(12) United States Patent
Bradley et al.

(10) Patent No.: US 11,606,941 B2
(45) Date of Patent: *Mar. 21, 2023

(54) ANIMAL MODELS AND THERAPEUTIC MOLECULES

(71) Applicant: Kymab Limited, Cambridge (GB)

(72) Inventors: Allan Bradley, Cambridge (GB); E-Chiang Lee, Cambridge (GB); Qi Liang, Cambridge (GB); Wei Wang, Cambridge (GB); Glenn Friedrich, Cambridge (GB)

(73) Assignee: Kymab Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/232,122

(22) Filed: Aug. 9, 2016

(65) Prior Publication Data

US 2016/0345552 A1 Dec. 1, 2016

Related U.S. Application Data

(63) Continuation of application No. 13/310,431, filed on Dec. 2, 2011, which is a continuation-in-part of application No. PCT/GB2011/050019, filed on Nov. 7, 2011, and a continuation-in-part of application No. PCT/GB2010/051122, filed on Jul. 7, 2010.

(60) Provisional application No. 61/355,666, filed on Jun. 17, 2010, provisional application No. 61/223,960, filed on Jul. 8, 2009.

(30) Foreign Application Priority Data

Jul. 8, 2009 (GB) ........................ 0911846
Jul. 28, 2009 (GB) ....................... 0913102

(51) Int. Cl.
| | | |
|---|---|---|
| *A01K 67/027* | (2006.01) | |
| *C12N 15/85* | (2006.01) | |
| *C07K 16/00* | (2006.01) | |
| *C07K 16/12* | (2006.01) | |
| *C07K 16/18* | (2006.01) | |
| *C07K 16/46* | (2006.01) | |
| *A61K 39/02* | (2006.01) | |
| *A61K 39/35* | (2006.01) | |
| *A61K 39/00* | (2006.01) | |

(52) U.S. Cl.
CPC ...... *A01K 67/0278* (2013.01); *A01K 67/0271* (2013.01); *A01K 67/0275* (2013.01); *A01K 67/0276* (2013.01); *A61K 39/107* (2013.01); *A61K 39/35* (2013.01); *C07K 16/00* (2013.01); *C07K 16/1203* (2013.01); *C07K 16/1239* (2013.01); *C07K 16/18* (2013.01); *C07K 16/462* (2013.01); *C12N 15/8509* (2013.01); *A01K 2207/15* (2013.01); *A01K 2217/072* (2013.01); *A01K 2217/075* (2013.01); *A01K 2217/15* (2013.01); *A01K 2227/105* (2013.01); *A01K 2267/01* (2013.01); *A61K 2039/505* (2013.01); *C07K 2317/14* (2013.01); *C07K 2317/21* (2013.01); *C07K 2317/24* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/567* (2013.01); *C07K 2317/76* (2013.01); *C07K 2317/92* (2013.01); *C12N 2015/8518* (2013.01)

(58) Field of Classification Search
CPC .................................. A01K 67/0278
See application file for complete search history.

(56) References Cited

U.S. PATENT DOCUMENTS

| | | | |
|---|---|---|---|
| 4,720,449 A | | 1/1988 | Borror et al. |
| 5,169,939 A | | 12/1992 | Gefter et al. |
| 5,545,806 A | | 8/1996 | Lonberg et al. |
| 5,545,807 A | | 8/1996 | Surani et al. |
| 5,565,321 A | | 10/1996 | Spriggs et al. |
| 5,633,425 A | | 5/1997 | Lonberg et al. |
| 5,770,429 A | | 6/1998 | Lonberg et al. |
| 5,789,215 A | | 8/1998 | Berns et al. |
| 5,807,715 A | * | 9/1998 | Morrison ............ C07K 16/00 435/326 |
| 5,939,598 A | | 8/1999 | Kucherlapati et al. |
| 5,948,600 A | | 9/1999 | Roschger et al. |
| 6,114,598 A | | 9/2000 | Kucherlapati et al. |
| 6,130,364 A | | 10/2000 | Jakobovits et al. |

(Continued)

FOREIGN PATENT DOCUMENTS

| | | |
|---|---|---|
| CA | 2307503 A1 | 11/2001 |
| CA | 2747534 A1 | 6/2010 |

(Continued)

OTHER PUBLICATIONS

Clark et al. (Nature Reviews: Genetics. 2003, 825-833.*
Niemann et al. (Rev. Sci, Tech. Off. Int. Spiz. 2005, (24), 285-298.*
Munoz et al. (2009) Stem Cell Rev. and Rep., vol. 5, 6-9.*
Hong et al. (2012, Stem Cells and Development, vol. 21(9), pp. 1571-1586.*

(Continued)

*Primary Examiner* — Anoop K Singh
(74) *Attorney, Agent, or Firm* — Nutter McClennen & Fish LLP

(57) ABSTRACT

The invention discloses methods for the generation of chimaeric human—non-human antibodies and chimaeric antibody chains, antibodies and antibody chains so produced, and derivatives thereof including fully humanised antibodies; compositions comprising said antibodies, antibody chains and derivatives, as well as cells, non-human mammals and vectors, suitable for use in said methods.

20 Claims, 57 Drawing Sheets

Specification includes a Sequence Listing.

(56) References Cited

U.S. PATENT DOCUMENTS

| | | | |
|---|---|---|---|
| 6,162,963 A | 12/2000 | Kucherlapati et al. | |
| 6,319,906 B1 | 11/2001 | Bennett et al. | |
| 6,395,487 B1 | 5/2002 | Bradley et al. | |
| 6,461,818 B1 | 10/2002 | Bradley et al. | |
| 6,596,541 B2 | 7/2003 | Murphy et al. | |
| 6,657,103 B1 | 12/2003 | Kucherlapati et al. | |
| 6,673,986 B1 | 1/2004 | Kucherlapati et al. | |
| 6,713,610 B1 | 3/2004 | Kucherlapati et al. | |
| 6,833,268 B1 | 12/2004 | Green et al. | |
| 6,914,128 B1 | 7/2005 | Salfeld et al. | |
| 6,992,235 B2 | 1/2006 | Bode et al. | |
| 6,998,514 B2 | 2/2006 | Bruggemann | |
| 7,105,348 B2 | 9/2006 | Murphy et al. | |
| 7,119,248 B1 | 10/2006 | Rajewsky et al. | |
| 7,205,140 B2 | 4/2007 | Gottschalk et al. | |
| 7,205,148 B2 | 4/2007 | Economides et al. | |
| 7,262,028 B2 | 8/2007 | Van Berkel et al. | |
| 7,294,754 B2 | 11/2007 | Poueymirou et al. | |
| 7,435,871 B2 | 10/2008 | Green et al. | |
| 7,501,552 B2 | 3/2009 | Lonberg et al. | |
| 7,605,237 B2 * | 10/2009 | Stevens | C07K 16/2866 530/350 |
| 7,605,238 B2 | 10/2009 | Korman et al. | |
| 7,910,798 B2 | 3/2011 | Tanamachi et al. | |
| 7,932,431 B2 | 4/2011 | Bruggemann | |
| 8,158,419 B2 | 4/2012 | Lonberg et al. | |
| 8,502,018 B2 | 8/2013 | Murphy et al. | |
| 8,592,644 B2 | 11/2013 | Harriman et al. | |
| 8,642,835 B2 | 2/2014 | MacDonald et al. | |
| 8,697,940 B2 | 4/2014 | MacDonald et al. | |
| 8,754,287 B2 | 6/2014 | MacDonald et al. | |
| 8,771,988 B2 | 7/2014 | Goepfert et al. | |
| 8,791,323 B2 * | 7/2014 | Murphy | A01K 67/0275 436/548 |
| 8,877,901 B2 | 11/2014 | Govindan | |
| 8,962,913 B2 | 2/2015 | Murphy | |
| 9,253,965 B2 | 2/2016 | Liang et al. | |
| 9,434,782 B2 | 9/2016 | Bradley et al. | |
| 9,445,581 B2 | 9/2016 | Bradley et al. | |
| 9,447,177 B2 | 9/2016 | Bradley et al. | |
| 9,504,236 B2 | 11/2016 | Bradley et al. | |
| 9,505,827 B2 | 11/2016 | Bradley et al. | |
| 9,783,593 B2 | 10/2017 | Bradley et al. | |
| 9,783,618 B2 | 10/2017 | Friedrich et al. | |
| 9,788,534 B2 | 10/2017 | Bradley et al. | |
| 9,896,516 B2 | 2/2018 | Bradley et al. | |
| 9,924,705 B2 | 3/2018 | Liang et al. | |
| 9,938,357 B2 | 4/2018 | Bradley et al. | |
| 9,938,358 B2 | 4/2018 | Bradley et al. | |
| 9,963,716 B2 | 5/2018 | Bradley et al. | |
| 10,064,398 B2 | 9/2018 | Bradley et al. | |
| 10,149,462 B2 | 12/2018 | Lee et al. | |
| 10,165,763 B2 | 1/2019 | Bradley et al. | |
| 10,226,033 B2 | 3/2019 | Bradley et al. | |
| 10,251,377 B2 | 4/2019 | Clube et al. | |
| 10,605,808 B2 | 3/2020 | Logtenberg et al. | |
| 10,667,501 B2 | 6/2020 | Germaschewski et al. | |
| 10,730,930 B2 | 8/2020 | Bradley et al. | |
| 10,774,155 B2 | 9/2020 | Bradley et al. | |
| 10,966,412 B2 | 4/2021 | Lee et al. | |
| 2002/0088016 A1 | 7/2002 | Bruggemann | |
| 2002/0183275 A1 | 12/2002 | Murphy et al. | |
| 2003/0070185 A1 | 4/2003 | Jakobovits et al. | |
| 2003/0108925 A1 | 6/2003 | Dix et al. | |
| 2003/0167489 A1 | 9/2003 | Rajewsky et al. | |
| 2003/0217373 A1 | 11/2003 | Green et al. | |
| 2004/0128703 A1 | 7/2004 | Shizuya | |
| 2004/0231012 A1 | 11/2004 | Bruggemann | |
| 2005/0048621 A1 | 3/2005 | Grasso et al. | |
| 2006/0008892 A1 | 1/2006 | Yacoby-Zeevi | |
| 2006/0015949 A1 | 1/2006 | Lonberg et al. | |
| 2006/0015957 A1 * | 1/2006 | Lonberg | A01K 67/0275 800/18 |
| 2006/0021074 A1 | 1/2006 | Kellermann et al. | |
| 2006/0199204 A1 | 9/2006 | Dix et al. | |
| 2007/0280945 A1 | 12/2007 | Stevens et al. | |
| 2008/0098490 A1 | 4/2008 | Jakobovits et al. | |
| 2009/0083870 A1 | 3/2009 | Horn et al. | |
| 2009/0083879 A1 | 3/2009 | Dhugga | |
| 2009/0093059 A1 | 4/2009 | Baszczynski et al. | |
| 2009/0209036 A1 | 8/2009 | Reynaud et al. | |
| 2009/0307787 A1 | 12/2009 | Grosveld et al. | |
| 2010/0011450 A1 | 1/2010 | Garcia et al. | |
| 2010/0069614 A1 | 3/2010 | Houtzager et al. | |
| 2010/0146647 A1 | 6/2010 | Logtenberg et al. | |
| 2010/0196367 A1 | 8/2010 | Day | |
| 2010/0330676 A1 | 12/2010 | Horowitz et al. | |
| 2011/0119779 A1 | 5/2011 | Shizuya et al. | |
| 2011/0138489 A1 | 6/2011 | Tanamachi et al. | |
| 2011/0145937 A1 | 6/2011 | MacDonald et al. | |
| 2011/0195454 A1 | 8/2011 | McWhirter et al. | |
| 2011/0236378 A1 | 9/2011 | Green et al. | |
| 2011/0283376 A1 | 11/2011 | Murphy et al. | |
| 2012/0021409 A1 | 1/2012 | McWhirter et al. | |
| 2012/0070861 A1 | 3/2012 | MacDonald et al. | |
| 2012/0073004 A1 | 3/2012 | MacDonald et al. | |
| 2012/0096572 A1 * | 4/2012 | Macdonald | A01K 67/0275 800/18 |
| 2012/0195910 A1 | 8/2012 | Wu et al. | |
| 2012/0204278 A1 | 8/2012 | Bradley et al. | |
| 2012/0233715 A1 | 9/2012 | Kuroiwa et al. | |
| 2012/0322108 A1 | 12/2012 | MacDonald et al. | |
| 2013/0039850 A1 | 2/2013 | Lonberg et al. | |
| 2013/0096287 A1 | 4/2013 | MacDonald et al. | |
| 2013/0102031 A1 | 4/2013 | King et al. | |
| 2013/0160153 A1 | 6/2013 | MacDonald et al. | |
| 2013/0198879 A1 | 8/2013 | McWhirter et al. | |
| 2013/0212719 A1 | 8/2013 | MacDonald et al. | |
| 2013/0243759 A1 | 9/2013 | Friedrich et al. | |
| 2013/0247235 A1 | 9/2013 | McWhirter et al. | |
| 2013/0254911 A1 | 9/2013 | MacDonald et al. | |
| 2013/0263293 A1 | 10/2013 | Bradley et al. | |
| 2013/0323790 A1 | 12/2013 | MacDonald et al. | |
| 2013/0323791 A1 | 12/2013 | MacDonald et al. | |
| 2013/0326647 A1 | 12/2013 | MacDonald et al. | |
| 2013/0333057 A1 | 12/2013 | MacDonald et al. | |
| 2014/0017228 A1 | 1/2014 | MacDonald et al. | |
| 2014/0017782 A1 | 1/2014 | Murphy et al. | |
| 2014/0041067 A1 | 2/2014 | Bradley et al. | |
| 2014/0120582 A1 | 5/2014 | Bradley et al. | |
| 2014/0130193 A1 | 5/2014 | MacDonald et al. | |
| 2014/0130194 A1 | 5/2014 | MacDonald et al. | |
| 2014/0137275 A1 | 5/2014 | MacDonald et al. | |
| 2014/0150125 A1 | 5/2014 | Bradley et al. | |
| 2014/0150126 A1 | 5/2014 | Bradley et al. | |
| 2014/0182003 A1 | 6/2014 | Bradley et al. | |
| 2014/0201854 A1 | 7/2014 | Bradley et al. | |
| 2014/0201856 A1 | 7/2014 | Bradley et al. | |
| 2014/0212416 A1 | 7/2014 | Friedrich et al. | |
| 2014/0213773 A1 | 7/2014 | MacDonald et al. | |
| 2014/0283150 A1 | 9/2014 | Bradley et al. | |
| 2014/0323327 A1 | 10/2014 | Bradley et al. | |
| 2014/0325690 A1 | 10/2014 | Bradley et al. | |
| 2014/0331339 A1 | 11/2014 | Bradley et al. | |
| 2014/0331343 A1 | 11/2014 | Bradley et al. | |
| 2014/0331344 A1 | 11/2014 | Friedrich et al. | |
| 2014/0356908 A1 | 12/2014 | Grosveld et al. | |
| 2014/0359797 A1 | 12/2014 | Bradley et al. | |
| 2015/0033369 A1 | 1/2015 | Bradley et al. | |
| 2015/0033372 A1 | 1/2015 | Bradley et al. | |
| 2015/0037337 A1 | 2/2015 | Friedrich et al. | |
| 2015/0040250 A1 | 2/2015 | Bradley et al. | |
| 2015/0082466 A1 | 3/2015 | Clube | |
| 2015/0113669 A1 | 4/2015 | Bradley et al. | |
| 2015/0133641 A1 | 5/2015 | Germaschewski et al. | |
| 2015/0196015 A1 | 7/2015 | MacDonald et al. | |
| 2015/0334998 A1 | 11/2015 | Bradley et al. | |
| 2016/0044900 A1 | 2/2016 | Bradley et al. | |
| 2016/0150768 A1 | 6/2016 | Bradley et al. | |
| 2016/0219846 A1 | 8/2016 | Liang | |
| 2016/0249592 A1 | 9/2016 | Bradley et al. | |
| 2016/0345551 A1 | 12/2016 | Bradley et al. | |
| 2016/0345552 A1 | 12/2016 | Bradley et al. | |
| 2016/0353719 A1 | 12/2016 | Friedrich et al. | |

(56) References Cited

U.S. PATENT DOCUMENTS

| | | | |
|---|---|---|---|
| 2017/0051045 A1 | 2/2017 | Bradley et al. |
| 2017/0071174 A1 | 3/2017 | Bradley et al. |
| 2017/0081423 A1 | 3/2017 | Bradley et al. |
| 2017/0094956 A1 | 4/2017 | Bradley et al. |
| 2017/0096498 A1 | 4/2017 | Bradley et al. |
| 2017/0099815 A1 | 4/2017 | Bradley et al. |
| 2017/0099816 A1 | 4/2017 | Bradley et al. |
| 2017/0099817 A1 | 4/2017 | Bradley et al. |
| 2017/0101482 A1 | 4/2017 | Bradley et al. |
| 2017/0101483 A1 | 4/2017 | Bradley et al. |
| 2017/0105396 A1 | 4/2017 | Bradley et al. |
| 2017/0135327 A1 | 5/2017 | Lee |
| 2017/0320936 A1 | 11/2017 | Bradley et al. |
| 2017/0354131 A1 | 12/2017 | Bradley et al. |
| 2018/0030121 A1 | 2/2018 | Bradley et al. |
| 2018/0142006 A1 | 5/2018 | Logtenberg et al. |
| 2018/0282761 A1 | 10/2018 | Bradley et al. |
| 2018/0295821 A1 | 10/2018 | Friedrich et al. |
| 2018/0298112 A1 | 10/2018 | Bradley et al. |
| 2019/0174729 A1 | 6/2019 | Lee et al. |
| 2019/0208753 A1 | 7/2019 | Clube |
| 2019/0327946 A1 | 10/2019 | Bradley et al. |
| 2020/0205384 A1 | 7/2020 | Friedrich et al. |
| 2020/0214274 A1 | 7/2020 | Lee et al. |
| 2020/0267952 A1 | 8/2020 | Germaschewski et al. |
| 2020/0317751 A1 | 10/2020 | Bradley et al. |
| 2020/0317752 A1 | 10/2020 | Bradley et al. |
| 2020/0337280 A1 | 10/2020 | Bradley et al. |
| 2020/0352144 A1 | 11/2020 | Bradley et al. |
| 2020/0352145 A1 | 11/2020 | Bradley et al. |
| 2020/0375158 A1 | 12/2020 | Bradley et al. |
| 2021/0079118 A1 | 3/2021 | Bradley et al. |
| 2021/0204530 A1 | 7/2021 | Lee et al. |

FOREIGN PATENT DOCUMENTS

| | | |
|---|---|---|
| CA | 2820824 A1 | 2/2012 |
| DE | 10251918 A1 | 5/2004 |
| EP | 1780272 A1 | 5/2007 |
| EP | 0937140 B1 | 9/2007 |
| EP | 2480676 B1 | 8/2012 |
| EP | 2517556 A2 | 10/2012 |
| EP | 2517556 B1 | 10/2012 |
| EP | 2517557 A2 | 10/2012 |
| EP | 2147594 A1 | 11/2013 |
| GB | 2398784 A | 9/2004 |
| GB | 2403475 A | 1/2005 |
| JP | 2004524841 A | 8/2004 |
| JP | 2005510253 A | 4/2005 |
| JP | 2008507257 A | 3/2008 |
| JP | 20100512749 A | 4/2010 |
| JP | 2011525808 A | 9/2011 |
| JP | 2012521211 A | 9/2012 |
| KR | 20050042792 A | 5/2005 |
| WO | WO-9004036 A1 | 4/1990 |
| WO | WO-9100906 A1 | 1/1991 |
| WO | WO-9110741 A1 | 7/1991 |
| WO | 9203918 A1 | 3/1992 |
| WO | WO-9312227 A1 | 6/1993 |
| WO | WO-9402602 A1 | 2/1994 |
| WO | WO-9404667 A1 | 3/1994 |
| WO | WO-9425585 A1 | 11/1994 |
| WO | WO-9630498 A1 | 10/1996 |
| WO | WO-9824884 A1 | 6/1998 |
| WO | WO-9824893 A2 | 6/1998 |
| WO | 9850431 A2 | 11/1998 |
| WO | WO-9945962 A1 | 9/1999 |
| WO | WO-0026373 A1 | 5/2000 |
| WO | 0071585 A1 | 11/2000 |
| WO | WO-0208409 A2 | 1/2002 |
| WO | WO-0236789 A2 | 5/2002 |
| WO | WO-0243478 A2 | 6/2002 |
| WO | WO-02053596 A2 | 7/2002 |
| WO | WO-02059263 A2 | 8/2002 |
| WO | WO-02066630 A1 | 8/2002 |
| WO | WO-02070648 A2 | 9/2002 |
| WO | WO-03006639 A1 | 1/2003 |
| WO | WO-03047336 A2 | 6/2003 |
| WO | WO-03061363 A2 | 7/2003 |
| WO | 2004009618 A2 | 1/2004 |
| WO | 2004044150 A2 | 5/2004 |
| WO | WO-2004050838 A2 | 6/2004 |
| WO | WO-2005003364 A2 | 1/2005 |
| WO | WO-2005004592 A2 | 1/2005 |
| WO | WO-2005019463 A1 | 3/2005 |
| WO | WO-2005058815 A2 | 6/2005 |
| WO | WO-2005092926 A2 | 10/2005 |
| WO | WO-2006008548 A2 | 1/2006 |
| WO | 2006029459 A1 | 3/2006 |
| WO | WO-2006044492 A2 | 4/2006 |
| WO | WO-2006055704 A2 | 5/2006 |
| WO | WO-2006068953 A2 | 6/2006 |
| WO | 2006117699 A2 | 11/2006 |
| WO | WO-2006122442 A1 | 11/2006 |
| WO | WO-2007085837 A1 | 8/2007 |
| WO | WO-2007096779 A2 | 8/2007 |
| WO | WO-2007143168 A2 | 12/2007 |
| WO | WO-2008022391 A1 | 2/2008 |
| WO | WO-2008054606 A2 | 5/2008 |
| WO | WO-2008070367 A2 | 6/2008 |
| WO | WO-2008076379 A2 | 6/2008 |
| WO | WO-2008081197 A1 | 7/2008 |
| WO | WO-2008094178 A2 | 8/2008 |
| WO | WO-2008103474 A1 | 8/2008 |
| WO | 2008108918 A1 | 9/2008 |
| WO | WO2007/117410 * | 10/2008 |
| WO | WO-2008118970 A2 | 10/2008 |
| WO | WO-2008122886 A2 | 10/2008 |
| WO | WO-2008151081 A1 | 12/2008 |
| WO | WO-2009013620 A2 | 1/2009 |
| WO | WO-2009018411 A1 | 2/2009 |
| WO | WO-2009023540 A1 | 2/2009 |
| WO | WO-2009076464 A2 | 6/2009 |
| WO | WO-2009080254 A1 | 7/2009 |
| WO | WO-2009097006 A2 | 8/2009 |
| WO | WO-2009118524 A2 | 10/2009 |
| WO | WO-2009129247 A2 | 10/2009 |
| WO | WO-2009143472 A2 | 11/2009 |
| WO | WO-2009157771 A2 | 12/2009 |
| WO | WO-2010039900 A2 | 4/2010 |
| WO | WO-2010070263 A1 | 6/2010 |
| WO | WO-2010077854 A1 | 7/2010 |
| WO | WO-2010097385 A1 | 9/2010 |
| WO | WO-2010109165 A2 | 9/2010 |
| WO | WO-2010113039 A1 | 10/2010 |
| WO | WO-2011004192 A1 | 1/2011 |
| WO | WO-2011008093 A1 | 1/2011 |
| WO | WO-2011014469 A1 | 2/2011 |
| WO | WO-2011056864 A1 | 5/2011 |
| WO | WO-2011062206 A1 | 5/2011 |
| WO | WO-2011062207 A1 | 5/2011 |
| WO | WO-2011071957 A1 | 6/2011 |
| WO | WO-2011072204 A1 | 6/2011 |
| WO | WO-2011097603 A1 | 8/2011 |
| WO | WO-2011146121 A1 | 11/2011 |
| WO | WO-2011158009 A1 | 12/2011 |
| WO | WO-2011163311 A1 | 12/2011 |
| WO | WO-2011163314 A1 | 12/2011 |
| WO | WO-2012018764 A1 | 2/2012 |
| WO | WO-2012023053 A2 | 2/2012 |
| WO | WO-2012064682 A1 | 5/2012 |
| WO | 2012/088313 A1 | 6/2012 |
| WO | WO-2012141798 A1 | 10/2012 |
| WO | WO-2012148873 A2 | 11/2012 |
| WO | WO-2013022782 A1 | 2/2013 |
| WO | WO-2013041844 A2 | 3/2013 |
| WO | WO-2013041845 A2 | 3/2013 |
| WO | WO-2013041846 A2 | 3/2013 |
| WO | WO-2013045916 A1 | 4/2013 |
| WO | WO-2013059230 A1 | 4/2013 |
| WO | WO-2013061078 A1 | 5/2013 |
| WO | WO-2013061098 A2 | 5/2013 |
| WO | WO-2013079953 A1 | 6/2013 |
| WO | WO-2013096142 A1 | 6/2013 |

(56) References Cited

FOREIGN PATENT DOCUMENTS

| WO | WO-2013116609 A1 | 8/2013 |
|---|---|---|
| WO | WO-2013130981 A1 | 9/2013 |
| WO | WO-2013134263 A1 | 9/2013 |
| WO | WO-2013144567 A1 | 10/2013 |
| WO | WO-2013166236 A1 | 11/2013 |
| WO | WO-2013171505 A1 | 11/2013 |
| WO | WO-2013176772 A1 | 11/2013 |
| WO | WO-2014093622 A2 | 6/2014 |
| WO | 2014130690 A1 | 8/2014 |
| WO | WO-2015049517 A2 | 4/2015 |
| WO | 2019008123 A2 | 1/2019 |

OTHER PUBLICATIONS

Butler Rev Scientifique et Technique Office International Des Epizooties. 1998, 17, 1, 43-70.*
Stevens et al. Pharma Focus Asia, 2008, 8, 72-74)/.*
Murphy et al. Slide Presentation dated Nov. 3, 2009, The Big and the Backward, slides 1-57).*
Aguilera et al. (EMBO 4(13B): 3689-3693, 1985).*
Lefranc et al ExpClin Immunogenet 2001;18:161-174.*
Valenzuela et al. Nature Biotechnology 2003 21:652-659).*
Adams Genomics. Dec. 2005; 86 (6):753-8.*
Zheng et al. Mol. Cell Biol. 2000, 20, 648-655).*
Oberdoerffer et al (Nucleic Acids Res. 2003, 31: e140.*
Torres and Kuhn, (Laboratory Protocols for Conditional Gene Targeting, 1997, p. 37-40.*
Stevens et al Expanded poster in 1st Mugen Conf. on animal model, Sept. pp. 1-6 (Year: 2006).*
Sakai et al PNAS, 96, 1526-1531 (Year: 1999).*
Sullivan et al The Journal of Biological Chemistry, 272, 17972-17980 (Year: 1997).*
U.S. Appl. No. 13/846,672, filed Mar. 18, 2013.
U.S. Appl. No. 13/875,892, filed May 2, 2013.
U.S. Appl. No. 14/080,630, filed Nov. 14, 2013.
U.S. Appl. No. 14/220,095, filed Mar. 19, 2014.
U.S. Appl. No. 14/226,698, filed Mar. 26, 2014.
U.S. Appl. No. 14/263,158, filed Apr. 28, 2014.
U.S. Appl. No. 14/263,176, filed Apr. 28, 2014.
U.S. Appl. No. 14/516,461, filed Oct. 16, 2014.
U.S. Appl. No. 15/018,670, filed Feb. 8, 2016.
U.S. Appl. No. 15/088,805, filed Apr. 1, 2016.
U.S. Appl. No. 15/095,315, filed Apr. 11, 2016.
U.S. Appl. No. 15/383,196, filed Dec. 19, 2016.
U.S. Appl. No. 15/383,202, filed Dec. 19, 2016.
1st International MUGEN Conference on Animal Models for Human Immunological Disease, Sep. 10-13, 2006—Athens Greece (Abstracts 1-52), 52 pages.
Adams D.J., et al., "Contemporary approaches for modifying the mouse genome," *Physiological Genomics*, vol. 34, 2008, pp. 225-238.
Adams D.J., et al., "Mutagenic Insertion and Chromosome Engineering Resource (MICER)," *Nature Genetics*, vol. 36 (8), Aug. 2004, pp. 867-871.
Affidavits Evidencing Murphy Slides as Printed Publication, dated Jun. 20, 2016, 84 pages.
Ahmed T., "Sanofi-aventis and Regeneron Extend Therapeutic Antibody Agreement," *PharmaDeals Review*, Nov. 2009, vol. 11, p. 115.
Arnaout R., et al., "High-Resolution Description of Antibody Heavy-Chain Repertoires in Humans," *PLoS One*, Aug. 2011, vol. 6 (8), pp. e22365-1-e22365-8.
Arthur J.S.C., et al., "Gene-Targeting Vectors," *Transgenesis Techniques, Principles and Protocols*, Third edition, Chapter 9, 2009 (24 pages, including cover sheet, copyright and preface pages and table of contents), pp. 127-144.
Asenbauer H., et al., "The immunoglobulin lambda light chain enhancer consists of three modules which synergize in activation of transcription," *European Journal of Immunology*, 1999, vol. 29, pp. 713-724.

Askew G.R., et al., "Site-Directed Point Mutations in Embryonic Stem Cells: A Gene-Targeting Tag-and-Exchange Strategy," *Molecular and Cellular Biology*, Jul. 1993, vol. 13 (7), pp. 4115-4124.
Atlas of Genetics and Cytogenetics in Oncology and Haematology, VPREB1 (pre-B lymphocyte 1), 5 pages. [Retrieved online at http://atlasgeneticsoncology.org/Genes/GC_VPREB1.html on May 25, 2015].
Auerbach W., et al., "Establishment and Chimera Analysis of 129/SvEv- and C57BL/6-Derived Mouse Embryonic Stem Cell Lines," BioTechniques, 2000, vol. 29 (5), pp. 1024-1032.
Avery S., Attorney for Applicant, Third-Party Pre-Issuance Submission Under 37 CFR Section 1.290 in U.S. Appl. No. 14/517,755, dated Jun. 26, 2015, 16 pages.
Baer A., et al., "Coping with kinetic and thermodynamic barriers: RMCE, an efficient strategy for the targeted integration of transgenes," *Current Opinions in Biotechnology*, Oct. 2001, vol. 12(5), pp. 473-480.
Baker A.M., et al., "Adaptation of TCR Expression Vectors for the Construction of Mouse-Human Chimeric MBP-SpecificTCR Transgenes," *Journal of Neuroscience Research*, 1996, vol. 45 (4), pp. 487-491.
Baker M.D., et al., "Homologous Recombination Between Transferred and Chromosomal Immunoglobulin Kappa Genes," *Molecular and Cellular Biology*, Oct. 1988, vol. 8 (10), pp. 4041-4047.
Barreto V.M., et al., "AID from bony fish catalyzes class switch recombination," *Journal of Experimental Medicine*, 2005, vol. 202 (6), pp. 733-738.
Bates J.G., et al., "Chromosomal Position of A $V_H$ Gene Segment Determines its Activation and Inactivation as A Substrate for V(D)J Recombination," *Journal of Experimental Medicine*, 2007, vol. 204 (13), pp. 3247-3256.
Beard C., et al., "Efficient Method to Generate Single-Copy Transgenic Mice by Site-Specific Integration in Embryonic Stem Cells," *Genesis*, 2006, vol. 44 (1), pp. 23-28.
Beck E., et al., "Nucleotide Sequence And Exact Localization Of The Neomycin Phosphotransferase Gene From Transposon Tn5," *Genesis*, 1982, vol. 19 (3), pp. 327-336.
Beck J.A., et al., "Genealogies of mouse inbred strains," *Nature Genetics*, 2000, vol. 24, pp. 23-25 (with supporting table and chart).
Beerli R.R., et al., "Mining Human Antibody Repertoires," *mAbs*, Jul./Aug. 2010, vol. 2 (4), pp. 365-378.
Bentham, A., Attorneys for Regeneron Pharmaceuticals, Inc., Opposition against EP2421357B1 in the name of Kymab Ltd. pertaining to Application No. 10734546.4, dated Jan. 9, 2017, 13 pages.
Berg D.E., et al., "Inverted Repeats of Tn5 are Transposable Elements," *Proceedings of the National Academy of Sciences U.S.A*, 1982, vol. 79 (8), pp. 2632-2635.
Bethke B., et al., "Segmental Genomic Replacement by Cre-Mediated Recombination: Genotoxic Stress Activation of the p53 Promoter in Single-Copy Transformants," *Nucleic Acids Research*, 1997, vol. 25 (14), pp. 2828-2834.
Bhattacharya P., et al., "Switch Region Identity Plays an Important Role in Ig Class Switch Recombination," *Journal of Immunology*, 2010, vol. 184 (11), pp. 6242-6248.
Billiard F., et al., "Ongoing Dll4-Notch Signaling is Required for T-Cell Homeostasis in the Adult Thymus," *European Journal of Immunology*, 2011, vol. 41 (8), pp. 2207-2216.
Birling M.C., et al., "Site-Specific Recombinases for Manipulation of the Mouse Genome," *Transgenesis Techniques, Principles and Protocols*, Third edition, Chapter 16, 2009 (25 pages, including cover sheet, copyright and preface pages and table of contents), pp. 245-263.
Blankenstein T., et al., "Immunoglobulin $V_H$ Region Genes of the Mouse are Organized in Overlapping Clusters," *European Journal of Immunology*, 1987, vol. 17 (9), pp. 1351-1357.
Board of Appeal of the European Patent Office, Datasheet for the Decision of Nov. 9, 2015 for Application No. 02709544.7, Case T 2220/14-3.3.08, 83 pages.
Bode J., et al., "The Transgeneticist's Toolbox: Novel Methods for The Targeted Modification of Eukaryotic Genomes," *Biological Chemistry*, Sep./Oct. 2000, vol. 381 (9-10), pp. 801-813.

(56) References Cited

OTHER PUBLICATIONS

Bogen B., et al., "A Rearranged $\lambda_2$ Light Gene Chain Retards but does not Exclude x and $\lambda_1$, Expression," *European Journal of Immunology*, 1991, vol. 21 (10), pp. 2391-2395.
Bolland D.J., et al., "Antisense Intergenic Transcription Precedes Igh D-To-J Recombination and is Controlled by the Intronic Enhancer Eμ," *Molecular and Cellular Biology*, 2007, vol. 27 (15), pp. 5523-5533.
Bonin A., et al., "Isolation, Microinjection, and Transfer of Mouse Blastocysts," *Methods in Molecular Biology*, Chapter 9, 2001, vol. 158, pp. 121-134.
Bornstein, G.G. et al., "Development of a new fully human anti-CD20 monoclonal antibody forthe treatment of B-cell malignancies", *Investigational New Drugs*, 2010, vol. 28, pp. 561-574.
Bottaro A., et al., "Deletion ofthe IgH Intronic Enhancer and Associated Matrix-Attachment Regions Decreases, but does not Abolish, Class Switching at the μ Locus," *International Immunology*, 1998, vol. 10 (6), pp. 799-806.
Bradley A., et al., "Formation of Germ-Line Chimaeras from Embryo-Derived Teratocarcinoma Cell Lines," *Nature*, 1984, vol. 309 (5965), pp. 255-256.
Bransteitter R., et al., "Activation-Induced Cytidine Deaminase Deaminates Deoxycytidine on Single-Stranded DNA but Requires the Action of RNase," *Proceedings of the National Academy of Sciences of the U.S.A.*, Apr. 2003, vol. 100 (7), pp. 4102-4107.
Brault V., et al., "Modeling Chromosomes in Mouse to Explore the Function of Genes, Genomic Disorders, and Chromosonal Organization," *PLoS Genetics*, Jul. 2006, vol. 2 (7), pp. e86-1-e86-9.
Breden F., et al., "Comparison of Antibody Repertoires Produced By HIV-1 Infection, Other Chronic and Acute Infections, and Systemic Autoimmune Disease," *PLoS One*, 2011, vol. 6 (3), pp. e16857.
Brezinschek H.P., et al., "Analysis ofthe Human $V_H$ Gene Repertoire," *Journal of Clinical Investigation*, 1997, vol. 99 (10), pp. 2488-2501.
Brüggemann M., et al., "A Repertoire of Monoclonal Antibodies with Human Heavy Chains from Transgenic Mice," *Proceedings of the National Academy of Sciences U.S.A*, 1989, vol. 86 (17), pp. 6709-6713.
Brüggemann M., "Human Antibody Expression in Transgenic Mice," *Archivum Immunologiae et Therapia Experimentalis*, 2001, vol. 49 (3), pp. 203-208.
Brüggemann M., et al., "Human Antibody Production in Transgenic Mice: Expression from 100 Kb ofthe Human IgH Locus," *European Journal of Immunology*, May 1991, vol. 21 (5), pp. 1323-1326.
Brüggemann M., et al., "Immunoglobulin Heavy Chain Locus of the Rat: Striking Homology to Mouse Antibody Genes," *Proceedings ofthe National Academy of Sciences U.S.A*, 1986, vol. 83 (16), pp. 6075-6079.
Brüggemann M., et al., "The Immunogenicity of Chimeric Antibodies," *The Journal of Experimental Medicine*, Dec. 1989, vol. 170 (6), pp. 2153-2157.
Brüggemann M., et al., "Strategies for Expressing Human Antibody Repertoires in Transgenic Mice," *Immunology Today*, Aug. 1996, vol. 17 (8), pp. 391-397.
Briney B.S., et al., "Human Peripheral Blood Antibodies with Long HCDR3s are Established Primarily at Original Recombination using A Limited Subset of Germline Genes," *PLoS One*, 2012, vol. 7 (5), pp. e36750-1-e36750-13.
Brocker C.N., et al., "Evolutionary Divergence and Functions of the ADAM and ADAMTS Gene Families," *Human Genomics*, 2009, vol. 4 (1), pp. 43-55.
Brüggemann M., "Human Monoclonal Antibodies from Translocus Mice," *Molecular Biology of B Cells*, Chapter 34, 2003, pp. 547-561.
Buehr M., et al., "Capture of Authentic Embryonic Stem Cells from Rat Blastocysts," *Cell*, 2008, vol. 135 (7), pp. 1287-1298.
Cadiñanos J., et al., "Generation of an Inducible and Optimized PiggyBac Transposon System," *Nucleic Acids Research*, 2007, vol. 35 (12), pp. e87.
Call L.M., et al., "A Cre-lox recombination system for the targeted integration of circular yeast artificial chromosomes into embryonic stem cells," *Human Molecular Genetics*, 2000, vol. 9 (12), pp. 1745-1751.
Carstea A.C., et al., "Germline Competence of Mouse ES and iPS Cell Lines: Chimera Technologies and Genetic Background," *World Journal of Stem Cells*, 2009, vol. 1 (1), pp. 22-29.
Carter T.C., et al., "Standardized Nomenclature for Inbred Strains of Mice," *Cancer Research*, 1952, vol. 12 (8), pp. 602-613.
Casrouge A., et al., "Size Estimate of the αβ TCR Repertoire of Naive Mouse Splenocytes," *The Journal of Immunology*, 2000, vol. 164 (11), pp. 5782-5787.
Chan A.C., et al., "Therapeutic Antibodies for Autoimmunity and Inflammation," *Nature Reviews Immunology*, 2010, vol. 10 (5), pp. 301-316.
Chen C., et al., "Immunoglobulin Heavy Chain Gene Replacement: A Mechanism of Receptor Editing," *Immunity*, 1995, vol. 3 (6), pp. 747-755.
Chen J., et al., "B Cell Development in Mice that Lack One or Both Immunoglobulin κ Light Chain Genes," *The EMBO Journal*, 1993, vol. 12 (3), pp. 821-830.
Chen Y., "PiggyBac Transposon-Mediated, Reversible Gene Transfer in Human Embryonic Stem Cells," *Stem Cells and Development*, Nov. 2010, vol. 19 (6), 9 pages.
Chia R., et al., "The origins and uses of mouse outbred stocks," *Nature Genetics*, 2005, vol. 37 (11), pp. 1181-1186.
Chinese Patent Office, First Office Action (English Translation) for Chinese Application No. 201180039668.1, dated Jan. 3, 2014, 6 pages.
Chinese Patent Office, First Office Action for Chinese Patent Application No. 201180039668.1, dated Jan. 3, 2014, 6 pages.
Chinese Patent Office, Office Action (English Translation) for Chinese Patent Application No. 201380029744.1, dated Nov. 10, 2016, 2 pages.
Chinese Patent Office, Office Action for Chinese Patent Application No. 201380027944.1, dated Nov. 10, 2016, 5 pages.
Chinese Patent Office, Search Report (English Translation), Chinese Patent Application No. 201180039668.1, dated Jan. 3, 2014, 2 pages.
Chinese Patent Office, Search Report, Chinese Patent Application No. 201180039668.1, dated Jan. 3, 2014, 1 page.
Cho C., "Testicular and Epididymal ADAMs: Expression and Function During Fertilization," *Nature Reviews Urology*, 2012, vol. 9 (10), pp. 550-560.
Choi I., et al., "Characterization and Comparative Genomic Analysis of Intronless Adams with Testicular Gene Expression," *Genomics*, 2004, vol. 83 (4), pp. 636-646.
Clark L.A., et al., "Trends in Antibody Sequence Changes During the Somatic Hypermutation Process," *The Journal of Immunology*, 2006, vol. 177 (1), pp. 333-340.
Clark M.R., "IgG Effector Mechanisms," *Chemical Immunology*, 1997, vol. 65, pp. 88-110.
Colbère-Garapin F., et al., "A New Dominant Hybrid Selective Marker for Higher Eukaryotic Cells," *Journal of Molecular Biology*, 1981, vol. 150 (1), pp. 1-14.
Collins F.S., et al., "A Mouse for All Reasons," *Cell*, 2007, vol. 128 (1), pp. 9-13.
Collins A.M., et al., "The reported germline repertoire of human immunoglobulin kappa chain genes is relatively complete and accurate," *Immunogenetics*, 2008, vol. 60, pp. 669-676.
Combriato G., et al., "Regulation of Human Igλ Light Chain Gene Expression by NF-κB1," *The Journal of Immunology*, 2002, vol. 168 (3), pp. 1259-1266.
Conrath K.E., et al., "Camel Single-domain Antibodies as Modular Building Units in Bispecific and Bivalent Antibody Constructs," *The Journal of Biological Chemistry*, 2001, vol. 276 (10), pp. 7346-7350.
Copeland N.G., et al., "Recombineering: A Powerful New Tool for Mouse Functional Genomics," *Nature Reviews Genetics*, 2001, vol. 2 (10), pp. 769-779.
Corbett S.J., et al., "Sequence of the Human Immunoglobulin Diversity (D) Segment Locus: A Systematic Analysis Provides No Evidence for the Use of DIR Segments, Inverted D Segments,

(56) References Cited

OTHER PUBLICATIONS

"Minor" D Segments or D-D Recombination," *Journal of Molecular Biology*, 1997, vol. 270 (4), pp. 587-597.
Corti D., et al., "A Neutralizing Antibody Selected from Plasma Cells that Binds to Group 1 and Group 2 Influenza A Hemagglutinins," *Science*, 2011, vol. 333 (6044), pp. 850-856.
Crouch E.E., et al., "Regulation of AID expression in the Immune Response," *Journal of Experimental Medicine*, May 2007, vol. 204 (5), pp. 1145-1156.
Cuesta A.M., et al., "Multivalent Antibodies: When Design Surpasses Evolution," *Trends in Biotechnology*, 2010, vol. 28 (7), pp. 355-362.
Davies N.P., et al., "Creation of Mice Expressing Human Antibody Light Chains by Introduction of a Yeast Artificial Chromosome Containing the Core Region of the Human Immunoglobulin κ Locus," *Nature Biotechnology*, Aug. 1993, vol. 11 (8), pp. 911-914.
D'Eustachio P., et al., "Mouse Chromosome 12," *Mammalian Genome*, 1998, vol. 8, pp. S241-S257.
De Bono B., et al., "VH Gene Segments in the Mouse and Human Genomes," *Journal of Molecular Biology*, 2004, vol. 342 (1), pp. 131-143.
De Kruif J., et al., "Human Immunoglobulin Repertoires Against Tetanus Toxoid Contain a Large and Diverse Fraction of High-Affinity Promiscuous $V_H$ Genes," *Journal of Molecular Biology*, 2009, vol. 387 (3), pp. 548-558.
De Saint Vincent B.R., et al., "Homologous Recombination in Mammalian Cells Mediates Formation of A Functional Gene from Two Overlapping Gene Fragments," *Proceedings of the National Academy of Sciences of the U.S.A*, 1983, vol. 80 (7), pp. 2002-2006.
De Wildt R.M.T., et al., "Analysis of Heavy and Light Chain Pairings Indicates that Receptor Editing Shapes the Human Antibody Repertoire," *Journal of Molecular Biology*, 1999, vol. 285, pp. 895-901.
Dechiara T.M., et al., "Producing Fully ES Cell-Derived Mice from Eight-Cell Stage Embryo Injections," *Methods in Enzymology*, Chapter 16, 2010, vol. 476, pp. 285-294.
Dechiara T.M., et al., "VelociMouse: Fully ES Cell-Derived F0-Generation Mice Obtained from the Injection of ES Cells into Eight-Cell-Stage Embryos," *Methods in Molecular Biology*, Chapter 16, 2009, vol. 530, pp. 311-324.
DeClerck P.J., et al., "Generation of Monoclonal Antibodies against autologous Proteins in Gene-inactivated Mice," *The Journal of Biological Chemistry*, Apr. 1995, vol. 270 (15), pp. 8397-8400.
Deftos, M., et al., "Defining the Genetic Origins of Three Rheumatoid Synovium-derived IgG Rheumatoid Factors," *Journal of Clinical Investigations*, Jun. 1994, vol. 93, pp. 2545-2553.
Deng C., et al., "Reexamination of Gene Targeting Frequency as a Function of the Extent of Homology Between the Targeting Vector and the Target Locus," *Molecular and Cellular Biology*, Aug. 1992, vol. 12 (8), pp. 3365-3371.
Denome R.M., et al., "Patterns of Polyadenylation Site Selection in Gene Constructs Containing Multiple Polyadenylation Signals," *Molecular and Cellular Biology*, 1988, vol. 8 (11), pp. 4829-4839.
Di Noia, J.M., et al., "Molecular Mechanisms of Antibody Somatic Hypermutation," *Annual Review of Biochemistry*, 2007, vol. 76, pp. 1-22.
Diez-Roux G., et al., "A High-Resolution Anatomical Atlas of the Transcriptome in the Mouse Embryo," *PLoS Biology*, 2011, vol. 9 (1), pp. 1-13.
Ding L., et al., "Generation of High-Affinity Fully Human Anti-Interleukin-8 Antibodies from its cDNA by Two-Hybrid Screening and Affinity Maturation in Yeast," *Protein Science*, 2010, vol. 19(10), pp. 1957-1966.
Doetschman T., et al., "Establishment of Hamster Blastocyst-Derived Embryonic Stem (ES) Cells," *Developmental Biology*, 1988, vol. 127 (1), pp. 224-227.
Doetschman T., et al., "Targeted Mutation of the Hprt Gene in Mouse Embryonic Stem Cells," *Proceedings of the National Academy of Sciences of the U.S.A*, 1988, vol. 85 (22), pp. 8583-8587.
Donohoe M.E., et al., "Transgenic Human λ5 Rescues the Murine λ5 Nullizygous Phenotype," *Journal of Immunology*, 2000, vol. 164, pp. 5269-5276.
Doyle A., et al., "The Construction of Transgenic and Gene Knockout/Knockin Mouse Models of Human Disease," *Transgenic Research*, 2012, vol. 21 (2), pp. 327-349.
Durbin R., "A Map of Human Genome Variation from Population-Scale Sequencing," *Nature*, 1000 Genomes Project Consortium, 2010, vol. 467 (7319), pp. 1061-1073.
Durdik J., et al., "Isotype Switching by a Microinjected μ Immunoglobulin Heavy Chain Gene in Transgenic Mice," *Proceedings of the National Academy of Sciences of the U.S.A*, 1989, vol. 86 (7), pp. 2346-2350.
Ebert A., et al., "The Distal $V_H$ Gene Cluster of the Igh Locus Contains Distinct Regulatory Elements with Pax5 Transcription Factor-Dependent Activity In Pro-B Cells," *Immunity*, Feb. 2011, vol. 34 (2), pp. 175-187.
Edwards D.R., et al., "The ADAM Metalloproteinases," *Molecular Aspects of Medicine*, 2008, vol. 29 (5), pp. 258-289.
Eisener-Dorman A.F., et al., "Cautionary Insights on Knockout Mouse Studies: The Gene or not the Gene?," *Brain, Behavior, and Immunity*, 2009, vol. 23 (3), pp. 318-324.
Ekiert D.C., et al., "A Highly Conserved Neutralizing Epitope On Group 2 Influenza A Viruses," *Science*, 2011, vol. 333 (6044), pp. 843-850.
Engel H., et al., "Expression level of a transgenic λ2 chain results in isotype exclusion and commitment to B1 cells," *European Journal of Immunology*, 1998, vol. 28, pp. 2289-2299.
European Patent Office, Alessandro Brero, Authorized officer, International Search Report for Application No. PCT/GB2012/052296, dated May 17, 2013, 30 pages, together with the Written Opinion of the International Searching Authority.
European Patent Office, Alessandro Brero, Authorized officer, International Search Report for Application No. PCT/GB2012/052297, dated Jun. 19, 2013, 24 pages, together with the Written Opinion of the International Searching Authority.
European Patent Office, Alessandro Brero, Authorized Officer, International Search Report for Application No. PCT/GB2012/052298, dated Jun. 13, 2013, 21 pages, together with the Written Opinion of the International Searching Authority.
European Patent Office, Examination Report for Application No. 12762378.3, dated Jun. 8, 2016, 5 pages.
European Patent Office, Extended European Search Report for Application No. 16189625.3, dated Nov. 23, 2016, 8 pages.
European Patent Office, Communication pursuant to Rule 114(2) EPC regarding 14772198.9, dated Mar. 30, 2016, 16 pages.
European Patent Office, European Search Report for Application No. 12194977.0, dated Jul. 5, 2013, 4 pages.
European Patent Office, Extended European Search Report for Application No. 12171791.2, dated Jun. 18, 2013, 5 pages.
European Patent Office, Extended European Search Report for Application No. 12195041.4, dated Nov. 18, 2013, 8 pages.
European Patent Office, Extended European Search Report for Application No. 14176740.0, dated Oct. 15, 2014, 7 pages.
European Patent Office, Extended European Search Report for Application No. 16151215.7, dated Mar. 16, 2016, 11 pages.
European Patent Office, F. Chambonnet, Authorized officer, International Search Report for Application No. PCT/GB2012/052380, dated Jan. 3, 2013, 17 pages, together with the Written Opinion of the International Searching Authority.
European Patent Office, Gaby Brouns, Authorized officer, International Search Report for Application No. PCT/GB2012/052956, dated Mar. 1, 2013, 14 pages, together with the Written Opinion of the International Searching Authority.
European Patent Office, Gaby Brouns, Authorized officer, International Search Report for Application No. PCT/GB2012/052960, dated Apr. 29, 2013, 19 pages, together with the Written Opinion of the International Searching Authority.
European Patent Office, Gaby Brouns, Authorized officer, International Search Report for Application No. PCT/GB2013/050682, dated Sep. 25, 2013, 16 pages, together with the Written Opinion of the International Searching Authority.

(56) References Cited

OTHER PUBLICATIONS

European Patent Office, Gaby Brouns, Authorized officer, International Search Report for Application No. PCT/GB2013/050683, dated Jul. 9, 2013, 11 pages, together with the Written Opinion of the International Searching Authority.
European Patent Office, Gaby Brouns, Authorized officer, International Search Report for Application No. PCT/GB2013/051280, dated Nov. 15, 2013, 19 pages, together with the Written Opinion of the International Searching Authority.
European Patent Office, Extended European Search Report for Application No. 15188522.5 dated Feb. 2, 2016, 15 pages.
European Patent Office, Examination Report for Application No. 12795841.1, dated Feb. 12, 2016, 5 pages.
European Patent Office, Examination Report for Application No. 13711119.1, dated Dec. 17, 2015, 6 pages.
European Patent Office, Examination Report for Application No. 13711119.1, dated Jul. 13, 2016, 6 pages.
European Patent Office, International Searching Authority, Examiners Report on Allowable Claims for Application No. PCT/GB2010/051122, dated Jan. 2004, 1 page.
European Patent Office, Extended European Search Report for Application No. 14196645.7, dated Jun. 26, 2015, 12 pages.
European Patent Office, Julien Landre, Authorized officer, International Search Report for Application No. PCT/GB2012/052670, dated Feb. 14, 2013, 12 pages, together with the Written Opinion of the International Searching Authority.
European Patent Office, Laurent Deleu, Authorized Officer, International Preliminary Report on Patentability Chapter II for Application No. PCT/GB2010/051122, date of completion Nov. 2, 2011, 33 pages.
European Patent Office, Laurent Deleu, Authorized officer, International Search Report for Application No. PCT/GB2010/051122, dated Sep. 29, 2010, 9 pages, together with the Written Opinion of the International Searching Authority.
European Patent Office, Laurent Deleu, Authorized officer, International Search Report for Application No. PCT/GB2011/050019, dated May 16, 2011, 12 pages, together with the Written Opinion of the International Searching Authority.
European Patent Office, Examination Report for Application No. 12194970.5, dated Sep. 23, 2013, 6 pages.
European Patent Office, Examination Report for Application No. 14176740.0, dated Jun. 6, 2016, 5 pages.
European Patent Office, Laurent Deleu, Examiner, Examination Report for Application No. 14176740.0, dated Oct. 23, 2015, 5 pages.
European Patent Office, Extended European Search Report for Application No. 12171793.8 dated Jun. 21, 2013, 8 pages.
European Patent Office, Extended European Search Report for Application No. 12194970.5, dated Jan. 23, 2013, 9 pages.
European Patent Office, Extended European Search Report for Application No. 12194977.0, dated Jul. 17, 2013, 8 pages.
European Patent Office, Extended European Search Report for Application No. 14170196.1, dated Oct. 8, 2014, 8 pages.
European Patent Office, Notice of opposition to a European patent, pertaining to Application No. 10734546.4, dated Jan. 23, 2013, 41 pages.
European Patent Office, Opposition against EP2421357 Animal Models and Therapeutic Molecules in the name of Kymab Limited pertaining to Application No. 10734546.4, dated Oct. 23, 2013, 44 pages.
European Patent Office, Opposition against EP2517557 Animal Models and Therapeutic Molecules in the name of Kymab Limited pertaining to Application No. 12171793.8, dated Jan. 17, 2017, 39 pages.
European Patent Office, Statement of Fact and Arguments in Support of Opposition pertaining to Application No. 10734546.4, dated Oct. 22, 2013, 41 pages.
European Patent Office, Invitation to Pay Additional Fees and, Where Applicable, Protest Fee, Application No. PCT/GB2012/052296, mailed on Jan. 24, 2013, 9 pages.

Evans J.P., "Fertilin β and Other ADAMs as Integrin Ligands: Insights into Cell Adhesion and Fertilization," *Bioessays*, 2001, vol. 23 (7), pp. 628-639.
Featherstone K., et al., "The Mouse Immunoglobulin Heavy Chain V-D Intergenic Sequence Contains Insulators that May Regulate Ordered V(D)J Recombination," *Journal of Biological Chemistry*, 2010, vol. 285 (13), pp. 9327-9338.
Feeney A.J., "Genetic and Epigenetic Control of V Gene Rearrangement Frequency," *Advances in Experimental Medicine and Biology*, Chapter 6, 2009, vol. 650, pp. 73-81.
Fell H.P. et al., "Homologous Recombination in Hybridoma Cells: Heavy Chain Chimeric Antibody Produced by Gene Targeting," *Proceedings of the National Academy of Sciences of the U.S.A*, 1989, vol. 86 (21), pp. 8507-8511.
Feng Y.Q., et al., "Site-Specific Chromosomal Integration in Mammalian Cells: Highly Efficient CRE Recombinase-Mediated Cassette Exchange," *Journal of Molecular Biology*, 1999, vol. 292 (4), pp. 779-785.
Feschotte C., et al., "DNA Transposons and the Evolution of Eukaryotic Genomes," *Annual Review of Genetics*, 2007, vol. 41, pp. 331-368.
Festing, M.F.W., et al., "Revised nomenclature for strain 129 mice," *Mammalian Genome*, 1999, vol. 10, p. 836.
Fleischer B., et al., "Reactivity of Mouse T-Cell Hybridomas Expressing Human Vβ Gene Segments With Staphylococcal And Streptococcal Superantigens," *Infection and Immunity*, Mar. 1996, vol. 64 (3), pp. 987-994.
Folger K.R., et al., "Patterns of Integration of DNA Microinjected into Cultured Mammalian Cells: Evidence for Homologous Recombination Between Injected Plasmid DNA Molecules," *Molecular and Cellular Biology*, 1982, vol. 2 (11), pp. 1372-1387.
Forconi F., et al., "The Normal IGHV1-69-Derived B-Cell Repertoire Contains Stereotypic Patterns Characteristic of Unmutated CLL," *Blood*, 2010, vol. 115 (1), pp. 71-77.
French Patent Office, INPI, Laurent Deleu, Authorized officer, International Search Report for Patent Application No. 1359518, dated Aug. 20, 2014, 3 pages.
Friedrich G., Statement of Dr. Glenn Friedrich, dated Mar. 3, 2016, 4 pages.
Fujieda S., et al., "Multiple Types of Chimeric Germ-Line Ig Heavy Chain Transcripts in Human B Cells: Evidence for Trans-Splicing of Human Ig RNA," *Journal of Immunology*, 1996, vol. 157 (8), pp. 3450-3459.
Fukita Y., et al., "Somatic Hypermutation in the Heavy Chain Locus Correlates with Transcription," *Immunity*, 1998, vol. 9 (1), pp. 105-114.
Gallo M.L., et al., "The Human Immunoglobulin Loci Introduced into Mice: V (D) and J Gene Segment Usage Similar to that of Adult Humans," *European Journal of Immunology*, 2000, vol. 30 (2), pp. 534-540.
Gama Sosa M.A., et al., "Animal Transgenesis: An Overview," *Brain Structure and Function*, 2010, vol. 214 (2-3), pp. 91-109.
Gavilondo J.V., et al., "Antibody Engineering at the Millennium," *BioTechniques*, Jul. 2000, vol. 29 (1), pp. 128-145.
Genbank (D. Muzny et al.), "Rattus norvegicus clone CH230-30N12, * Sequencing in Progress *, 6 unordered pieces," Accession No. AC111740, Nov. 9, 2002, 42 pages. [Retrieved from the Internet: http://www.ncbi.nlm.nih.gov/nuccore/AC111740 on Feb. 28, 2013].
Genbank, "DNA Sequence of the Human Immunoglobulin D Segment Locus," Accession No. X97051.1 S64822, Aug. 6, 2014, 29 pages. [Retrieved from the Internet: http://www.ncbi.nlm.nih.gov/nuccore/X97051].
Genbank, "DNA Sequence of the Human Immunoglobulin D Segment Locus," Accession No. X97051.1 S64822, updated Mar. 3, 2015, 26 pages.
Genbank, "*Homo sapiens* immunoglobulin heavy-chain (IGHV2-5) gene, IGHV2-5*10 allele, partial sequence," Accession No. KF698731.1, dated Nov. 18, 2013, 1 page.
Genbank, "Mus musculus strain 129S1/SvImJ chromosome 12 genomic sea locus group 129S1/SvImJ 129S1/SVIMJ_MMCHR12_CTG1," NCBI Reference Sequence No. NT_114985.3, dated May 5, 2014, 1 page.

(56) References Cited

OTHER PUBLICATIONS

Gerdes T., et al., "Physical Map of the Mouse λ Light Chain and Related Loci," *Immunogenetics*, 2002, vol. 54 (1), pp. 62-65.

Gerstein R.M., et al., "Isotype Switching of an Immunoglobulin Heavy Chain Transgene Occurs by DNA Recombination Between Different Chromosomes," *Cell*, 1990, vol. 63 (3), pp. 537-548.

Geurts A.M., et al., "Knockout Rats Via Embryo Microinjection of Zinc-Finger Nucleases," *Science*, 2009, vol. 325 (5939), p. 433.

Giallourakis C.C., et al., "Elements Between the IgH Variable (V) and Diversity (D) Clusters Influence Antisense Transcription and Lineage-Specific V(D)J Recombination," *Proceedings of the National Academy of Sciences of the U.S.A.*, 2010, vol. 107 (51), pp. 22207-22212.

Giraldo P., et al., "Size Matters: Use of YACs, BACs and PACs in Transgenic Animals," *Transgenic Research*, 2001, vol. 10 (2), pp. 83-103.

Giusti A.M., et al., "Hypermutation is Observed only in Antibody H Chain V Region Transgenes that have Recombined with Endogenous Immunoglobulin H DNA: Implications for the Location of cis-acting Elements Required for Somatic Mutation," *The Journal of Experimental Medicine*, Mar. 1993, vol. 177 (3), pp. 797-809.

Glanville J., et al., "Naive Antibody Gene-Segment Frequencies are Heritable and Unaltered by Chronic Lymphocyte Ablation," *Proceedings of the National Academy of Sciences of the U.S.A*, Dec. 2011, vol. 108 (50), pp. 20066-20071.

Glaser S. et al., "Current issues in mouse genome engineering," *Nature Genetics*, Nov. 2005, Vo. 37 (11), pp. 1187-1193.

Gluzman Y., "SV40-Transformed Simian Cells Support the Replication of Early SV40 Mutants," *Cell*, 1981, vol. 23 (1), pp. 175-182.

Goldman I.L., et al., "Transgenic Animals in Medicine: Integration and Expression of Foreign Genes, Theoretical and Applied Aspects," *Medical Science Monitor*, 2004, vol. 10 (11), pp. RA274-RA285.

Goodhardt M., et al., "Rearrangement and Expression of Rabbit Immunoglobulin κ Light Chain Gene in Transgenic Mice," *Proceedings of the National Academy of Sciences of the U.S.A.*, 1987, vol. 84 (12), pp. 4229-4233.

Gorman J.R., et al., "The Igκ 3' Enhancer Influences the Ratio of Igκ Versus Igλ B Lymphocytes," *Immunity*, 1996, vol. 5 (3), pp. 241-252.

Gorny M.K., et al., "Human Anti-V3 HIV-1 Monoclonal Antibodies Encoded by the VH5-51/VL Lambda Genes Define A Conserved Antigenic Structure," *PLoS One*, 2011, vol. 6 (12), pp. e27780-1-e27780-10.

Goyenechea B., et al., "Cells Strongly Expressing Igκ Transgenes Show Clonal Recruitment of Hypermutation: A Role for Both MAR and the Enhancers," *EMBO Journal*, 1997, vol. 16 (13), pp. 3987-3994.

Grandea A.G., III., et al., "Human antibodies reveal a protective epitope that is highly conserved among human and nonhuman influenza A viruses," *Proceedings of the National Academy of Sciences ofthe U.S.A.*, Jul. 2010, vol. 107 (28), pp. 12658-12663.

Gratz S. et al., "Genome Engineering of *Drosophila* with the CRISPR RNA-Guided Cas9 Nuclease," *Genetics*, Aug. 2013, vol. 194, pp. 1029-1035.

Green L.L., "Antibody Engineering via Genetic Engineering of the Mouse: XenoMouse Strains are a Vehicle for the Facile Generation of Therapeutic Human Monoclonal Antibodies," *Journal of Immunological Methods*, Dec. 1999, vol. 231 (1-2), pp. 11-23.

Green L.L., et al., "Antigen-Specific Human Monoclonal Antibodies from Mice Engineered with Human Ig Heavy and Light Chain YACs," *Nature Genetics*, May 1994, vol. 7 (1), pp. 13-21.

Green L.L., et al., "Regulation of B Cell Development by Variable Gene Complexity in Mice Reconstituted with Human Immunoglobulin Yeast Artificial Chromosomes," *The Journal of Experimental Medicine*, Aug. 1998, vol. 188 (3), pp. 483-495.

Grippo V., et al., "The Heavy Chain Variable Segment Gene Repertoire in Chronic Chagas' Heart Disease," *The Journal of Immunology*, Dec. 2009, vol. 182 (12), pp. 8015-8025.

Grund M., European Patent Attorney, Grund Intellectual Property Group, Third-Party Observations according to Article 115 EPC regarding 11705964.2, dated Apr. 30, 2014, 4 pages.

Grund M., European Patent Attorney, Grund Intellectual Property Group, Third-Party Observations according to Article 115 EPC regarding 11705964.2, dated Aug. 5, 2016, 11 pages.

Grund M., European Patent Attorney, Grund Intellectual Property Group, Third-Party Observations according to Article 115 EPC regarding 11705964.2, dated Oct. 9, 2013, 8 pages.

Grund M., European Patent Attorney, Grund Intellectual Property Group, Third-Party Observations according to Article 115 EPC regarding 12171791.2, dated Aug. 4, 2014, 6 pages.

Grund M., European Patent Attorney, Grund Intellectual Property Group, Third-Party Observations according to Article 115 EPC regarding 12171791.2, dated Dec. 19, 2014, 7 pages.

Grund M., European Patent Attorney, Grund Intellectual Property Group, Third-Party Observations according to Article 115 EPC regarding 12171791.2, dated Feb. 26, 2014, 9 pages.

Grund M., European Patent Attorney, Grund Intellectual Property Group, Third-Party Observations according to Article 115 EPC regarding 12171793.8, dated Jun. 25, 2014, 7 pages.

Grund M., European Patent Attorney, Grund Intellectual Property Group, Third-Party Observations according to Article 115 EPC regarding 12194970.5, dated Apr. 25, 2014, 6 pages.

Grund M., European Patent Attorney, Grund Intellectual Property Group, Third-Party Observations according to Article 115 EPC regarding 12194970.5, dated Aug. 12, 2014, 5 pages.

Grund M., European Patent Attorney, Grund Intellectual Property Group, Third-Party Observations according to Article 115 EPC regarding 12194970.5, dated Mar. 5, 2014, 9 pages.

Grund M., European Patent Attorney, Grund Intellectual Property Group, Third-Party Observations according to Article 115 EPC regarding 12194970.5, dated Nov. 15, 2013, 6 pages.

Grund M., European Patent Attorney, Grund Intellectual Property Group, Third-Party Observations according to Article 115 EPC regarding 12194970.5, dated Sep. 9, 2013, 11 pages.

Grund M., European Patent Attorney, Grund Intellectual Property Group, Third-Party Observations according to Article 115 EPC regarding 12194977.0, dated Mar. 26, 2014, 4 pages.

Grund M., European Patent Attorney, Grund Intellectual Property Group, Third-Party Observations according to Article 115 EPC regarding 12194977.0, dated May 12, 2015, 5 pages.

Grund M., European Patent Attorney, Grund Intellectual Property Group, Third-Party Observations according to Article 115 EPC regarding 12195041.4, dated Jul. 30, 2014, 5 pages.

Grund M., European Patent Attorney, Grund Intellectual Property Group, Third-Party Observations according to Article 115 EPC regarding 12762377.5, dated Jun. 20, 2017, 4 pages.

Grund M., European Patent Attorney, Grund Intellectual Property Group, Third-Party Observations according to Article 115 EPC regarding 12762377.5, dated Feb. 12, 2016, 8 pages.

Grund M., European Patent Attorney, Grund Intellectual Property Group, Third-Party Observations according to Article 115 EPC regarding 12762377.5, dated May 22, 2015, 7 pages.

Grund M., European Patent Attorney, Grund Intellectual Property Group, Third-Party Observations according to Article 115 EPC regarding 12762378.3, dated Feb. 15, 2017, 6 pages.

Grund M., European Patent Attorney, Grund Intellectual Property Group, Third-Party Observations according to Article 115 EPC regarding 12772122.3, dated Mar. 12, 2015, 5 pages.

Grund M., European Patent Attorney, Grund Intellectual Property Group, Third-Party Observations according to Article 115 EPC regarding 12772122.3, dated May 17, 2016, 7 pages.

Grund M., European Patent Attorney, Grund Intellectual Property Group, Third-Party Observations according to Article 115 EPC regarding 12795606.8, dated Aug. 22, 2014, 8 pages.

Grund M., European Patent Attorney, Grund Intellectual Property Group, Third-Party Observations according to Article 115 EPC regarding 12795606.8, dated Feb. 26, 2014, 6 pages.

Grund M., European Patent Attorney, Grund Intellectual Property Group, Third-Party Observations according to Article 115 EPC regarding 12795606.8, dated Mar. 26, 2015, 4 pages.

(56) References Cited

OTHER PUBLICATIONS

Grund M., European Patent Attorney, Grund Intellectual Property Group, Third-Party Observations according to Article 115 EPC regarding 13711119.1, dated Dec. 9, 2015, 7 pages.
Grund M., European Patent Attorney, Grund Intellectual Property Group, Third-Party Observations according to Article 115 EPC regarding 13711119.1, dated Jul. 5, 2016, 7 pages.
Grund M., European Patent Attorney, Grund Intellectual Property Group, Third-Party Observations according to Article 115 EPC regarding 13711120.9, dated May 17, 2016, 11 pages.
Grund M., European Patent Attorney, Grund Intellectual Property Group, Third-Party Observations according to Article 115 EPC regarding 14176740.0, dated Aug. 10, 2015, 13 pages.
Grund M., European Patent Attorney, Grund Intellectual Property Group, Third-Party Observations according to Article 115 EPC regarding 14176740.0, dated Nov. 2, 2016, 4 pages.
Grund M., European Patent Attorney, Grund Intellectual Property Group, Third-Party Observations according to Article 115 EPC regarding 16151215.7, dated Mar. 1, 2017, 4 pages.
Grund M., European Patent Attorney, Grund Intellectual Property Group, Third-Party Observations according to Article 115 EPC regarding 16189625.3, dated Mar. 23, 2017, 5 pages.
Grund M., European Patent Attorney, Grund Intellectual Property Group, Third-Party Observations regarding Application No. PCT/GB2012/052297, dated Jan. 17, 2014, 3 pages.
Grund M., European Patent Attorney, Grund Intellectual Property Group, Third-Party Observations regarding Application No. PCT/GB2012/052298, dated Jan. 17, 2014, 4 pages.
Grund M., European Patent Attorney, Grund Intellectual Property Group, Third-Party Observations regarding Application No. PCT/GB2012/052380, dated Jan. 24, 2014, 4 pages.
Grund M., European Patent Attorney, Grund Intellectual Property Group, Third-Party Observations regarding Application No. PCT/GB2012/052956, dated Mar. 26, 2014, 2 pages.
Grund M., European Patent Attorney, Grund Intellectual Property Group, Third-Party Observations regarding Application No. PCT/GB2012/052960, dated Apr. 2, 2014, 3 pages.
Grund M., European Patent Attorney, Grund Intellectual Property Group, Third-Party Observations regarding Application No. PCT/GB2013/050682, dated Jul. 28, 2014, 3 pages.
Grund M., European Patent Attorney, Grund Intellectual Property Group, Third-Party Observations regarding Application No. PCT/GB2013/050683, dated Jul. 28, 2014, 2 pages.
Grund M., European Patent Attorney, Grund Intellectual Property Group, Third-Party Observations regarding Application No. PCT/US2012/026416, dated Jun. 6, 2013, 2 pages.
Grund M., European Patent Attorney, Grund Intellectual Property Group, Third-Party Observations according to Article 115 EPC regarding 11705964.2, dated Feb. 26, 2015, 5 pages.
Gu H., et al., "Independent Control of Immunoglobulin Switch Recombination at Individual Switch Regions Evidenced Through Cre-loxP-Mediated Gene Targeting," *Cell*, 1993, vol. 73 (6), pp. 1155-1164.
Guan C., et al., "A Review of Current Large-Scale Mouse Knockout Efforts," *Genesis*, vol. 48, 2010, pp. 73-85.
Guerrero C., et al., "The Bleomycin Resistance Gene of Transposon Tn5 is an Excellent Marker for Transformation of Corynebacteria," *Applied Microbiology and Biotechnology*, 1992, vol. 36 (6), pp. 759-762.
Guirouilh-Barbat J., et al., "Is homologous recombination really an error-free process?", *Frontiers in Genetics*, Jun. 2014, vol. 5 (175), 15 pages.
Guntaka R.V., "Transcription Termination and Polyadenylation in Retroviruses," *Microbiological Reviews*, 1993, vol. 57 (3), pp. 511-521.
Guo Y., et al., "A Preliminary Analysis of the Immunoglobulin Genes in the African Elephant (*Loxodonta africana*)," *PLoS ONE*, Feb. 2011, vol. 6 (2), pp. e16889-1-e16889-14.

Hagiwara S., "Transgenic Expression of VpreB-3 Under the Control of the Immunoglobulin Heavy Chain Enhancer and SV40 Promoter," *Kobe Journal of Medical Sciences*, 1996, vol. 42 (1), pp. 43-59 (abstract only).
Hamers-Caterman C., et al., "Naturally occurring antibodies devoid of light chains," *Nature*, Jun. 1993, vol. 363, pp. 446-448.
Han C., et al., "Comprehensive Analysis of Reproductive ADAMs: Relationship of ADAM4 and ADAM6 with an ADAM Complex Required for Fertilization in Mice," *Biology of Reproduction*, 2009, vol. 80 (5), pp. 1001-1008.
Harding F.A., et al., "Class Switching in Human Immunoglobulin Transgenic Mice," *Annals of the New York Academy of Sciences*, 1995, vol. 764, pp. 536-546.
Hasty P., et al., "Target Frequency and Integration Pattern for Insertion and Replacement Vectors in Embryonic Stem Cells," *Molecular and Cellular Biology*, 1991, vol. 11 (9), pp. 4509-4517.
Hendricks J., et al., "Organization of the Variable Region of the Immunoglobulin Heavy-Chain Gene Locus of the Rat," *Immunogenetics*, 2010, vol. 62 (7), pp. 479-486.
Herschbach Jarrell B., Third-Party Pre-Issuance Submission Under 37 CFR Section 1.290 in U.S. Appl. No. 14/052,259, dated Aug. 6, 2014, 7 pages.
Hewitt S.L., et al., "Association between the Igk and Igh immunoglobulin loci mediated by the 3' Igk enhancer Induces 'decontraction' of the Igh locus in pre-B cells," *Nature Immunology*, Apr. 2008, vol. 9 (4), pp. 396-404.
Houdebine L.M., "The Methods to Generate Transgenic Animals and to Control Transgene Expression," *Journal of Biotechnology*, 2002, vol. 98 (2-3), pp. 145-160.
Houdebine L.M., "Transgenic Animal Models in Biomedical Research," *Methods in Molecular Biology*, Chapter 10, 2007, vol. 360, pp. 163-202.
Houldsworth J., et al., "Comparative Genomic Hybridization: An Overview," *The American Journal of Pathology*, Dec. 1994, vol. 145 (6), pp. 1253-1260.
Hsu E., et al., "The plasticity of immunoglobulin gene systems in evolution," *Immunology Reviews*, vol. 210, Apr. 2006, pp. 8-26.
Huang C., et al., "Structural Basis of Tyrosine Sulfation and $V_H$-Gene Usage in Antibodies that Recognize the HIV Type 1 Coreceptor-Binding Site on gp120," *Proceedings of the National Academy of Sciences of the U.S.A.*, 2004, vol. 101 (9), pp. 2706-2711.
Huang D., et al., "Sequence Analyses of Three Immunoglobulin G Anti-virus Antibodies Reveal Their Utilization of Autoantibody-related Immunoglobulin Vh Genes, but Not Vλ Genes," *Journal of Clinical Investigations*, Dec. 1992, vol. 90, pp. 2197-2208.
Huber V.C., et al., "Distinct Contributions of Vaccine-Induced Immunoglobulin G1 (IgG1) and IgG2a Antibodies to Protective Immunity Against Influenza," *Clinical and Vaccine Immunology*, 2006, vol. 13(9), pp. 981-990.
Hudziak R.M., et al., "Establishment of Mammalian Cell Lines Containing Multiple Nonsense Mutations and Functional Suppressor tRNA Genes," *Cell*, 1982, vol. 31 (1), pp. 137-146.
Huovila A.J., et al., "Shedding Light on ADAM Metalloproteinases," *Trends in Biochemical Sciences*, 2005, vol. 30 (7), pp. 413-422.
Iglesias-Ussel M.D., et al., "Forced Expression of AID Facilitates the Isolation of Class Switch Variants from Hybridoma Cells," *Journal of Immunological Methods*, 2006, vol. 316 (1-2), pp. 59-66.
Ivics Z., et al., "The Expanding Universe of Transposon Technologies for Gene and Cell Engineering," *Mobile DNA*, 2010, vol. 1 (1), 15 pages.
Ivics Z., et al., "The Sleeping Beauty Transposable Element: Evolution, Regulation and Genetic Applications," *Current Issues in Molecular Biology*, 2004, vol. 6 (1), pp. 43-55.
Izsvák Z., et al., "Sleeping Beauty Transposition: Biology and Applications for Molecular Therapy," *Molecular Therapy*, 2004, vol. 9 (2), pp. 147-156.
Jacob H.J., et al., "Gene Targeting in the Rat: Advances and Opportunities," *Trends in Genetics*, 2010, vol. 26 (12), pp. 510-518.
Jakobovits A., et al., "From XenoMouse Technology to Panitumumab, the First Fully Human Antibody Product from Transgenic Mice," *Nature Biotechnology*, 2007, vol. 25 (10), pp. 1134-1143.

(56) References Cited

OTHER PUBLICATIONS

Jakobovits A., "Production of Fully Human Antibodies by Transgenic Mice," *Current Opinion in Biotechnology*, 1995, vol. 6 (5), pp. 561-566.

Jakobovits A., "The Long-Awaited Magic Bullets: Therapeutic Human Monoclonal Antibodies from Transgenic Mice," *Expert Opinion Investigational Drugs*, 1998, vol. 7 (4), pp. 607-614.

Janeway C.A. et al., "The rearrangement of antigen-receptor gene segments controls lymphocyte development," Immunobiology: The Immune System in Health and Disease, 5th Edition, Aug. 2015, 13 pages. [Retrieved from the Internet: http://www.ncbi.nlm.nih.gov/books/NBK27113/].

Janeway et al., "Structural Variation in Immunoglobulin Constant Regions," *Immunobiology: The Immune System in Health and Disease*, 5th Edition, 2001, 5 pages.

Janssens R., et al., "Generation of Heavy-Chain-only Antibodies in Mice," *Proceedings of the National Academy of Sciences of the U.S.A.*, 2006, vol. 103 (41), pp. 15130-15135.

Jasper, P.J., et al., "B lymphocyte deficiency in IgH-transgenic rabbits," *European Journal of Immunology*, 2007, vol. 37, pp. 2290-2299.

Jendreyko N., et al., "Intradiabodies, Bispecific, Tetravalent Antibodies forthe Simultaneous Functional Knockout of Two Cell Surface Receptors," *The Journal of Biological Chemistry*, 2003, vol. 278 (48), pp. 47812-47819.

Jessen K.A., et al., "Molecular Analysis of Metastasis in a Polyomavirus Middle T Mouse Model: the Role of Osteopontin," *Breast Cancer Research*, 2004, vol. 6 (3), pp. R157-R169.

Johnston C.M., et al., "Complete Sequence Assembly and Characterization ofthe C57BL/6 Mouse Ig Heavy Chain V Region," *The Journal of Immunology*, 2006, vol. 176 (7), pp. 4221-4234.

Jones B.T., Attorney for Applicant, Third-Party Pre-Issuance Submission Under 37 CFR Sec. 1.290 in U.S. Appl. No. 15/016,211, filed Oct. 4, 2016, 59 pages.

Jones B.T., Attorney for Applicant, Third-Party Pre-Issuance Submission Under 37 CFR Sec. 1.290 in U.S. Appl. No. 15/018,670, filed Aug. 12, 2016, 26 pages.

Jones B.T., Attorney for Applicant, Third-Party Pre-Issuance Submission Under 37 CFR Sec. 1.290 in U.S. Appl. No. 15/095,315, filed Sep. 16, 2016, 26 pages.

Jones B.T., Attorney for Applicant, Third-Party Pre-Issuance Submission Under 37 CFR Sec. 1.290 in U.S. Appl. No. 15/360,502, filed May 8, 2017, 40 pages.

Jones B.T., Attorney for Applicant, Third-Party Pre-Issuance Submission Under 37 CFR Sec. 1.290 in U.S. Appl. No. 15/383,188, filed May 30, 2017, 33 pages.

Jones B.T., Attorney for Applicant, Third-Party Pre-Issuance Submission Under 37 CFR Sec. 1.290 in U.S. Appl. No. 15/383,196, filed May 8, 2017, 25 pages.

Jones B.T., Attorney for Applicant, Third-Party Pre-Issuance Submission Under 37 CFR Sec. 1.290 in U.S. Appl. No. 15/383,202, filed May 3, 2017, 23 pages.

Jones B.T., Attorney for Applicant, Third-Party Pre-Issuance Submission Under 37 CFR Sec. 1.290 in U.S. Appl. No. 15/214,963, filed Mar. 2, 2017, 42 pages.

Jung D., et al., "Mechanism and Control of V(D)J Recombination at the Immunoglobulin Heavy Chain Locus," *Annual Review of Immunology*, 2006, vol. 24, pp. 541-570.

Kaminski D.A., et al., "Antibody Class Switching differs among SJL, C57BL/6 and 129 Mice," *International Immunology*, 2007, vol. 19 (4), pp. 545-556.

Karu A.E., et al., "Recombinant Antibody Technology," *ILAR Journal / National Research Council, Institute of Laboratory Animal Resources*, 1995, vol. 37 (3), pp. 132-141.

Kaushik A., et al., "Novel Insight into Antibody Diversification from Cattle," *Veterinary Immunology and Immunopathology*, 2002, vol. 87 (3-4), pp. 347-350.

Kawasaki K., et al., "One-Megabase Sequence Analysis of the Human Immunoglobulin λ Gene Locus," *Genome Research*, 1997, vol. 7, pp. 250-261.

Kellermann S., et al., "Developing the XENOMOUSE® Technology for Evaluating Immunogenicity," AntibOZ 2: An International Forum to Predict the Next Wave of Protein-based Therapies and Immuno Diagnostics, 2004, *AntibOZ 2 Conference*, Australia, 1 page (abstract only).

Kenter A.L., et al., "Three-Dimensional Architecture of the IgH Locus Facilitates Class Switch Recombination," *Annals of the New York Academy of Sciences*, 2012, vol. 1267, pp. 86-94.

Köhrer C., et al., "Import of Amber and Ochre Suppressor tRNAs into Mammalian Cells: a General Approach to Site-Specific Insertion of Amino Acid Analogues into Proteins," *Proceedings of the National Academy of Sciences of the U.S.A.*, 2001, vol. 98 (25), pp. 14310-14315.

Kim J.Y., et al., "CHO Cells in Biotechnology for Production of Recombinant Proteins: Current State and Further Potential," *Applied Microbiology Biotechnology*, 2012, vol. 93 (3), pp. 917-930.

Kim T., et al., "Expression and Relationship of Male Reproductive ADAMs in Mouse," *Biology of Reproduction*, 2006, vol. 74 (4), pp. 744-750.

Kindt T.J. et al., "Organization and Expression of Immunoglobulin Genes," *Immunology*, Sixth edition, Chapter 5, 2007 (36 pages, including coversheet and copyright page), pp. 111-144.

Kingzette M., et al., "Trans-Chromosomal Recombination within the Ig Heavy Chain Switch Region in B Lymphocytes," *Proceedings of the National Academy of Sciences of the U.S.A.*, 1998, vol. 95 (20), pp. 11840-11845.

Kitamura D., et al., "A B Cell-Deficient Mouse by Targeted Disruption of the Membrane Exon ofthe Immunoglobulin β Chain Gene," *Nature*, 1991, vol. 350 (6317), pp. 423-426.

Kondo S., et al., "Highly improved Gene Targeting by Germline-Specific Cas9 Expression in *Drosophila*," *Genetics*, vol. 195, Nov. 2013, pp. 715-721 (Abstract).

Kondo S., et al., "Highly improved Gene Targeting by Germline-Specific Cas9 Expression in *Drosophila*," *Genetics*, vol. 195, Nov. 2013, pp. 715-721.

Kostenuik P. J., et al., "Denosumab, a Fully Human Monoclonal Antibody to RANKL, Inhibits Bone Resorption and Increases BMD in Knock-in Mice that Express Chimeric (Murine/Human) RANKL," *Journal of Bone and Mineral Research*, 2009, vol. 24 (2), pp. 182-195.

Kotzamanis G., et al., "Recombining Overlapping BACs into a Single Larger BAC," *BMC Biotechnology*, 2004, vol. 4 (1), 10 pages.

Kouskoff V., et al., "Cassette Vectors Directing Expression of T Cell Receptor Genes in Transgenic Mice," *Journal of Immunological Methods*, 1995, vol. 180 (2), pp. 273-280.

Krause J.C., et al., "Epitope-Specific Human Influenza Antibody Repertoires Diversify by B Cell Intraclonal Sequence Divergence and Interclonal Convergence," *Journal of Immunology*, 2011, vol. 187 (7), pp. 3704-3711.

Krutskikh A., et al., "Epididymal Protein Rnase10 is Required for Post-Testicular Sperm Maturation and Male Fertility," *The FASEB Journal*, 2012, vol. 26 (10), pp. 4198-4209.

Kucherlapati R.S., et al., "Homologous Recombination Between Plasmids in Mammalian Cells can be Enhanced by Treatment of Input DNA," *Proceedings of the National Academy of Sciences of the U.S.A.*, 1984, vol. 81 (10), pp. 3153-3157.

Kuraoka M., et al., "AID Expression During B-Cell Development: Searching for Answers," *Immunologic Research*, 2011, vol. 49 (1-3), pp. 3-13.

Kuroiwa Y., et al., "Sequential Targeting ofthe Genes Encoding Immunoglobulin-μ and Prion Protein in Cattle," *Nature Genetics*, 2004, vol. 36 (7), pp. 775-780.

Kuzin I.I., et al, "Requirement for enhancer specificity in immunoglobulin heavy chain locus regulation," *Journal of Immunology*, Jun. 2008, vol. 180 (11), pp. 7443-7450.

Laffleur B., et al., "Production of Human or Humanized Antibodies in Mice," *Methods in Molecular Biology*, Chapter 9, 2012, vol. 901, pp. 149-159.

Largaespada D.A., "Transposon Mutagenesis in Mice," *Methods in Molecular Biology*, vol. 530, 2009, pp. 379-390.

Laventie B., et al., "Heavy Chain-Only Antibodies and Tetravalent Bispecific Antibody Neutralizing *Staphylococcus aureus* Leukotoxins,"

(56) References Cited

OTHER PUBLICATIONS

*Proceedings of the National Academy of Sciences of the U.S.A.,* 2011, vol. 108 (39), pp. 16404-16409.
Le Mouellic H., et al., "Pattern of Transcription of the Homeo Gene Hox-3.1 in the Mouse Embryo," *Genes & Development*, 1988, vol. 2 (1), pp. 125-135.
Lee E., et al., "Complete Humanization of the Mouse Immunoglobulin Loci Enables Efficient Therapeutic Antibody Discovery," *Nature Biotechnology*, 2014, vol. 32 (4), pp. 356-363.
Lee E., et al., "The Application of Transgenic Mice for Therapeutic Antibody Discovery," *Methods in Molecular Biology*, Chapter 8, 2012, vol. 901, pp. 137-148.
Lee H., et al., "Human C5aR Knock-in Mice Facilitate the Production and Assessment of Anti-Inflammatory Monoclonal Antibodies," *Nature Biotechnology*, 2006, vol. 24 (10), pp. 1279-1284.
Lefranc M., Appendix 1P, Abbreviations and Useful Data, "Nomenclature of the Human Immunoglobulin Genes," *Current Protocols in Immunology*, 2000, Supp. 40, pp. A.1P.1-A.1P.37.
Lefranc M.P., et al., "IGHJ group," The Immunoglobulin FactsBook, *IMGT*, the international ImMunoGeneTics database, May 2001, 4 pages (including cover sheet and copyright pages).
Lefranc M.P., et al., Excerpts from "The Immunoglobulin FactsBook," *IMGT*, the international ImMunoGeneTics database, May 2001, 455 pages.
Lefranc M.P., et al., "Immunoglobulin Lambda (IGL) Genes of Human and Mouse," *Molecular Biology of B Cells*, Chapter 4, p. 47, 2004 (Edtrs. Honjo et al.).
Lefranc M.P., "Nomenclature of the Human Immunoglobulin Heavy (IGH) Genes," *Experimental and Clinical Immunogenetics*, 2001, vol. 18 (2), pp. 100-116.
Lefranc M.P., "Nomenclature of the Human Immunoglobulin Lambda (IGL) Genes," *Experimental and Clinical Immunogenetics*, 2001, vol. 18 (4), pp. 242-254.
Levin A.M., et al., "Optimizing the affinity and specificity of proteins with molecular display," *Molecular Biosystems*, 2006, vol. 2, pp. 49-57.
Li H., et al., "Genetic Diversity of the Human Immunoglobulin Heavy Chain $V_H$ Region," *Immunological Reviews*, Dec. 2002, vol. 190, pp. 53-68.
Li L., et al., "Transgenic Mice with a Diverse Human T Cell Antigen Receptor Repertoire," *Nature Medicine*, 2010, vol. 16 (9), pp. 1029-1034.
Li M., Second Declaration of Dr. Meng (Amy) Li, dated Sep. 5, 2016, 2 pages.
Li M.A., et al., "Crafting Rat Genomes with Zinc Fingers," *Nature Biotechnology*, 2011, vol. 29 (1), pp. 39-41.
Li P., et al., "Germline Competent Embryonic Stem Cells Derived from Rat Blastocysts," *Cell*, 2008, vol. 135 (7), pp. 1299-1310.
Li X., et al., "The Minimum Internal and External Sequence Requirements for Transposition of the Eukaryotic Transformation Vector PiggyBac," *Molecular Genetics & Genomics*, 2001, vol. 266(2), pp. 190-198.
Liang Q., et al., "Extensive genomic copy number variation in embryonic stem cells," *Proceedings of the National Academy of Sciences of the U.S.A.*, Nov. 2008, vol. 105 (45), pp. 17453-17456.
Liao J., et al., "Generation of Induced Pluripotent Stem Cell Lines from Adult Rat Cells," *Cell Stem Cell*, 2009, vol. 4 (1), pp. 11-15.
Little M., et al., "Generation of a Large Complex Antibody Library from Multiple Donors," *Journal of Immunological Methods*, 1999, vol. 231 (1-2), pp. 3-9.
Liu L., et al., "Potent and Broad Anti-HIV-1 Activity Exhibited by a Glycosyl-Phosphatidylinositol-Anchored Peptide derived from the Cdr H3 of Broadly Neutralizing Antibody PG16," *Journal of Virology*, 2011, vol. 85 (17), pp. 8467-8476.
Lonberg N., "Human Antibodies from Transgenic Animals," *Nature Biotechnology*, 2005, vol. 23(9), pp. 1117-1125.
Lonberg N., "Fully Human Antibodies from Transgenic Mouse and Phage Display Platforms," *Current Opinion in Immunology*, 2008, vol. 20 (4), pp. 450-459.
Loveslati B.Y., et al., "A Study of Gm Allotypes and Immunoglobulin Heavy Gamma IGHG Genes in Berbers, Arabs and Sub-Saharan Africans from Jerba Island, Tunisia," *European Journal of Immunogenetics*, 2001, vol. 28 (5), pp. 531-538.
Luby T.M., et al., "The μ Switch Region Tandem Repeats are Important, but not Required, for Antibody Class Switch Recombination," *The Journal of Experimental Medicine*, 2001, vol. 193 (2), pp. 159-168.
Luciw P.A., et al., "Location and Function of Retroviral and SV40 Sequences that Enhance Biochemical Transformation after Microinjection of DNA," *Cell*, 1983, vol. 33 (3), pp. 705-716.
Luo G., et al., "Chromosomal Transposition of a Tc1/Mariner-like Element in Mouse Embryonic Stem Cells," *Proceedings of the National Academy of Sciences of the U.S.A.*, 1998, vol. 95 (18), pp. 10769-10773.
Lyon C., Attorney for Applicant, Third-Party Pre-Issuance Submission Under 37 CFR Sec. 1.290 in U.S. Appl. No. 14/056,700, dated Nov. 28, 2014, 6 pages.
Lyon C., Attorney for Applicant, Third-Party Pre-Issuance Submission Under 37 CFR Sec. 1.290 in U.S. Appl. No. 14/056,707, dated Nov. 28, 2014, 10 pages.
Lyon C., Attorney for Applicant, Third-Party Pre-Issuance Submission Under 37 CFR Sec. 1.290 in U.S. Appl. No. 13/846,672, dated Mar. 17, 2015, 32 pages.
Lyon C., Attorney for Applicant, Third-Party Pre-Issuance Submission Under 37 CFR Sec. 1.290 in U.S. Appl. No. 13/875,892, dated May 5, 2015, 49 pages.
Lyon C., Attorney for Applicant, Third-Party Pre-Issuance Submission Under 37 CFR Sec. 1.290 in U.S. Appl. No. 13/886,511, dated May 5, 2015, 18 pages.
Lyon C., Attorney for Applicant, Third-Party Pre-Issuance Submission Under 37 CFR Sec. 1.290 in U.S. Appl. No. 14/040,405, dated Jan. 16, 2015, 18 pages.
Lyon C., Attorney for Applicant, Third-Party Pre-Issuance Submission Under 37 CFR Sec. 1.290 in U.S. Appl. No. 14/040,427, dated Jan. 16, 2015, 20 pages.
Lyon C., Attorney for Applicant, Third-Party Pre-Issuance Submission Under 37 CFR Sec. 1.290 in U.S. Appl. No. 14/056,434, dated Dec. 15, 2014, 6 pages.
Lyon C., Attorney for Applicant, Third-Party Pre-Issuance Submission Under 37 CFR Sec. 1.290 in U.S. Appl. No. 14/080,630, dated Oct. 31, 2014, 8 pages.
Lyon C., Attorney for Applicant, Third-Party Pre-Issuance Submission Under 37 CFR Sec. 1.290 in U.S. Appl. No. 14/137,902, dated Nov. 13, 2014, 9 pages.
Lyon C., Attorney for Applicant, Third-Party Pre-Issuance Submission Under 37 CFR Sec. 1.290 in U.S. Appl. No. 14/220,080, dated Jul. 28, 2015, 28 pages.
Lyon C., Attorney for Applicant, Third-Party Pre-Issuance Submission Under 37 CFR Sec. 1.290 in U.S. Appl. No. 14/220,095, dated Aug. 4, 2015, 19 pages.
Lyon C., Attorney for Applicant, Third-Party Pre-Issuance Submission Under 37 CFR Sec. 1.290 in U.S. Appl. No. 14/220,099, dated Apr. 29, 2015, 43 pages.
Lyon C., Attorney for Applicant, Third-Party Pre-Issuance Submission Under 37 CFR Sec. 1.290 in U.S. Appl. No. 14/226,706, dated Jul. 28, 2015, 53 pages.
Lyon C., Attorney for Applicant, Third-Party Pre-Issuance Submission Under 37 CFR Sec. 1.290 in U.S. Appl. No. 14/263,158, dated Apr. 29, 2015, 16 pages.
Lyon C., Attorney for Applicant, Third-Party Pre-Issuance Submission Under 37 CFR Sec. 1.290 in U.S. Appl. No. 14/263,176, dated Apr. 29, 2015, 16 pages.
Lyon C., Attorney for Applicant, Third-Party Pre-Issuance Submission Under 37 CFR Sec. 1.290 in U.S. Appl. No. 14/497,054, dated Oct. 21, 2015, 81 pages.
Lyon C., Attorney for Applicant, Third-Party Pre-Issuance Submission Under 37 CFR Sec. 1.290 in U.S. Appl. No. 14/498,685, dated Sep. 18, 2015, 37 pages.
Lyon C., Attorney for Applicant, Third-Party Pre-Issuance Submission Under 37 CFR Sec. 1.290 in U.S. Appl. No. 14/516,461, dated Aug. 4, 2015, 27 pages.

(56) References Cited

OTHER PUBLICATIONS

Lyon C., Attorney for Applicant, Third-Party Pre-Issuance Submission Under 37 CFR Sec. 1.290 in U.S. Appl. No. 14/543,359, dated Nov. 13, 2015, 36 pages.

Lyon C., Attorney for Applicant, Third-Party Pre-Issuance Submission Under 37 CFR Sec. 1.290 in U.S. Appl. No. 14/226,698, dated Jun. 3, 2015, 53 pages.

Ma B., et al., "Human Antibody Expression in Transgenic Rats: Comparison of Chimeric IgH Loci with Human $V_H$, D and $J_H$ but Bearing Different Rat C-Gene Regions," *Journal of Immunological Methods*, 2013, vols. 400-401, pp. 78-86.

MacDonald L., Curriculum Vitae of Lynn E. MacDonald, Ph.D., 3 pages.

MacDonald L., Declaration of Lynn E. MacDonald with Exhibits, dated Feb. 3, 2015, relating to International Application No. PCT/US02/04500 (Published as WO02/066630 A1), 13 pages.

MacDonald L., Declaration of Lynne E. MacDonald, dated Jun. 29, 2016, 4 pages.

MacDonald L., et al., Expanded Poster: "Velocigene® Technology Extended to Humanization of Several Megabases of Complex Gene Loci," Sep. 2006, 6 pages.

MacDonald L., et al., Poster (Exhibit IJR-47): "Velocigene® Technology Extended to Humanization of Several Megabases of Complex Gene Loci," and evidence of unavailability, Sep. 2006, 42 pages.

MacDonald L., et al., "Velocigene® Technology Extended to Humanization of Several Megabases of Complex Gene Loci," (Abstract—21) 1st International MUGEN Conference on Animal Models for Human Immunological Disease, Athens Greece, Sep. 10-13, 2006, 1 page.

MacDonald L.E., et al., "Precise and in Situ Genetic Humanization of 6 Mb of Mouse Immunoglobulin Genes," *Proceedings of the National Academy of Sciences of the U.S.A.*, 2014, vol. 111 (14), pp. 5147-5152.

Mack M., et al., "A Small Bispecific Antibody Construct Expressed as a Functional Single-Chain Molecule with High Tumor Cell Cytotoxicity," *Proceedings of the National Academy of Sciences of the U.S.A.*, 1995, vol. 92 (15), pp. 7021-7025.

Magadán S., et al., "Production of Antigen-Specific Human Monoclonal Antibodies: Comparison of Mice Carrying IgH/κ or IgH/κ/λ transloci," *Biotechniques*, 2002, vol. 33 (3), pp. 680, 682, 684 passim.

Magdelaine-Beuzelin C., et al., "Structure-function relationships of the variable domains of monoclonal antibodies approved for cancer treatment," *Critical Reviews in Oncology Hematology*, 2007, vol. 64, pp. 210-225.

Maitta R.W., et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," *Infection and Immunity*, 2004, vol. 72 (1), pp. 196-208.

Makris J.C., et al., "Mutational Analysis of Insertion Sequence 50 (IS50) and Transposon 5 (Tn5) Ends," *Proceedings of the National Academy of Sciences of the U.S.A.*, 1988, vol. 85 (7), pp. 2224-2228.

Mallender W.D., et al., "Construction, Expression, and Activity of a Bivalent Bispecific Single-Chain Antibody," *The Journal of Biological Chemistry*, 1994, vol. 269 (1), pp. 199-206.

Manis J.P., et al., "Mechanism and Control of Class-Switch Recombination," *Trends in Immunology*, 2002, vol. 23 (1), pp. 31-39.

Marcello M.R., et al., "Lack of Tyrosylprotein Sulfotransferase-2 Activity Results in Altered Sperm-Egg Interactions and Loss of ADAM3 and ADAM6 in Epididymal Sperm," *The Journal of Biological Chemistry*, 2011, vol. 286 (15), pp. 13060-13070.

Marchalonis J.J., et al., "Emergence of the immunoglobulin family: conservation in protein sequence and plasticity in gene organization," *Glycobiology*, vol. 6, 1996, pp. 657-663.

Mårtensson I.L., et al., "Role of the Surrogate Light Chain and the Pre-B-Cell Receptor in Mouse B-Cell Development," *Immunology*, 2000, vol. 101 (4), pp. 435-441.

Martinez C., et al., "The Mouse (*Mus musculus*) Immunoglobulin Kappa Variable (IGKV) Genes and Joining (IGKJ) Segments," *Experimental and Clinical Immunogenetics*, Jul. 1998, vol. 15, pp. 184-193.

Martínez P., et al., "Antibody Synthesis in Vitro," Encyclopedia of Life Sciences, 2005, pp. 1-8.

Martinez-Jean C., et al., "Nomenclature and Overview of the Mouse (*Mus musculus* and *Mus* sp.) Immunoglobulin Kappa (IGK) Genes," *Experimental and Clinical Immunogenetics*, 2001, vol. 18(4), pp. 255-279.

Matthews V.B., et al., "A Locus Affecting Immunoglobulin Isotype Selection (Igis1) Maps to the MHC Region in C57BL, BALB/c and NOD Mice," *Immunology and Cell Biology*, 2001, vol. 79 (6), pp. 576-582.

Mattila P.S., et al., "Extensive Allelic Sequence Variation in the J Region of the Human Immunoglobulin Heavy Chain Gene Locus," *European Journal of Immunology*, 1995, vol. 25 (9), pp. 2578-2582.

Maul R.W., et al., "AID and Somatic Hypermutation," *Advances in Immunology*, Chapter 6, 2010, vol. 105, pp. 159-191.

McCreath K.J., et al., "Production of Gene-Targeted Sheep by Nuclear Transfer from Cultured Somatic Cells," *Nature*, 2000, vol. 405 (6790), pp. 1066-1069.

McMurry M.T., et al., "Enhancer Control of Local Accessibility to V(D)J Recombinase," *Molecular and Cellular Biology*, Aug. 1997, vol. 17 (8), pp. 4553-4561.

Mejía J.E., et al., "The Assembly of Large BACs by in Vivo Recombination," *Genomics*, 2000, vol. 70(2), pp. 165-170.

Mendez M.J., et al., "Functional Transplant of Megabase Human Immunoglobulin Loci Recapitulates Human Antibody Response in Mice," *Nature Genetics*, Feb. 1997, vol. 15 (2), pp. 146-156.

Mester G., European Patent Attorney, Grund Intellectual Property Group, Third-Party Observations according to Article 115 EPC regarding 12778780.2, dated Sep. 30, 2016, 5 pages.

Mgi, "Guidelines for Nomenclature of Mouse and Rat Strains," International Committee on Standardized Genetic Nomenclature for Mice / Rat Genome and Nomenclature Committee; Chairpersons: J.T. Eppig and G. Levan, Oct. 2011, 11 pages. [printed: Mar. 6, 2012—http://www.informatics.jax.org/mgihome/nomen/strains.shtml].

Mills F.C., et al., "Enhancer Complexes Located Downstream of Both Human Immunoglobulin Cα Genes," *The Journal of Experimental Medicine*, Sep. 1997, vol. 186 (6), pp. 845-858.

Milner E.C., et al., "Polymorphism and Utilization of Human $V_H$ Genes," *Annals of the New York Academy of Sciences*, 1995, vol. 764, pp. 50-61.

Minaee S., et al., "Mapping and Functional Analysis of Regulatory Sequences in the Mouse λ5-VpreB1 Domain," *Molecular Immunology*, 2005, vol. 42 (11), pp. 1283-1292.

Mir K.U., "Sequencing Genomes: From Individuals to Populations," *Briefings in Functional Genomics & Proteomics*, 2009, vol. 8 (5), pp. 367-378.

Müller U., "Ten Years of Gene Targeting: Targeted Mouse Mutants, from Vector Design to Phenotype Analysis," *Mechanisms of Development*, 1999, vol. 82 (1-2), pp. 3-21.

Moffatt S., et al., "PEGylated J591 mAb loaded in PLGA-PEG-PLGA tri-block copolymer for targeted delivery: In vitro evaluation in human prostate cancer cells," *International Journal of Pharmaceutics*, 2006, vol. 317, pp. 10-13.

Monaco A.P., et al., "YACs, BACs, PACs and MACs: Artificial Chromosomes as Research Tools," *Trends in Biotechnology*, Jul. 1994, vol. 12 (7), pp. 280-286.

Moran N., "Mouse Platforms Jostle for Slice of Humanized Antibody Market," *Nature Biotechnology*, Apr. 2013, vol. 31 (4), pp. 267-268.

Moreau P., et al., "The SV40 72 Base Repair Repeat has a Striking Effect on Gene Expression Both in SV40 and Other Chimeric Recombinants," *Nucleic Acids Research*, 1981, vol. 9 (22), pp. 6047-6068.

Moreno R.D., et al., "The Emerging Role of Matrix Metalloproteases of the ADAM Family in Male Germ Cell Apoptosis," *Spermatogenesis*, 2011, vol. 1 (3), pp. 195-208.

Mortuza F.Y., et al., "Immunoglobulin Heavy-Chain Gene Rearrangement in Adult Acute Lymphoblastic Leukemia Reveals Pref-

(56) References Cited

OTHER PUBLICATIONS erential Usage of $J_H$-Proximal Variable Gene Segments," *Blood*, 2001, vol. 97 (9), pp. 2716-2726.
Mullins L.J., et al., "Transgenesis in the Rat and Larger Mammals," Perspective Series: Molecular Medicine in Genetically Engineered Animals, *Journal of Clinical Investigation*, Apr. 1996, vol. 97 (7), pp. 1557-1560.
Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," cited in an IDS in U.S. Appl. No. 14/192,051 of MacDonald et al., dated Oct. 6, 2014, 62 pages.
Murphy A., "VelocImmune: Immunoglobulin Variable Region Humanized Mice," *Recombinant Antibodies for Immunotherapy*, 1st Edition, Chapter 8, 2009, pp. 100-108.
Murphy A.J., et al., "Mice with megabase humanization of their Immunoglobulin Genes Generate Antibodies as Efficiently as Normal Mice," *Proceedings of the National Academy of Sciences of the U.S.A.*, 2014, vol. 111 (14), pp. 5153-5158.
Murphy K., et al., The Generation of Lymphocyte Antigen Receptors, excerpt from *Janeway's Immunobiology*, Seventh edition, Chapter 4, 2008, p. 158.
Muyrers J.P.P., et al., "Rapid Modification of Bacterial Artificial Chromosomes by ET-Recombination," *Nucleic Acids Research*, 1999, vol. 27 (6), pp. 1555-1557.
Nadel B., et al., "Sequence of the Spacer in the Recombination Signal Sequence Affects V(D)J Rearrangement Frequency and Correlates with Nonrandom Vκ Usage in Vivo," *The Journal of Experimental Medicine*, 1998, vol. 187 (9), pp. 1495-1503.
Nagle M., "Regeneron Helps Make Sanofi Velocimmune to its 'Weak' Pipeline," 2007, 2 pages.
Nandi A.K., et al., "Regulated Expression of Genes Inserted at the Human Chromosomal β-globin Locus by Homologous Recombination," *Proceedings of the National Academy of Sciences of the U.S.A.*, 1988, vol. 85 (11), pp. 3845-3849.
Narayanan K., et al., "Bacterial Artificial Chromosome Mutagenesis Using Recombineering, Article ID: 971296," Journal of Biomedicine and Biotechnology, 2010, vol. 2011, Article ID No. 971296, 10 pages.
Narayanan K., et al., "Efficient and Precise Engineering of a 200 kb β-Globin Human/Bacterial Artificial Chromosome in *E. coli* DH10B using an Inducible Homologous Recombination System," *Gene Therapy*, 1999, vol. 6 (3), pp. 442-447.
Nelson A.L., et al., "Development Trends for Human Monoclonal Antibody Therapeutics," *Nature Reviews Drug Discovery*, 2010, vol. 9 (10), pp. 767-774.
Neuberger M.S., et al., "Isotype Exclusion and Transgene Down-Regulation in Immunoglobulin-λ Transgenic Mice," *Nature*, Mar. 1989, vol. 338 (6213), pp. 350-352.
Neuberger M.S., et al., "Somatic Hypermutation," *Current Opinion in Immunology*, 1995, vol. 7 (2), pp. 248-254.
Neuberger M.S., "Expression and regulation of immunoglobulin heavy chain gene transfected into lymphoid cells," *The EMBO Journal*, 1983, vol. 2 (8), pp. 1373-1378.
New Zealand Patent Office, Simon Maguire, Authorized Officer, Further Examination Report for Patent No. 623756, dated Sep. 9, 2015, 3 pages.
Nicholson I.C., et al., "Antibody Repertoires of Four- and Five-Feature Translocus Mice Carrying Human Immunoglobulin Heavy Chain and κ and λ Light Chain Yeast Artificial Chromosomes," *Journal of Immunology*, 1999, vol. 163 (12), pp. 6898-6906.
Nucleotide Sequence RID Y55HBK1W114, accessed Aug. 6, 2014, 2 pages.
Oancea A.E., et al., "Expression of the (recombinant) Endogenous Immunoglobulin Heavy-Chain Locus Requires the Intronic Matrix Attachment Regions," *Molecular and Cellular Biology*, 1997, vol. 17 (5), pp. 2658-2668.

Ohlin M., et al., "The Human Antibody Repertoire to Infectious Agents: Implications for Disease Pathogenesis," Molecular Immunology, 2003, vol. 40 (1), pp. 1-11.
Ohm-Laursen L., et al., "Identification of Two New Alleles, IGHV3-23*04 and IGHJ6*04, and the Complete Sequence of the IGHV3-h Pseudogene in the Human Immunoglobulin Locus and their Prevalences in Danish Caucasians," *Immunogenetics*, 2005, vol. 57 (9), pp. 621-627.
Osborn M.J., et al., "High-Affinity IgG Antibodies Develop Naturally in Ig-Knockout Rats Carrying Germline Human IgH/Igκ/Igλ Loci Bearing the Rat $C_H$ Region," *Journal of Immunology*, 2013, vol. 190 (4), pp. 1481-1490.
Osoegawa K., et al., "Bacterial Artificial Chromosome Libraries for Mouse Sequencing and Functional Analysis," *Genome Research*, 2000, vol. 10 (1), pp. 116-128.
Oumard A., et al., "Recommended method for chromosome exploitation: RMCE-based cassette-exchange systems in animal cell biotechnology," *Cytotechnology*, 2006, vol. 50, pp. 93-108.
Parng C.L., et al., "Gene Conversion Contributes to Ig Light Chain Diversity in Cattle," *Journal of Immunology*, 1996, vol. 157 (12), pp. 5478-5486.
Pear W.S., et al., "Localization of the Rat Immunoglobulin Heavy Chain Locus to Chromosome 6," *Immunogenetics*, 1986, vol. 23 (6), pp. 393-395.
Pelham H., et al., "Expression of a Drosophila Heat Shock Protein in Mammalian Cells: Transient Association with Nucleoli After Heat Shock," *Philosophical Transactions of the Royal Society B: Biological Sciences*, 1984, vol. 307 (1132), pp. 301-307.
Pera M.F., et al., "Human embryonic stem cells," *Journal of Cell Science*, 2000, vol. 113, pp. 5-10.
Pérez-Luz S., et al., "Factor VIII mRNA expression from a BAC carrying the intact locus made by homologous recombination," *Genomics*, 2007, vol. 90, pp. 610-619.
Perlot T., et al., "Antisense Transcripts from Immunoglobulin Heavy-Chain Locus V(D)J and Switch Regions," *Proceedings of the National Academy of Sciences of the U.S.A.*, 2008, vol. 105 (10), pp. 3843-3848.
Perlot T., et al., "Cis-Regulatory Elements and Epigenetic Changes control genomic rearrangements of the IgH locus," *Advances in Immunology*, Chapter 1, 2008, vol. 99, pp. 1-32.
Pettersson S., et al., "A second B cell-specific enhancer 3' of the immunoglobulin heavychain locus," *Nature*, Mar. 1990, vol. 344, pp. 165-168.
Pettitt S.J., et al., "Agouti C57BL/6N Embryonic Stem Cells for Mmouse Genetic Resources," *Nature Methods*, 2009, vol. 6 (7), pp. 493-495.
Plasterk R.H., et al., "Resident Aliens: the Tc1/Mariner Superfamily of Transposable Elements," *Trends Genetics*, 1999, vol. 15(8), pp. 326-332.
Pobursky K., Third-Party Pre-Issuance Submission Under 37 CFR 1.290 in U.S. Appl. No. 13/843,528, dated Mar. 18, 2014, 14 pages.
Pobursky K., Third-Party Pre-Issuance Submission Under 37 CFR 1.290 in U.S. Appl. No. 13/433,084, dated Apr. 1, 2014, 15 pages.
Pobursky K., Third-Party Pre-Issuance Submission Under 37 CFR 1.290 in U.S. Appl. No. 13/434,361, dated Apr. 1, 2014, 15 pages.
Pobursky K., Third-Party Pre-Issuance Submission Under 37 CFR 1.290 in U.S. Appl. No. 13/740,727, dated May 27, 2014, 25 pages.
Ponsel D., et al., "High Affinity, Developability and Functional Size: the Holy Grail of Combinatorial Antibody by Library Generation," *Molecules*, 2011, vol. 16 (5), pp. 3675-3700.
Popov A.V., et al., "A Human Immunoglobulin λ Locus is Similarly Well Expressed in Mice and Humans," *The Journal of Experimental Medicine*, 1999, vol. 189 (10), pp. 1611-1620.
Pramanik S., et al., "Segmental Duplication as One of the Driving Forces Underlying the Diversity of the Human Immunoglobulin Heavy Chain Variable Gene Region," *BMC Genomics*, Jan. 2011, vol. 12 (1), p. 78.
Presta L., "Molecular engineering and design of therapeutic antibodies," *Current Opinion in Immunology*, 2008, vol. 20, pp. 460-470.
Primakoff P., et al., "Penetration, Adhesion, and Fusion in Mammalian Sperm-Egg Interaction," *Science*, 2002, vol. 296 (5576), pp. 2183-2185.

(56) References Cited

OTHER PUBLICATIONS

Primakoff P., et al., "The ADAM Gene Family: Surface Proteins with Adhesion and Protease Activity," *Trends Genetics*, 2000, vol. 16 (2), pp. 83-87.
Printout of PDF file available from the University of California website presented in support of European opposition in the name of Kymab Ltd. pertaining to Application No. EP12171793.8 as filed on Jan. 19, 2017, 4 pages. [http://www.research.uci.edu/facilities-services/tmf/presentations/Mouse_ES_CellLine].
Prosser H.M., et al., "A Resource of Vectors and ES Cells for Targeted Deletion of MicroRNAs in Mice," *Nature Biotechnology*, 2011, vol. 29 (9), pp. 840-845.
Prosser H.M., et al., "Mosaic Complementation Demonstrates a Regulatory Role for Myosin Vila in Actin Dynamics of Stereocilia," *Molecular and Cellular Biology*, 2008, vol. 28 (5), pp. 1702-1712.
Pruzina S., et al., "Human Monoclonal Antibodies to HIV-1 gp140 from Mice Bearing YAC-Based Human Immunoglobulin Transloci," *Protein Engineering, Design & Selection*, 2011, vol. 24 (10), pp. 791-799.
Puente X.S., et al., "Comparative Genomic Analysis of Human and Chimpanzee Proteases," *Genomics*, 2005, vol. 86 (6), pp. 638-647.
Qi N.R., et al., "A New Transgenic Rat Model of Hepatic Steatosis and the Metabolic Syndrome," *Hypertension*, 2005, vol. 45 (5), pp. 1004-1011.
Qu S., et al., "Gene Targeting of ErbB3 Using a Cre-Mediated Unidirectional DNA Inversion Strategy," *Genesis*, 2006, vol. 44 (10), pp. 477-486.
Ramírez-Solis R., et al., "Chromosome Engineering in Mice," *Nature*, 1995, vol. 378 (6558), pp. 720-724.
Ramsden D.A., et al., "Conservation of Sequence in Recombination Signal Sequence Spacers," *Nucleic Acids Research*, 1994, vol. 22 (10), pp. 1785-1796.
Ray P., et al., "Ectopic Expression of a c-kit$^{VV42}$ Minigene in Transgenic Mice: Recapitulation of W Phenotypes and Evidence for c-kit Function in Melanoblast Progenitors," *Genes & Development*, 1991, vol. 5 (12A), pp. 2265-2273.
Raynard S.J., et al., "Cis-Acting Regulatory Sequences Promote High-Frequency Gene Conversion between Repeated Sequences in Mammalian Ccells," *Nucleic Acids Research*, 2004, vol. 32 (19), pp. 5916-5927.
Reddy S.T., et al., "Monoclonal Antibiotics Isolated without Screening by Analysing the Variable-Gene Repertoire of Plasma Cells," *Nature Biotechnology*, 2010, vol. 28 (9), pp. 965-971.
Regeneron Pharmaceuticals, Inc., et al., "Big Pharma Vies for Mice," *Nature Biotechnology*, 2007, vol. 25 (6), pp. 613.
Regeneron Pharmaceuticals, Inc., Press Release—"Astellas Licenses Regeneron's VelocImmune® Technology for Discovering Human Monoclonal Antibodies," dated Mar. 30, 2007, 2 pages.
Regeneron Pharmaceuticals, Inc., Press Release—"AstraZeneca Licenses Regeneron's VelocImmune® Technology for Discovering Human Monoclonal Antibodies—AstraZeneca Is First Licensee of Novel VelocImmune Technology License Fees Total up to $120 Million Over Six Years," dated Feb. 5, 2007, 2 pages.
Regeneron Pharmaceuticals, Inc., Press Release—"Regeneron Initiates Major Global Collaboration with Sanofi-aventis of Develop and Commercialize Fully-Human Therapeutic Antibodies," dated Nov. 29, 2007, 2 pages.
Ren S.Y., et al., "Targeted Insertion Results in a Rhombomere 2-Specific Hoxa2 Knockdown and Ectopic Activation of Hoxa1 Expression," *Developmental Dynamics*, 2002, vol. 225 (3), pp. 305-315.
Renaut L., et al., "Affinity Maturation of Antibodies: Optimized Methods to Generate High-Quality ScFv Libraries and Isolate IgG Candidates by High-Throughput Screening," *Antibody Engineering: Methods and Protocols*, Second Edition, Chapter 26, 2012, vol. 907, pp. 451-461.
Retter I., et al., "Sequence and Characterization ofthe Ig Heavy Chain Constant and Partial Variable Region ofthe Mouse Strain 129S1," *The Journal of Immunology*, 2007, vol. 179 (4), pp. 2419-2427.
Ricker M., European Patent Attorney, Opposition against EP2421357B1 in the name of Kymab Limited Statement of Facts and Arguments pertaining to Application No. 10734546.4, dated Oct. 23, 2013, 29 pages.
Ristevski S., "Making Better Transgenic Models: Conditional, Temporal, and Spatial Approaches," *Molecular Biotechnology*, 2005, vol. 29 (2), pp. 153-163.
Rivera J., et al., "Genetic Background and the Dilemma of Translating Mouse Studies to Humans," *Immunity*, 2008, vol. 28 (1), pp. 1-4.
Rock E.P., et al., "CDR3 Length in Antigen-specific Immune Receptors", *Journal of Experimental Medicine*, Jan. 1994, vol. 179, pp. 323-328.
Rodríguez C.I., et al., "High-Efficiency Deleter Mice Show that FLPe is an Alternative to Cre-loxP," *Nature Genetics*, 2000, vol. 25 (2), pp. 139-140.
Rogozin I.B., et al., "Cutting edge: DGYW/WRCH is a Better Predictor of Mmutability at G:C bases in Lg Hypermutation than the Widely Accepted RGYW/RCY Motif and Probably Reflects a Two-Step Activation-Induced Cytidine Deaminase-Triggered Process," *The Journal of Immunology*, 2004, vol. 172 (6), pp. 3382-3384.
Rosner K., et al., "Third Complementarity-Determining Region of Mutated $V_H$ Immunoglobulin Genes Contains Shorter V, D, J, P, and N Components than Non-Mutated Genes," *Immunology*, 2001, vol. 103 (2), pp. 179-187.
Rusk N., "Making Mice at High Speed," *Nature Methods*, Mar. 2007, vol. 4 (3), pp. 196-197.
Sabbattini P., et al., "Analysis of Mice with Single and Multiple Copies of Transgenes Reveals a Novel Arrangement for the $\lambda 5$-$V_{preB1}$ Locus Control Region," *Molecular and Cellular Biology*, Jan. 1999, vol. 19 (1), pp. 671-679.
Sakai E., et al., "Recombination and Transcription of the Endogenous Ig Heavy Chain Locus is Effected by the Ig Heavy Chain Intronic Enhancer Core Region in the Absence of the Matrix Attachment Regions," *Proceedings of the National Academy of Sciences of the U.S.A.*, 1999, vol. 96(4), pp. 1526-1531.
Sarkar A., et al., "Molecular Evolutionary Analysis of the Widespread PiggyBac Transposon Family and Related "Domesticated" Sequences," *Molecular Genetics & Genomics*, 2003, vol. 270 (2), pp. 173-180.
Sasso E.H., et al., "Ethnic Differences of Polymorphism of an Immunoglobulin $V_H3$ Gene," *Journal of Clinical Investigation*, 1995, vol. 96 (3), pp. 1591-1600.
Sasso E.H., et al., "Expression of the Immunoglobulin $V_H$ Gene 51p1 is Proportional to its Germline Gene Copy Number," *Journal of Clinical Investigation*, 1996, vol. 97 (9), pp. 2074-2080.
Sauer B., et al., "Cre-Stimulated Recombination at loxP-Containing DNA Sequences Placed into the Mammalian Genome," *Nucleic Acids Research*, 1989, vol. 17 (1), pp. 147-161.
Sauer B., et al., "Site-Specific DNA Recombination in Mammalian Cells by the Cre Recombinase of Bacteriophage P1," *Proceedings of the National Academy of Sciences of the U.S.A.*, 1988, vol. 85 (14), pp. 5166-5170.
Sauer B., "Functional Expression ofthe cre-lox Site-Specific Recombination System in the Yeast *Saccharomyces cerevisiae*," *Molecular and Cellular Biology*, 1987, vol. 7 (6), pp. 2087-2096.
Scapini P., et al., "Myeloid Cells, BAFF, and IFN-$\gamma$ Establish an Inflammatory Loop that Exacerbates Autoimmunity in Lyn-Deficient Mice," *The Journal of Experimental Medicine*, Jul. 2010, vol. 207 (8), pp. 1757-1773.
Schlake T., et al., "Use of Mutated FLP Recognition Target (FRT) Sites forthe Exchange of Expression Cassettes at Defined Chromosomal Loci," *Biochemistry*, 1994, vol. 33 (43), pp. 12746-12751.
Schnütgen F., et al., "A Directional Strategy for Monitoring Cre-Mediated Recombination at the Cellular Level in the Mouse," *Nature Biotechnology*, 2003, vol. 21 (5), pp. 562-565.
Schonewald, S.L., Attorney for Applicant, Third-Party Pre-Issuance Submission Under 37 CFR Sec. 1.290 in U.S. Appl. No. 14/220,074, dated Jul. 12, 2016, 46 pages.
Schonewald, S.L., Attorney for Applicant, Third-Party Pre-Issuance Submission Under 37 CFR Sec. 1.290 in U.S. Appl. No. 14/750,870, dated Aug. 10, 2016, 34 pages.

(56) References Cited

OTHER PUBLICATIONS

Schonewald, S.L., Attorney for Applicant, Third-Party Pre-Issuance Submission Under 37 CFR Sec. 1.290 in U.S. Appl. No. 14/818,162, dated May 24, 2016, 47 pages.
Schonewald, S.L., Attorney for Applicant, Third-Party Pre-Issuance Submission Under 37 CFR Sec. 1.290 in U.S. Appl. No. 14/935,010, dated Aug. 19, 2016, 27 pages.
Schroeder Jr. H.W, et al., "Preferential Utilization of Conserved Immunoglobulin Heavy Chain Variable Gene Segments During Human Fetal Life," *Proceedings of the National Academy of Sciences of the U.S.A.*, 1990, vol. 87 (16), pp. 6146-6150.
Schroeder, Jr. H.W., "Similarity and divergence in the development and expression of the mouse and human antibody repertoires," *Developmental and Comparative Immunology*, vol. 30, 2006, pp. 119-135.
Schröck E., et al., "Comparative Genomic Hybridization (CGH)--Detection of Unbalanced Genetic Aberrations Using Conventional and Micro-Array Techniques," *Current Protocols in Cytometry*, Chapter 8, 2001, Unit 8.12.1, Supplement 18, 30 pages.
Schweinfest C.W., et al., "A Heat-Shock-Inducible Eukaryotic Expression Vector," *Gene*, 1988, vol. 71 (1), pp. 207-210.
Scott C.T., "Mice with a Human Touch," *Nature Biotechnology*, 2007, vol. 25 (10), pp. 1075-1077.
Seals D.F., et al., "The ADAMs Family of Metalloproteases: Multidomain Proteins with Multiple Functions," *Genes & Development*, 2003, vol. 17 (1), pp. 7-30.
Seed B., "Purification of Genomic Sequences from Bacteriophage Libraries by Recombination and Selection in Vivo," *Nucleic Acids Research*, 1983, vol. 11 (8), pp. 2427-2445.
Seidl K.J., et al., "An Expressed neo$^r$ Cassette Provides Required Functions ofthe 1γ2b Exon for Class Switching," *International Immunology*, 1998, vol. 10 (11), pp. 1683-1692.
Seidl K.J., et al., "Position-Dependent Inhibition of Class-Switch Recombination by PGK-neo$^r$ Cassettes Inserted into the Immunoglobulin Heavy Chain Constant Region Locus," *Proceedings of the National Academy of Sciences of the U.S.A.*, Mar. 1999, vol. 96 (6), pp. 3000-3005.
Sekiguchi J., et al., "The Mechanism of V(D)J Recombination," *Molecular Biology of B Cells*, Chapter 5, 2004, pp. 61-82.
Sen R., et al., "Multiple Nuclear Factors Interact with the Immunoglobulin Enhancer Sequences," *Cell*, 1986, vol. 46 (5), pp. 705-716.
Seong E., et al., "To Knockout in 129 or in C57BL/6: That is the Question," *Trends in Genetics*, 2004, vol. 20 (2), pp. 59-62.
Sequence Listing to WO2008054606A2, 163 pages.
Serwe M., et al., "V(D)J Recombination in B Cells is Impaired but not Blocked by Targeted Deletion of the Immunoglobulin Heavy Chain Intron Enhancer," *The EMBO Journal*, 1993, vol. 12(6), pp. 2321-2327.
Sharon J., et al., "Expression of a VHC Kappa Chimaeric Protein in Mouse Myeloma Cells," *Nature*, 1984, vol. 309 (5966), pp. 364-367.
Shaul Y., et al., "Homologous Recombination Between a Defective Virus and a Chromosomal Sequence in Mammalian Cells," *Proceedings of the National Academy of Sciences of the U.S.A.*, 1985, vol. 82 (11), pp. 3781-3784.
Shi B., et al., "Comparative Analysis of Human and Mouse Immunoglobulin Variable Heavy Regions from IMGT/LIGM-DB with IMGT/HighV-QUEST," *Theoretical Biology and Medical Modelling*, 2014, vol. 11, pp. 1-11.
Shi Y.P., et al., "The Mapping of Transgenes by Fluorescence in Situ Hybridization on G-Banded Mouse Chromosomes," *Mammalian Genome*, 1994, vol. 5 (6), pp. 337-341.
Shih H.H., "Discovery Process for Antibody-Based Therapeutics," *Development of Antibody-Based Therapeutics*, Chapter 2, 2012, pp. 9-32.
Shimizu A., et al., "Immunoglobulin Double-Isotype Expression by Trans-mRNA in a Human Immunoglobulin Transgenic Mouse," *Proceedings of the National Academy of Sciences of the U.S.A.*, 1989, vol. 86 (20), pp. 8020-8023.

Shore, D.E., Attorney for Applicant, Third-Party Pre-Issuance Submission Under 37 CFR Sec. 1.290 in U.S. Appl. No. 14/543,359, filed Mar. 3, 2017, 16 pages.
Shore, D.E., Attorney for Applicant, Third-Party Pre-Issuance Submission Under 37 CFR Sec. 1.290 in U.S. Appl. No. 15/199,575, filed May 31, 2017, 37 pages.
Shultz L.D., et al., "Humanized Mice in Translational Biomedical Research," *Nature Reviews / Immunology*, 2007, vol. 7 (2), pp. 118-130.
Sigmund C.D., "Viewpoint: Are Studies in Genetically Altered Mice Out of Control?," *Arteriosclerosis, Thrombosis, and Vascular Biology*, Jun. 2000, vol. 20 (6), pp. 1425-1429.
Simpson E.M., et al., "Genetic Variation Among 129 Substrains and its Importance for Targeted Mutagenesis in Mice," *Nature Genetics*, 1997, vol. 16 (1), pp. 19-27.
Sirac C., et al., "Role of the Monoclonal κ Chain V Domain and Reversibility of Renal Damage in a Transgenic Model of Acquired Fanconi Syndrome," *Blood*, 2006, vol. 108 (2), pp. 536-543.
Skarnes W.C., et al., "A Conditional Knockout Resource for the Genome-Wide Study of Mouse Gene Function," *Nature*, 2011, vol. 474 (7351), pp. 337-342.
Skoultchi A.I., et al., "Expression of Genes Inserted at the Human β-Globin Locus by Homologous Recombination," *Progress in Clinical and Biological Research*, 1987, vol. 251, pp. 581-594.
Smith K.R., "Gene Transfer in Higher Animals: Theoretical Considerations and Key Concepts," *Journal of Biotechnology*, 2002, vol. 99 (1), pp. 1-22.
Smithies O., "Direct Alteration of a Gene in the Human Genome," *Journal of Inherited Metabolic Disease*, 1986, vol. 9 (Suppl. 1), pp. 92-97.
Smithies O., et al., "Insertion of DNA Sequences into the Human Chromosomal β-Globin Locus by Homologous Recombination," *Nature*, 1985, vol. 317 (6034), pp. 230-234.
Sohn J., et al., "Somatic Hypermutation of an Immunoglobulin μ Heavy Chain Transgene," *The Journal of Experimental Medicine*, 1993, vol. 177 (2), pp. 493-504.
Song K., et al., "Accurate Modification of a Chromosomal Plasmid by Homologous Recombination in Human Cells," *Proceedings of the National Academy of Sciences of the U.S.A.*, 1987, vol. 84 (19), pp. 6820-6824.
Sonoda E., et al., "B Cell Development Under the Condition of Allelic Inclusion," *Immunity*, 1997, vol. 6 (3), pp. 225-233.
Sopher B., et al., "Efficient recombination-based methods for bacterial artificial chromosome fusion and mutagenesis," *Gene*, 2006, vol. 371, pp. 136-143.
Sorrell D.A., et al., "Targeted modification of mammalian genomes," *Biotechnology Advances*, vol. 23, 2005, pp. 431-469.
Soukharev S., et al., "Segmental Genomic Replacement in Embryonic Stem Cells by Double Lox Targeting," *Nucleic Acids Research*, 1999, vol. 27 (18), pp. e21.
Spanopoulou E., et al., "Functional Immunoglobulin Transgenes Guide Ordered B-Cell Differentiation in Rag-1-Deficient Mice," *Genes & Development*, 1994, vol. 8 (9), pp. 1030-1042.
Stavnezer J., et al., "Mechanism and Regulation of Class Switch Recombination," *Annual Review of Immunology*, 2008, vol. 26, pp. 261-292.
Stein R., et al., "Characterization of a humanized IgG4 anti-HLA-DR monoclonal antibody that lacks effector cell functions but retains direct antilymphoma activity and increases the potency of rituximab," *Blood*, Oct. 2006, vol. 108 (8), pp. 2736-2744.
Stephen R., Kymab Limited Statement of Facts and Evidence in opposition to EP2550363, Olswang LLP, dated Sep. 10, 2015, 22 pages.
Stephen R., Olswang, Response to Examination Report dated Jun. 6, 2016 for Application No. 14176740.0, as filed with the European Patent Office on Oct. 10, 2016, 4 pages.
Stephen R., Olswang, Response to Search Report dated Oct. 15, 2014 for Application No. 14176740.0, as filed with the European Patent Office on May 12, 2015, 4 pages.
Stephen R., Olswang, Response to Third-Party Observations dated Aug. 10, 2015 and Examination Report dated Oct. 23, 2015 for Application No. 14176740.0, as filed with the European Patent Office on Apr. 23, 2016, 6 pages.

(56) References Cited

OTHER PUBLICATIONS

Stevens S., et al., Expanded Poster: "VelocImmune™: Humanization of immunoglobulin loci using VelociGene® technology," Sep. 2006, 6 pages.
Stevens S., et al., Poster (Exhibit IJR-46): "VelocImmune™: Humanization of immunoglobulin loci using VelociGene® technology," and evidence of unavailability, Sep. 2006, 42 pages.
Stevens S. et al., "VelocImmune™: Humanization of immunoglobulin loci using VelociGene® technology," (Abstract—4) Presented at 1st International MUGEN Conference on Animal Models for Human Immunological Disease, Athens, Greece, Sep. 10-13, 2006, 1 page.
Storb U., et al., "Physical Linkage of Mouse λ Genes by Pulsed-Field Gel Electrophoresis Suggests that the Rearrangement Process Favors Proximate Target Sequences," *Molecular and Cellular Biology*, 1989, vol. 9 (2), pp. 711-718.
Sun Y., et al., "Repertoire of Human Antibodies against the Polysaccharide Capsule of *Streptococcus pneumoniae* Serotype 6B," *Infection and Immunity*, Mar. 1999, vol. 67 (3), pp. 1172-1179.
Suárez E., et al., "Rearrangement of Only One Human IGHV Gene is Sufficient to Generate a Wide Repertoire of Antigen Specific Antibody Responses in Transgenic Mice," *Molecular Immunology*, 2006, vol. 43 (11), pp. 1827-1835.
Takeda S., et al., "Construction of Chimaeric Processed Immunoglobulin Genes Containing Mouse Variable and Human Constant Region Sequences," *Nature*, Apr. 1985, vol. 314 (6010), pp. 452-454.
Taki S., et al., "Targeted Insertion of a Variable Region Gene into the Immunoglobulin Heavy Chain Locus," *Science*, 1993, vol. 262 (5137), pp. 1268-1271.
Talbot P., et al., "Cell Adhesion and Fertilization: Steps in Oocyte Transport, Sperm-Zona Pellucida Interactions, and Sperm-Egg Fusion," *Biology of Reproduction*, 2003, vol. 68 (1), pp. 1-9.
Tan L.K., et al., "A Human-Mouse Chimeric Immunoglobulin Gene with a Human Variable Region is Expressed in Mouse Myeloma Cells," *Journal of Immunology*, Nov. 1985, vol. 135 (5), pp. 3564-3567.
Tanimoto Y., et al., "Embryonic Stem Cells Derived from C57BL/6J and C57BL/6N Mice," *Comparative Medicine*, Aug. 2008, vol. 58 (4), pp. 347-352.
Taylor L.D., et al., "Human Immunoglobulin Transgenes Undergo Rearrangement, Somatic Mutation and Class Switching in Mice that Lack Endogenous IgM," *International Immunology*, 1994, vol. 6(4), pp. 579-591.
Te Riele H., et al., "Highly Efficient Gene Targeting in Embryonic Stem Cells through Homologous Recombination with Isogenic DNA Constructs," *Proceedings of the National Academy of Sciences of the U.S.A.*, 1992, vol. 89 (11), pp. 5128-5132.
The Jackson Laboratory, "Breeding Strategies for Maintaining Colonies of Laboratory Mice," *A Jackson Laboratory Resource Manual*, 2007, pp. 1-29.
Thomas K.R., et al., "High Frequency Targeting of Genes to Specific Sites in the Mammalian Genome," *Cell*, 1986, vol. 44 (3), pp. 419-428.
Thomas K.R., et al., "Introduction of Homologous DNA Sequences into Mammalian Cells Induces Mutations in the Cognate Gene," *Nature*, 1986, vol. 324 (6092), pp. 34-38.
Thomas K.R., et al., "Site-Directed Mutagenesis by Gene Targeting in Mouse Embryo-Derived Stem Cells," *Cell*, 1987, vol. 51 (3), pp. 503-512.
Thykjaer T., et al., "Gene Targeting Approaches Using Positive-Negative Selection and Large Flanking Regions," *Plant Molecular Biology*, 1997, vol. 35 (4), pp. 523-530.
Tomizuka K., et al., "Double Trans-Chromosomic Mice: Maintenance of Two Individual Human Chromosome Fragments Containing Ig Heavy and κ Loci and Expression of Fully Human Antibodies," *Proceedings of the National Academy of Sciences of the U.S.A.*, Jan. 2000, vol. 97 (2), pp. 722-727.
Tonegawa S., "Somatic Generation of Antibody Diversity," *Nature*, Apr. 1983, vol. 302 (5909), pp. 575-581.
Tong C., et al., "Production of p53 gene knockout rats by homologous recombination in embryonic stem cells," *Nature*, Sep. 2010, vol. 467 (7312), pp. 211-213.
Tuaillon N., et al., "Human immunoglobulin heavy-chain minilocus recombination in transgenic mice: Gene-segment use in μ and γ transcripts," *Proceedings of the National Academy of Sciences of the U.S.A.*, Apr. 1993, vol. 90, pp. 3720-3724.
Tucker P.W., et al., "Mouse IgA Heavy Chain Gene Sequence: Implications for Evolution of Immunoglobulin Hinge Axons," *Proceedings of the National Academy of Sciences of the U.S.A.*, Dec. 1981, vol. 78 (12), pp. 7684-7688.
Ungrin M.D., et al., "Strict Control of Telomerase Activation Using Cre-Mediated Inversion," *BMC Biotechnology*, 2006, vol. 6, pp. 1-9, 2006.
United Kingdom Intellectual Property Office, Combined Search and Examination Report under Sections 17 and 18(3) for Application No. GB1317410.7, dated Nov. 21, 2013, 8 pages.
United Kingdom Intellectual Property Office, Combined Search and Examination Report under Sections 17 and 18(3) for Application No. GB1317447.9, dated Jan. 14, 2014, 7 pages.
United Kingdom Intellectual Property Office, Corrected Search Report Under Section 17 for Application No. GB1122047.2, dated Apr. 20, 2012, 5 pages.
United Kingdom Intellectual Property Office, Search Report under Section 17 for Application No. GB1116122.1, dated Feb. 2, 2012, 1 page.
Urquhart-Dykes & Lord LLP, Third-Party Observation for Application No. EP20140772198, dated Dec. 14, 2015, 8 pages.
USPTO, Excerpts from U.S. Appl. No. 14/682,859, filed Apr. 9, 2015, including Applicant-initiated Interview Summary; Amendments to the Claims and Information Disclosure Statement, 14 pages.
Van Der Weyden L., et al., "Mouse Chromosome Engineering for Modeling Human Disease," *Europe PMC Funders Group*, Author Manuscript, Dec. 2008, 32 pages.
Van Dijk M., Declaration of Marcus Van Dijk with exhibits, Apr. 30, 2016, 139 pages.
Van Loo, P.F., et al., "Surrogate-Light-Chain Silencing Is Not Critical for the Limitation of Pre-B Cell Expansion but Is for the Termination of Constitutive Signaling," *Immunity*, Sep. 2007, vol. 27, pp. 468-480.
Van Snick J.L., et al., "Genetic Control of Rheumatoid Factor Production in the Mouse. Role of Genes Linked to the Immunoglobulin Heavy Chain Locus and to the Major Histocompatibility Complex," *Arthritis and Rheumatism*, Sep. 1983, vol. 26 (9), pp. 1085-1090.
Van Spriel A.B., et al., "Immunotherapeutic Perspective for Bispecific Antibodies," *Immunology Today*, 2000, vol. 21 (8), pp. 391-397.
Vasicek T.J., et al., "Structure and Expression of the Human Immunoglobulin λ Genes," *The Journal of Experimental Medicine*, 1990, vol. 172 (2), pp. 609-620.
Vassilieva S., et al., "Establishment of SSEA-1- and Oct-4-Expressing Rat Embryonic Stem-Like Cell Lines and Effects of Cytokines of the IL-6 Family on Clonal Growth," *Experimental Cell Research*, 2000, vol. 258 (2), pp. 361-373.
Venken K.J.T., et al., "P[acman]: a BAC Transgenic Platform for Targeted Insertion of Large DNA Fragments in *D. melanogaster*," *Science*, 2006, vol. 314 (5806), pp. 1747-1751.
Vieira P., et al., "The half-lives of serum immunoglobulins in adult mice," *European Journal of Immunology*, 1988, vol. 18, pp. 313-316.
Vollmer J., et al., "Antigen Contacts by Ni-Reactive TCR: Typical αβ Chain Cooperation Versus a Chain-Dominated Specificity," *International Immunology*, 2000, vol. 12 (12), pp. 1723-1731.
Vora K.A., et al., "Altering the Antibody Repertoire via Transgene Homologous Recombination: Evidence for Global and Clone-Autonomous Regulation of Antigen-Driven B Cell Differentiation," *The Journal of Experimental Medicine*, 1995, vol. 181 (1), pp. 271-281.
Wagner S.D., et al., "Antibodies Generated from Human Immunoglobulin Miniloci in Transgenic Mice," *Nucleic Acids Research*, 1994, vol. 22 (8), pp. 1389-1393.

(56) References Cited

OTHER PUBLICATIONS

Wallace H.A.C., et al., "Manipulating the Mouse Genome to Engineer Precise Functional Syntenic Replacements with Human Sequence," *Cell*, 2007, vol. 128 (1), pp. 197-209.
Wang M., et al., "AID Upmutants Isolated Using a High-Throughput Screen Highlight the Immunity/Cancer Balance Limiting DNA Deaminase Activity," *Nature Structural & Molecular Biology*, 2009, vol. 16 (7), pp. 769-776.
Wang M., et al., "Altering the Spectrum of Immunoglobulin V Gene Somatic Hypermutation by Modifying the Active Site of AID," *The Journal of Experimental Medicine*, 2010, vol. 207 (1), pp. 141-153.
Wang T.T., et al., "Catching a Moving Target," *Science*, 2011, vol. 333 (6044), pp. 834-835.
Wang W., et al., "Chromosomal Transposition of PiggyBac in Mouse Embryonic Stem Cells," *Proceedings of the National Academy of Sciences of the U.S.A.*, 2008, vol. 105 (27), pp. 9290-9295.
Wang X., et al., "Recombination, transcription, and diversity of a partially germline-joined VH in a mammal," *Immunogenetics*, 2012, vol. 64, pp. 713-717.
Wang Y., et al., "Many Human Immunoglobulin Heavy-Chain IGHV Gene Polymorphisms have been Reported in Error," *Immunology and Cell Biology*, 2008, vol. 86 (2), pp. 111-115.
Wasserman R., et al., "The Pattern of Joining ($J_H$) Gene Usage in the Human IgH Chain Is Established Predominantly at the B PreCursor Cell Stage," *The Journal of Immunology*, Jul. 1992, vol. 149(2), pp. 511-516.
Waterhouse P., et al., "Combinatorial Infection and in Vivo Recombination: a Strategy for Making Large Phage Antibody Repertoires," *Nucleic Acids Research*, 1993, vol. 21 (9), pp. 2265-2266.
Waterston R.H., et al., "Initial Sequencing and Comparative Analysis of the Mouse Genome," *Nature*, Dec. 2002, vol. 420 (6915), pp. 520-562.
Webpage corroborating non-confidential nature of 2006 MUGEN Conference, Athens (www.mugen.noe.org), accessed Aug. 9, 2016, 4 pages.
Weichhold G.M., et al., "Megabase Inversions in the Human Genome as Physiological Events," *Nature*, Sep. 1990, vol. 347 (6288), pp. 90-92.
Weichhold G.M., et al., "The Human Immunoglobulin κ Locus Consists of Two Copies that are Organized in Opposite Polarity," *Genomics*, 1993, vol. 16 (2), pp. 503-511.
Weiner L.M., "Fully Human Therapeutic Monoclonal Antibodies," *Journal of Immunology*, Jan./Feb. 2006, vol. 29 (1), pp. 1-9.
White J.K., et al., "Genome-Wide Generation and Systematic Phenotyping of Knockout Mice Reveals New Roles for Many Genes," *Cell*, 2013, vol. 154 (2), pp. 452-464.
Wikipedia, "Monoclonal antibody," 2008, 8 pages.
Wikipedia, "Polyclonal antibodies," 2008, 5 pages.
Wilke K., et al., "Diagnosis of Haploidy and Triploidy Based on Measurement of Gene Copy Number by Real-Time PCR," *Human Mutation*, 2000, vol. 16 (5), pp. 431-436.
Wilkie T.M., et al., "Analysis of the Integrant in MyK-103 Transgenic Mice in which Males Fail to Transmit the Integrant," *Molecular and Cellular Biology*, 1987, vol. 7 (5), pp. 1646-1655.
Williams G.S., et al., "Unequal VH Gene Rearrangement Frequency within the Large $V_H$7183 Gene Family is not due to Recombination Signal Sequence Variation, and Mapping of the Genes Shows a Bias of Rearrangement Based on Chromosomal Location," *Journal of Immunology*, 2001, vol. 167 (1), pp. 257-263.
Williams K., Attorney for Applicant, Third-Party Pre-Issuance Submission Under 37 CFR 1.290 in U.S. Appl. No. 14/600,829, dated Apr. 1, 2016, 18 pages.
Williams K., Attorney for Applicant, Third-Party Pre-Issuance Submission Under 37 CFR 1.290 in U.S. Appl. No. 14/679,949, dated Apr. 1, 2016, 18 pages.
Wuerffel R., et al., "S-S Synapsis During Class Switch Recombination is Promoted by Distantly Located Transcriptional Elements and Activation-Induced Deaminase," *Immunity*, Nov. 2007, vol. 27 (5), pp. 711-722.
Xiao X., et al., "Germline-like predecessors of broadly neutralizing antibodies lack measurable binding to HIV-1 envelope glycoproteins: Implications for evasion of immune responses and design of vaccine immunogens," *Biochemical and Biophysical Communications*, 2009, vol. 390, pp. 404-409.
Xu L., et al., "Combinatorial Surrobody Libraries," *Proceedings of the National Academy of Sciences of the U.S.A.*, 2008, vol. 105 (31), pp. 10756-10761.
Xu Y., et al., "Deletion of the Igκ Light Chain Intronic Enhancer/Matrix Attachment Region Impairs but does not Abolish VκJκ Rearrangement," *Immunity*, Apr. 1996, vol. 4 (4), pp. 377-385.
Yamada M., et al., "Preferential Utilization of Specific Immunoglobulin Heavy Chain Diversity and Joining Segments in Adult Human Peripheral Blood B Lymphocytes," *Journal of Experimental Medicine*, Feb. 1991, vol. 173, pp. 395-407.
Yancopoulos G.D., et al., "Preferential Utilization of the Most $J_H$-Proximal $V_H$ Gene Segments in Pre-B-Cell Lines," *Nature*, 1984, vol. 311 (5988), pp. 727-733.
Yang X.W., et al., "Homologous Recombination Based Modification in *Escherichia coli* and Germline Transmission in Transgenic Mice of a Bacterial Artificial Chromosome," *Nature Biotechnology*, Sep. 1997, vol. 15 (9), pp. 859-865.
Yu C.C.K., et al., "Differential Usage of $V_H$ Gene Segments is Mediated by cis Elements," *Journal of Immunology*, 1998, vol. 161 (7), pp. 3444-3454.
Yu Y., et al., "Engineering Chromosomal Rearrangements in Mice," *Nature Reviews Genetics*, 2001, vol. 2(10), pp. 780-790.
Zemlin M., et al., "Expressed Murine and Human CDR-H3 Intervals of Equal Length Exhibit Distinct Repertoires that Differ in their Amino Acid Composition and Predicted Range of Structures," *Journal of Molecular Biology*, 2003, vol. 334 (4), pp. 733-749.
Zhang X., et al., "Combination of overlapping bacterial artificial chromosones by a two-step recombinogenic engineering method," *Nucleic Acids Research*, 2003, vol. 31 (15), pp. e81-1-e81-6.
Zhang Y., et al., "A New Logic for DNA Engineering Using Recombination in *Escherichia coli*," *Nature Genetics*, 1998, vol. 20 (2), pp. 123-128.
Zhao S., "A Comprehensive BAC Resource," *Nucleic Acids Research*, 2001, vol. 29 (1), pp. 141-143.
Zhao Y., et al., "Physical Mapping of the Bovine Immunoglobulin Heavy Chain Constant Region Gene Locus," *Journal of Biological Chemistry*, Sep. 2003, vol. 278 (37), pp. 35024-35032.
Zheng J., et al., "Immunoglobulin Gene Transcripts Have distinctive $V_H DJ_H$ Recombination Characteristics in Human Epithelial Cancer Cells", *Journal of Biological Chemistry*, Mar. 2009, vol. 284 (20), pp. 13610-13619.
Zou X., et al., "Removal of the BIP-Retention Domain in Cμ Permits Surface Deposition and Developmental Progression Without L-Chain," *Molecular Immunology*, 2008, vol. 45 (13), pp. 3573-3579.
Zou X., et al., "Subtle differences in antibody responses and hypermutation of lambda λ chains in mice with a disrupted x contact region," *European Journal of Immunology*, 1995, vol. 25, pp. 2154-2162.
Zou Y., et al., "Cre-loxP-Mediated Gene Replacement: a Mouse Strain Producing Humanized Antibodies," *Current Biology*, 1994, vol. 4 (12), pp. 1099-1103.
U.S. Appl. No. 15/690,183, filed Aug. 29, 2017.
Baxendale H.E., et al., "Natural human antibodies to pneumococcus have distinctive molecular characteristics and protect against pneumococcal disease," *Clinical and Experimental Immunology*, 2007, vol. 151, pp. 51-60.
Forsman A., et al., "Llama Antibody Fragments with Cross-Subtype Human Immunodeficiency Virus Type I (HIV-I)-Neutralizing Properties and High Affinity for HIV-1 gp120," *Journal of Virology*, Dec. 2008, vol. 82 (24), pp. 12069-12081.
Jones B.T., Attorney for Applicant, Third-Party Pre-Issuance Submission Under 37 CFR Sec. 1.290 in U.S. Appl. No. 15/251,969, filed May 4, 2017, 22 pages.
Jones B.T., Attorney for Applicant, Third-Party Pre-Issuance Submission Under 37 CFR Sec. 1.290 in U.S. Appl. No. 15/383,101, filed May 30, 2017, 32 pages.

(56) References Cited

OTHER PUBLICATIONS

O'Dea, T.P., Attorney for Applicant, Third-Party Pre-Issuance Submission Under 37 CFR Sec. 1.290 in U.S. Appl. No. 15/385,348, filed Jul. 28, 2017, 48 pages.

O'Dea, T.P., Attorney for Applicant, Third-Party Pre-Issuance Submission Under 37 CFR Sec. 1.290 in U.S. Appl. No. 15/385,372, filed Jul. 28, 2017, 48 pages.

Suárez E., et al., "Human monoclonal antibodies produced in transgenic BABκ,λ mice recognising idiotypic immunoglobulins of human lymphoma cells," *Molecular Immunology*, 2004, vol. 41, pp. 519-526.

Zhu Z., et al., "Cross-Reactive HIV-1-Neutralizing Human Monoclonal Antibodies Identified from a Patient with 2F5-Like Antibodies," *Journal of Virology*, Nov. 2011, vol. 85 (21), pp. 11401-11408.

Adekar S.P., et al., "A Natural Human IgM Antibody that Neutralizes Botulinum Neurotoxin in vivo," *Hybridoma*, 2008, vol. 27 (2), pp. 65-69.

Aizenshtein E., et al., "Immunological complex for enhancement of innate immune response in passive vaccination," *Vaccine*, Jan. 2013, vol. 31 (4), pp. 626-631 [abstract only—1 page].

Australian IP Office, Examination Report No. 1 for Standard Patent Application for Application No. 2016244295, dated Aug. 18, 2017, 4 pages.

Boyd S.D., et al., "Individual Variation in the Germline Ig Gene Repertoire Inferred from Variable Region Gene Rearrangements," *The Journal of Immunology*, Jun. 2010, vol. 184 (12), pp. 6986-6992.

Bradley A., Declarations of Allan Bradley (Tanamachi/Grosveld), as submitted in U.S. Appl. No. 13/416,684, 5 pages.

Bradley A., Declaration of Allan Bradley (commercial success), with exhibits, as submitted in U.S. Appl. No. 13/416,684, dated Feb. 12, 2015, 15 pages.

Bradley A., Declaration of Allan Bradley (mouse strain), with exhibits, as submitted in U.S. Appl. No. 13/416,684, dated Feb. 12, 2015, 68 pages.

Brüggemann M., et al., "Selection Strategies III: Transgenic Mice," in *Handbook of Therapeutic Antibodies—Technologies, Emerging Developments and Approved Therapeutics*, 2010, Chapter 4, pp. 69-91.

Camboni M., et al., "Active and passive immunization strategies based on the SDPM1 peptide demonstrate pre-clinical efficacy in the APPswePSEN1dE9 mouse model for Alzheimer's disease," *Neurobiology of Disease*, Feb. 2014, vol. 52, pp. 31-43 [abstract only—2 pages].

Davis C.G., et al., "Antibody Engineering, Methods and Protocols, *Methods in Mol. Biol.*, Chapter 10: Production of Human Antibodies from Transgenic Mice," 2004, pp. 191-200.

Delves P.J., et al., "Antibodies," Chapter 3, *Roitt's Essential Immunology*, Eleventh edition, 2006, pp. 37-60.

Dörner T., et al., "Delineation of Selective Influences Shaping the Mutated Expressed Human Ig Heavy Chain Repertoire," *The Journal of Immunology*, Mar. 1998, vol. 160 (6), pp. 2831-2841.

Dörner T., et al., "Analysis of the targeting of the hypermutational machinery and the impact of subsequent selection on the distribution of nucleotide changes in human $V_H DJ_H$ rearrangements," *Immunologic Reviews*, Apr. 1998, vol. 162 (1), pp. 161-171.

Dörner T., et al., "Somatic hypermutation of human immunoglobulin heavy chain genes: targeting of RGYW motifs on both DNA strands," *European Journal of Immunology*, 1998, vol. 28, pp. 3384-3396.

Dübel S., et al., "Therapeutic Antibodies—From Past to Future," in *Handbook of Therapeutic Antibodies—Technologies, Emerging Developments and Approved Therapeutics*, 2010, Chapter 1 (excerpt: pp. 3-5).

European Patent Office, Examination Report for Application No. 15188522.5, dated Aug. 11, 2017, 6 pages.

European Patent Office, Extended European Search Report for Application No. 17174426.1, dated Sep. 14, 2017, 10 pages.

European Patent Office, Opposition against EP2604110 Animal Models and Therapeutic Molecules in the name of Kymab Limited pertaining to Application No. 12194777.0, dated Aug. 28, 2017, 73 pages.

European Patent Office, Opposition against EP2758535 Antibodies, Variable Domains and Chains Tailored for Human Use in the name of Kymab Limited pertaining to Application No. 12772122.3, dated Aug. 9, 2017, 75 pages.

Genbank, "*Homo sapiens* partial IGHJ6 gene for immunoglobulin heavy joining 6, exon 1, allele 4," AJ879487.1, dated Jul. 26, 2016, 1 page.

Giudicelli V., et al., "IMGT/GENE-DB: a comprehensive database for human and mouse immunoglobulin and T cell receptor genes," *Nucleic Acids Research*, 2005, vol. 33, pp. D256-D261.

He Y., et al., "Efficient Isolation of Novel Human Monoclonal Antibodies with Neutralizing Activity Against HIV-1 from Transgenic Mice Expressing Human Ig Loci," *The Journal of Immunology*, 2002, vol. 169, pp. 595-605.

HGNC (HUGO Gene Nomenclature Committee), "Gene Family: Immunoglobulin Heavy Locus at 14q32.33 (IGH)," 4 pages. [retrieved on Jul. 31, 2017 at http://www.genenames.ora/cgi-bin/genefamilies/set/349].

Hülseweh B., et al., "Human-like antibodies neutralizing Western equine encephalitis virus," *mAbs*, May/Jun. 2014, vol. 6 (3), pp. 718-727.

Imbimbo B.P., et al., "Solanezumab for the treatment of mild-to-moderate Alzheimer's disease," *Expert Review of Clinical Immunology*, Feb. 2012, vol. 8 (2), pp. 135-149 [abstract only—1 page].

IMGT, *the International ImMunoGeneTics Information system database*, IMGT/GENE-DB entry for *Homo sapiens* IGHD3-9, 2007, 2 pages.

IMGT, *the International ImMunoGeneTics Information system database*, "Alignment of alleles: Human IGHJ6," dated Jun. 29, 2011, 1 page.

IMGT, *the International ImMunoGeneTics Information system database*, IMGT/GENE-DB entry for *Homo sapiens* IGHJ6, dated Jul. 26, 2017, version 3.1.17, 2 pages.

IMGT, *the International ImMunoGeneTics Information system database*, "IMGT/GENE-DB reference sequences," Nucleotide sequences of the four human IGHJ6 alleles, dated Jul. 26, 2017, version 3.1.17, 1 page.

IMGT, *the International ImMunoGeneTics Information system database*, "IMGT/GENE-DB reference sequences," Amino acid sequences of the four human IGHJ6 alleles, dated Jul. 26, 2017, version 3.1.17, 7 pages.

Jackson S.M., et al., "Human B Cell Subsets," *Advances in Immunology*, Chapter 5, 2008, vol. 98, pp. 151-224.

Kim S.J., et al., "Antibody Engineering for the Development of Therapeutic Antibodies," *Mol. Cells*, 2005, vol. 20 (1), pp. 17-29.

Kriangkum J., et al., "Molecular Characterization of Waldenstrom's Macroglobulinemia Reveals Frequent Occurrence of Two B-Cell Clones Having Distinct IgH VDJ Sequences," *Clinical Cancer Research*, Apr. 2007, vol. 13 (7), pp. 2005-2013.

Lee E., et al., "Use of IGHJ and IGHD gene mutations in analysis of immunoglobulin sequences for the prognosis of chronic lymphocytic leukemia," *Leukemia Research*, 2007, vol. 31, pp. 1247-1252.

Lonberg N., et al., "Human Antibodies from Transgenic Mice," *Intern. Rev. Immunol.*, 1995, vol. 13, pp. 65-93.

Lonberg N., "Human Monoclonal Antibodies from Transgenic Mice," *Therapeutic Antibodies. Handbook of Experimental Pharmacology*, 2008, pp. 69-97.

Mårtensson I.L., et al., "The pre-B-cell receptor," *Current Opinion in Immunology*, 2007, vol. 19, pp. 137-142.

O'Dea, T.P., Attorney for Applicant, Third-Party Pre-Issuance Submission Under 37 CFR Sec. 1.290 in U.S. Appl. No. 15/383,342, filed Aug. 7, 2017, 32 pages.

Potter K.N., et al., "Features of the overexpressed V1-69 genes in the unmutated subset of chronic lymphocytic leukemia are distinct from those in the healthy elderly repertoire," *Blood*, Apr. 2003, vol. 101 (8), pp. 3082-3084.

Prak E.T.L, et al., "B cell receptor editing in tolerance and autoimmunity," *Annals of the New York Academy of Sciences*, Jan. 2011, vol. 1217, pp. 96-121.

(56) References Cited

OTHER PUBLICATIONS

Raaphorst F.M., et al., "Human Ig heavy chain CDR3 regions in adult bone marrow pre-B cells display an adult phenotype of diversity: evidence for structural selection of $D_H$ amino acid sequences," *International Immunology*, Oct. 1997, vol. 9 (10), pp. 1503-1515.

Ricker M., European Patent Attorney, Opposition against EP2758535 in the name of Kymab Limited Statement of Facts and Arguments pertaining to Application No. 12772122.3, dated Aug. 9, 2017, 42 pages.

Rudolf M.P., et al., "Molecular basis for nonanaphylactogenicity of a monoclonal anti-IgE antibody," *Journal of Immunology*, Jul. 2010, vol. 165 (2), pp. 813-819.

Ruiz M., et al., "The Human Immunoglobulin Heavy Diversity (IGHD) and Joining (IGHJ) Segments," *Experimental and Clinical Immunogenetics*, 1999, vol. 16, pp. 173-184.

Russell N.D., et al., "Production of Protective Human Antipneumococcal Antibodies by Transgenic Mice with Human Immunoglobulin Loci," *Infection and Immunity*, Apr. 2000, vol. 68 (4), pp. 1820-1826.

Shore D.E., Attorney for Applicant, Third-Party Pre-Issuance Submission Under 37 CFR Sec. 1.290 in U.S. Appl. No. 15/088,805, filed Nov. 17, 2017, 44 pages.

Siman-Tov D.D., et al., "Differentiation of a passive vaccine and the humoral immune response toward infection: Analysis of phage displayed peptides," *Vaccine*, Jan. 2006, vol. 24, pp. 607-612.

Taylor L.D., et al., "A transgenic mouse that expresses a diversity of human sequence heavy and light chain immunoglobulins," *Nucleic Acids Research*, 1992, vol. 20 (23), pp. 6287-6295.

Table S1 (pdf version of the Excel supplementary information available online), 60 pages.

Table S2 (pdf version of the Excel supplementary information available online), 14 pages.

U.S. Appl. No. 13/886,511, filed May 3, 2013.
U.S. Appl. No. 14/226,706, filed Mar. 26, 2014.
U.S. Appl. No. 14/498,685, filed Sep. 26, 2014.
U.S. Appl. No. 14/543,359, filed Nov. 17, 2014.
U.S. Appl. No. 15/656,897, filed Jul. 21, 2017.
U.S. Appl. No. 15/948,709, filed Apr. 9, 2018.

1st International MUGEN Conference on Animal Models for Human Immunological Disease, Sep. 10-13, 2006—Athens Greece (Scientific Programme & Presentations), 4 pages.

An Z., Therapeutic Monoclonal Antibodies from Bench to Clinic, 2009, 4 pages.

Australian IP Office, Notification of material filed by a third-party for Application No. 2012311288 in the name of Kymab Ltd., Applicant, dated Nov. 20, 2017, 14 pages.

Bentham A., Ja Kemp, European Patent Attorney, Statement of Fact and Arguments in Support of Opposition against EP2527557 in the name of Kymab Limited pertaining to Application No. 12171793.8, dated Jan. 11, 2017, 32 pages.

Bentham A., Ja Kemp, European Patent Attorney, Final Written Submissions for Application No. 12171793.8, dated May 17, 2018, 20 pages.

Bradshaw, et al., "*Handbook of Cell Signalling*," 2010, Chapter 5, p. 33 (excerpt).

Brüggemann M., "The Preparation of Human Antibodies from Mice Harbouring Human Immunoglobulin Loci," *Transgenic Animals. Generation and Use*, 1997, Chapter 58, Part IV, Section A, pp. 397-402 (including cover and copyright pages).

Burton D.R., et al., "Antibody vs. HIV in a clash of evolutionary titans," *Proceedings of the National Academy of Sciences of the U.S.A*, Oct. 2005, vol. 102 (42), pp. 14943-14948.

Calame K., et al., "Regulation of immunoglobulin gene transcription," *Immunoglobulin Genes*, 2nd edition, Chapter 18, 1995, pp. 397-422.

Collis A.V.J., et al., "Analysis of the Antigen Combining Site: Correlations Between Length and Sequence Composition of the Hypervariable Loops and the Nature of the Antigen," *Journal of Molecular Biology*, 2003, vol. 325, pp. 337-354.

European Patent Office, Communication pursuant to Rule 114(2) EPC regarding 17196235.0, dated Dec. 4, 2018, 23 pages.

European Patent Office, Examination Report for Application No. 13723933.1, dated Jan. 17, 2018, 6 pages.

European Patent Office, Examination Report for Application No. 16151215.7, dated Jan. 23, 2017, 5 pages.

European Patent Office, Extended European Search Report for Application No. 17196214.5, dated Jan. 2, 2018, 13 pages.

European Patent Office, Extended European Search Report for Application No. 18153171.6, dated Jun. 28, 2018, 15 pages.

European Patent Office, Notice of Opposition to a European Patent EP2517557 in the name of Kymab Limited pertaining to Application No. 12171793.8, dated Jan. 11, 2017, 7 pages.

European Patent Office, Opposition against EP 2798950 Animal Models and Therapeutic Molecules in the name of Kymab Limited pertaining to Application No. 14170196.1, dated Jan. 18, 2018, 33 pages.

Evans M.J., Declaration of Martin J. Evans with appendices, dated Dec. 23, 2016, 99 pages.

Frigerio B., et al., "Antibody Engineering as Opportunity for Selection and Organization of Anti-HIV Therapeutic Agents," *The Open Autoimmunity Journal*, 2010, vol. 2, pp. 127-138.

Genbank, "*Homo sapiens* DNA, immunoglobulin heavy-chain variable region, complete sequence, 5 of 5," AB019441.1, dated Jun. 18, 2018, 36 pages.

Goding J.W., "Differences Between Conventional and Monoclonal Serology," *Monoclonal Antibodies: Principles and Practice, Production and Application of Monoclonal Antibodies in Cell Biology, Biochemistry and Immunology*, 1996, Third Edition, Section 7.3, pp. 129-130.

Grund M., European Patent Attorney, Grund Intellectual Property Group, Third-Party Observations according to Article 115 EPC regarding 12171793.8, dated Oct. 10, 2013, 10 pages.

Grund M., European Patent Attorney, Grund Intellectual Property Group, Third-Party Observations according to Article 115 EPC regarding 12171793.8, dated Mar. 17, 2015, 4 pages.

Grund M., European Patent Attorney, Grund Intellectual Property Group, Third-Party Observations according to Article 115 EPC regarding 12171793.8, dated May 22, 2015, 5 pages.

Grund M., European Patent Attorney, Grund Intellectual Property Group, Third-Party Observations according to Article 115 EPC regarding 14781635.9, dated May 18, 2018, 4 pages.

Grund M., European Patent Attorney, Grund Intellectual Property Group, Third-Party Observations according to Article 115 EPC regarding 17174426.1, dated Jun. 27, 2018, 7 pages.

Grund M., European Patent Attorney, Grund Intellectual Property Group, Third-Party Observations according to Article 115 EPC regarding 17196235.0, dated Nov. 27, 2018, 22 pages.

Ichihara Y., et al., "Organization of human immunoglobulin heavy chain diversity gene loci," *The EMBO Journal*, 1988, vol. 7, No. 13, pp. 4141-4150.

Janeway C.A. et al., "Structure of the Antibody Molecule and the Immunoglobulin Genes," excerpts from *Immunobiology: The Immune System in Health and Disease*, 4th Edition, 1999, 4 pages.

Kelley S.K., et al., "Preclinical pharmacokinetics, pharmacodynamics, and activity of a humanized anti-CD40 antibody (SGN-40) in rodents and non-human primates," *British Journal of Pharmacology*, 2006, vol. 148, pp. 1116-1123.

Kumar R., et al., "A novel strategy for efficient production of anti-V3 human scFvs against HIV-1 clade C," *BMC Biotechnology*, Nov. 2012, vol. 12 (87), 15 pages.

Lee E-Chiang, "Declaration of E-Chiang Lee," Jun. 13, 2016, 8 pages.

Li Z., et al., "The generation of antibody diversity through somatic hypermutation and class switch recombination," *Genes & Development*, 2004, vol. 18, pp. 1-11.

Lonberg N., et al., "Antigen-specific human antibodies from mice comprising four distinct genetic modifications," *Nature*, Apr. 1994, vol. 368, pp. 856-859.

Maconald L., Declaration of Lynne E. Macdonald, dated May 16, 2018, including Annex 1, 10 pages.

(56) References Cited

OTHER PUBLICATIONS

Meier I.D., et al., "Short DNA sequences inserted for gene targeting can accidentally interfere with off-target gene expression," The FASEB Journal, Research Communication, Jun. 2010, vol. 24, pp. 1714-1724.
Missirlis P.I., et al., "A high-throughout screen identifying sequence and promiscuity characteristics of the loxP spacer region in Cre-mediated recombination," BMC Genomics, Apr. 2006, vol. 7(73), 13 pages.
Muramatsu M., et al., "Specific Expression of Activation-induced Cytidine Deaminase (AID), a Novel Member of the RNA-editing Deaminase Family in Germinal Center B Cells," 1999, The Journal of Biological Chemistry, vol. 274 (26), pp. 18470-18476.
Newcombe C., et al., "Antibody production: Polyclonal-derived biotherapeutics," Journal of Chromatography B, 2007 vol. 848, pp. 2-7.
Okada A., et al., "The variable region gene assembly mechanism," Immunoglobulin Genes, 2$^{nd}$ edition, Chapter 10, 1995, pp. 205-234.
Pinaud E., et al., "The IgH Locus 3' Regulatory Region: Pulling the Strings from Behind," Advances in Immunology, Chapter 2, 2011, vol. 11, pp. 27-70.
Shore D.E., Attorney for Applicant, Third-Party Pre-Issuance Submission Under 37 CFR Sec. 1.290 in U.S. Appl. No. 15/656,897, filed May 4, 2018, 55 pages.
Shore D.E., Attorney for Applicant, Third-Party Pre-Issuance Submission Under 37 CFR Sec. 1.290 in U.S. Appl. No. 15/690,183, filed Feb. 28, 2018, 60 pages.
Shore D.E., Attorney for Applicant, Third-Party Pre-Issuance Submission Under 37 CFR Sec. 1.290 in U.S. Appl. No. 15/786,281, filed Jun. 27, 2018, 63 pages.
Shore D.E., Attorney for Applicant, Third-Party Pre-Issuance Submission Under 37 CFR Sec. 1.290 in U.S. Appl. No. 15/786,281, filed Jun. 27, 2018 (Second Submission), 62 pages.
Shore D.E., Attorney for Applicant, Third-Party Pre-Issuance Submission Under 37 CFR Sec. 1.290 in U.S. Appl. No. 15/786,281, filed Jun. 27, 2018 (Third Submission), 53 pages.
Shore D.E., Attorney for Applicant, Third-Party Pre-Issuance Submission Under 37 CFR Sec. 1.290 in U.S. Appl. No. 15/948,709, filed Jan. 10, 2019, 43 pages.
Shore D.E., Attorney for Applicant, Third-Party Pre-Issuance Submission Under 37 CFR Sec. 1.290 in U.S. Appl. No. 15/955,216, dated Feb. 5, 2019, 64 pages.
Stephen R., Olswang LLP, Response to Third-Party Observations for Application No. 12171793.8, as filed with the European Patent Office on Apr. 17, 2015, 3 pages.
Stephen R., Olswang LLP, Response to Summons and Preliminary Opinion pertaining to Patent No. EP 2517557 for Application No. 12171793.8, as filed with the European Patent Office on May 17, 2018, 4 pages.
Stephen R., Olswang LLP, Response to Opposition (as filed by Regeneron Pharmaceuticals, Inc. on Jan. 11, 2017) for Application No. 12171793.8, as filed with the European Patent Office on Jun. 23, 2017, 8 pages.
Stephen R., Olswang LLP, Response to Opposition in the name of Kymab Limited filed against EP2758535B1, dated Mar. 22, 2018, 26 pages.
Sullivan P.M., et al., "Targeted Replacement of the Mouse Apolipoprotein E Gene with the Common Human APOE3 Allele Enhances Diet-induced Hypercholesterolemia and Atherosclerosis" The Journal of Biological Chemistry, 1997, vol. 272, No. 2, pp. 17972-17980.
Zwick M.B., et al., "The Long Third Complementarity-Determining Region of the Heavy Chain Is Important in the Activity of the Broadly Neutralizing Anti-Human Immunodeficiency Virus Type 1 Antibody 2F5," Journal of Virology, Mar. 2004, vol. 78 (6), pp. 3155-3161.
[No Author Listed] IMGT Repertoire (IG and TR), Gene table: human (Homo sapiens) IGHD, created Apr. 18, 1997, last updated Jan. 17, 2020; retrieved from the internet under: http://www.imgt.org/IMGTrepertoire/. 3 pages.

Balbás P., et al., "Chromosomal Editing in Escherichia coli. Vectors for DNA Integration and Excision," Molecular Biotechnology, Sep. 2001, vol. 19(1), pp. 1-12.
Bradley A., et al., "Modifying the Mouse: Design and Desire," Biotechnology, May 1992, vol. 10(5), pp. 534-539.
Carpenter A.J., et al., "Construction, Characterization, and Complementation of a Conditional-Lethal DNA Topoisomerase IIalpha Mutant Human Cell Line," Molecular Biology of the Cell, Dec. 2004, vol. 15(12), pp. 5700-5711.
Deonarain R., et al., "Impaired Antiviral Response and Alpha/Beta Interferon Induction in Mice Lacking Beta Interferon," Journal of Virology, Apr. 2000, vol. 74(4), pp. 3404-3409.
European Patent Office, Examination Report for Application No. 13723933.1, dated Mar. 3, 2020, 7 pages.
Gutterson N.I., et al., "Replacement and Amplification of Bacterial Genes With Sequences Altered in Vitro," Proc. Natl. Acad. Sci. USA, Aug. 1983, vol. 80(16), pp. 4894-4898.
Hasty P., et al., "Introduction of a Subtle Mutation Into the Hox-2.6 Locus in Embryonic Stem Cells," Nature, Mar. 1991, vol. 350(6315), pp. 243-246.
Itzhaki J.E., et al., "Targeted Breakage of a Human Chromosome Mediated by Cloned Human Telomeric DNA," Nature Genetics, Dec. 1992, vol. 2(4), pp. 283-287.
Itzhaki J.E., et al., "Construction by Gene Targeting in Human Cells of a "Conditional" CDC2 Mutant That Rereplicates Its DNA,", Nature Genetics, Mar. 1997, vol. 15(3), pp. 258-265.
Japanese Patent Office, Pre-Appeal Report—Application No. 2017-021028—Appeal No. 2020-000300, mailed Mar. 17, 2020, together with English translation, 13 pages.
Koller B.H., et al. "Altering Genes in Animals by Gene Targeting," Annu. Rev. Immunol., 1992, vol. 10, pp. 705-730.
Kuzminov A., "DNA Replication Meets Genetic Exchange: Chromosomal Damage and Its Repair by Homologous Recombination," Proc. Natl. Acad. Sci. USA, Jul. 2001, vol. 98(15), pp. 8461-8468.
Law M., et al., "Antibodies Against Viruses: Passive and Active Immunization," Current Opinion in Immunology, Aug. 2008, vol. 20(4), pp. 486-492.
Logtenberg T., "Antibody Cocktails: Next-Generation Biopharmaceuticals With Improved Potency," Trends in Biotechnology, Sep. 2007, vol. 25(9), pp. 390-394.
Ogle, Ph.D., J.M., European Patent Attorney of Hoffman Eitle, Reply to Statement of Grounds of Appeal In re Opposition against EP2758535 dated Feb. 26, 2020, 80 pages.
Ogle, Ph.D., J.M., European Patent Attorney of Hoffman Eitle, Written Submission in preparation to/during oral proceedings In re Opposition against EP2792236 dated Apr. 17, 2020, 14 pages.
Porter A., Resume Imperial College London, retrieved from the Internet under https://www.imperial.ac.uk/people/andy.porter on May 21, 2020. 2 pages.
Porter A.C., et al., "Role of the B Subunit of the Escherichia coli Proton-Translocating ATPase. A Mutagenic Analysis," Journal of Biological Chemistry, Jul. 1985, vol. 260(13), pp. 8182-8187.
Porter, Andrew, First Declaration, dated Oct. 11, 2018, 31 pages (Evidence in Support of Opposition thereto by Regeneron Pharmaceuticals, Inc. for Application No. 14176740.0).
Porter, Andrew, Second Decarlaration, dated Apr. 14, 2020, 8 pages (Evidence in Support of Opposition thereto by Regeneron Pharmaceuticals, Inc. for Application No. 14176740.0).
Porteus M., "Using Homologous Recombination to Manipulate the Genome of Human Somatic Cells," Biotechnology and Genetic Engineering Reviews, 2007, vol. 24, pp. 195-212.
Rojas G., et al., "Efficient Construction of a Highly Useful Phage-Displayed Human Antibody Repertoire", Biochemical and Biophysical Research Communications, Nov. 2005, vol. 336(4), pp. 1207-1213.
Rothstein R., "Targeting, Disruption, Replacement, and Allele Rescue: Integrative DNA Transformation in Yeast," Methods in Enzymology, 1991, vol. 194, pp. 281-301.
Rubinstein M., et al., "Introduction of a Point Mutation Into the Mouse Genome by Homologous Recombination in Embryonic Stem Cells Using a Replacement Type Vector With a Selectable Marker," Nucleic Acids Research, Jun. 1993, vol. 21(11), pp. 2613-2617.

(56) References Cited

OTHER PUBLICATIONS

Scherer S., et al., "Replacement of Chromosome Segments With Altered DNA Sequences Constructed in Vitro," Proc. Natl. Acad. Sci. USA, Oct. 1979, vol. 7 6(10), pp. 4951-4955.
Shaw, D.J., Ja Kemp, European Patent Attorney, Response to Summons to attend Oral Proceedings In re Opposition against EP2757875 in the name of Kymab Limited pertaining to Application No. 12762378.8, dated Apr. 16, 2020, 21 pages.
Stephen R., Olswang LLP, Response to Appeal in the name of Kymab Limited filed against EP2798950, dated Mar. 12, 2020, 23 pages.
Stephen R., Olswang LLP, Response to Grounds of Appeal in the name of Kymab Limited filed against EP2517557, dated Apr. 29, 2019, 18 pages.
Valancius V., et al., "Testing an "In-Out" Targeting Procedure for Making Subtle Genomic Modifications in Mouse Embryonic Stem Cells," Molecular and Cellular Biology, Mar. 1991, vol. 11(3), pp. 1402-1408.
Anderson P.S. et al., "Extensive restrictions in the VH sequence usage of the human antibody response against the Rhesus D Antigen," Molecular Immunology, Jan. 2007, vol. 44, pp. 412-422.
Bostrom, J. et al., Variants of the Antibody Herceptin That Interact with HER2 and VEGF at the Antigen Binding Site, Science, Mar. 2009, vol. 323, pp. 1610-1614.
Canadian IP Office, Office Action for Application No. 2,857,569, dated Jan. 14, 2019, 5 pages.
Canadian IP Office, Protest and Submission of Prior Art, Application No. 2,802,591, dated Nov. 13, 2019, 18 pages.
Chapal, N. et al., "Thyroid Peroxidase Autoantibodies Obtained from Random Single Chain Fv Libraries Contain The Same Heavy/Light Chain Combinations as Occur in Vivo," Endocrinology, 2001, vol. 142(11), pp. 4710-4750.
Dewitt, William S., et al., A Public Database of Memory and Naive B-Cell Receptor Sequences, PLOS ONE, Aug. 2016, 18 pages.
European Patent Office, Decision rejecting the opposition (Art. 101(2) EPC) for Application No. 10 010 741.6, dated Apr. 25, 2018, 44 pages.
European Patent Office, Examination Report for Application No. 13723933.1, dated Mar. 18, 2020, 6 pages.
European Patent Office, Irmgard Scheffzyk, Authorized officer, International Search Report for Application No. PCT/EP2018/068309, dated Jan. 15, 2019, 14 pages, together with the Written Opinion of the International Searching Authority.
European Patent Office, Examination Report for Application No. 12778780.2, dated Oct. 14, 2016, 3 pages.
European Patent Office, Examination Report for Application No. 17174426.1, dated Feb. 5, 2020 (with Annex), 11 pages.
Ewert, H.T. et al., "Biophysical Properties of human antibody variable domains," J. Mol. Biol., Jan. 2003, vol. 325(3), pp. 531-553.
GENBANK "Immunoglobulin Heavy Chain Variable Region (*Homo sapiens*)," Accession No. BAA75060, dated Jul. 2, 2008, 1 page.
Goodnow, Christopher Carl, Declaration, dated Aug. 29, 2017, 7 pages (Evidence in Support of Opposition thereto by Regeneron Pharmaceuticals, Inc. for Application No. 2011266843).
Goodnow, Christopher Carl, Declaration, dated Jan. 29, 2016, 21 pages (Evidence in Support of Opposition thereto by Regeneron Pharmaceuticals, Inc. for Application No. 2011266843).
Goodnow, Christopher Carl, Second Declaration, dated Jul. 4, 2016, 9 pages (Evidence in Support of Opposition thereto by Regeneron Pharmaceuticals, Inc. for Application No. 2011266843).
Grund M., European Patent Attorney, Grund Intellectual Property Group, Third-Party Observations according to Article 115 EPC regarding 15188522.5, dated Mar. 13, 2019, 3 pages.
Grund M., European Patent Attorney, Grund Intellectual Property Group, Third-Party Observations according to Article 115 EPC regarding 17174426.1, dated Feb. 11, 2019, 5 pages.
Ignatovich O. et al., "The creation of diversity in the human immunoglobulin V(lambda) repertoire," Journal of Molecular Biology, vol. 268, p. 69-77 (Apr. 1997).
Ignatovich O., et al., "Dominance of intrinsic genetic factors in shaping the human immunoglobulin Vλ repertoire", Journal of Molecular Biology, Nov. 1999, vol. 294, pp. 457-465.
Nicholson I.C., et al., "Antibody Repertoires of Four- and Five-Feature Translocus Mice Carrying Human mmunoglobulin Heavy Chain and ☐ and ☐ Light Chain Yeast Artificial Chromosomes," Journal of Immunology, 1999, vol. 163(12), pp. 6898-6906.
Ogle, Ph.D., J.M., European Patent Attorney of Hoffman Eitle, Statement of Grounds of Appeal (Corrected version) In re Opposition against EP2758535 dated Feb. 26, 2020, 83 pages.
Ogle, Ph.D., J.M., European Patent Attorney of Hoffman Eitle, Statement of Grounds of Appeal In re Opposition against EP2758535 dated Feb. 26, 2020, 80 pages.
Pavlicek A., et al., "Ancient Transposable Elements, Processed Pseudogenes, and Endogenous Retroviruses," Genomic Disorders, Chapter 4, 2006, pp. 57-72.
Ren L., et al., "Silencing of the immunoglobulin heavy chain locus by removal of all eight constant-region genes in a 200-kb region," Genomics, Aug. 2004, vol. 84, pp. 686-695.
Richardson, C. et al., "Molecular Basis of 9G4 B cell Autoreactivity in Human Systemic Lupus Erythematosus," The Journal of Immunology, vol. 191(10), pp. 4926-4939 (Nov. 2013).
Rourke J., Declaration of Jeffrey Rourke, Registered Patent Attorney for Regeneron Pharmaceuticals, Inc.—In the matter of Patent Acceptance 2011266843 in the Name of Kymab Limited and In the Matter of Opposition thereto by Regeneron Pharmaceuticals, Inc., dated Jan. 29, 2016, 5 pages.
Sleeman, Mark W., First Declaration, dated Jan. 29, 2016, 24 pages (Evidence in Support of Opposition thereto by Regeneron Pharmaceuticals, Inc. for Application No. 2011266843).
Sleeman, Mark W., Second Declaration, dated Jul. 4, 2016, 7 pages (Evidence in Support of Opposition thereto by Regeneron Pharmaceuticals, Inc. for Application No. 2011266843).
Sleeman, Mark W., Third Declaration, dated Jan. 5, 2018, 9 pages (Evidence in Support of Opposition thereto by Regeneron Pharmaceuticals, Inc. for Application No. 2011266843).
Stephen R., Olswang LLP, Patentee's Response to Third-Party Observations dated Aug. 10, 2015 and Examination Report dated Oct. 23, 2015 to the European Patent Office with corresponding claims for Application No. 14176740.0, dated Apr. 23, 2016, 13 pages.
Stephen R., Olswang LLP, Response to Examination Report dated Jun. 6, 2016 for Application No. 14176740.0, as filed with the European Patent Office on Oct. 10, 2016, 4 pages.
Stephen R., Olswang LLP, Response to Examination Report dated Nov. 10, 2016 to the European Patent Office with corresponding claims for Application No. 14176740.0 on Mar. 17, 2017, 13 pages.
Stephen R., Olswang LLP, Response to Search Report dated Oct. 15, 2014 for Application No. 14176740.0, as filed with the European Patent Office on May 12, 2015, 4 pages.
Van Dijk, Marcus, Third Declaration, dated Mar. 28, 2018, 6 pages (Evidence in Support of Opposition thereto by Regeneron Pharmaceuticals, Inc. for Application No. 2011266843).
European Patent Office, Notice of Opposition to a European Patent EP2758534 in the name of Kymab Limited pertaining to Application No. 12762377.5, dated Apr. 29, 2020, 6 pages.
Betz A.G., et al., "Elements Regulating Somatic Hypermutation of an Immunoglobulin κ Gene: Critical Role for the ntron Enhancer/Matrix Attachment Region," Cell, Apr. 1994, vol. 77, pp. 239-248.
Brazilian Patent Office, Lucia Aparecida Mendonca, Preliminary Office Action for Application No. BR112012000536-7, dated Jul. 7, 2010, 12 pages.
Brazilian Patent Office, Lucia Aparecida Mendonca, Preliminary Office Action (English translation) for Application No. BR112012000536-7, dated Jul. 7, 2010, 1 page.
Chinese Patent Office, First Office Action for Application No. 201610821299.6, dated Jun. 23, 2020, 15 pages.
Chinese Patent Office, First Office Action (English translation) for Application No. 201610821299.6, dated Jun. 23, 2020, 19 pages.
Dafhnis-Calas F., et al., "Iterative in vivo assembly of large and complex transgenes by combining the activities of ϕC31 integrase and Cre recombinase," Nucleic Acids Research, Dec. 2005, vol. 33(22), pp. e189-1-e189-14.

(56) References Cited

OTHER PUBLICATIONS

Defranco, Anthony L., Ph.D., Declaration, Interparties Review AIA No. IPR2019-01578 U.S. Pat. No. 9,505,827), dated Sep. 9, 2019, 121 pages.
European Patent Office, Notice of Opposition to a European Patent EP2758534 in the name of Kymab Limited pertaining to Application No. 12762377.5, dated May 4, 2020, 6 pages.
Friedrich G., Statement of Dr. Glenn Friedrich, dated Mar. 31, 2014, 9 pages.
Friedrich G., Statement of Dr. Glenn Friedrich, dated Oct. 16, 2014, 9 pages.
Gibson D.G., et al., "Complete Chemical Synthesis, Assembly, and Cloning of a Mycoplasma genitalium Genome," Science, Feb. 2008, vol. 319, pp. 1215-1220.
Gondo Y., et al., Next-generation gene targeting in the mouse for functional genomics,nBMB reports, Jul. 2009, vol. 42(6), pp. 315-323.
Hasty P., et al., "Gene targeting, principles, and practice in mammalian cells," Gene Targeting, A Practical Approach, 2nd Edition, Oxford, 2000, pp. 1-175, including cover pages (XP055500641).
IMGT, the International ImMunoGeneTics Information system database, IMGT/GENE-DB entry for Homo sapiens IGHJ6, dated Jul. 26, 2017, version 3.1.17, 4 pages.
International Bureau of WIPO, Third-Party Observations regarding Application No. PCT/EP2018/068309, dated Aug. 14, 2019, 6 pages.
Japanese Patent Office, Notice of Reasons for Rejection—Application No. 2017-021028, dated Dec. 21, 2018, together with English translation, 11 pages.
Japanese Patent Office, Decision of Rejection—Application No. 2017-021028, dated Sep. 9, 2019, together with English translation, 9 pages.
Japanese Patent Office, Notice of Reasons for Rejection—Application No. 2016-548441, dated Aug. 5, 2019, together with English translation, 12 pages.
Japanese Patent Office, Notice of Reasons for Rejection—Application No. 2018-088749, dated May 27, 2019, together with English translation, 11 pages.
Japanese Patent Office, Notice of Reasons for Rejection—Application No. 2017-017360, dated Mar. 19, 2018, together with English translation, 7 pages.
Kotzamanis G., et al., "Construction of human artificial chromosome vectors by recombineering," Gene, 2005, vol. 351, pp. 29-38.
Lerner, R.A., "Rare antibodies from combinatorial libraries suggests an S.O.S. component of the human mmunological repertoire," Mol. BioSyst., Apr. 2011, vol. 7(4), pp. 1004-1012.
Liu X., et al., "Trisomy Eight in ES Cells Is a Common Potential Problem in Gene Targeting and Interferes With Germ Line Transmission," Developmental Dynamics, vol. 209, 1997, pp. 85-91.
Mitra R., et al., "PiggyBac can bypass DNA synthesis during cut and paste transposition," The EMBO Journal, 2008, vol. 27, pp. 1097-1109.
Morrison S.L., et al. "Vectors and Approaches for the Eukaryotic Expression of Antibodies and Antibody Fusion Proteins," Antibody Engineering, 2nd Edition, Chapter 9, 1995, 31 pages.
Muyrers J.P.P., et al., "Techniques: Recombinogenic engineering—new options for cloning and manipulating DNA," Trends in Biochemical Sciences, May 2001, vol. 26(5), pp. 325-331.
Odegard V.H., et al., "Targeting of somatic hypermutation," Nature Reviews—Immunology, Aug. 2006, vol. 6, pp. 573-583.
Ogle, Ph.D., J.M., European Patent Attorney of Hoffman Eitle, Opposition to EP 2 792 236 (Application No. 14176740.0) dated Feb. 28, 2020, 56 pages.
Ogle, Ph.D., J.M., European Patent Attorney of Hoffman Eitle, Reply to Statement of Grounds of Appeal (Corrected version) In re Opposition against EP2758535 dated Feb. 26, 2020, 83 pages.
Perera, W.S., et al., "Comparison between hybridoma and Fab/phage anti-RhD: Their V gene usage and pairings," Disease Markers, 2000, vol. 16, pp. 15-19.
Richardson, C. et al., "Molecular Basis of 9G4 B cell Autoreactivity in Human Systemic Lupus Erythematosus," The Journal of Immunology, Nov. 2013, vol. 191(10), pp. 4926-4939.
Sabouri, Z., et al., "Redemption of autoantibodies on anergic B cells by variable-region glycosylation and mutation away from self-reactivity," Proceedings of the National Academy of Sciences of the United States of America, Early Edition, May 2014, pp. E2567-E2575.
Schaller, M. et al., "The splenic autoimmune response to ADAMTS13 in thrombotic thrombocytopenic purpura contains recurrent antigen-binding CDR3 motifs," Blood, Nov. 2014, vol. 124(23), pp. 3469-3479.
Schonewald, Stephanie L., Choate Hall & Stewart LLP, Petition for Inter Parties Review—AIA Review No. IPR2019-01577, filed Sep. 20, 2019, 86 pages.
Schonewald, Stephanie L., Choate Hall & Stewart LLP, Petition for Inter Parties Review—AIA Review No. IPR2019-01578, filed Sep. 20, 2019, 83 pages.
Schonewald, Stephanie L., Choate Hall & Stewart LLP, Petition for Inter Parties Review—AIA Review No. IPR2019-01579, filed Sep. 20, 2019, 84 pages.
Schonewald, Stephanie L., Choate Hall & Stewart LLP, Petition for Inter Parties Review—AIA Review No. IPR2019-01580, filed Sep. 20, 2019, 87 pages.
Schonewald, Stephanie L., Choate Hall & Stewart LLP, Petition for Inter Parties Review—AIA Review No. IPR2020-00389, filed Jan. 3, 2020, 89 pages.
Sharan S.K., et al., "Recombineering: a homologous recombination-based method of genetic engineering," Nature Protocols, 2009, vol. 4(2), pp. 206-223.
Sheng Y., et al., "Transformation of Escherichia coli with large DNA molecules by electroporation," Nucleic Acids Research, 1995, vol. 23, Issue No. 11, pp. 1990-1996.
Shore D.E., Attorney for Applicant, Third-Party Pre-Issuance Submission Under 37 CFR Sec. 1.290 in U.S. Appl. No. 16/216,666, filed Dec. 11, 2019, 42 pages.
Shore D.E., Attorney for Applicant, Third-Party Pre-Issuance Submission Under 37 CFR Sec. 1.290 in U.S. Appl. No. 16/353,870, filed Dec. 20, 2019, 104 pages.
Siegel, D.L. et al., "Section 5: Structural/genetic analysis of mAbs to blood group antigens. Coordinator's Report," Transfus. Clin. Biol., 2002, vol. 9, pp. 83-97.
Sleeman, Mark W., First Declaration (Evidence in Support of Opposition thereto by Regeneron Pharmaceuticals, Inc. for Application No. 2011266843), dated Jan. 29, 2016, 24 pages.
Sleeman, Mark W., Second Declaration (Evidence in Support of Opposition thereto by Regeneron Pharmaceuticals, Inc. for Application No. 2011266843), dated Jul. 4, 2016, 7 pages.
Sleeman, Mark W., Third Declaration (Evidence in Support of Opposition thereto by Regeneron Pharmaceuticals, Inc. for Application No. 2011266843), dated Jan. 25, 2018, 9 pages.
Sosio M., et al., "Assembly of large genomic segments in artificial chromosomes by homologous recombination in Escherichia coli," Nucleic Acids Research, 2001, vol. 29(7), pp. e37-1-e37-8.
Stacey A., et al., "Use of Double-Replacement Gene Targeting To Replace the Murine α-Lactalbumin Gene with Its Human Counterpart in Embryonic Stem Cells and Mice," Molecular and Cellular Biology, Feb. 1994, vol. 14(2), pp. 1009-1016.
Stephen R., Olswang LLP, Response to Examination Report dated Jun. 6, 2016 to the European Patent Office with corresponding claims for Application No. 14176740.0, dated Oct. 10, 2016, 11 pages.
Stephen R., Olswang LLP, Response to Search Report dated Oct. 15, 2014 to the European Patent Office with corresponding claims for Application No. 14176740.0, dated May 12, 2015, 10 pages.
Stephen R., Olswang LLP, Response to Third-Party Observations dated Aug. 10, 2015 and Examination Report dated Oct. 23, 2015 to the European Patent Office with corresponding claims for Application No. 14176740.0, dated Apr. 23, 2016, 13 pages.
Stephen R., Olswang LLP, Response to Examination Report dated Nov. 10, 2016 to the European Patent Office with corresponding claims for Application No. 14176740.0 dated Mar. 17, 2017, 13 pages.

(56) References Cited

OTHER PUBLICATIONS

Traggiai, E. et al., "An efficient method to make human monoclonal antibodies from memory B cells: potent neutralization of SARS coronavirus," Nature Medicine, Aug. 2004, vol. 10(8), pp. 871-875.
Tung J.W., "Phenotypically distinct B cell development pathways map to the three B cell lineages in the mouse," Proceedings of the National Academy of Sciences of the U.S.A., Apr. 2006, vol. 103(16), pp. 6293-6298.
U.S. Patent and Trademark Office, Before the Patent and Appeal Board, AIA Review No. IPR2019-01577, Decision (Denying Institution of Inter Parties Review 35 U.S.C. Sec. 314), dated Apr. 1, 2020, 20 pages.
U.S. Patent and Trademark Office, Before the Patent and Appeal Board, AIA Review No. IPR2019-01578, Decision (Denying Institution of Inter Parties Review 35 U.S.C. Sec. 314), dated Apr. 1, 2020, 17 pages.
U.S. Patent and Trademark Office, Before the Patent and Appeal Board, AIA Review No. IPR2019-01579, Decision (Denying Institution of Inter Parties Review 35 U.S.C. Sec. 314), dated Mar. 20, 2020, 20 pages.
U.S. Patent and Trademark Office, Before the Patent and Appeal Board, AIA Review No. IPR2019-01580, Decision (Denying Institution of Inter Parties Review 35 U.S.C. Sec. 314), dated Mar. 18, 2020, 26 pages.
U.S. Patent and Trademark Office, Before the Patent and Appeal Board, AIA Review No. IPR2020-00389, Decision (Denying Institution of Inter Parties Review 35 U.S.C. Sec. 314), dated May 26, 2020, 21 pages.
Van Dijk, Marcus, Third Declaration (Evidence in Support of Opposition thereto by Regeneron Pharmaceuticals, Inc. for Application No. 2011266843), dated Mar. 28, 2018, 6 pages.
Wozniak-Knopp G., et al., "Introducing antigen-binding sites in structural loops of immunoglobulin constant domains: Fc fragments with engineered HER2/neu-binding sites and antibody properties," Protein Engineering Design & Selection, 2010, vol. 23(4), pp. 289-297.
Wu H., et al., "Double replacement: Strategy for efficient introduction of subtle mutations into the murine Colla-1 gene by homologous recombination in embryonic stem cells," Proc. National Academy of Sciences of the U.S.A., Mar. 1994, vol. 91, pp. 2819-2823.
Xu Z., et al., "Site-specific recombination in Schizosaccharomyces pombe and systematic assembly of a 400kb transgene array iin mammalian cells using the integrase of Steptomyces phage φBt1," Nucleic Acids Research, Dec. 2007, vol. 36(1), pp. e9-1-e9-9.
Yusa K., et al., "Generation of transgene-free induced pluripotent mouse stem cells by the piggyBac transposon," Nature Methods, May 2009, vol. 6, Issue No. 5, pp. 363-371.
Yusa K., et al., "Targeted gene correction of a1-antitrypsin deficiency in induced pluripotent stem cells," Nature, Oct. 2011, vol. 478, Issue No. 7369, pp. 391-394.
U.S. Appl. No. 16/216,666, filed Dec. 11, 2018.
U.S. Appl. No. 16/296,033, filed Mar. 7, 2019.
U.S. Appl. No. 16/353,870, filed Mar. 14, 2019.
[No Author Listed] IMGT Repertoire (IG and TR), Gene table: human (*Homo sapiens*) IGHJ4, created Oct. 17, 1997, last updated Mar. 30, 2021, 606 pages. [retrieved from the internet under: http://www.imgt.org/IMGTrepertoire/Proteins/alleles/index.php?species=Homo%20sapiens&group=IGHJ&gene=IGHJ4].
Brevini T.A.L., "Embryonic Stem Cells in Domestic Animals, No shortcuts to pig embryonic stem cells," ScienceDirect/Theriogenology, vol. 74, 2010, pp. 544-550.
Daukss, Dana M., Third-Party Pre-Issuance Submission Under 37 CFR 1.290 in U.S. Appl. No. 16/725,707, dated Dec. 28, 2020, 46 pages.
Daukss, Dana M., Third-Party Pre-Issuance Submission Under 37 CFR 1.290 in U.S. Appl. No. 16/869,416, dated Apr. 6, 2021, 28 pages.
Daukss, Dana M., Third-Party Pre-Issuance Submission Under 37 CFR 1.290 in U.S. Appl. No. 16/870,365, dated Mar. 15, 2021, 36 pages.
Daukss, Dana M., Third-Party Pre-Issuance Submission Under 37 CFR 1.290 in U.S. Appl. No. 16/870,365, dated Mar. 15, 2021, 45 pages (Second Submission).
Daukss, Dana M., Third-Party Pre-Issuance Submission Under 37 CFR 1.290 in U.S. Appl. No. 16/886,057, dated Apr. 1, 2021, 31 pages.
Daukss, Dana M., Third-Party Pre-Issuance Submission Under 37 CFR 1.290 in U.S. Appl. No. 16/886,394, dated Apr. 1, 2021, 33 pages.
Daukss, Dana M., Third-Party Pre-Issuance Submission Under 37 CFR 1.290 in U.S. Appl. No. 16/905,557, dated Mar. 9, 2021, 67 pages.
Daukss, Dana M., Third-Party Pre-Issuance Submission Under 37 CFR 1.290 in U.S. Appl. No. 16/905,557, dated Mar. 9, 2021, 63 pages (Second Submission).
Daukss, Dana M., Third-Party Pre-Issuance Submission Under 37 CFR 1.290 in U.S. Appl. No. 16/721,326, dated Mar. 25, 2021, 36 pages.
Daukss, Dana M., Third-Party Pre-Issuance Submission Under 37 CFR 1.290 in U.S. Appl. No. 16/721,326, dated Mar. 25, 2021, 30 pages (Second Submission).
Defranco, Anthony L., Ph.D., Declaration, Interparties Review AIA No. IPR2019-01579 U.S. Pat. No. 9,447,177), dated Sep. 20, 2019, 103 pages.
European Patent Office, Examination Report for Application No. 13723933.1, dated Feb. 21, 2019, 7 pages.
European Patent Office, Examination Report for Application No. 18743421.2, dated Feb. 26, 2021, 3 pages.
Genbank, Mus musculus immunoglobulin heavy chain locus constant region and partial variable region, strain 129S1, NCBI Reference Sequence No. AJ851868.3, dated Jul. 26, 2007, 23 pages.
Genbank, "Mus musculus Ig kappa germline J-C region: J1-5 and C genes, and flanks," GenBank No. L80040.1, dated Sep. 2, 2003, 5 pages.
Genbank, *Homo sapiens* immunoglobulin heavy chain (IGH.1@) on chromosome 14, NCBI Ref. Sequence No. NG_001019.1, dated Jun. 26, 2002, 261 pages.
Ploegh, Hidde Dr., Declaration, submittted in U.S. Appl. No. 14/046,291 (now U.S. Pat. No. 10,526,630) dated Jul. 12, 2018, 123 pages.
Winter D.B., et al., "Insertion of 2 KB of Bacteriophage DNA Between An Immunoglobulin Promoter and Leader Exon Stops Somatic Hypermutation in a κ Transgene," Molecular Immunology, 1997, vol. 34, Issue No. 5, pp. 359-366.
U.S. Appl. No. 14/080,630, filed Nov. 14, 2013, issued Jan. 1, 2019 as U.S. Pat. No. 10,165,763.
U.S. Appl. No. 14/220,074, filed Mar. 19, 2014.
Ozawa T., et al., "Amplification and analysis of cDNA generated from a single cell by 5'-RACE: application to isolation of antibody heavy and light chain variable gene sequences from single B cells,," BioTechniques—Short Technical Reports, 2006, vol. 40, Issue No. 4, pp. 469-478.
Ronai D., et al., "Variegated Expression of the Endogenous Immunoglobulin Heavy-Chain Gene in the Absence of the Intronic Locus Control Region," Molecular and Cellular Biology, Oct. 1999, vol. 19, Issue No. 10, pp. 7031-7040.
Shiokawa S., et al., "IgM Heavy Chain Complementarity-Determining Region 3 Diversity Is Constrained by Genetic and Somatic Mechanisms Until Two Months After Birth," Journal of Immunology, May 1999, vol. 162, Issue No. 10, pp. 6060-6070.
U.S. Appl. No. 09/552,219, filed Apr. 19, 2000, issued May 28, 2002 as U.S. Pat. No. 6,395,487.
U.S. Appl. No. 09/552,626, filed Apr. 19, 2000, issued Oct. 8, 2002 as U.S. Pat. No. 6,461,818.
U.S. Appl. No. 13/310,431, filed Dec. 2, 2011.
U.S. Appl. No. 13/416,684, filed Mar. 9, 2012, issued Sep. 20, 2016 as U.S. Pat. No. 9,447,177.
U.S. Appl. No. 13/433,084, filed Mar. 28, 2012, issued Sep. 20, 2016 as U.S. Pat. No. 9,445,581.
U.S. Appl. No. 13/434,361, filed Mar. 29, 2012, issued Feb. 9, 2016 as U.S. Pat. No. 9,253,965.
U.S. Appl. No. 13/740,727, filed Jan. 14, 2013, issued Nov. 29, 2016 as U.S. Pat. No. 9,505,827.

(56) References Cited

OTHER PUBLICATIONS

U.S. Appl. No. 13/846,672, filed Mar. 18, 2013, issued Oct. 17, 2017 as U.S. Pat. No. 9,788,534.
U.S. Appl. No. 13/875,892, filed May 2, 2013, issued Oct. 10, 2017 as U.S. Pat. No. 9,783,593.
U.S. Appl. No. 14/040,405, filed Sep. 27, 2013.
U.S. Appl. No. 14/040,427, filed Sep. 27, 2013.
U.S. Appl. No. 14/052,259, filed Oct. 11, 2013.
U.S. Appl. No. 14/056,434, filed Oct. 17, 2013.
U.S. Appl. No. 14/056,700, filed Oct. 17, 2013.
U.S. Appl. No. 14/056,707, filed Oct. 17, 2013.
U.S. Appl. No. 14/080,630, filed Nov. 14, 2013, issued Jan. 1, 2019 as U.S. Patent No. 10,165,763.
U.S. Appl. No. 14/137,902, filed Dec. 20, 2013, issued Sep. 6, 2016 as U.S. Pat. No. 9,434,782.
U.S. Appl. No. 14/220,074, filed Mar. 19, 2014, issued Jul. 6, 2021 as U.S. Patent No. 11,051,497.
U.S. Appl. No. 14/220,080, filed Mar. 19, 2014.
U.S. Appl. No. 14/220,095, filed Mar. 19, 2014, issued Oct. 10, 2017 as U.S. Pat. No. 9,783,618.
U.S. Appl. No. 14/220,099, filed Mar. 19, 2014.
U.S. Appl. No. 14/226,698, filed Mar. 26, 2014, issued May 8, 2018 as U.S. Pat. No. 9,963,716.
U.S. Appl. No. 14/497,054, filed Sep. 25, 2014.
U.S. Appl. No. 14/498,685, filed Sep. 26, 2014, issued Apr. 9, 2019 as U.S. Pat. No. 10,251,377.
U.S. Appl. No. 14/516,461, filed Oct. 16, 2014, issued Sep. 4, 2018 as U.S. Pat. No. 10,064,398.
U.S. Appl. No. 14/543,359, filed Nov. 17, 2014, issued Jun. 2, 2020 as U.S. Pat. No. 10,667,501.
U.S. Appl. No. 14/750,870, filed Jun. 25, 2015.
U.S. Appl. No. 14/818,162, filed Aug. 4, 2015.
U.S. Appl. No. 14/935,010, filed Nov. 6, 2015, issued Nov. 29, 2016 as U.S. Pat. No. 9,504,236.
U.S. Appl. No. 15/016,211, filed Feb. 4, 2016.
U.S. Appl. No. 15/018,670, filed Feb. 8, 2016, issued Mar. 27, 2018 as U.S. Pat. No. 9,924,705.
U.S. Appl. No. 15/088,805, filed Apr. 1, 2016, issued Dec. 11, 2018 as U.S. Pat. No. 10,149,462.
U.S. Appl. No. 15/095,315, filed Apr. 11, 2016, issued Feb. 20, 2018 as U.S. Pat. No. 9,896,516.
U.S. Appl. No. 15/199,575, filed Jun. 30, 2016.
U.S. Appl. No. 15/214,963, filed Jul. 20, 2016.
U.S. Appl. No. 15/251,969, filed Aug. 30, 2016.
U.S. Appl. No. 15/360,502, filed Nov. 23, 2016.
U.S. Appl. No. 15/369,595, filed Dec. 5, 2016.
U.S. Appl. No. 15/383,101, filed Dec. 19, 2016.
U.S. Appl. No. 15/383,188, filed Dec. 19, 2016.
U.S. Appl. No. 15/383,196, filed Dec. 19, 2016, issued Apr. 10, 2018 as U.S. Pat. No. 9,938,357.
U.S. Appl. No. 15/383,202, filed Dec. 19, 2016, issued Apr. 10, 2018 as U.S. Pat. No. 9,938,358.
U.S. Appl. No. 15/383,342, filed Dec. 19, 2016.
U.S. Appl. No. 15/383,353, filed Dec. 19, 2016.
U.S. Appl. No. 15/385,348, filed Dec. 20, 2016.
U.S. Appl. No. 15/385,372, filed Dec. 20, 2016.
U.S. Appl. No. 15/656,897, filed Jul. 21, 2017, issued Aug. 4, 2020 as U.S. Pat. No. 10,730,930.
U.S. Appl. No. 15/690,183, filed Aug. 29, 2017, issued Mar. 12, 2019 as U.S. Pat. No. 10,226,033.
U.S. Appl. No. 15/786,281, filed Oct. 17, 2017.
U.S. Appl. No. 15/948,709, filed Apr. 9, 2018, issued Sep. 15, 2020 as U.S. Pat. No. 10,774,155.
U.S. Appl. No. 15/955,216, filed Apr. 17, 2018.
U.S. Appl. No. 15/973,376, filed May 7, 2018.
U.S. Appl. No. 16/216,666, filed Dec. 11, 2018, issued Apr. 6, 2021 as U.S. Pat. No. 10,996,412.
U.S. Appl. No. 16/296,033, filed Mar. 7, 2019; issued Apr. 12, 2022 as U.S. Pat. No. 11,297,810.
U.S. Appl. No. 16/353,870, filed Mar. 14, 2019; issued Apr. 12, 2022 as U.S. Pat. No. 11,297,811.
U.S. Appl. No. 16/721,326. filed Dec. 19, 2019.
U.S. Appl. No. 16/725,707, filed Dec. 23, 2019.
U.S. Appl. No. 16/869,416, filed May 7, 2020.
U.S. Appl. No. 16/870,365, filed May 8, 2020.
U.S. Appl. No. 16/870,413, filed May 8, 2020.
U.S. Appl. No. 16/886,057, filed May 28, 2020.
U.S. Appl. No. 16/886,394, filed May 28, 2020.
U.S. Appl. No. 16/905,537, filed Jun. 18, 2020.
U.S. Appl. No. 16/905,557, filed Jun. 18, 2020.
U.S. Appl. No. 17/020,997, filed Sep. 15, 2020.
U.S. Appl. No. 17/180,258, filed Feb. 19, 2021.
U.S. Appl. No. 17/368,266, filed Jul. 6, 2021.
Muñoz-López M., et al., "DNA Transposons: Nature and Applications in Genomics," Current Genomics, 2010, vol. 11, pp. 115-128.
Ni J.M., et al., "Transposon tools hopping in vertebrates," Briefings In Functional Genomics and Proteomics, 2008, vol. 7, Issue No. 6, pp. 444-453.
Nicholls, James, Ja Kemp, Reply to Patentee's Grounds of Appeal, Opposition roceedings in relation to EP Patent No. 3,028,564 B1 (Appln No. EP1615124.0), dated Nov. 24, 2021, 12 pages.
Nicholls, James, Ja Kemp, Statement of Facts and Arguments in Support of Opposition, Opposition proceedings in relation to EP Patent No. 3,622,813 B1 (Appln. No. EP19207050.6), dated Nov. 17, 2021, 56 pages.
Ogle, Ph.D., J.M., European Patent Attorney of Hoffman Eitle, Reply to Patentee's Response of Nov. 16, 2018 In Re Opposition against EP 3028564 (European Appln. No. 16151214.0), dated Feb. 12, 2019, 28 pages.
Ogle, Ph.D., J.M., European Patent Attorney of Hoffman Eitle, Subsequent Written Submission in Response to Patentee's Written Submissions of Jan. 10, 2020 and Jan. 27, 2020 In Re Opposition against EP 3028564 European Appln. No. 16151214.0), dated Feb. 11, 2020, 10 pages.
Patil V.M., et al., "Transgenic animals and drug development: A review," Indian Journal of Public Health Research & Development, Jun. 2011, vol. 2, Issue No. 1, pp. 106-109.
Porter, Andrew, Declaration for Kymab, Ltd. relating to Patent No. EP 2,792,236 B1, dated Aug. 10, 2018, 24 pages.
Ravetch, J.V., et al., "Structure of the human immunoglobulin μ locus: Characterization of embryonic and rearranged J and D genes," Cell, Dec. 1981, vol. 27, Issue No. 3, Part 2, pp. 583-591.
Romo-Gonzalez, "Novel substitution polymorphisms of human immunoglobulin VH genes in Mexicans," Human Immunology, 2005, vol. 66, pp. 732-740.
Roskos L.K., et al., "Measuring Immunity," Chapter 13—Human Antiglobulin Responses, Editor(s): Michael T. Lotze, Angus W. Thomson, Academic Press, London, United Kingdom, 2005, pp. 172-186, ISBN 9780124559004 [retrieved online: https://doi.org/10.1016/B978-012455900-4/50275-0].
Scarselli, M., et al., "Epitope Mapping of a Bactericidal Monoclonal Antibody against the Factor H Binding Protein of Neisseria meningitidis," The Journal of Molecular Biology, Feb. 2009, vol. 386(1), pp. 97-108.
Sinzelle L., et al., "Transposition of a reconstructed Harbinger element in human cells and functional homology with two transposon-derived cellular genes," Proceedings of the National Academy of Sciences of the U.S.A., Mar. 2008, vol. 105, Issue No. 12, pp. 4715-4720.
Stephen, R., Cameron McKenna Nabarro Olswang LLP, Response to Opposition to EP 3028564 (Application No. 16151214.0) with supporting documents, dated Nov. 16, 2018, 164 pages.
Throsby M., et al., "Heterosubtypic Neutralizing Monoclonal Antibodies Cross-Protective against H5N1 and H1N1 Recovered from Human IgM+ Memory B Cells," PLoS One, Dec. 2008, vol. 3, Issue No. 12, pp. e3942-1-e3942-15.
U.S. Patent and Trademark Office, Office Action issued for U.S. Appl. No. 13/310,431, dated Sep. 7, 2021, 109 pages.
University of California Santa Cruz, "Human Genome Browser GRCh37/hg19 Assembly," Feb. 2009, 3 pages.

(56) References Cited

OTHER PUBLICATIONS

Volpe J.M., et al., "Large-scale analysis of human heavy chain V(D)J recombination patterns," Immunome Research, 2008, vol. 4, Issue No. 3, 10 pages.

Voronina V.A., et al., "Deletion of Adam6 in Mus musulus leads to male subfertility an deficits in sperm ascent into the oviduct," Biology of Reproduction, 2019, vol. 100, Issue No. 3, pp. 686-696.

Wilson, M.H., et al., "PiggyBack Transposon-mediated Gene Transfer in Human Cells, The American Society of Gene Therapy, Molecular Therapy," Jan. 2007, vol. 15, Issue No. 1, pp. 136-145.

Woloschak G.E., et al., "Regulation of κ / λ Immunoglobulin Light Chain Expression in Normal Murine Lymphocytes," Molecular Immunology, 1987, vol. 24, Issue No. 7, pp. 751-757.

Woltjen K. et al., "piggyBac transposition reprograms fibroblast to induced pluripotent stem cells," Nature, Apr. 2009, vol. 458, pp. 766-771.

Wooddard L.E.et al., "piggyBac-ing models and new therapeutic strategies," Trends in Biotechnology, Sep. 2015, vol. 33, Issue No. 9, pp. 525-533.

Xu J.L., et al., "Diversity in the CDR3 Region of VH Is Sufficient for Most Antibody Specificities," Immunity, vol. 13, Jul. 2000, pp. 37-45.

Yang C., et al., "Mutant PFN1 causes ALS phenotypes and progressive motor neuron degeneration in mice by a gain of toxicity," Proceedings of the National Academy of Sciences of the U.S.A., Sep. 2016, vol. 113, Issue No. 41, pp. E6209-E6218.

Zimmerman, A., et al., "Immunoglobulin light chain (IgL) genes in zebrafish: Genomic configurations and inversional rearrangements between (VL-JL-CL) gene clusters," Developmental and comparative immunology, 2008, vol. 32(4), pp. 421-434.

[No Author Listed] Exemplary allele distribution for IgHV3-72 (3 pages) [retrieved from the internet Apr. 29, 2021: http://www.imgt.org/IMGTrepertoire/Proteins/taballeles/human/IGH/IGHV/Hu_IGHVall.html].

[No Author Listed] Exemplary allele distribution for IgHV3-73 (3 pages) [retrieved from the internet Apr. 29, 2021: http://www.imgt.org/IMGTrepertoire/Proteins/taballeles/human/IGH/IGHV/Hu_IGHVall.html].

[No Author Listed] IMGT Repertoire (IG and TR), Locus representation: Human (*Homo sapiens*) IGK, dated Nov. 26, 2021, 3 pages [retrieved from the internet under: http://www.imgt.org/IMGrepertoire/index.php?section=LocusGenes&repertoire=locus&species=human&group=IGK/].

[No Author Listed] IMGT Repertoire, Gene table: Protein display: Human IGH C-Regions, last updated Jun. 9, 2021, 1 page [retrieved from the internet under: http://www.imgt.org/IMGTrepertoire/Proteins/protein/human/IGH/IGHC/Hu_IGHCallgenes.html].

Almagro J.C., et al., "Therapeutic Monoclonal Antibodies from Bench to Clinic," Part IV—Antibody Engineering, Chapter 13: Antibody Engineering: Humanization, Affinity Maturation, and Selection Techniques, 2009, pp. 311-334, including cover and copyright pages, Edited by Zhiqiang An, John Wiley & Sons, Inc., ISBN 978-0-470-11791-0 [retrieved online: https://doi.org/10.1002/9780470485408.ch13].

Brezinschek H.P., et al., "Analysis of the Heavy Chain Repertoire of Human Peripheral B Cells Using Single-Cell Polymerase Chain Reaction," The Journal of Immunology, vol. 155, 1995, pp. 190-202.

Bychowski M.E., Third-Party Pre-Issuance Submission Under 37 CFR 1.290 in U.S. Appl. No. 17/020,997, dated Sep. 10, 2021, 66 pages.

Casadevall A., et al., "Serum Therapy Revisited: Animal Models of Infection and Development of Passive Antibody Therapy," Antimicrobial Agents and Chemotherapy, Aug. 1994, vol. 38, Issue No. 8, pp. 1695-1702.

Casadevall A., et al., "The convalescent sera option for containing COVID-19," The Journal of Clinical Investigation, 2020, vol. 130, Issue No. 4, pp. 1545-1548.

Chen J., et al., "RAG-2-deficient blastocyst complementation: An assay of gene function in lymphocyte development," Proceedings of the National Academy of Sciences of the U.S.A., Immunology, May 1993, vol. 90, pp. 4528-4532.

Clark K.J., et al., "Pigs taking wing with transposons and recombinases," Genome Biology, 2007, vol. 8, Suppl. I, Article S13, 16 pages.

Daukss, Dana M., Third-Party Pre-Issuance Submission Under 37 CFR 1.290 in U.S. Appl. No. 16/870,413, dated Jun. 1, 2021, 34 pages.

Daukss, Dana M., Third-Party Pre-Issuance Submission Under 37 CFR 1.290 in U.S. Appl. No. 16/870,413, dated Jun. 1, 2021, 40 pages (Second Submission).

Daukss, Dana M., Third-Party Pre-Issuance Submission Under 37 CFR 1.290 in U.S. Appl. No. 16/905,537, dated Apr. 23, 2021, 47 pages.

Daukss, Dana M., Third-Party Pre-Issuance Submission Under 37 CFR 1.290 in U.S. Appl. No. 17/180,258, dated Oct. 13, 2021, 52 pages.

DICTIONARY.com, Definition of "population" 2021, 8 pages [retrieved online: https://www.dictionary.com/browse/population].

Ebersbach H., et al., "Antigen Presentation for the Generation of Binding Molecules," Methods of Molecular Biology, 2012, Chaper 1: Antigen Presentation for the Generation of Binding Molecules, 19 pages.

Eisen H.N., et al., "Variations in Affinities of Antibodies during the Immune Response," Biochemistry, Feb. 1964, vol. 3, Issue No. 7, pp. 996-1008.

European Patent Office, Extended European Search Report for Application No. 20188009.3, dated May 3, 2021, 17 pages.

European Patent Office, Decision of Technical Board of Appeal 3.3.04, relating to Application No. EP11705964.2 (Patent No. EP2582230), dated Apr. 26, 2019 (including Datasheet and Notice of Decision to Refuse), 10 pages.

European Patent Office, Summons to Attend Oral Proceedings pursuant to Rule 115(1) EPC, relating to Application No. EP11705964.2 (Patent No. EP2582230), dated Jul. 4, 2017, 10 pages.

European Patent Office, Minutes of the oral proceedings before the Opposition Division, relating to Application No. EP12716101.6 (Patent No. EP2550363), with supporting documents, dated May 26, 2017, 62 pages.

European Patent Office, Notice of Opposition to European Patent EP3241435 in the name of Kymab Limited pertaining to Application No. 17174426.1, dated Mar. 3, 2022, 44 pages.

European Patent Office, Notice of Opposition, together with Statement of Fact and Arguments In Support of Opposition related to European Patent EP2989894 in the name of Kymab Limited pertaining to Application No. 15188522.5, dated May 17, 2021, 34 pages.

European Patent Office, Notice of Opposition,.together with Ground of Opposition and accompanying cited documents, related to European Patent EP3128009 in the name of Kymab Limited pertaining to Application No. 16189625.3, dated May 6, 2021, 55 pages.

Fraser M.J., et al., "Prescise excision of TTAA-specific lepidopteran transposons piggyBac (IFP2) and tagalong (TFP3) from the baculovirus genome in cell lines from two species of Lepidoptera," Insect. Molecular Biology, 1996, vol. 5, Issue No. 2, pp. 141-151.

Fraser, N., et al., "The VH gene repertoire of splenic B cells and somatic hypermutation in systemic lupus erythematosus," Arthritis Research and Therapy, 2003, vol. 5, Issue No. 2, pp. R114-R121.

Genecards, "IGKV1-13 Gene—Immunoglobulin Kappa Va . . . Pseudogene," IGKV1-13 Gene—GeneCards | IGKV1-13 Pseudogene, dated Nov. 4, 2021, 14 pages [retrieved online Apr. 11, 2021, https://www.genecards.org/cgi-bin/carddisp.pl?gene=IGKV1-13].

Grund M., European Patent Attorney, Grund Intellectual Property Group, Third-Party Observations according to Article 115 EPC regarding 18153154.2, dated Mar. 18, 2022, 3 pages.

Grund M., European Patent Attorney, Grund Intellectual Property Group, Third-Party Observations according to Article 115 EPC regarding 13723933.1, dated Sep. 20, 2021, 5 pages.

Grund M., European Patent Attorney, Grund Intellectual Property Group, Third-Party Observations according to Article 115 EPC regarding 18153171.6, dated Feb. 2, 2022, 6 pages.

(56) References Cited

OTHER PUBLICATIONS

Grund M., European Patent Attorney, Grund Intellectual Property Group, Third-Party Observations according to Article 115 EPC regarding 19207052.2, dated Oct. 28, 2021, 5 pages.
Grund M., European Patent Attorney, Grund Intellectual Property Group, Third-Party Observations according to Article 115 EPC regarding 20171931.7, dated Dec. 13, 2021, 5 pages.
Grund M., European Patent Attorney, Grund Intellectual Property Group, Third-Party Observations according to Article 115 EPC regarding 20191651.7, dated Nov. 24, 2021, 7 pages.
Hayes Emily A.L., Mewburn Ellis LLP, Supplemental Response on behalf of Regeneron Pharmaceuticals, Inc. regarding Opposition filed Sep. 16, 2021 relating to European Patent No. 3,128,009 (European Appln. No. 16189625.3), dated Dec. 7, 2021, 17 pages.
Hjelm B., et al., "Generation of monospecific antibodies based on affinity capture of polyclonal antibodies," Protein Science, 2011, vol. 20, pp. 1824-1835.
Hohn B., et al., "Elimination of selection markers from transgenic plants," Current Opinion in Biotechnology, Plant biotechnology, 2001, vol. 12, pp. 139-143.
Ivics Z., et al., "Transposon-mediated genome manipulation in vertebrates," Nature Methods, Jun. 2009, vol. 6, Issue No. 6, pp. 415-422 (including Errata sheet).
Japanese Patent Office, Notice of Reasons for Rejection—Application No. 2021-026065, dated Mar. 22, 2022, together with English translation, 16 pages.
Jefferis R., et al., "Human immunoglobulin allotypes," mAbs, Jul./Aug. 2009, vol. 1, Issue No. 4, pp. 1-7.
Jones B.T., Attorney for Applicant, Third-Party Pre-Issuance Submission Under 37 CFR Sec. 1.290 in U.S. Appl. No. 15/232,122, filed Mar. 13, 2017, 32 pages.
Kaji K., et al., "Virus-free induction of pluripotency and subsequent excision of reprogramming factors," Nature, Apr. 2009, vol. 458, pp. 771-776.
Khodarovich Y.M., et al., "Expression of Eukaryotic Recombinant Proteins and Deriving Them from the Milk of Transgenic Animals," Applied Biochemistry and Microbiology, Problems and Aspects, 2013, vol. 49, Issue No. 9, pp. 711-722.
Kilpatrick K.E., et al., "Rapid Development of Affinity Matured Monoclonal Antibodies Using RIMMS," Hybridoma, 1997, vol. 16, Issue No. 4, pp. 381-389.
Kokubu C. et al., "A transposon-based chromosomal engineering method to survey a large cis-regulatory andscape in mice," Nature Genetics, Aug. 2009, vol. 41, Issue No. 8, pp. 946-954.
Little M., et al., "Of mice and men: hybridoma and recombinant antibodies," Review Immunology Today, Aug. 2000, vol. 21, Issue No. 8, pp. 364-370.
Liu L., et al., "Igh V3-23*01 and its allele V3-23*03 differ in their capacity to form the canonical human antibody combining site specific for the capsular polysaccharide of Haemophilus influenzae type b," Immunogenetics, 2003, vol. 55, pp. 336-338.
Maksimenko O.G., et al., "Use of Transgenic Animals in Biotechnology: Prospect and Problems," ACTA Naturae, Reviews, 2013, vol. 5, Issue No. 1, pp. 33-46.
Merriam Webster Dictionary, Definition of "population" 2021, 8 pages [retrieved online: https://www.merriam-webster.com/dictionary/population].
Murphy A., "Declaration of Andrew J. Murphy," including Slide Presentation dated Nov. 3, 2009, at Wellcome Trust Advanced Course: Genetic Manipulation of ES Cells, in Hirixton, UK, entitled "BAC-based Modifications of the Mouse Genome: The Big and the Backward," including course timetables, 72 pages.
Chinese Patent Office, Office Action (English Translation) for Chinese Patent Application No. 201610821299.6, dated Jun. 15, 2020, 19 pages.
Chinese Patent Office, Office Action for Chinese Patent Application No. 201610821299.6, dated Jun. 15, 2020, 15 pages.
Ejima D., "Effective elution of antibodies by arginine and arginine derivatives in affinity column chromatography," Analytical Biochemistry, 2005, vol. 345, pp. 250-257.
England, Nicholas Dr., 37 C.F.R. Rule 1.132 Declaration, dated Dec. 21, 2016, 6 pages.
Finn, C.A., "Rreproductive Capacity and Litter Size In Mice: Effect of Age and Environment," J. Reprod. Fertil., 1963, vol. 6, pp. 205-214.
Genbank, "*H.sapiens* immunoglobulin heavy chain J region, B1C haplotype," Accession No. X86356, 2 pages.
Genbank, "Human Ig germline J6-region, partial cds," Accession No. M63030, 1 page.
Grund M., European Patent Attorney, Grund Intellectual Property Group, Third-Party Observations according to Article 115 EPC regarding 19207052.2, dated Aug. 19, 2020, 4 pages.
Ivanov I.I., et al., "Development of the Expressed Ig CDR-H3 Repertoire Is Marked by Focusing of Constraints in Length, Amino Acid Use, and Charge That Are First Established in Early B Cell Progenitors," The Journal of Immunology, Jun. 2005, vol. 174, pp. 7773-7780.
Shore, D.E., Attorney for Applicant, Third-Party Pre-Issuance Submission Under 37 CFR Sec. 1.290 in U.S. Appl. No. 16/296,033, filed Jul. 14, 2020, 75 pages.
Shore, D.E., Attorney for Applicant, Third-Party Pre-Issuance Submission Under 37 CFR Sec. 1.290 in U.S. Appl. No. 16/296,033, filed Jul. 14, 2020, 78 pages (2nd Submission).
Decloux, A.M., Attorney for Applicant Amendment and Response After Final Rejection—U.S. Appl. No. 13/846,672, filed May 10, 2016, 20 pages.
Defranco, Anthony L., Ph.D., Declaration, dated Sep. 9, 2019, 113 pages.
Stevens, S., "Human Antibody Discovery VelocImmune—A novel platform", pp. 72-74, Pharma Focus Asia, Issue 8, 2008.†

\* cited by examiner
† cited by third party

Distribution of JH Usage Within Each VHs

| | JH1 | JH2 | JH3 | JH4 | JH5 | JH6 |
|---|---|---|---|---|---|---|
| V2-5 | | 1 | 5 | 5 | 2 | 1 |
| V4-4 | 1 | 1 | 1 | 1 | | 8 |
| V1-3 | 1 | 6 | 6 | 49 | 13 | 40 |
| V1-2 | | 1 | 4 | 1 | | 1 |
| V6-1 | | 1 | 4 | 18 | 1 | 29 |
| Total | 2 | 9 | 16 | 74 | 16 | 79 |

The data includes 196 independent sequences.

Distribution of DH Usage Within Each VHs

The data includes 196 independent sequences.

Fig. 43

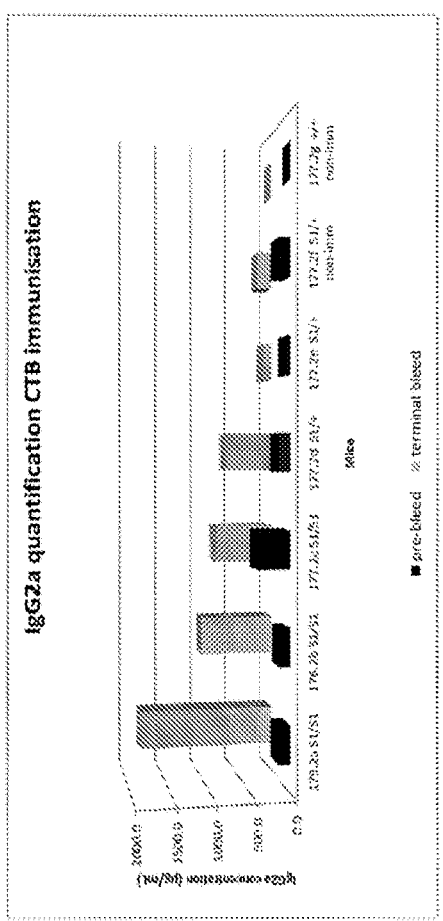
FIG. 54E
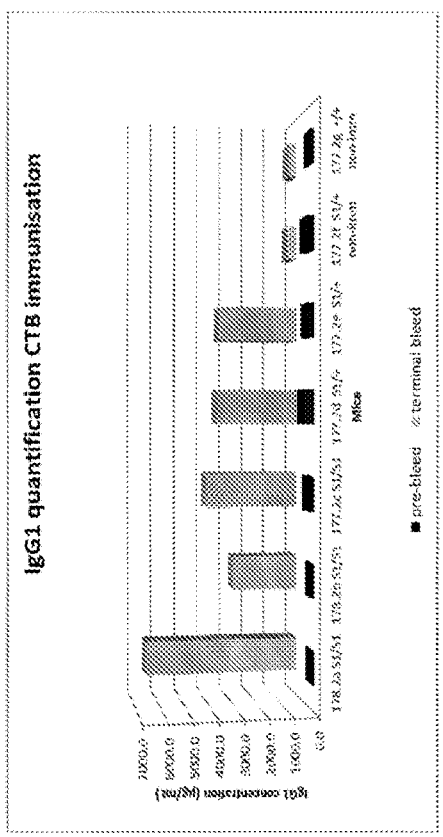
FIG. 54G
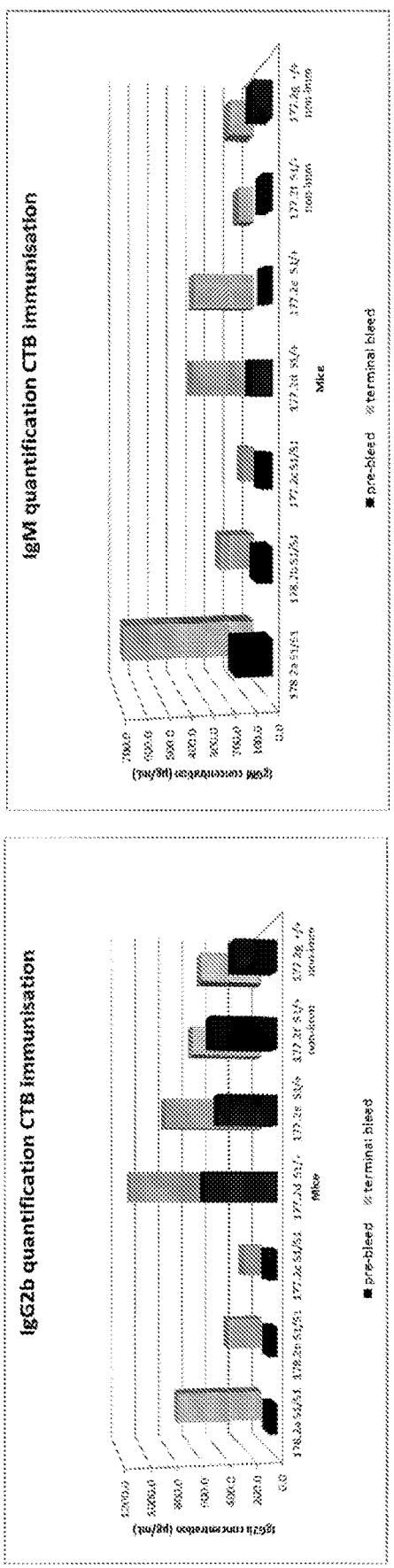
FIG. 54F
FIG. 54H

ANIMAL MODELS AND THERAPEUTIC MOLECULES

CROSS-REFERENCE TO RELATED APPLICATIONS

This application is a continuation of U.S. patent application Ser. No. 13/310,431, filed Dec. 2, 2011, which is a continuation-in-part of PCT/GB2010/051122 filed Jul. 7, 2010, which claims the benefit of U.S. Provisional Application No. 61/223,960 filed Jul. 8, 2009; U.S. Provisional Application No. 61/355,666 filed Jun. 17, 2010; GB Patent Application No.: 0911846.4 filed Jul. 8, 2009; and GB Patent Application No.: 0913102.0 filed Jul. 28, 2009, the entire contents of which are incorporated herein by reference. U.S. patent application Ser. No. 13/310,431, filed Dec. 2, 2011, is also a continuation-in-part of PCT/GB2011/050019, filed Jan. 7, 2011, which claims the benefit of PCT/GB2010/051122, filed Jul. 7, 2010, and claims the benefit of U.S. Provisional Application No. 61/355,666 filed Jun. 17, 2010. The entire contents of each of the above named applications are hereby incorporated by reference in their entirety.

SEQUENCE LISTING

The attached sequence listing is hereby incorporated by reference in its entirety.

BACKGROUND

The present invention relates inter alia to non-human animals and cells that are engineered to contain exogenous DNA, such as human immunoglobulin gene DNA, their use in medicine and the study of disease, methods for production of non-human animals and cells, and antibodies and antibody chains produced by such animals and derivatives thereof.

In order to get around the problems of humanizing antibodies a number of companies set out to generate mice with human immune systems. The strategy used was to knockout the heavy and light chain loci in ES cells and complement these genetic lesions with transgenes designed to express the human heavy and light chain genes. Although fully human antibodies could be generated, these models have several major limitations:

(i) The size of the heavy and light chain loci (each several Mb) made it impossible to introduce the entire loci into these models. As a result the transgenic lines recovered had a very limited repertoire of V-regions, most of the constant regions were missing and important distant enhancer regions were not included in the transgenes.

(ii) The very low efficiency of generating the large insert transgenic lines and the complexity and time required to cross each of these into the heavy and light chain knockout strains and make them homozygous again, restricted the number of transgenic lines which could be analysed for optimal expression.

(iii) Individual antibody affinities rarely reached those which could be obtained from intact (non-transgenic) animals.

WO2007117410 discloses chimaeric constructs for expressing chimaeric antibodies.

WO2010039900 discloses knock in cells and mammals having a genome encoding chimaeric antibodies.

The present invention provides, inter alia, a process for the generation in non-human mammals of antibodies that comprise a human Ig variable region, and further provides non-human animal models for the generation of such antibodies.

SUMMARY OF THE INVENTION

All nucleotide co-ordinates for the mouse are those corresponding to NCBI m37 for the mouse C57BL/6J strain, e.g. April 2007 ENSEMBL Release 55.37 h, e.g. NCBI37 July 2007 (NCBI build 37) (e.g. UCSC version mm9 see World Wide Web (www) genome.ucsc.edu and World Wide Web (www) genome.ucsc.edu/FAQ/FAQreleases.html) unless otherwise specified. Human nucleotides coordinates are those corresponding to GRCh37 (e.g. UCSC version hg 19, World Wide Web (www) genome.ucsc.edu/FAQ/FAQreleases.html), February 2009 ENSEMBL Release 55.37, or are those corresponding to NCBI36, Ensemble release 54 unless otherwise specified. Rat nucleotides are those corresponding to RGSC 3.4 Dec. 2004 ENSEMBL release 55.34w, or Baylor College of Medicine HGSC v3.4 Nov. 2004 (e.g., UCSC rn4, see World Wide Web (www) genome.ucsc.edu and World Wide Web (www) genome.ucsc.edu/FAQ/FAQreleases.html) unless otherwise specified.

In the present invention, methods are disclosed for constructing a chimaeric human heavy and light chain loci in a non-human mammal, for example a mouse. Reference to work in mice herein is by way of example only, and reference to mice is taken to include reference to all non-human mammals unless otherwise apparent from the disclosure, with mice being preferred as the non-human mammal.

In one aspect the invention relates to a non-human mammal whose genome comprises:
 (a) a plurality of human IgH V regions, one or more human D regions and one or more human J regions upstream of the host non-human mammal constant region; and
 (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;
wherein the non-human mammal is able to produce a repertoire of chimaeric antibodies, or chimaeric light or heavy chains, having a non-human mammal constant region and a human variable region.

In one aspect the invention relates to non-human mammal whose genome comprises
 (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
 (b) optionally one or more human IgH V regions, one or more human D regions and one or more human J regions upstream of the host non-human mammal constant region;
wherein the non-human mammal is able to produce a repertoire of chimaeric antibodies, or chimaeric light or heavy chains, having a non-human mammal constant region and a human variable region.

In one aspect the invention relates to non-human mammalian cell whose genome comprises
  (a) a plurality of human IgH V regions, one or more human D regions and one or more human J regions upstream of the host non-human mammal constant region and
  (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region.

In one aspect the invention relates to a non-human mammalian cell whose genome comprises
  (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
  (b) optionally one or more human IgH V regions, one or more human D regions and one or more human J regions upstream of the host non-human mammal constant region;

In a further aspect the invention relates to a method for producing a non-human cell or mammal comprising inserting into a non-human mammal cell genome, such as an ES cell genome;
  (a) a plurality of human IgH V regions, one or more human D regions and one or more human J regions upstream of the host non-human mammal constant region; and
  (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region; respectively, the insertion being such that the non-human cell or mammal is able to produce a repertoire of chimaeric antibodies having a non-human mammal constant region and a human variable region, wherein steps (a) and (b) can be carried out in either order and each of steps (a) and (b) can be carried out in a stepwise manner or as a single step. Insertion may be by homologous recombination.

In a further aspect the invention relates to a method for producing an antibody or antibody chain specific to a desired antigen the method comprising immunizing a transgenic non-human mammal as disclosed herein with the desired antigen and recovering the antibody or antibody chain.

In a further aspect the invention relates to a method for producing a fully humanised antibody comprising immunizing a transgenic non-human mammal as disclosed herein with the desired antigen, recovering the antibody or cells producing the antibody and then replacing the non-human mammal constant region with a human constant region, for example by protein or DNA engineering.

In a further aspect the invention relates to humanised antibodies and antibody chains produced according to the present invention, both in chimaeric (for example, mouse-human) and fully humanised form, as well as fragments and derivatives of said antibodies and chains, and use of said antibodies, chains and fragments in medicine, including diagnosis.

In a further aspect the invention relates to use of a non-human mammal as described herein as a model for the testing of drugs and vaccines.

In one aspect the invention relates to a non-human mammal whose genome comprises:
  (a) a plurality of human IgH V regions, one or more human D regions and one or more human J regions upstream of the host non-human mammal constant region; and
  (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;
wherein the non-human mammal is able to produce a repertoire of chimaeric antibodies or antibody chains having a non-human mammal constant region and a human variable region.

In a further aspect the invention relates to a non-human mammal whose genome comprises:
  (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
  (b) optionally one or more human IgH V regions, one or more human D regions and one or more human J regions upstream of the host non-human mammal constant;
wherein the non-human mammal is able to produce a repertoire of chimaeric antibodies having a non-human mammal constant region and a human variable region.

Optionally the non-human mammal genome is modified to prevent expression of fully host-species specific antibodies.

In one aspect the inserted human DNA comprises at least 50% of the human heavy chain variable (V) genes, such as at least 60%, at least 70%, at least 80%, at least 90%, and in one aspect all of the human V genes.

In one aspect the inserted human DNA comprises at least 50% of the human heavy chain diversity (D) genes, such as at least 60%, at least 70%, at least 80%, at least 90%, and in one aspect all of the human D genes.

In one aspect the inserted human DNA comprises at least 50% of the human heavy chain joining (J) genes, such as at least 60%, at least 70%, at least 80%, at least 90%, and in one aspect all of the human J genes.

In one aspect the inserted human DNA comprises at least 50% of the human light chain Variable (V) genes, such as at least 60%, at least 70%, at least 80%, at least 90%, and in one aspect all of the human light chain V genes.

In one aspect the inserted human DNA comprises at least 50% of the human light chain joining (J) genes, such as at least 60%, at least 70%, at least 80%, at least 90%, and in one aspect all of the human light chain J genes.

The inserted human genes may be derived from the same individual or different individuals, or be synthetic or represent human consensus sequences.

Although the number of V D and J regions is variable between human individuals, in one aspect there are considered to be 51 human V genes, 27 D and 6 J genes on the heavy chain, 40 human V genes and 5 J genes on the kappa light chain and 29 human V genes and 4 J genes on the lambda light chain (Janeway and Travers, Immunobiology, Third edition)

In one aspect the human heavy chain locus inserted into the non-human mammal contains the full repertoire of human V, D and J regions, which in the genome is in functional arrangement with the non-human mammal constant regions such that functional chimaeric antibodies can be produced between the human variable and non-human mammal constant regions. This total inserted human heavy chain genetic material is referred to herein as the human IgH VDJ region, and comprises DNA from a human genome that encodes all the exons encoding human V, D and J portions and suitably also the associated introns. Similarly, reference to the human Ig light chain kappa V and J regions herein refers to human DNA comprising all the exons encoding V and J regions and suitably also the associated introns of the human genome. Reference to the human Ig light chain lambda V and J regions herein refers to human DNA comprising all the exons encoding V and J regions and suitably also the associated introns of the human genome.

Human variable regions are suitably inserted upstream of a non-human mammal constant region, the latter comprising all of the DNA required to encode the full constant region or a sufficient portion of the constant region to allow the formation of an effective chimaeric antibody capable of specifically recognising an antigen.

In one aspect the chimaeric antibodies or antibody chains have a part of a host constant region sufficient to provide one or more effector functions seen in antibodies occurring naturally in a host mammal, for example that they are able interact with Fc receptors, and/or bind to complement.

Reference to a chimaeric antibody or antibody chain having a host non mammal constant region herein therefore is not limited to the complete constant region but also includes chimaeric antibodies or chains which have all of the host constant region, or a part thereof sufficient to provide one or more effector functions. This also applies to non-human mammals and cells and methods of the invention in which human variable region DNA may be inserted into the host genome such that it forms a chimaeric antibody chain with all or part of a host constant region. In one aspect the whole of a host constant region is operably linked to human variable region DNA.

The host non-human mammal constant region herein is preferably the endogenous host wild-type constant region located at the wild type locus, as appropriate for the heavy or light chain. For example, the human heavy chain DNA is suitably inserted on mouse chromosome 12, suitably adjacent the mouse heavy chain constant region.

In one aspect the insertion of the human DNA, such as the human VDJ region is targeted to the region between the J4 exon and the Cμ locus in the mouse genome IgH locus, and in one aspect is inserted between co-ordinates 114,667,090 and 114,665,190, or at co-ordinate 114,667,091, after 114,667,090. In one aspect the insertion of the human DNA, such as the human light chain kappa VJ is targeted into mouse chromosome 6 between co-ordinates 70,673,899 and 70,675,515, suitably at position 70,674,734, or an equivalent position in the lambda mouse locus on chromosome 16.

In one aspect the host non-human mammal constant region for forming the chimaeric antibody may be at a different (non endogenous) chromosomal locus. In this case the inserted human DNA, such as the human variable VDJ or VJ region(s) may then be inserted into the non-human genome at a site which is distinct from that of the naturally occurring heavy or light constant region. The native constant region may be inserted into the genome, or duplicated within the genome, at a different chromosomal locus to the native position, such that it is in a functional arrangement with the human variable region such that chimaeric antibodies of the invention can still be produced.

In one aspect the human DNA is inserted at the endogenous host wild-type constant region located at the wild type locus between the host constant region and the host VDJ region.

Reference to location of the variable region upstream of the non-human mammal constant region means that there is a suitable relative location of the two antibody portions, variable and constant, to allow the variable and constant regions to form a chimaeric antibody or antibody chain in vivo in the mammal. Thus, the inserted human DNA and host constant region are in functional arrangement with one another for antibody or antibody chain production.

In one aspect the inserted human DNA is capable of being expressed with different host constant regions through isotype switching. In one aspect isotype switching does not require or involve trans switching. Insertion of the human variable region DNA on the same chromosome as the relevant host constant region means that there is no need for trans-switching to produce isotype switching.

As explained above, the transgenic loci used for the prior art models were of human origin, thus even in those cases when the transgenes were able to complement the mouse locus so that the mice produced B-cells producing fully human antibodies, individual antibody affinities rarely reached those which could be obtained from intact (non-transgenic) animals. The principal reason for this (in addition to repertoire and expression levels described above) is the fact that the control elements of the locus are human. Thus, the signalling components, for instance to activate hyper-mutation and selection of high affinity antibodies are compromised.

In contrast, in the present invention, host non-human mammal constant regions are maintained and it is preferred that at least one non-human mammal enhancer or other control sequence, such as a switch region, is maintained in functional arrangement with the non-human mammal constant region, such that the effect of the enhancer or other control sequence, as seen in the host mammal, is exerted in whole or in part in the transgenic animal.

This approach above is designed to allow the full diversity of the human locus to be sampled, to allow the same high expression levels that would be achieved by non-human mammal control sequences such as enhancers, and is such that signalling in the B-cell, for example isotype switching using switch recombination sites, would still use non-human mammal sequences.

A mammal having such a genome would produce chimaeric antibodies with human variable and non-human mammal constant regions, but these could be readily humanized, for example in a cloning step. Moreover the in vivo efficacy of these chimaeric antibodies could be assessed in these same animals.

In one aspect the inserted human IgH VDJ region comprises, in germline configuration, all of the V, D and J regions and intervening sequences from a human.

In one aspect 800-1000 kb of the human IgH VDJ region is inserted into the non-human mammal IgH locus, and in one aspect a 940, 950 or 960 kb fragment is inserted. Suitably this includes bases 105,400,051 to 106,368,585 from human chromosome 14.

In one aspect the inserted IgH human fragment consists of bases 105,400,051 to 106,368,585 from chromosome 14. In one aspect the inserted human heavy chain DNA, such as DNA consisting of bases 105,400,051 to 106,368,585 from chromosome 14, is inserted into mouse chromosome 12 between the end of the mouse J4 region and the Eμ region, suitably between co-ordinates 114,667,090 and 114,665, 190, or at co-ordinate 114,667,091, after 114,667,090. In one aspect the insertion is between co-ordinates 114,667,089 and 114,667,090 (co-ordinates refer to NCBI m37, for the mouse C57BL/6J strain), or at equivalent position in another non-human mammal genome.

In one aspect the inserted human kappa VJ region comprises, in germline configuration, all of the V and J regions and intervening sequences from a human. Suitably this includes bases 88,940,356 to 89,857,000 from human chromosome 2, suitably approximately 917 kb. In a further aspect the light chain VJ insert may comprise only the proximal clusters of V segments and J segments. Such an insert would be of approximately 473 kb. In one aspect the human light chain kappa DNA, such as the human IgK fragment of bases 88,940,356 to 89,857,000 from human chromosome 2, is suitably inserted into mouse chromosome 6 between co-ordinates 70,673,899 and 70,675,515, suitably at position 70,674,734. These co-ordinates refer to NCBI36 for the human genome, ENSEMBL Release 54 and NCBIM37 for the mouse genome, relating to mouse strain C57BL/6J.

In one aspect the human lambda VJ region comprises, in germline configuration, all of the V and J regions and intervening sequences from a human.

Suitably this includes analogous bases to those selected for the kappa fragment, from human chromosome 2.

A cell or non-human mammal of the invention, in one embodiment, comprises an insertion of human heavy chain variable region DNA between co-ordinates 114, 666, 183 and 114, 666, 725, such as between 114 666 283 and 114 666 625, optionally between co-ordinates 114,666,335 and 114, 666,536, optionally between 114,666,385 and 114,666,486, or between 114,666,425 and 114,666,446, or between 114, 666,435 and 114,666,436 of mouse chromosome 12 with reference to NCBIM37 for the mouse genome, relating to mouse strain C57BL/6J or an equivalent position of mouse chromosome 12 from a different mouse strain or an equivalent position in the genome of another non-human vertebrate, e.g., a rat. The insertion between co-ordinates 114, 666,435 and 114,666,436 relating to mouse strain C57BL/6J is equivalent to an insertion between co-ordinates 1207826 and 1207827 on chromosome 12 with reference to the 129/SvJ genomic sequence of the GenBank® access number NT114985.2. An insertion may be made at equivalent position in another genome, such as another mouse genome. In an example of this embodiment, the cell or mammal of the invention comprises a human IgH VDJ region which comprises or consists of nucleotides 106,328,851-107,268,544, such as nucleotides 106,328,901-107,268,494, such as nucleotides 106,328,941-107,268,454, such as nucleotides 106,328,951-107,268,444 of human Chromosome 14, with reference to the GRCH37/hg19 sequence database, or insertion of equivalent nucleotides relating to chromosome 14 from a different human sequence or database. The human insertion may be made between the regions indicated above.

A cell or mammal of the invention, in one embodiment, comprises an insertion of the human kappa VJ region, suitably comprising or consisting of, in germline configuration, all of the V and J regions and intervening sequences from a human, the insertion of the human DNA being made between co-ordinates 70,673,918-70,675,517, such as between co-ordinates 70, 674,418 and 70 675, 017, such as between co-ordinates 70,674, 655-70,674,856, such as between co-ordinates 70,674, 705-70,674,906, such as between co-ordinates 70,674, 745-70,674,766, such as between co-ordinates 70,674,755 and 70,674,756 of mouse chromosome 6, numbering with reference to NCBIM37 for the mouse genome, relating to mouse strain C57BL/6J, or an insertion at an equivalent position in another genome, such as another mouse genome. In an example of this embodiment, a cell or mammal of the invention comprises an insertion of nucleotides 89,159,079-89,630,437 and/or 89,941,714-90,266,976 of human chromosome 2 with reference to the GRCH37/hg19 sequence database (or equivalent nucleotides relating to chromosome 2 from a different human sequence or database), such as an insertion of these 2 discrete fragments without the intervening sequence, or an insertion of the complete 89,159,079-90,266,976 region.

The insertion may comprise, or consist, of:
(i) nucleotides 89,158,979-89,630,537, such as 89,159, 029-89,630,487, such as 89,159,069-89,630,447, such as 89,159,079-89,630,437, optionally in addition to fragment (ii) below
(ii) nucleotides 89,941,614-90,267,076, such as 89,941, 664-90,267,026, such as 89, 941,704-90,266,986, such as 89,941,714-90,266,976; optionally in addition to fragment (i)
(iii) nucleotides 89,158,979-90,267,076, such as nucleotides 89,159,079-90,266,976.

The human insertion may be made between the regions indicated above.

In an embodiment, a cell or mammal of the invention comprises an insertion of a human lambda region which comprises at least one human Jλ region (e.g., a germline region) and at least one human Cλ region (e.g., a germline region), optionally $C_\lambda 6$ and/or $C_\lambda 7$. For example, the cell or mammal comprises a plurality of human Jλ regions, optionally two or more of $J_\lambda 1$, $J_\lambda 2$, $J_\lambda 6$ and $J_\lambda 7$, optionally all of $J_\lambda 1$, $J_\lambda 2$, $J_\lambda 6$ and $J_\lambda 7$. In an example, the cell or mammal comprises at least one human $J_\lambda$-$C_\lambda$ cluster, optionally at least $J_\lambda 7$-$C_\lambda 7$.

In one aspect the human JC cluster is inserted 3' of the last endogenous J lambda or is inserted 3' of the last endogenous J kappa region, suitably immediately 3' of these sequences, or substantially immediately 3' of these sequences.

In one aspect the insertion into the mouse lambda locus is made downstream of the endogenous C1 gene segment, for example where there is a 3' J1C1 cluster, suitably immediately 3' of the C1 segment, or substantially immediately 3' of the segment.

In one aspect (e.g. cell or non-human mammal) a human JC cluster is inserted into a kappa locus and any resulting cell or animal is heterozygous at that locus, such that the cell has one chromosome with human lambda DNA inserted into the kappa locus, and another chromosome with human kappa DNA at the endogenous kappa locus.

In an embodiment, a cell or mammal of the invention comprises a human EA enhancer.

A cell or mammal may of the invention comprise an inserted human lambda VJ region, suitably comprising or consisting of, in germline configuration, all of the V and J regions and intervening sequences from a human, the inserted region comprises or consisting of nucleotides 22,375,509-23,327,984, such as nucleotides 22,375,559-23, 327,934, such as nucleotides 22,375,599-23,327,894, such as nucleotides 22,375,609-23,327,884 from human Chromosome 22, with reference to the GRCH37/hg19 sequence database, or equivalent DNA from another human sequence or database. The insertion into the mouse genome may be made between co-ordinates 19,027,763 and 19,061,845, such as between co-ordinates 19, 037, 763 and 19, 051, 845, such as between co-ordinates 19,047,451 and 19,047,652, such as between co-ordinates 19,047,491 and 19,047,602, such as between co-ordinates 19,047,541 and 19,047,562, such as between co-ordinates 19,047,551 and 19,047,552 of mouse Chromosome 16 (with reference to NCBIM37 for the mouse genome, relating to mouse strain C57BL/6J, equivalent to co-ordinates 1,293,646-1,293,647 of the 129 SvJ genomic sequence in the sequence file of NT_039630.4), or may be an insertion at an equivalent position in other genome, such as another mouse genome. The insertion of the human lambda nucleic acid into the mouse genome may alternatively be made between co-ordinates 70,673,918 and 70,675,517, such as between co-ordinates 70, 674,418 and 70 675, 017, such as between co-ordinates 70,674,655 and 70,674,856, such as between co-ordinates 70,674,705 and 70,674,806, such as between co-ordinates 70,674,745 and 70,674,766, such as between co-ordinates 70,674,755 and 70,674,756 of mouse Chromosome 6 (with reference to NCBIM37 for the mouse genome, relating to mouse strain C57BL/6J) or equivalent in another genome. The human insertion may be made between the regions indicated above.

All specific human fragments described above may vary in length, and may for example be longer or shorter than defined as above, such as 500 bases, 1 KB, 2K, 3K, 4K, 5 KB, 10 KB, 20 KB, 30 KB, 40 KB or 50 KB or more, which suitably comprise all or part of the human V(D)J region, whilst preferably retaining the requirement for the final insert to comprise human genetic material encoding the complete heavy chain region and light chain region, as appropriate, as described above.

In one aspect the 5' end of the human insert described above is increased in length. Where the insert is generated in a stepwise fashion then the increase in length is generally in respect of the upstream (5') clone.

In one aspect the 3' end of the last inserted human gene, generally the last human J gene to be inserted is less than 2 kb, preferably less than 1 KB from the human-mouse join region.

In one aspect the non-human mammal comprises some or all of the human light chain kappa VJ region as disclosed herein but not the human light chain lambda VJ region.

In one aspect the cell or non-human mammal comprises a fully human lambda locus (lambda VJC regions from a human), a chimaeric kappa locus (human kappa VJ regions operatively linked to a host kappa constant region) and a chimaeric heavy chain locus, having a human VDJ region operatively linked to a host heavy chain constant region.

In a further aspect the genome comprises an insertion of V, D (heavy chain only) and J genes as described herein at the heavy chain locus and one light chain locus, or at the heavy chain locus and both light chain loci. Preferably the genome is homozygous at one, or both, or all three loci.

In another aspect the genome may be heterozygous at one or more of the loci, such as heterozygous for DNA encoding a chimaeric antibody chain and native (host cell) antibody chain.

In one aspect the genome may be heterozygous for DNA capable of encoding 2 different antibody chains of the invention, for example, comprising 2 different chimaeric heavy chains or 2 different chimaeric light chains.

In one aspect the invention relates to a non-human mammal or cell, and methods for producing said mammal or cell, as described herein, wherein the inserted human DNA, such as the human IgH VDJ region and/or light chain V, J regions are found on only one allele and not both alleles in the mammal or cell. In this aspect a mammal or cell has the potential to express both an endogenous host antibody heavy or light chain and a chimaeric heavy or light chain.

In a further aspect of the invention the human VDJ region, or light chain VJ region, is not used in its entirety, but parts of the equivalent human VDJ or VJ region, such as the exons, from other species may be used, such as one or more V, D, or J exons from other species, or regulatory sequences from other species. In one aspect the sequences used in place of the human sequences are not human or mouse. In one aspect the sequences used may be from rodent, or, primate such as chimp. For example, 1, 2, 3, 4, or more, or all of the J regions from a primate other than a human may be used to replace, one, 2, 3, 4, or more or all of the human J exons in the VDJ/VJ region of the cells and animals of the invention.

In a further aspect the inserted human DNA, such as the human IgH VDJ region, and/or light chain VJ regions, may be inserted such that they are operably linked in the genome with a mu constant region from a non-human, non-mouse species, such as a rodent or primate sequence, such as a rat sequence.

Other non-human, non-mouse species from which DNA elements may be used in the present invention include rabbits, lamas, dromedary, alpacas, camels and sharks.

In one aspect the inserted human DNA, such as the human VDJ or VJ region, is not operably linked to the endogenous host mu sequence but rather to a non-host mu sequence.

Operable linkage suitably allows production of an antibody heavy or light chain comprising the human variable region.

In one aspect the inserted human DNA, such as the human IgH VDJ region (and/or light chain VJ regions) may be inserted into the host chromosome together with mu constant region nucleic acid which is not host mu constant region nucleic acid, and preferably is a mu constant region from a non-mouse, non-human species. Suitably the inserted human DNA, such as the human VDJ region (and/or light chain VJ regions) is operably linked to a non-human, non-mouse mu, and is able to form a chimaeric antibody heavy or light chain. In another aspect a non-mouse, non-human mu may be inserted into the host chromosome on a separate genetic element to that of the human variable region, or at a different location in the genome, suitably operably linked to the variable region such that a chimaeric antibody heavy or light can be formed.

In an additional aspect the invention relates to a non-human mammal or a cell whose genome comprises a plurality of human IgH V regions, one or more human D regions and one or more human J regions upstream of a host non-human mammal light chain constant region, arranged such that the cell or mammal is able to express a chimaeric antibody chain. The invention also relates to a non-human mammal or a cell whose genome additionally or alternatively comprises a plurality of human Ig light chain V regions, and one or more human J regions upstream of a host non-human mammal heavy chain constant region, such that the cell or mammal is able to express a chimaeric antibody chain. The cell or mammal may be able to express an antibody having both heavy and light chains, including at least one chimaeric antibody chain, as disclosed above.

The inserted human heavy chain variable regions may be any of those described herein, and may be inserted at the positions described above for insertion 5' of the lambda and kappa constant regions. Likewise the inserted human light chain variable regions may be those described above, and may be inserted at the positions described above for insertion 5' of the heavy chain constant region.

For example, the genome or the cell or non-human mammal of the invention may encode an antibody comprising an antibody chain having a human heavy chain variable region upstream of a mouse light chain constant region, or an antibody chain having a human light chain variable region upstream of a mouse heavy chain constant region, in combination with one of:
- a fully human antibody light chain;
- a fully human antibody heavy chain;
- a non-human vertebrate (e.g., mouse or rat) antibody light chain;
- a non-human vertebrate (e.g., mouse or rat) antibody heavy chain;
- a chimaeric non-human vertebrate (e.g., mouse or rat)—human antibody chain;
- an antibody chain having a human heavy chain variable region upstream of a non-human vertebrate (e.g., mouse or rat) light chain constant region;
- an antibody chain having a human light chain variable region upstream of a non-human vertebrate (e.g., mouse or rat) heavy chain constant region.

The invention also relates to a transgene encoding a plurality of human IgH V regions, one or more human D regions and one or more human J regions upstream of a host non-human mammal light chain constant region, optionally comprised within a vector.

The invention also relates to a transgene encoding a plurality of human Ig light chain V regions, and one or more human light chain J regions upstream of a host non-human mammal heavy chain constant region, optionally comprised within a vector.

In one aspect the invention relates to a cell, or non-human mammal, the genome of which comprises: one or more human Ig light chain kappa V regions and one or more human Ig light chain kappa J regions upstream of all or part of the human kappa constant region.

In another aspect the invention relates to a cell, or non-human mammal, the genome of which comprises: one or more human Ig light chain lambda V regions and one or more human Ig light chain lambda J regions upstream of all or part of the human lambda constant region.

Suitably the light chain VJ and C regions are able to form antibody chains in vivo capable of specifically reacting with an antigen.

In one aspect of the invention there is no non-human coding sequence in the inserted light chain region.

In such aspects a human kappa and/or lambda region is inserted into the genome, in combination with insertion of the heavy chain VDJ region or part thereof, upstream of the host heavy chain constant region as disclosed herein.

The cell or non-human mammal of the invention may comprise:
(a) a plurality of human IgH V regions, one or more human D regions and one or more human J regions upstream of the host non-human mammal constant region; and
(b) one or more human Ig light chain kappa V regions and one or more human Ig light chain kappa J regions upstream of all or part of the non-human kappa constant region, wherein the non-human mammal is able to produce a repertoire of antibodies having an antibody chain comprising non-human mammal constant region and a human variable region.

The cell or non-human mammal of the invention may comprise
(a) a plurality of human IgH V regions, one or more human D regions and one or more human J regions upstream of the host non-human mammal constant region; and
one or more human Ig light chain lambda V regions and one or more human Ig light chain lambda J regions upstream of the host non-human mammal lambda constant region;
wherein the non-human mammal is able to produce a repertoire of antibodies having an antibody chain comprising a non-human mammal constant region and a human variable region.

Suitably the insertion of the human VJC light chain DNA, or part thereof as disclosed above, is made at the equivalent mouse locus. In one aspect the human light chain kappa VJC DNA, or part thereof, is inserted immediately upstream or downstream of the mouse kappa VJC region. In one aspect, the human light chain lambda VJC region or part thereof is inserted immediately upstream or downstream of the mouse lambda VJC region. In one aspect only the human kappa VJC locus is inserted and not the human lambda VJC locus. In one aspect only the human lambda VJC locus is inserted and not the human kappa VJC locus. Insertions may be made using the techniques disclosed herein, and suitably do not remove the host sequences from the genome. In one aspect the non-human mammal host VJC sequences may be inactivated in some way, by mutation, or inversion, or by insertion of the human variable region DNA, or by any other means. In one aspect the cell or non-human mammal of the invention may comprise an insertion of the complete VJC human region.

The human kappa variable region DNA might be inserted into the genome in functional arrangement with a lambda constant region, for example inserted upstream of a lambda constant region. Alternatively human lambda region variable DNA might be inserted in functional arrangement with a kappa constant region, for example inserted upstream of a kappa constant region.

In one aspect one or more non-human mammal control sequences such as the enhancer sequence(s) is maintained upstream of the nonhuman mammal Mu constant region, suitably in its native position with respect to the distance from the constant region.

In one aspect one or more non-human mammal control sequences such as an enhancer sequence(s) are maintained downstream of the nonhuman mammal Mu constant region, suitably in its native position with respect to the distance from the constant region.

In one aspect a non-human mammal switch sequence, suitably the endogenous switch sequence, is maintained upstream of the non-human mammal Mu constant region, suitably in its native position with respect to distance from the constant region.

In such location the host enhancer or switch sequences are operative in vivo with the host constant region sequence(s).

In one aspect a switch sequence is neither human, nor native in the non-human mammal, for example in one aspect a non-human mammal switch sequence is not a mouse or human switch sequence. The switch sequence may be, for example, a rodent or primate sequence, or a synthetic sequence. In particular the switch sequence may be a rat sequence where the non-human mammal is a mouse. By way of example, a mouse or human constant mu sequence may be placed under the control of a switch sequence from a rat, or chimp, or other switch sequence, suitably capable of allowing isotype switching to occur in vivo.

In one aspect the switch sequence of the invention is a switch sequence comprising 3, 4, 5, 6 or more (up to 82) contiguous repeats of the repeat sequence GGGCT (SEQ ID no 46-50), such as a rat switch sequence. By "rat switch" herein it is meant that the switch is a wild-type switch corresponding to a switch from a rat genome or derived from such a switch.

In one aspect the switch sequence of the invention is a rat switch sequence comprising the following repeats: GAGCT (296 repeats; SEQ ID No 18), GGGGT (50 repeats; SEQ ID No 19), and GGGCT (83 repeats; SEQ ID No 20).

In one example the rat switch sequence comprises or consists of the sequence of SEQ ID no 1.

In these embodiments, and where the non-human mammal is a mouse or the cell is a mouse cell, the switch is optionally a rat switch as described herein.

Alternatively, the switch sequence present in cells or mammal of the invention is a mouse switch, e.g., is from a mouse such as a mouse 129 strain or mouse C57 strain, or from a strain derived therefrom, optionally comprising or consisting of the sequence of SEQ ID no 4 or 5. By "mouse switch" herein it is meant that the switch is a wild-type switch corresponding to a switch from a mouse genome or derived from such a switch. In this embodiment, and where the non-human mammal is a mouse or the cell is a mouse cell, the mouse switch sequence is optionally the endogenous switch or is a mouse switch from another mouse strain.

The cell or mammal of the invention may therefore comprise a human or non-human mammal switch sequence and a human or non-human mammal enhancer region or regions. They may be upstream of a human or non-human mammal constant region. Preferably the control sequences are able to direct expression or otherwise control the production of antibodies comprising a constant region with which they are associated. One combination envisaged is a rat switch with mouse enhancer sequences and mouse constant regions in a mouse cell.

In one aspect the invention relates to a cell, preferably a non-human cell, or non-human mammal comprising an immunoglobulin heavy chain or light chain locus having DNA from 3 or more species. For example, the cell or animal may comprise host cell constant region DNA, one or more human V, D or J coding sequences and one or more non-human, non-host DNA regions that are able to control a region of the immunoglobulin locus, such as a switch sequence, promoter or enhancer which are able to control expression or isotype switching in vivo of the Ig DNA. In one aspect the cell or animal is a mouse and comprises additionally human DNA from the human Ig locus and additionally a non-mouse DNA sequence, such as a rat DNA sequence, capable of regulation of the mouse or human DNA.

In another aspect the invention relates to a cell, preferably non-human cell, or non-human mammal comprising an immunoglobulin heavy chain or light chain locus having DNA from 2 or more different human genomes. For example, it could comprise heavy chain V(D)J sequences from more than one human genome within a heavy or light chain, or heavy chain VDJ DNA from one genome and light chain VJ sequences from a different genome.

In one aspect the invention relates to a DNA fragment or cell or non-human mammal comprising an immunoglobulin heavy chain or light chain locus, or part thereof, having DNA from 2 or more species, where one species contributes a non-coding region such as a regulatory region, and the other species coding regions such as V, D, J or constant regions.

In one aspect the human promoter and/or other control elements that are associated with the different human V, D or J regions are maintained after insertion of the human VDJ into the mouse genome.

In a further aspect one or more of the promoter elements, or other control elements, of the human regions, such as the human V regions, are optimised to interact with the transcriptional machinery of a non-human mammal.

Suitably a human coding sequence may be placed under the control of an appropriate non-human mammal promoter, which allows the human DNA to be transcribed efficiently in the appropriate non-human animal cell. In one aspect the human region is a human V region coding sequence, and a human V region is placed under the control of a non-human mammal promoter.

The functional replacement of human promoter or other control regions by non-human mammal promoter or control regions may be carried out by use of recombineering, or other recombinant DNA technologies, to insert a part of the human Ig region (such as a human V region) into a vector (such as a BAC) containing a non-human Ig region. The recombineering/recombinant technique suitably replaces a portion of the non-human (e.g. mouse) DNA with the human Ig region, and thus places the human Ig region under control of the non-human mammal promoter or other control region. Suitably the human coding region for a human V region replaces a mouse V region coding sequence. Suitably the human coding region for a human D region replaces a mouse D region coding sequence. Suitably the human coding region for a human J region replaces a mouse J region coding sequence. In this way human V, D or J regions may be placed under the control of a non-human mammal promoter, such as a mouse promoter.

In one aspect the only human DNA inserted into the non-human mammalian cell or animal are V, D or J coding regions, and these are placed under control of the host regulatory sequences or other (non-human, non-host) sequences, In one aspect reference to human coding regions includes both human introns and exons, or in another aspect simply exons and no introns, which may be in the form of cDNA.

It is also possible to use recombineering, or other recombinant DNA technologies, to insert a non-human-mammal (e.g. mouse) promoter or other control region, such as a promoter for a V region, into a BAC containing a human Ig region. A recombineering step then places a portion of human DNA under control of the mouse promoter or other control region.

The approaches described herein may also be used to insert some or all of the V, D and J regions from the human heavy chain upstream of a light chain constant region, rather than upstream of the heavy chain constant region. Likewise some or all of the human light chain V and J regions may be inserted upstream of the heavy chain constant region. Insertion may be at the endogenous constant region locus, for example between the endogenous constant and J region, and may be of some, or all, of the V, D or J genes alone, excluding promoter or enhancer sequences, or may be of some, or all, of the V, D or J genes with one or more or all respective promoter or enhancer sequences. In one aspect the full repertoire of V, D or J fragments in germline orientation may be inserted upstream and in functional arrangement with a host constant region.

Thus the present invention allows V and/or D and/or J regions from a human, or any species, to be inserted into a chromosome of a cell from a different species that comprises a constant region, allowing a chimaeric antibody chain to be expressed.

In one aspect the invention requires only that some human variable region DNA is inserted into the genome of a non-human mammal in operable arrangement with some, or all, of the human heavy chain constant region at the region of the endogenous heavy chain constant region locus such that an antibody chain can be produced. In this aspect of the invention and where human light chain DNA is additionally inserted, the light chain DNA insertion can be in the form of a completely human construct, having both human variable DNA and human constant region DNA, or have human variable region DNA and constant region DNA from a non-human, non-host species. Other variations are also possible, such as insertion of both of the light chain human variable region and host genome constant region. In addition the insertion of said light chain transgenes need not be at the equivalent endogenous locus, but may be anywhere in the genome. In such a scenario the cell or mammal may produce chimaeric heavy chains (comprising human variable region DNA and mouse constant region DNA) and light chains comprising human variable and human constant region DNA. Thus in one aspect of the invention the lambda and or kappa human variable region DNA can be inserted upstream of the endogenous locus, or downstream, or indeed on a different chromosome to the endogenous locus, and inserted with or without constant region DNA.

As well insertion of human light chain DNA upstream of the host non-human mammal constant region, a further aspect of the invention relates to insertion of one or both light chain human variable regions downstream of the equivalent endogenous locus constant region, or elsewhere in the genome.

Generally, insertion of human variable region DNA at or close to the equivalent endogenous locus in the recipient genome is preferred, for example within 1, 2, 3, 4, 5, 6, 7, 8, 9, or 10 kb of the boundary (upstream or downstream) of a host immunoglobulin locus.

Thus in one aspect the invention can relate to a cell or non-human mammal whose genome comprises:
 (a) a plurality of human IgH V regions, one or more human D regions and one or more human J regions upstream of the host non-human mammal constant region; and
 (b) one or more human Ig light chain kappa V regions and one or more human Ig light chain kappa J regions, and/or, one or more human Ig light chain lambda V regions and one or more human Ig light chain lambda J regions;
wherein the non-human mammal is able to produce a repertoire of chimaeric antibodies, or chimaeric light or heavy chains, having a non-human mammal constant region and a human variable region.

In one particular aspect the genome of the cell or non-human mammal comprises:
 a plurality of human IgH V regions, one or more human D regions and one or more human J regions upstream of the host non-human mammal constant region;
 one or more human Ig light chain kappa V regions and one or more human Ig light chain kappa J regions upstream of the host non-human mammal kappa constant region, and
 one or more human Ig light chain lambda V regions and one or more human Ig light chain lambda J regions downstream of the host non-human mammal lambda constant region,
 optionally in which the human lambda variable region may be inserted upstream or downstream of the endogenous host lambda locus in operable linkage with a human lambda constant region, such that the non-human mammal or cell can produce fully human antibody light chains and chimaeric heavy chains.

In a further, different, aspect of the invention, the use of the methods of the invention allows a locus to be built up in a stepwise manner by sequential insertions, and thus allows for the insertion of human variable DNA together with human or non-human constant region DNA at any suitable location in the genome of a non-human host cell. For example, methods of the invention can be used to insert human immunoglobulin variable region DNA together with constant region DNA from the host genome anywhere in the genome of a non-human host cell, allowing a chimaeric antibody chain to be produced from a site other than the endogenous heavy region. Any human heavy chain or light chain DNA construct contemplated above can be inserted into any desired position into the genome of a non-human host cell using the techniques described herein. The present invention thus also relates to cells and mammals having genomes comprising such insertions.

The invention also relates to a vector, such as a BAC, comprising a human V, D or J region in a functional arrangement with a non-human mammal promoter, or other control sequence, such that the expression of the human V, D or J region is under the control of the non-human mammal promoter in a cell of the non-human mammal, such as an ES cell, in particular once inserted into the genome of that cell.

The invention also relates to cells and non-human mammals containing said cells, which cells or mammals have a human V, D or J region in a functional arrangement with a non-human mammal promoter, or other control sequence, such that the expression of the human V, D or J region is under the control of the non-human mammal promoter in the cells or mammal.

Generally, one aspect of the invention thus relates to a non-human mammal host cell capable of expression of a human V, D or J coding sequence under the control of a host promoter or control region, the expression capable of producing a humanised antibody having a human variable domain and non-human mammal constant region.

In one aspect the invention relates to a cell, such as a non mammalian cell, such as an ES cell, the genome of which comprises
 (a) a plurality of human IgH V regions, one or more human D regions and one or more human J regions upstream of the host non-human mammal constant region; and
 (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;

In another aspect the invention relates to a cell, such as a non-human mammal cells, such as ES cells whose genome comprises
 (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and (b) optionally one or more human IgH V regions, one or more human D regions and one or more human J regions upstream of the host non-human mammal constant region In one aspect the cell is an ES cell is capable of developing into a non-human mammal able to produce a repertoire of antibodies which are chimaeric, said chimaeric antibodies having a non-human mammal constant region and a human variable region. Optionally the genome of the cell is modified to prevent expression of fully host-species specific antibodies.

In one aspect the cell is an induced pluripotent stem cell (iPS cell).

In one aspect cells are isolated non-human mammalian cells.

In one aspect a cell as disclosed herein is preferably a non-human mammalian cell.

In one aspect the cell is a cell from a mouse strain selected from C57BL/6, M129 such as 129/SV, BALB/c, and any hybrid of C57BL/6, M129 such as 129/SV, or BALB/c.

The invention also relates to a cell line which is grown from or otherwise derived from cells as described herein, including an immortalised cell line. The cell line may comprise inserted human V, D or J genes as described herein, either in germline configuration or after rearrangement following in vivo maturation. The cell may be immortalised by fusion (e.g., electrofusion or using PEG according to standard procedures) to a tumour cell (e.g., P3X63-Ag8.653 (obtainable from LGC Standards; CRL-1580), SP2/0-Ag14 (obtainable from ECACC), NSI or NS0), to provide an antibody producing cell and cell line, or be made by direct cellular immortalisation.

The present invention also relates to vectors for use in the invention. In one aspect such vectors are BACs (bacterial artificial chromosomes). It will be appreciated that other cloning vectors may be used in the invention, and therefore reference to BACs herein may be taken to refer generally to any suitable vector.

In one aspect BACs used for generation of human DNA to be inserted, such as the VDJ or VJ regions are trimmed so that in the final human VDJ or VJ region or part thereof in the non-human mammal, no sequence is duplicated or lost when compared to the original human genomic sequence.

In one aspect the invention relates to a vector comprising an insert, preferably comprising a region of human DNA from some of the human VDJ or VJ locus, flanked by DNA which is not from that locus. The flanking DNA may comprise one or more selectable markers or one or more site specific recombination sites. In one aspect the vector comprises 2 or more, such as 3, heterospecific and incompatible site specific recombination sites. In one aspect the site specific recombination sites may be loxP sites, or variants thereof, or FRT sites or variants thereof. In one aspect the vector comprises one or more transposon ITR (inverted terminal repeat) sequences.

In one aspect the non-human animals of the invention suitably do not produce any fully humanised antibodies. In one aspect this is because there is no DNA inserted from the human constant region. Alternatively there is no human constant region DNA in the genome capable of forming an antibody in conjunction with the inserted human variable region DNA component, for example due to mutation within any human constant region DNA or distance from any constant region human DNA and human variable region DNA.

In one aspect human light chain constant region DNA may be included in the cell genome, such that a fully human lambda or kappa human antibody chain might be generated, but this would only be able to form an antibody with a chimaeric heavy chain, and not produce a fully human antibody having human variable and constant regions.

In one aspect the non-human mammal genome is modified to prevent expression of fully host-species specific antibodies. Fully host species specific antibodies are antibodies that have both variable and constant regions from the host organism. In this context the term 'specific' is not intended to relate to the binding of the antibodies produced by the cells or animals of the invention but rather to the origin of the DNA which encodes those antibodies.

In one aspect the non-human mammal genome is modified to prevent expression of the native (fully host species specific) antibodies in the mammal by inactivation of all or a part of the host non-human mammal Ig loci. In this context, inactivation or prevention of endogenous antibody or gene segment usage (using any inactivation technique described herein) is, for example, substantially complete inactivation or prevention (substantially 100%, i.e., essentially none (e.g., less than 10, 5, 4, 3, 2, 1 or 0.5%) of the endogenous antibody chain (e.g., no endogenous heavy chains) is expressed). This can be determined, for example, at the antibody chain (protein) level by assessing the antibody repertoire produced by the non-human vertebrate, mammal or at the nucleotide level by assessing mRNA transcripts of antibody chain loci, e.g., using RACE. In an embodiment, inactivation is more than 50% (i.e., 50% or less of the antibodies or transcripts are of an endogenous antibody chain), 60%, 70%, 80%, 85%, 90%, 95%, 96%, 97%, 98% or 99%. For example, in an embodiment, endogenous heavy chain expression is substantially inactivated such that no more than 85%, 90%, 95%, 96%, 97%, 98% or 99% of the heavy chain repertoire of the vertebrate (mammal) is provided by endogenous heavy chains. For example, endogenous heavy chain expression is substantially inactivated such that substantially none of the heavy chain repertoire of the vertebrate (mammal) is provided by endogenous heavy chains. For example, in an embodiment, endogenous heavy chain expression is substantially inactivated such that no more than 85%, 90%, 95%, 96%, 97%, 98% or 99% of the kappa chain repertoire of the vertebrate (mammal) is provided by endogenous kappa chains. For example, endogenous kappa chain expression is substantially inactivated such that substantially none of the kappa chain repertoire of the vertebrate (mammal) is provided by endogenous kappa chains. For example, in an embodiment, endogenous heavy chain expression is substantially inactivated such that no more than 85%, 90%, 95%, 96%, 97%, 98% or 99% of the lambda chain repertoire of the vertebrate (mammal) is provided by endogenous lambda chains. For example, endogenous lambda chain expression is substantially inactivated such that substantially none of the lambda chain repertoire of the vertebrate (mammal) is provided by endogenous lambda chains.

In one aspect this is achieved by inversion of all or part of the non-human mammal VDJ region, or VJ region, optionally by insertion of one or more site specific recombinase sites into the genome and then use of these sites in recombinase-mediated excision or inversion of all or a part of the non-human mammal Ig locus. In one aspect a double inversion, may be employed, the first to move the V(D)Js away from the endogenous locus and then a more local inversion which puts them in the correct orientation. In one aspect a single loxP site is used to invert the non-human mammal VDJ region to a centromeric locus or telomeric locus.

In one example, a mouse or mouse cell of the invention comprises inverted endogenous heavy chain gene segments (e.g., VH, D and JH, such as the entire endogenous heavy chain VDJ region) that are immediately 3' of position 119753123, 119659458 or 120918606 on an endogenous mouse chromosome 12. Optionally, the genome of the mouse or cell is homozygous for said chromosome 12.

The invention also provides: —

A cassette for inversion and inactivation of endogenous non-human vertebrate (e.g., mouse or rat) antibody chain gene segments, the segments being part of an antibody chain locus sequence on a chromosome of a non-human vertebrate (e.g., mouse or rat) cell (e.g., ES cell) wherein the sequence is flanked at its 3' end by a site-specific recombination site (e.g., lox, rox or frt), the cassette comprising a nucleotide sequence encoding an expressible label or selectable marker and a compatible site-specific recombination site (e.g., lox, rox or frt) flanked by a 5' and a 3' homology arm, wherein the homology arms correspond to or are homologous to adjacent stretches of sequence in the cell genome on a different chromosome or on said chromosome at least 10, 15, 20, 25, 30, 35, 40, 45 or 50 mb away from the endogenous gene segments.

The invention also provides: —

A cassette for inversion and inactivation of endogenous mouse antibody heavy chain gene segments, the segments being part of a heavy chain locus sequence on chromosome 12 of a mouse cell (e.g., ES cell) wherein the sequence is flanked at its 3' end by a site-specific recombination site (e.g., lox, rox or frt), the cassette comprising a nucleotide sequence encoding an expressible label or selectable marker and a compatible site-specific recombination site (e.g., lox, rox or frt) flanked by a 5' and a 3' homology arm, wherein the homology arms correspond to or are homologous to adjacent stretches of sequence in the mouse cell genome on a different chromosome or on chromosome 12 at least 10, 15, 20, 25, 30, 35, 40, 45 or 50 mb away from the endogenous gene segments.

The invention provides: —

A cassette for inversion and inactivation of endogenous mouse antibody heavy chain gene segments, the segments being part of a heavy chain locus sequence on chromosome 12 of a mouse cell (e.g., ES cell) wherein the sequence is flanked at its 3' end by a site-specific recombination site (e.g., lox, rox or frt), the cassette comprising a nucleotide sequence encoding an expressible label or selectable marker and a compatible site-specific recombination site (e.g., lox, rox or frt) flanked by a 5' and a 3' homology arm, wherein (i) the 5' homology arm is mouse chromosome 12 DNA from coordinate 119753124 to coordinate 119757104 and the 3' homology arm is mouse chromosome 12 DNA from coordinate 119749288 to 119753123; or (ii) the 5' homology arm is mouse chromosome 12 DNA from coordinate 119659459 to coordinate 119663126 and the 3' homology arm is mouse chromosome 12 DNA from coordinate 119656536 to 119659458; or (iii) the 5' homology arm is mouse chromosome 12 DNA from coordinate 120918607 to coordinate 120921930 and the 3' homology arm is mouse chromosome 12 DNA from coordinate 120915475 to 120918606.

Embodiment (i) results in an inversion of mouse chromosome 12 from coordinate 119753123 to coordinate 114666436.

Embodiment (ii) results in an inversion of mouse chromosome 12 from coordinate 119659458 to coordinate 114666436

Embodiment (iii) results in an inversion of mouse chromosome 12 from coordinate 12091806 to coordinate 114666436.

Thus, the invention provides a mouse or mouse cell whose genome comprises an inversion of a chromosome 12, wherein the inversion comprises inverted endogenous heavy chain gene segments (e.g., VH, D and JH, such as the entire endogenous heavy chain VDJ region); wherein the mouse comprises a transgenic heavy chain locus comprising a plurality of human VH gene segments, a plurality of human D segments and a plurality of human JH segments operably connected upstream of an endogenous constant region (e.g., C mu) so that the mouse or cell (optionally following differentiation into a B-cell) is capable of expressing an antibody comprising a variable region comprising sequences derived from the human gene segments; and wherein the inversion is (i) an inversion of mouse chromosome 12 from coordinate 119753123 to coordinate 114666436; (ii) an inversion of mouse chromosome 12 from coordinate 119659458 to coordinate 114666436; or (iii) an inversion of mouse chromosome 12 from coordinate 12091806 to coordinate 114666436.

In one embodiment, the endogenous gene segments are from a 129-derived mouse cell (e.g., segments from an AB2.1 cell) and the homology arms are isogenic DNA (i.e., identical to 129-derived endogenous sequences demarcated by the respective coordinates stated in (i) to (iii) above). Thus, no new sequence is created by homologous recombination using these homology arms. In another embodiment, the arms are from a mouse strain that is different from the endogenous strain. The site-specific recombination sites are mutually compatible and mutually inverted such that, on expression of an associated recombinase enzyme (eg, Cre, Dre or Flp), recombination between the site in the inserted inversion cassette and the site flanking the endogenous gene segments is carried out, thereby inverting and moving the endogenous gene segments far upstream (5') of their original location in the heavy chain locus. This inactivates endogenous heavy chain expression. Similarly, light chain inactivation can be performed by choosing the homology arms of the inversion cassette with reference to a chromosomal region spaced at least 10, 15, 20, 25, 30, 35, 40, 45 or 50 mb away from the endogenous light chain locus, the latter comprising a site-specific recombination site that is compatible with the site in the inversion cassette.

In one embodiment, the expressible label is a fluorescent label, e.g., GFP or a variant thereof (eg, YFP, CFP or RFP). Thus, a label is used instead of a selection marker, such as one that confers resistance to allow for selection of transformants.

The invention provides a method of inactivating gene segments of an endogenous antibody locus, the method comprising
(i) Providing a non-human vertebrate cell (eg, an ES cell, e.g., a mouse ES cell) whose genome comprises an antibody chain locus comprising endogenous variable region gene segments;
(ii) Targeting a site-specific recombination site to flank the 3' of the 3'-most of said endogenous gene segments;
(iii) Targeting a second site-specific recombination site at least 10 mb away from said endogenous gene segments, the second site being compatible with the first site inverted with respect to the first site;

(iv) Expressing a recombinase compatible with said sites to effect site-specific recombination between said sites, thereby inverting and moving said gene segments away from said locus, wherein the endogenous gene segments are inactivated; and (v) Optionally developing the cell into a progeny cell or vertebrate (e.g., mouse or rat) whose genome is homozygous for the inversion.

The genome of the progeny cell or vertebrate can comprise transgenic heavy and/or light chain loci, each capable of expressing antibody chains comprising human variable regions. Optionally, endogenous heavy and kappa light chain expression is inactivated by inverting endogenous heavy and kappa variable region gene segments according to the method of the invention. Optionally, endogenous lambda chain expression is also inactivated in this way.

In an alternative to the method and inversion cassettes of the invention, instead of inverting and moving variable region gene segments only, other parts of the endogenous locus can alternatively or additionally be inverted and moved to effect inactivation. For example, one or more endogenous regulatory elements (e.g., Smu and/or Emu) and/or one or more endogenous constant regions (e.g., Cmu and/or Cgamma) can be inverted and moved.

Sites that "flank" in the above contexts of the invention can be provided such that a site-specific recombination site immediately flanks the endogenous sequence or is spaced therefrom, e.g., by no more than 250, 200, 250, 100, 50 or 20 kb in the 3' direction.

In one aspect the non-human mammal genome into which human DNA is inserted comprises endogenous V, (D) and J regions, and the endogenous sequences have not been deleted.

The invention comprises a method for insertion of multiple DNA fragments into a DNA target, suitably to form a contiguous insertion in which the inserted fragments are joined together directly without intervening sequences. The method is especially applicable to the insertion of a large DNA fragment into a host chromosome which can be carried out in a stepwise fashion.

In one aspect the method comprises insertion of a first DNA sequence into a target, the sequence having a DNA vector portion and a first sequence of interest (X1); insertion of a second DNA sequence into the vector portion of the first sequence, the second DNA sequence having a second sequence of interest (X2) and a second vector portion; and then excising any vector sequence DNA separating X1 and X2 to provide a contiguous X1X2, or X2X1 sequence within the target. There is optionally insertion of a further one or more DNA sequences, each DNA sequence having a further sequence of interest (X3, . . . ) and a further vector portion, into the vector portion of the preceding DNA sequence, to build up a contiguous DNA fragment in the target.

The DNA target for insertion of the first DNA sequence may be a specific site or any point in the genome of a particular cell.

The general method is described herein in relation to the insertion of elements of the human VDJ region, but is applicable to insertion of any DNA region, from any organism, and in particular insertion of large DNA fragments of >100 kB, such as 100-250 kb, or even larger, such as that of the TCR or HLA. Features and approaches described herein in respect of the VDJ insertion may be equally applied to the any of the methods disclosed In one aspect the inserted DNA is human DNA, such as the human VDJ or VJ region, is built up in the genome of a cell, such as an ES cell, in a stepwise manner using 2, 3, 4, 5, 6, 7, 8, 9, 10, 11, 12, 13, 14, 15, 20 or more separate insertions for each heavy chain or light chain region. Fragments are suitably inserted at the same or substantially the same cell locus, e.g. ES cell locus, one after another, to form the complete VDJ or VJ region, or part thereof. The present invention also relates to cells and non-human animals comprising intermediates in the process whose genomes may comprise only a partial VDJ region, such as only human variable region DNA.

In a further aspect the method for producing a transgenic non-human mammal comprises the insertion of human VDJ or VJ regions upstream of the host non-human mammal constant region by step-wise insertion of multiple fragments by homologous recombination, preferably using an iterative process. Suitably fragments of approximately 100 KB from the human VDJ and VJ locus are inserted, suitably to form part of, or a complete, VDJ or VJ region after the final iteration of the insertion process, as disclosed herein.

In one aspect the insertion process commences at a site where an initiation cassette has been inserted into the genome of a cell, such as an ES cell, providing a unique targeting region. In one aspect the initiation cassette is inserted in the non-human mammal heavy chain locus, for use in insertion of human heavy chain DNA. Similarly an initiation cassette may be inserted in the non-human mammal light chain locus, for use in insertion of human light chain VJ DNA The initiation cassette suitably comprises a vector backbone sequence with which a vector having a human DNA fragment in the same backbone sequence can recombine to insert the human DNA into the cell (e.g. ES) cell genome, and suitably a selection marker, such as a negative selection marker. Suitably the vector backbone sequence is that of a BAC library, to allow BACs to be used in the construction of the ES cells and mammals. The vector backbone sequence may however be any sequence which serves as a target site into which a homologous sequence can insert, for example by homologous recombination, for example RMCE, and is preferably not DNA encoding any of the VDJ or constant region.

In one aspect the insertion of the first DNA fragment into an initiation cassette is followed by insertion of a second DNA fragment into a portion of the first DNA fragment, suitably a part of the vector backbone of the second DNA fragment. In one aspect an inserted DNA fragment comprises a part of the human VDJ region flanked by 5' and/or 3' sequences that are not from the human VDJ region. In one aspect the 5' and/or 3' flanking sequences may each contain one or more selectable markers, or be capable of creating a selectable system once inserted into the genome. In one aspect one or both flanking sequences may be removed from the genome in vitro, or in vivo, following insertion. In one aspect the method comprises insertion of a DNA fragment followed by selection of both 5' and 3' ends of the inserted fragment flanking the human VDJ DNA. In one aspect the iterative insertion is made by insertion of DNA fragments at the 5' end of the previous inserted fragment, and in this aspect there may be deletion in vivo of the vector DNA which separates the inserted human DNA sequences, to provide a contiguous human DNA sequence.

In one aspect insertion of human VDJ DNA into a genome may be achieved without leaving any flanking DNA in the genome, for example by transposase mediate DNA excision. One suitable transposase is the Piggybac transposase.

In one aspect the first human variable region fragment is inserted by homologous recombination at the initiation cassette backbone sequence and then the DNA of any negative selection marker and initiation cassette are subsequently removed by recombination between recombinase target sequences, such as FRT using in this example, FLPase expression. Generally repeated targeted insertions at the (e.g. BAC) backbone initiation sequence and subsequent removal by rearrangement between recombinase target sequences are repeated to build up the entire human VDJ region upstream of the host non-mammal constant region.

In one aspect a selectable marker or system may be used in the method. The marker may be generated upon insertion of a DNA fragment into a genome, for example forming a selectable marker in conjunction with a DNA element already present in the genome.

In one aspect the cell (e.g. ES) cell genome does not contain 2 identical selectable markers at the same time during the process. It can be seen that the iterative process of insertion and selection can be carried out using only 2 different selection markers, as disclosed in the examples herein, and for example the third selectable marker may be identical to the first marker, as by the time of insertion of the third vector fragment the first vector fragment and the first marker has been removed.

In one aspect a correct insertion event, is confirmed before moving to the next step of any multistep cloning process, for example by confirmation of BAC structure using high density genomic arrays to screen ES cells to identify those with intact BAC insertions, sequencing and PCR verification.

Initiation Cassette (Also Called a "Landing Pad")

The invention also relates to a polynucleotide 'landing pad' sequence, the polynucleotide comprising nucleic acid regions homologous to regions of a target chromosome to allow for insertion by homologous recombination into the target chromosome, and comprising a nucleic acid site which permits recombinase-driven insertion of nucleic acid into the landing pad. The invention also relates to vectors, cells and mammals of the invention comprising a landing pad as disclosed herein inserted into the genome of the cell.

The landing pad optionally comprises a non-endogenous S-mu, e.g. a rat S-mu switch The landing pad optionally comprises (in 5' to 3' orientation) a mouse Eµ sequence, a non-human, non-mouse (e.g. rat) Switch p and at least a portion of a mouse Cµ or the entire mouse Cµ.

The rat switch sequence optionally comprises or consists of SEQ ID NO 1.

The landing pad optionally comprises the 5' homology arm of SEQ ID NO 6.

The landing pad optionally has the sequence of SEQ ID 2 or SEQ ID NO 3.

In one embodiment, the landing pad comprises an expressible label. For example the label is a fluorescent label, e.g., GFP or a variant thereof (e.g., YFP, CFP or RFP). Thus, a label is used instead of a selection marker (such as one that confers resistance to allow for selection of transformants).

In an embodiment, the landing pad comprises 5' and 3' homology arms for insertion into the cell genome using homologous recombination. The homology arms can be isogenic DNA (e.g., identical to 129-derived endogenous sequences of when a 129-derived ES cell is used). Thus, no new sequence is created by homologous recombination using these homology arms. In another embodiment, the arms are from a mouse strain that is different from the endogenous strain (ES cell strain).

The methods of the invention include methods wherein the landing pad sequence comprises any of the configurations or sequences as disclosed herein.

Another method of the invention comprises the step of insertion of the landing pad into a mouse chromosome by homologous recombination between mouse J1-4 and mouse C mu sequences.

Another method of the invention comprises the step of insertion of the landing pad into the mouse chromosome 12 by homologous recombination between mouse J1-4 and E mu.

In one aspect the method uses site specific recombination for insertion of one or more vectors into the genome of a cell, such as an ES cell. Site specific recombinase systems are well known in the art and may include Cre-lox, and FLP/FRT or combinations thereof, in which recombination occurs between 2 sites having sequence homology.

Additionally or alternatively to any particular Cre/Lox or FLP/FRT system described herein, other recombinases and sites that may be used in the present invention include Dre recombinase, rox sites, and PhiC31 recombinase.

Suitable BACs are available from the Sanger centre, see "A genome-wide, end-sequenced 129Sv BAC library resource for targeting vector construction". Adams D J, Quail M A, Cox T, van der Weyden L, Gorick B D, Su Q, Chan W I, Davies R, Bonfield J K, Law F, Humphray S, Plumb B, Liu P, Rogers J, Bradley A. Genomics. 2005 December; 86(6):753-8. Epub 2005 Oct. 27. The Wellcome Trust Sanger Institute, Hinxton, Cambridgeshire CB10 1SA, UK. BACs containing human DNA are also available from, for example, Invitrogen™. A suitable library is described in Osoegawa K et al, Genome Research 2001. 11: 483-496.

In one aspect a method of the invention specifically comprises:
(1) insertion of a first DNA fragment into a non-human ES cell, the fragment containing a first portion of human VDJ or VJ region DNA and a first vector portion containing a first selectable marker;
(2) optionally deletion of the a part of the first vector portion;
(3) insertion of a second DNA fragment into a non-human ES cell containing the first DNA fragment, the insertion occurring within the first vector portion, the second DNA fragment containing a second portion of the human VDJ or VJ region and a second vector portion containing a second selectable marker,
(4) deletion of the first selectable marker and first vector portion, preferably by a recombinase enzyme action;
(5) insertion of a third DNA fragment into a non-human ES cell containing the second DNA fragment, the insertion occurring within the second vector portion, the third DNA fragment containing a third portion of the human VDJ or VJ region and a third vector portion containing third selectable marker,
(6) deletion of the second selectable marker and second vector portion; and
(7) iteration of the steps of insertion and deletion, as necessary, for fourth and further fragments of the human VDJ or VJ human regions, as necessary, to produce an ES cell with a part or all of the human VDJ or VJ region inserted as disclosed herein, and suitably to remove all the vector portions within the ES cell genome.

In another aspect the invention comprises
(1) insertion of DNA forming an initiation cassette into the genome of a cell;
(2) insertion of a first DNA fragment into the initiation cassette, the first DNA fragment comprising a first portion of a human DNA and a first vector portion containing a first selectable marker or generating a selectable marker upon insertion;

(3) optionally removal of part of the vector DNA (4) insertion of a second DNA fragment into the vector portion of the first DNA fragment, the second DNA fragment containing a second portion of human DNA and a second vector portion, the second vector portion containing a second selectable marker, or generating a second selectable marker upon insertion;

(5) optionally, removal of any vector DNA to allow the first and second human DNA fragments to form a contiguous sequence; and (6) iteration of the steps of insertion of human VDJ DNA and vector DNA removal, as necessary, to produce a cell with all or part of the human VDJ or VJ region sufficient to be capable of generating a chimaeric antibody in conjunction with a host constant region, wherein the insertion of one, or more, or all of the DNA fragments uses site specific recombination.

In one aspect the non-human mammal is able to generate a diversity of at least $1\times10^6$ different functional chimaeric immunoglobulin sequence combinations.

In one aspect the targeting is carried out in ES cells derived from the mouse C57BL/6N, C57BL/6J, 129S5 or 129Sv strain.

In one aspect non-human animals, such as mice, are generated in a RAG-1-deficient or a RAG-2-deficient background, or other suitable genetic background which prevents the production of mature host B and T lymphocytes.

In one aspect the non-human mammal is a rodent, suitably a mouse, and cells of the invention, are rodent cells or ES cells, suitably mouse ES cells.

The ES cells of the present invention can be used to generate animals using techniques well known in the art, which comprise injection of the ES cell into a blastocyst followed by implantation of chimaeric blastocystys into females to produce offspring which can be bred and selected for homozygous recombinants having the required insertion. In one aspect the invention relates to a chimeric animal comprised of ES cell-derived tissue and host embryo derived tissue. In one aspect the invention relates to genetically-altered subsequent generation animals, which include animals having a homozygous recombinants for the VDJ and/or VJ regions.

In a further aspect the invention relates to a method for producing an antibody specific to a desired antigen the method comprising immunizing a transgenic non-human mammal as above with the desired antigen and recovering the antibody (see e.g. Harlow, E. & Lane, D. 1998, $5^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259). Suitably an immunogenic amount of the antigen is delivered. The invention also relates to a method for detecting a target antigen comprising detecting an antibody produced as above with a secondary detection agent which recognises a portion of that antibody.

In a further aspect the invention relates to a method for producing a fully humanised antibody comprising immunizing a transgenic non-human mammal as above with the desired antigen, recovering the antibody or cells expressing the antibody, and then replacing the non-human mammal constant region with a human constant region. This can be done by standard cloning techniques at the DNA level to replace the non-human mammal constant region with an appropriate human constant region DNA sequence—see e.g. Sambrook, J and Russell, D. (2001, 3'd edition) Molecular Cloning: A Laboratory Manual (Cold Spring Harbor Lab. Press, Plainview, N.Y.).

In a further aspect the invention relates to humanised antibodies and antibody chains produced according to the present invention, both in chimaeric and fully humanised form, and use of said antibodies in medicine. The invention also relates to a pharmaceutical composition comprising such an antibodies and a pharmaceutically acceptable carrier or other excipient.

Antibody chains containing human sequences, such as chimaeric human—non-human antibody chains, are considered humanised herein by virtue of the presence of the human protein coding regions region. Fully humanised antibodies may be produced starting from DNA encoding a chimaeric antibody chain of the invention using standard techniques.

Methods for the generation of both monoclonal and polyclonal antibodies are well known in the art, and the present invention relates to both polyclonal and monoclonal antibodies of chimaeric or fully humanised antibodies produced in response to antigen challenge in non-human mammals of the present invention.

In a yet further aspect, chimaeric antibodies or antibody chains generated in the present invention may be manipulated, suitably at the DNA level, to generate molecules with antibody-like properties or structure, such as a human variable region from a heavy or light chain absent a constant region, for example a domain antibody; or a human variable region with any constant region from either heavy or light chain from the same or different species; or a human variable region with a non-naturally occurring constant region; or human variable region together with any other fusion partner. The invention relates to all such chimaeric antibody derivatives derived from chimaeric antibodies identified according to the present invention.

In a further aspect, the invention relates to use of animals of the present invention in the analysis of the likely effects of drugs and vaccines in the context of a quasi-human antibody repertoire.

The invention also relates to a method for identification or validation of a drug or vaccine, the method comprising delivering the vaccine or drug to a mammal of the invention and monitoring one or more of: the immune response, the safety profile; the effect on disease.

The invention also relates to a kit comprising an antibody or antibody derivative as disclosed herein and either instructions for use of such antibody or a suitable laboratory reagent, such as a buffer, antibody detection reagent.

The invention also relates to a method for making an antibody, or part thereof, the method comprising providing:
(i) a nucleic acid encoding an antibody, or a part thereof, obtained according to the present invention; or
(ii) sequence information from which a nucleic acid encoding an antibody obtained according to the present invention, or part thereof, can be expressed to allow an antibody to be produced.

The present invention also relates to a chimaeric antibody comprising a human variable region and a non-human vertebrate or mammal (optionally a rat or mouse) constant region (optionally a C gamma or C mu), wherein the antibody is encoded by a nucleotide sequence corresponding to the nucleotide sequence of a chimaeric heavy chain locus of a cell (optionally a B-cell, ES cell or hybridoma), the locus comprising a non-human vertebrate constant region nucleotide sequence and a rearranged VDJ nucleotide sequence produced by the in vivo rearrangement of a human V region, a human D region and a human J region, the V region being selected from one of a V1-3 region, V2-5 region, V4-4 region, V1-2 region or V6-1 region, and optionally a V1-3 or V6-1 segment. Optionally, the J region is any of JH1, JH2, JH3, JH4, JH5 or JH6, and in one aspect is JH4 or JH6. The D region is, in one aspect, any D3-9, D3-10, D6-13 or D6-19. In one example, rearranged VDJ nucleotide sequence is produced by the in vivo rearrangement of human V1-3 and JH4 (optionally with D3-9, D6-13 or D-19); or V1-3 and JH6 (optionally with D3-9, D3-10, D6-13 or D-19); or V6-1 and JH4 (optionally with D3-9, D3-10, D6-13 or D-19); or V6-1 and JH6 (optionally with D3-9, D3-10, D6-13 or D-19). In one example the rearranged VDJ nucleotide sequence is produced by the in vivo rearrangement of human V6-1 DH3-10, V1-3 DH3-10, V1-3 DH6-19, V1-3 Dh3-9 or V6-1 DH6-19. In one aspect the antibody comprises any combination exemplified in the Examples and Figures herein. Optionally, the in vivo rearrangement is in a cell (e.g., B cell or ES cell) derived from the same non-human vertebrate species as the constant region sequence (e.g., a mouse B cell or ES cell). The invention also relates to a non-human vertebrate or mammal cell (e.g., a B-cell or ES cell or hybridoma) whose genome comprises a chimaeric heavy chain locus as described above in this paragraph. The invention also relates to a non-human vertebrate or mammal (e.g., a mouse or rat) whose genome comprises a chimaeric heavy chain locus as described above in this paragraph.

The present invention also relates to a non-human vertebrate or mammal having a genome encoding a chimaeric antibody, the chimaeric antibody comprising a human variable region and a non-human vertebrate or mammal (optionally a rat or mouse) constant region (optionally a C gamma or C mu), the mammal:
  expressing more V1-3 antibodies than V2-5, V4-4, V1-2 or V6-1 antibodies; and/or
  expressing more V1-3 JH4 or V1-3 JH6 antibodies than any of, individually, V1-3 JH1, V1-3 JH2, V1-3 JH3 or V1-3 JH5 antibodies, and/or
  expressing more V6-1 JH4 or V6-1 JH6 antibodies than any of, individually, V6-1 JH1, V6-1 JH2, V6-1 JH3 or V6-1 JH5 antibodies and/or
  expressing a greater number of V1-3 DH3-10 antibodies than antibodies V1-3 with any other D region. Expression of antibodies can be assessed by methods readily available to the skilled person and as conventional in the art. For example, expression can be assessed at the mRNA level as shown in the examples below.

The invention also relates to a chimaeric antibody comprising a human variable region and a non-human vertebrate or mammal (optionally a rat or mouse) constant region (optionally a light chain constant region), wherein the antibody is obtainable from a mammal (optionally a rat or mouse) whose genome comprises an antibody chain locus comprising a germline human kappa V1-8 and germline human kappa J1 sequence, and wherein the antibody is obtainable by in vivo recombination in said mammal of the V1-8 and J1 sequences and wherein the antibody has a variable region sequence which is different from that which is encoded by germline human kappa V1-8 and germline human kappa J1sequences. Thus, in this aspect of the invention the human germline sequences are able to undergo productive rearrangement to form a coding sequence which, in conjunction with the non-human constant region sequence, can be expressed as a chimaeric antibody chain having at least a complete human variable region and a non-human constant region. This is in contrast (as the examples show below) to the combination of the germline human kappa V1-8 and germline human kappa J1sequences per se, which do not provide for an antibody coding sequence (due to the inclusion of stop codons). In one aspect the rearranged sequence of the chimaeric antibody is a result of somatic hypermutation. In one aspect the antibody is a kappa antibody; in another aspect the antibody comprises a non-human heavy chain constant region (e.g., a rat or mouse C gamma or C mu). The antibody sequence optionally comprises a $X_1X_2$ T F G Q, where $X_1X_2$=PR, RT, or PW (SEQ ID No 21); optionally a $X_1X_2$ TFGQGTKVEIKRADA (SEQ ID No 22) motif. Such motifs are not found in the equivalent position in the germline sequence as shown in the examples. The invention also relates to a non-human vertebrate or mammal cell (e.g., a B-cell or ES cell or hybridoma) whose genome comprises a chimaeric antibody chain locus as described above in this paragraph. The invention also relates to a non-human vertebrate or mammal (e.g., a mouse or rat) whose genome comprises a chimaeric antibody chain locus as described above in this paragraph.

The invention also relates to a chimaeric antibody comprising a human variable region and a non-human vertebrate or mammal (optionally a rat or mouse) constant region (optionally a light chain constant region), wherein the antibody is obtainable from a mammal (optionally a rat or mouse) whose genome comprises an antibody chain locus comprising a germline human kappa V1-6 and germline human kappa J1 sequence, and wherein the antibody is obtainable by in vivo recombination in said mammal of the V1-6 and J1 sequences and wherein the antibody has a variable region sequence which is different from that which is encoded by germline human kappa V1-6 and germline human kappa J1sequences. Thus, in this aspect of the invention the human germline sequences are able to undergo productive rearrangement to form a coding sequence which, in conjunction with the non-human constant region sequence, can be expressed as a chimaeric antibody chain having at least a complete human variable region and a non-human constant region. This is in contrast (as the examples show below) to the combination of the germline human kappa V1-6 and germline human kappa J1sequences per se, which do not provide for an antibody coding sequence (due to the inclusion of stop codons). In one aspect the rearranged sequence of the chimaeric antibody is a result of somatic hypermutation. In one aspect the antibody is a kappa antibody; in another aspect the antibody comprises a non-human heavy chain constant region (e.g., a rat or mouse C gamma or C mu). The antibody sequence optionally comprises a $X_3X_4$ T F G Q, where $X_3X_4$=PR or PW (SEQ ID No 23); optionally a $X_3X_4$ T F G Q G T K V E I K R A D A (SEQ ID No 24) motif. Such motifs are not found in the equivalent position in the germline sequence as shown in the examples. The invention also relates to a non-human vertebrate or mammal cell (e.g., a B-cell or ES cell or hybridoma) whose genome comprises a chimaeric antibody chain locus as described above in this paragraph. The invention also relates to a non-human vertebrate or mammal (e.g., a mouse or rat) whose genome comprises a chimaeric antibody chain locus as described above in this paragraph.

The invention also relates to a chimaeric antibody comprising a human variable region and a non-human (optionally a rat or mouse) constant region (optionally a C gamma or C mu or a C kappa), wherein the antibody is obtainable from a mammal (optionally a rat or mouse) whose genome comprises an antibody chain locus comprising a germline human kappa V1-5 and germline human kappa J1 sequence, and wherein the antibody is obtainable by in vivo recombination in said mammal of the V1-5 and J1 sequences. The invention also relates to a non-human vertebrate or mammal cell (e.g., a B-cell or ES cell or hybridoma) whose genome comprises a chimaeric antibody chain locus as described above in this paragraph. The invention also relates to a non-human vertebrate or mammal (e.g., a mouse or rat) whose genome comprises a chimaeric antibody chain locus as described above in this paragraph.

The invention also relates to a chimaeric antibody comprising a human variable region and a non-human (optionally a rat or mouse) constant region (optionally a C gamma or C mu or a C kappa), wherein the antibody is obtainable from a mammal (optionally a rat or mouse) whose genome comprises an antibody chain locus comprising a germline human kappa V1-5 and germline human kappa J4 sequence, and wherein the antibody is obtainable by in vivo recombination in said mammal of the V1-5 and J4 sequences. The invention also relates to a non-human vertebrate or mammal cell (e.g., a B-cell or ES cell or hybridoma) whose genome comprises a chimaeric antibody chain locus as described above in this paragraph. The invention also relates to a non-human vertebrate or mammal (e.g., a mouse or rat) whose genome comprises a chimaeric antibody chain locus as described above in this paragraph.

Antibodies of the invention may be isolated, in one aspect being isolated from the cell or organism in which they are expressed.

A non-human mammal whose genome comprises:
(a) the human IgH VDJ region upstream of the host non-human mammal constant region; and
(b) the human Ig light chain kappa V and J regions upstream of the host non-human mammal kappa constant region and/or the human Ig light chain lambda V and J regions upstream of the host non-human mammal lambda constant region;

wherein the non-human mammal is able to produce a repertoire of chimaeric antibodies having a non-human mammal constant region and a human variable region, and optionally wherein the non-human mammal genome is modified to prevent expression of fully host-species specific antibodies.

A non-human mammal ES cell whose genome comprises:
(a) the human IgH V, D and J region upstream of a non-human mammal constant region; and
(b) the human Ig locus light chain kappa V and J regions upstream of the host non-human mammal kappa constant region, and/or the human Ig locus light chain lambda V and J regions upstream of the host non-human mammal lambda constant region wherein the ES cell is capable of developing into a non-human mammal, being able to produce a repertoire of antibodies which are chimaeric, having a non-human mammal constant region and a human variable region.

A method for producing a transgenic non-human mammal able to produce a repertoire of chimaeric antibodies, the antibodies having a non-human mammal constant region and a human variable region, the method comprising inserting by homologous recombination into a non-human mammal ES cell genome
(a) the human IgH VDJ region upstream of the host non-human mammal heavy chain constant region, and
(b) the human IgL VJ region for lambda or kappa chains upstream of the host non-human mammal lambda or kappa chain constant region, respectively
such that the non-human mammal is able to produce a repertoire of chimaeric antibodies having a non-human mammal constant region and a human variable region, wherein steps (a) and (b) can be carried out in either order and each of steps (a) and (b) can be carried out in a stepwise manner or as a single step.

In one aspect the insertion of human VDJ or VJ regions upstream of the host non-human mammal constant region is accomplished by step-wise insertion of multiple fragments by homologous recombination.

In one aspect the step-wise insertions commence at a site where an initiation cassette has been inserted into the genome of an ES cell providing a unique targeting region consisting of a BAC backbone sequence and a negative selection marker.

In one aspect the first human variable region fragment is inserted by homologous recombination at the initiation cassette BAC backbone sequence and said negative selection marker and initiation cassette are subsequently removed by recombination between recombinase target sequences.

In one aspect repeated targeted insertions at the BAC backbone initiation sequence and subsequent removal of the backbone by rearrangement between recombinase target sequences is repeated to build up the entire human VDJ region upstream of the host non-mammal constant region.

Insertion of Human Variable Region Gene Segments Precisely within the Endogenous Mouse JH4-Cmu Intron There is further provided a cell or non human mammal according to the invention wherein the mammal is a mouse or the cell is a mouse cell and wherein the insertion of the human heavy chain DNA is made in a mouse genome between coordinates 114,667,091 and 114,665,190 of mouse chromosome 12.

There is further provided a cell or non human mammal according to the invention wherein the insertion of the human heavy chain DNA is made at coordinate 114,667,091.

There is further provided a cell or non human mammal according to the invention wherein the human IgH VDJ region comprises nucleotides 105,400,051 to 106,368,585 from human chromosome 14 (coordinates refer to NCBI36 for the human genome).

There is further provided a method, cell or non human mammal according to the invention wherein a human coding region DNA sequence is in a functional arrangement with a non-human mammal control sequence, such that transcription of the human DNA is controlled by the non-human mammal control sequence. In one example, the initiation cassette is inserted between the mouse J4 and C alpha exons. There is further provided an initiation cassette suitable for use in the method comprising a vector backbone sequence and a selection marker.

The invention provides the following aspects (starting at aspect number 103):—

103. A cell or non human mammal according to any one of the above configurations, examples, embodiments or aspects, wherein the mammal is a mouse or the cell is a mouse cell and wherein the insertion of the human heavy chain DNA is made in a mouse genome between coordinates 114,667,091 and 114,665,190 of mouse chromosome 12.

104. A cell or non human mammal according to any one of the above configurations, examples, embodiments or aspects, wherein the insertion of the human heavy chain DNA is made at coordinate 114,667,091.

105. A cell or mammal according to any one of the above configurations, examples, embodiments or aspects, wherein the human IgH VDJ region comprises nucleotides 105,400,051 to 106,368,585 from human chromosome 14 (coordinates refer to NCBI36 for the human genome).
106. A method, cell or mammal according to any one of the above configurations, examples, embodiments or aspects, wherein a human coding region DNA sequence is in a functional arrangement with a non-human mammal control sequence, such that transcription of the human DNA is controlled by the non-human mammal control sequence.
107. A method according to aspect 106 wherein the initiation cassette is inserted between the mouse J4 and C alpha exons.
108. An initiation cassette suitable for use in the method of aspect 107 comprising a vector backbone sequence and a selection marker.

Inactivation of Endogenous Antibody Chain Expression by Insertion of Human Antibody Variable Region Gene Segments 109. A non-human vertebrate (optionally a mouse or rat) or non-human vertebrate cell (optionally a mouse or rat cell) having a genome that
   (i) comprises a transgenic antibody chain locus capable of expressing an antibody chain comprising a human variable region (optionally following antibody gene rearrangement); and
   (ii) is inactivated for endogenous non-human vertebrate antibody chain expression; wherein the transgenic locus comprises
   (iii) a DNA sequence comprising a plurality of human antibody variable region gene segments inserted between endogenous antibody variable region gene segments and an endogenous antibody constant region, whereby endogenous antibody chain expression is inactivated.

The transgenic locus is a heavy chain or light chain locus.

Inactivation of endogenous heavy chain expression in non-human vertebrates such as mice and rats has involved the deletion of all or part of the endogenous heavy chain VDJ region (including sequences between gene segments). The ADAM6 genes are present in the endogenous mouse VDJ region. In mouse, there are two copies of ADAM6 (ADAM6a, ADAM6b) located between the VH and D gene segments in the IgH locus of chromosome 12 (in the intervening region between mouse VH5-1 and D1-1 gene segments). These two adjacent intronless ADAM6 genes have 95% nucleotide sequence identity and 90% amino acid identity. In human and rat, there is only one ADAM6 gene. Expression pattern analysis of mouse ADAM6 shows that it is exclusively expressed in testis [1]. Although ADAM6 transcripts can be detected in lymphocytes, it is restricted to the nucleus, suggesting that the transcription of ADAM6 gene in particular was due to transcriptional read-through from the D region rather than active messenger RNA production [2]. In rat, ADAM6 is on chromosome 6. Mature ADAM6 protein is located on the acrosome and the posterior regions of sperm head. Notably, ADAM6 forms a complex with ADAM2 and ADAM3, which is required for fertilization in mice [3]. Reference [4] implicates ADAM6 in a model where this protein interacts with ADAM3 after ADAM6 is sulphated by TPST2, sulphation of ADAM6 being critical for stability and/or complex formation involving ADAM6 and ADAM3, and thus ADAM6 and ADAM3 are lost from Tpst2-null sperm. The study observes that Tpst2-deficient mice have male infertility, sperm mobility defects and possible abnormalities in sperm-egg membrane interactions.

Thus, the maintenance of ADAM6 expression in sperm is crucial for fertility. Thus, it is thought that transgenic male mice and rats in which ADAM6 genes have been deleted are not viably fertile. This hampers breeding of colonies and hampers the utility of such mice as transgenic antibody-generating platforms. It would be desirable to provide improved non-human transgenic antibody-generating vertebrates that are fertile.

[1]. Choi I, et. al., Characterization and comparative genomic analysis of intronless Adams with testicular gene expression. Genomics. 2004 April; 83(4):636-46.
[2]. Featherstone K, Wood A L, Bowen A J, Corcoran A E. The mouse immunoglobulin heavy chain V-D intergenic sequence contains insulators that may regulate ordered V(D)J recombination. J Biol Chem. 2010 Mar. 26; 285 (13):9327-38. Epub 2010 Jan. 25.
[3]. Han C, et. al., Comprehensive analysis of reproductive ADAMs: relationship of ADAM4 and ADAM6 with an ADAM complex required for fertilization in mice. Biol Reprod. 2009 May; 80(5):1001-8. Epub 2009 Jan. 7.
[4]. Marcello et al, Lack of tyrosylprotein sulfotransferase-2 activity results in altered sperm-egg interactions and loss of ADAM3 and ADAM6 in epididymal sperm, J Biol Chem. 2011 Apr. 15; 286(15):13060-70. Epub 2011 Feb. 21.

According to aspect 109 of the invention, inactivation does not involve deletion of the VDJ region or part thereof including endogenous ADAM6, but instead inactivation by insertion allows for the preservation of endogenous ADAM6 and thus does not risk infertility problems.

The final mouse resulting from the method (or a mouse derived from a cell produced by the method) is in one embodiment a male, so that the invention improves upon the prior art male transgenic mice that are infertile as a result of genomic manipulation. Fertile mice produce sperm that can fertilise eggs from a female mouse. Fertility is readily determined, for example, by successfully breeding to produce an embryo or child mouse. In another embodiment, the method of the invention makes the final female mouse. Such females are, of course, useful for breeding to create male progeny carrying ADAM6 and which are fertile.

In one embodiment of aspect 109, the genome is homozygous for the transgenic locus. For example, the genome is homozygous for endogenous ADAM6 genes.

In one embodiment of the vertebrate of aspect 109, the genome is inactivated for expression of endogenous heavy and kappa (and optionally also lambda) chains.

In one embodiment, in part (iii) of aspect 109 said DNA comprises human VH, D and JH gene segments or human VL and JL gene segments (e.g., Vκ and Jκ gene segments). In an example, the DNA comprises a landing pad having a selectable marker, e.g., a HPRT gene, neomycin resistance gene or a puromycin resistance gene; and/or a promoter.

In one embodiment, in part (iii) of aspect 109 the endogenous gene segments are the entire endogenous VDJ region of a heavy chain locus and/or the endogenous constant region is a Cmu or Cgamma.

In one embodiment, in part (iii) of aspect 109 the endogenous gene segments are the entire endogenous VJ region of a kappa chain locus and/or the endogenous constant region is a Ckappa In one embodiment, in part (iii) of aspect 109 the endogenous gene segments are the entire endogenous VJ region of a lambda chain locus and/or the endogenous constant region is a Clambda.

The non-human vertebrate cell can be a hybridoma, B-cell, ES cell or an IPS cell. When the cell is an ES cell or IPS cell, the endogenous antibody chain expression is inactivated following differentiation of the cell into a progeny B-cell (e.g., in a B-cell in a non-human vertebrate).

The invention further provides:—

110. The vertebrate or cell according to aspect 109, wherein said plurality of human antibody gene segments comprises at least 11 human V segments and/or at least 6 human J segments, e.g. at least 11 human VH gene segments and at least 6 human JH segments and optionally also at least 27 human D segments; optionally with the human inter-gene segment intervening sequences. In an embodiment, the human antibody gene segments are provided by a stretch of DNA sequence of human chromosome 14, comprising the gene segments and intervening sequences in germline configuration.

111. The vertebrate or cell according to aspect 109 or 110, wherein said inserted DNA sequence comprises a human nucleotide sequence comprising said antibody gene segments, wherein the nucleotide sequence is at least 110, 130, 150, 170, 190, 210, 230, 250, 270 or 290 kb. In an embodiment, the nucleotide sequence corresponds to a stretch of DNA sequence of human chromosome 14, comprising the gene segments and intervening sequences in germline configuration, e.g., at least a sequence corresponding to the nucleotide sequence from coordinate 106328951 to coordinate 106601551 of a human chromosome 14, e.g., a sequence in the GRCH37/hg19 sequence database.

112. The vertebrate or cell according to aspect 109, wherein the transgenic locus is a light chain kappa locus and the human antibody gene segments are between the 3'-most endogenous Jk gene segment and endogenous Ck; optionally wherein the human antibody gene segments comprise five functional human JA-CA clusters and at least one human VA gene segment, e.g., at least a sequence corresponding to the nucleotide sequence from coordinate 23217291 to 23327884 of a lambda locus found on a human chromosome 22.

113. The vertebrate or cell according to any one of aspects 109 to 112, wherein the transgenic locus is a heavy chain locus and the human antibody gene segments are between the 3'-most endogenous JH gene segment (e.g., JH4 in a mouse genome) and endogenous Cmu.

114. The vertebrate or cell according to any one of aspects 109 to 113, wherein the genome is homozygous for said transgenic locus.

115. A mouse or mouse cell or a rat or rat cell according to any one of aspects 109 to 114.

116. A method of making a non-human vertebrate cell (optionally a mouse or rat cell), the method comprising
(a) providing a non-human ES cell whose genome comprises an endogenous antibody chain locus comprising endogenous antibody variable region gene segments and an endogenous antibody constant region; and
(b) making a transgenic antibody chain locus by inserting into said endogenous locus a DNA sequences comprising a plurality of human antibody variable region gene segments between said endogenous antibody variable region gene segments and said endogenous constant region, so that the human antibody variable region gene segments are operably connected upstream of the endogenous constant region, whereby a non-human vertebrate ES cell is produced that is capable of giving rise to a progeny cell in which endogenous antibody expression is inactivated and wherein the progeny is capable of expressing antibodies comprising human variable regions; and
(c) optionally differentiating said ES cell into said progeny cell or a non-human vertebrate (e.g., mouse or rat) comprising said progeny cell.

117. The method according to aspect 116, wherein said plurality of human antibody gene segments comprises at least 11 human V segments.

118. The method according to aspect 116 or 117, wherein said plurality of human antibody gene segments comprises at least 6 human J segments.

119. The method according to aspect 116, 117 or 118, wherein a human nucleotide sequence is inserted in step (b), the nucleotide sequence comprising said antibody gene segments, wherein the nucleotide sequence is at least 110 kb.

120. The method according to any one of aspects 110 to 113, wherein the endogenous locus is a heavy chain locus and the human antibody gene segments are between the 3'-most endogenous JH gene segment and endogenous Cmu.

121. The method according to any one of aspects 116 to 120, wherein the progeny cell is homozygous for said transgenic locus.

In one embodiment of the method of aspect 116, the method comprises inactivating the genome for expression of endogenous heavy and kappa (and optionally also lambda) chains.

In one embodiment of the method of aspect 116, in part (b) said DNA sequence comprises human VH, D and JH gene segments or human VL and JL gene segments (e.g., Vκ and Jκ gene segments). In an example, the DNA comprises a landing pad having a selectable marker, e.g., a HPRT gene, neomycin resistance gene or a puromycin resistance gene; and/or a promoter.

In one embodiment, in part (b) of aspect 116 the endogenous gene segments are the entire endogenous VDJ region of a heavy chain locus and/or the endogenous constant region is a Cmu or Cgamma.

In one embodiment, in part (b) of aspect 116 the endogenous gene segments are the entire endogenous VJ region of a kappa chain locus and/or the endogenous constant region is a Ckappa In one embodiment, in part (b) of aspect 116 the endogenous gene segments are the entire endogenous VJ region of a lambda chain locus and/or the endogenous constant region is a Clambda.

The non-human vertebrate cell can be a hybridoma, B-cell, ES cell or an IPS cell. When the cell is an ES cell or IPS cell, the endogenous antibody chain expression is inactivated following differentiation of the cell into a progeny B-cell (e.g., in a B-cell in a non-human vertebrate).

The invention further provides: —

The method according to aspect 116, wherein said inserted DNA sequence comprises a human nucleotide sequence comprising said human antibody gene segments, wherein the nucleotide sequence is at least 110, 130, 150, 170, 190, 210, 230, 250, 270 or 290 kb. In an embodiment, the nucleotide sequence corresponds to a stretch of DNA sequence of human chromosome 14, comprising the gene segments and intervening sequences in germline configuration, e.g., at least a sequence corresponding to the nucleotide sequence from coordinate 106328951 to coordinate 106601551 of a human chromosome 14, e.g., a sequence in the GRCH37/hg19 sequence database.

The method according to aspect 116, wherein the transgenic locus is a light chain kappa locus and the human antibody gene segments are between the 3'-most endogenous Jk gene segment and endogenous Ck; optionally wherein the human antibody gene segments comprise five functional human JA-CA clusters and at least one human VA gene segment, e.g., at least a sequence corresponding to the nucleotide sequence from coordinate 23217291 to 23327884 of a lambda locus found on a human chromosome 22.

The method according to aspect 116, wherein, wherein the transgenic locus is a heavy chain locus and the human antibody gene segments are inserted between the 3'-most endogenous JH gene segment (e.g., JH4 in a mouse genome) and endogenous Cmu.

122. The method according to any one of aspects 116 to 121, comprising making the genome of the progeny homozygous for said transgenic locus.

Isolating Antibodies from Transgenic Non-Human Vertebrates of the Invention & Useful Antigen-Specific Antibodies of Therapeutically-Relevant Affinities 123. A method of isolating an antibody that binds a predetermined antigen, the method comprising
    (a) providing a vertebrate (optionally a mammal; optionally a mouse or rat according to any one of the above configurations, examples, embodiments or aspects;
    (b) immunising said vertebrate with said antigen (optionally wherein the antigen is an antigen of an infectious disease pathogen);
    (c) removing B lymphocytes from the vertebrate and selecting one or more B lymphocytes expressing antibodies that bind to the antigen;
    (d) optionally immortalising said selected B lymphocytes or progeny thereof, optionally by producing hybridomas therefrom; and
    (e) isolating an antibody (e.g., and IgG-type antibody) expressed by the B lymphocytes.
124. The method of aspect 123, comprising the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.
125. The method of aspect 123 or 124, further comprising making a mutant or derivative of the antibody produced by the method of aspect 122 or 123.
    As demonstrated by the examples below, the non-human vertebrates of the invention are able to produce antigen-specific antibodies of sub-50 nM affinity with human sequences in their CDR3 regions. Thus, the invention further provides:—
126. An antibody or fragment (eg, a Fab or $Fab_2$) thereof comprising variable regions that specifically bind a predetermined antigen with a sub-50 nM affinity (optionally sub-40, 30, 20, 10, 1, 0.1 or 0.01 nM) as determined by surface plasmon resonance, wherein the antibody is isolated from a non-human vertebrate (optionally a mammal; optionally a mouse or rat) according to any one of the above configurations, examples, embodiments or aspects and comprises heavy chain CDR3s (as defined by Kabat) encoded by a rearranged VDJ of said vertebrate, wherein the VDJ is the product of rearrangement in vivo of a human JH gene segment of a heavy chain locus of said vertebrate with D (optionally a human D gene segment of said locus) and VH gene segments.

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (e.g., using Hepes buffered saline at pH7.6 (also referred to as HBS-EP)).

In one embodiment, the SPR is carried out at a physiological salt level, e.g., 150 mM NaCl.

In one embodiment, the SPR is carried out at a detergent level of no greater than 0.05% by volume, e.g., in the presence of P20 (polysorbate 20; e.g., Tween-20™) at 0.05% and EDTA at 3 mM.

In one example, the SPR is carried out at 25° C. or 37° C. in a buffer at pH7.6, 150 mM NaCl, 0.05% detergent (e.g., P20) and 3 mM EDTA. The buffer can contain 10 mM Hepes. In one example, the SPR is carried out at 25° C. or 37° C. in HBS-EP. HBS-EP is available from Teknova Inc. (California; catalogue number H8022).

In an example, the affinity of the antibody is determined using SPR by
1. Coupling anti-mouse (or other relevant non-human vertebrate) IgG (e.g., Biacore BR-1008-38) to a biosensor chip (e.g., GLM chip) such as by primary amine coupling;
2. Exposing the anti-mouse IgG (non-human vertebrate antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, e.g., under an SPR condition discussed above (e.g., at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, e.g., using a model inherent to the ProteOn XPR36™ analysis software.

The invention also relates to an scFv, diabody or other antibody fragment comprising a VH and VL domain from an antibody or fragment of aspect 126 (optionally following affinity maturation, e.g., by phage display).

In one embodiment, the antigen is a serpin, e.g., ovalbumin, antithrombin or antitrypsin. Serpins are a group of proteins with similar structures that were first identified as a set of proteins able to inhibit proteases. The acronym serpin was originally coined because many serpins inhibit chymotrypsin-like serine proteases (serine protease inhibitors). The first members of the serpin superfamily to be extensively studied were the human plasma proteins antithrombin and antitrypsin, which play key roles in controlling blood coagulation and inflammation, respectively. Initially, research focused upon their role in human disease: antithrombin deficiency results in thrombosis and antitrypsin deficiency causes emphysema. In 1980 Hunt and Dayhoff made the surprising discovery that both these molecules share significant amino acid sequence similarity to the major protein in chicken egg white, ovalbumin, and they proposed a new protein superfamily.

127. An antibody or fragment that is identical to an antibody of aspect 126 or a derivative thereof (optionally a derivative whose constant regions are human and/or an affinity matured derivative) that specifically binds said antigen with a sub-50 nM affinity as determined by surface plasmon resonance.

128. A pharmaceutical composition comprising an antibody or fragment of aspect 126 or 127 and a pharmaceutically-acceptable diluent, excipient or carrier.

129. A nucleotide sequence encoding a heavy chain variable region of an antibody or fragment of aspect 126 or 127, optionally as part of a vector (e.g., an expression vector).

130. The nucleotide sequence of aspect 129, wherein the sequence is a cDNA derived from a B-cell of the vertebrate from which the antibody of aspect 126 is isolated, or is identical to such a cDNA.

131. An isolated host cell (e.g., a hybridoma or a CHO cell or a HEK293 cell) comprising a nucleotide sequence according to aspect 129 or 130.

132. A method of isolating an antibody that binds a predetermined antigen, the method comprising
   (a) providing a vertebrate (optionally a mammal; optionally a mouse or rat according to any one of the above configurations, examples, embodiments or aspects;
   (b) immunising said vertebrate with said antigen;
   (c) removing B lymphocytes from the vertebrate and selecting a B lymphocyte expressing an antibody that binds to the antigen with sub-nM affinity, wherein the antibody is according to aspect 126;
   (d) optionally immortalising said selected B lymphocyte or progeny thereof, optionally by producing hybridomas therefrom; and
   (e) isolating an antibody (e.g., and IgG-type antibody) expressed by the B lymphocyte.

133. The method of aspect 132, comprising the step of isolating from said B lymphocyte nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

134. The method of aspect 132 or 133, further comprising making a mutant or derivative of the antibody produced by the method of aspect 132 or 133.

Inactivation by Inversion of Endogenous VDJ to Genome Desert Regions

135. A mouse or mouse cell comprising inverted endogenous heavy chain gene segments (e.g., VH, D and JH, such as the entire endogenous heavy chain VDJ region) that are immediately 3' of position 119753123, 119659458 or 120918606 on an endogenous mouse chromosome 12, wherein the mouse comprises a transgenic heavy chain locus comprising a plurality of human VH gene segments, a plurality of human D segments and a plurality of human JH segments operably connected upstream of an endogenous constant region (e.g., C mu) so that the mouse or cell (optionally following differentiation into a B-cell) is capable of expressing an antibody comprising a variable region comprising sequences derived from the human gene segments.

136. The mouse or cell of aspect 135, wherein the genome of the mouse or cell is homozygous for said chromosome 12.

137. A cassette for inversion and inactivation of endogenous non-human vertebrate (e.g., mouse or rat) antibody chain gene segments, the segments being part of an antibody chain locus sequence on a chromosome of a non-human vertebrate (e.g., mouse or rat) cell (e.g., ES cell) wherein the sequence is flanked at its 3' end by a site-specific recombination site (e.g., lox, rox or frt), the cassette comprising a nucleotide sequence encoding an expressible label or selectable marker and a compatible site-specific recombination site (e.g., lox, rox or frt) flanked by a 5' and a 3' homology arm, wherein the homology arms correspond to or are homologous to adjacent stretches of sequence in the cell genome on a different chromosome or on said chromosome at least 10 mb away from the endogenous gene segments.

138. A cassette for inversion and inactivation of endogenous mouse antibody heavy chain gene segments, the segments being part of a heavy chain locus sequence on chromosome 12 of a mouse cell (e.g., ES cell) wherein the sequence is flanked at its 3' end by a site-specific recombination site (e.g., lox, rox or frt), the cassette comprising a nucleotide sequence encoding an expressible label or selectable marker and a compatible site-specific recombination site (e.g., lox, rox or frt) flanked by a 5' and a 3' homology arm, wherein (i) the 5' homology arm is mouse chromosome 12 DNA from coordinate 119753124 to coordinate 119757104 and the 3' homology arm is mouse chromosome 12 DNA from coordinate 119749288 to 119753123; (ii) the 5' homology arm is mouse chromosome 12 DNA from coordinate 119659459 to coordinate 119663126 and the 3' homology arm is mouse chromosome 12 DNA from coordinate 119656536 to 119659458; or (iii) the 5' homology arm is mouse chromosome 12 DNA from coordinate 120918607 to coordinate 120921930 and the 3' homology arm is mouse chromosome 12 DNA from coordinate 120915475 to 120918606.

139. A method of inactivating gene segments of an endogenous antibody locus, the method comprising
   (i) Providing a non-human vertebrate cell (e.g., an ES cell, e.g., a mouse ES cell) whose genome comprises an antibody chain locus comprising endogenous variable region gene segments;
   (ii) Targeting a site-specific recombination site to flank the 3' of the 3'-most of said endogenous gene segments;
   (iii) Targeting a second site-specific recombination site at least 10 mb away from said endogenous gene segments, the second site being compatible with the first site inverted with respect to the first site;
   (iv) Expressing a recombinase compatible with said sites to effect site-specific recombination between said sites, thereby inverting and moving said gene segments away from said locus, wherein the endogenous gene segments are inactivated; and
   (v) Optionally developing the cell into a progeny cell or vertebrate (e.g., mouse or rat) whose genome is homozygous for the inversion.

140. A mouse or mouse cell whose genome comprises an inversion of a chromosome 12, wherein the inversion comprises inverted endogenous heavy chain gene segments (e.g., VH, D and JH, such as the entire endogenous heavy chain VDJ region); wherein the mouse comprises a transgenic heavy chain locus comprising a plurality of human VH gene segments, a plurality of human D segments and a plurality of human JH segments operably connected upstream of an endogenous constant region (e.g., C mu) so that the mouse or cell (optionally following differentiation into a B-cell) is capable of expressing an antibody comprising a variable region comprising sequences derived from the human gene segments; and wherein the inversion is (i) an inversion of mouse chromosome 12 from coordinate 119753123 to coordinate 114666436; (ii) an inversion of mouse chromosome 12 from coordinate 119659458 to coordinate 114666436; or (iii) an inversion of mouse chromosome 12 from coordinate 12091806 to coordinate 114666436.

Other aspects include:

A method for producing an antibody specific to a desired antigen the method comprising immunizing a non-human mammal as disclosed herein with the desired antigen and recovering the antibody or a cell producing the antibody.

A method for producing a fully humanised antibody comprising immunizing a non-human mammal as disclosed herein and then replacing the non-human mammal constant region of an antibody specifically reactive with the antigen with a human constant region, suitably by engineering of the nucleic acid encoding the antibody.

A method, cell or mammal as disclosed herein wherein a human coding region DNA sequence is in a functional arrangement with a non-human mammal control sequence, such that transcription of the DNA is controlled by the non-human mammal control sequence. In one aspect the human coding region V, D or J region is in a functional arrangement with a mouse promoter sequence.

The invention also relates to a humanised antibody produced according to any methods disclosed herein and use of a humanised antibody so produced in medicine.

BRIEF DESCRIPTION OF THE FIGURES

FIG. 39 illustrates Distribution of JH Usage Within Each VHs FIG. 40 illustrates Distribution of DH Usage Within Each VHs FIG. 43 illustrates Joint Diversity Produces Functional CDS FIGS. 54E-54H illustrate normal IgH isotypes in transgenic mice (S1) immunised with 100 μg Cholera Toxin B subunit.

SEQUENCES

Figure 1:
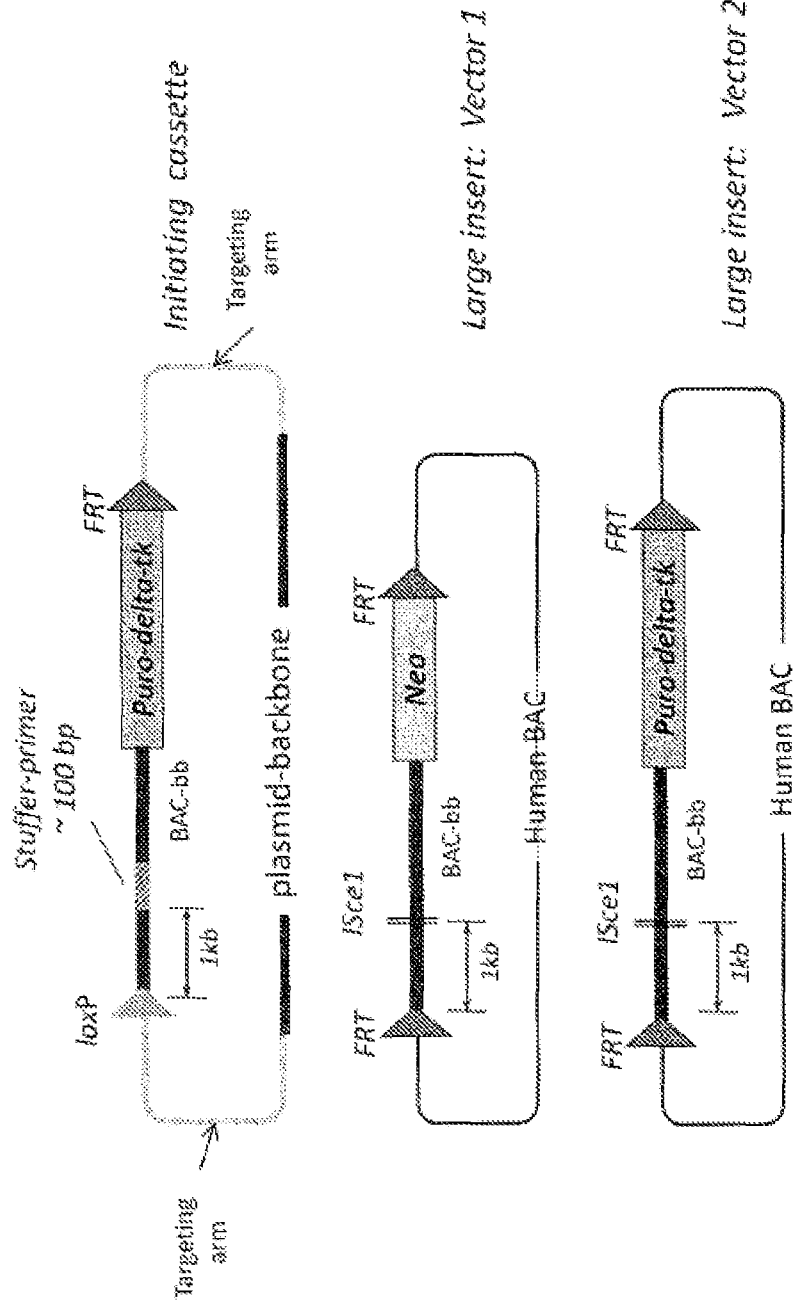
FIGS. 1-8 show an iterative process for insertion of a series of human BACs into a mouse Ig locus

SEQ ID No 1 is a Rat switch sequence

SEQ ID No 2 is a landing pad targeting vector (long version)

SEQ ID No 3 is a landing pad targeting vector (shorter version)

SEQ ID No 4 is the mouse strain 129 switch

SEQ ID No 5 is the mouse strain C57 switch

SEQ ID No 6 is the 5' homology arm of a landing pad

SEQ ID No 7 is oligo HV2-5

SEQ ID No 8 is oligo HV4-4

SEQ ID No 9 is oligo HV1-3

SEQ ID No 10 is oligo HV1-2

SEQ ID No 11 is oligo HV6-1

SEQ ID No 12 is oligo Cμ

SEQ ID No 13 is oligo KV1-9
SEQ ID No 14 is oligo KV1-8
SEQ ID No 15 is oligo KV1-6
SEQ ID No 16 is oligo KV1-5
SEQ ID No 17 is oligo Cκ
SEQ ID Nos 18-20 are rat switch sequences
SEQ ID No 21 is $X_1X_2$ T F G Q, where $X_1X_2$=PR, RT, or PW
SEQ ID No 22 is $X_1X_2$ T F G Q G T K V E I K R A D A, where $X_1X_2$=PR, RT, or PW;
SEQ ID No 23 is $X_3X_4$ T F G Q, where $X_3X_4$=PR or PW
SEQ ID No 24 is $X_3X_4$ T F G Q G T K V E I K R A D A, where $X_3X_4$=PR or PW
SEQ ID No 25 is Primer E1554
SEQ ID No 26 is Primer E1555
SEQ ID No 27 is Primer ELP1352_Cγ1
SEQ ID No 28 is Primer ELP1353_Cγ2b
SEQ ID No 29 is Primer ELP1354_Cγ2a
SEQ ID No 30 is Primer ELP1356_VH4-4
SEQ ID No 31 is Primer ELP1357_VH1-2,3
SEQ ID No 32 is Primer ELP1358_VH6-1
SEQ ID No 33 is Primer mIgG1_2 rev
SEQ ID No 34 is Primer mIgG2b rev
SEQ ID No 35 is Primer mIgG2a_2 rev
SEQ ID No 36 is Primer mCH1 unirev
SEQ ID No 37 is Primer mCH1 unirev_2
SEQ ID Nos 38-45 are CDRH3 sequences
SEQ ID Nos 46-50 is 3, 4, 5, 6 or more (up to 82) repeats of GGGCT
SEQ ID NOs 51-55 are heavy chain CDR1 sequences against CTB (cloned and reference)
SEQ ID NOs 56-60 are heavy chain CDR2 sequences against CTB (cloned and reference)
SEQ ID NOs 61-63 are heavy chain CDR3 sequences against CTB (cloned and reference)
SEQ ID NOs 64-68 are J Region sequences against CTB (cloned and reference)

DETAILED DESCRIPTION OF THE INVENTION

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims.

The use of the word "a" or an when used in conjunction with the term "comprising" in the claims and/or the specification may mean "one," but it is also consistent with the meaning of "one or more," "at least one," and "one or more than one." The use of the term or in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As a source of antibody gene segment sequences, the skilled person will also be aware of the following available databases and resources (including updates thereof) the contents of which are incorporated herein by reference:

The Kabat Database (G. Johnson and T. T. Wu, 2002; World Wide Web (www) kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII tool, and a range of utilities is available for sequence alignment, sequence subgroup classification, and the generation of variability plots. See also Kabat, E. A., Wu, T. T., Perry, H., Gottesman, K., and Foeller, C. (1991) *Sequences of Proteins of Immunological Interest,* 5th ed., NIH Publication No. 91-3242, Bethesda, Md., which is incorporated herein by reference, in particular with reference to human gene segments for use in the present invention.

KabatMan (A. C. R. Martin, 2002; World Wide Web (www) bioinf.org.uk/abs/simkab.html). This is a web interface to make simple queries to the Kabat sequence database.

IMGT (the International ImMunoGeneTics Information System®; M.-P. Lefranc, 2002; World Wide Web (www) imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

V-BASE (I. M. Tomlinson, 2002; World Wide Web (www) mrc-cpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Müller) that allows the assignment of rearranged antibody V genes to their closest germline gene segments.

Antibodies—Structure and Sequence (A. C. R. Martin, 2002; World Wide Web (www) bioinf.org.uk/abs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

AAAAA (A Ho's Amazing Atlas of Antibody Anatomy; A. Honegger, 2001; World Wide Web (www) unizh.ch/~antibody). This resource includes tools for structural analysis, modeling, and engineering. It adopts a unifying scheme for comprehensive structural alignment of antibody and T-cell-receptor sequences, and includes Excel macros for antibody analysis and graphical representation.

WAM (Web Antibody Modeling; N. Whitelegg and A. R. Rees, 2001; World Wide Web (www) antibody.bath.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

Mike's Immunoglobulin Structure/Function Page (M. R. Clark, 2001; World Wide Web (www) path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

The Antibody Resource Page (The Antibody Resource Page, 2000; World Wide Web (www) antibodyresource.com). This site describes itself as the "complete guide to antibody research and suppliers." Links to amino acid sequencing tools, nucleotide antibody sequencing tools, and hybridoma/cell-culture databases are provided.

Humanization by Design (J. Saldanha, 2000; World Wide Web (www) people.cryst.bbk.ac.uk/~ubcg07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, *Methods in Molecular Biology*™, Human Press. Also at World Wide Web (www) blogsua.com/pdf/antibody-engineering-methods-and-protocolsantibody-engineering-methods-and-protocols.pdf Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The following examples are put forth so as to provide those of ordinary skill in the art with a complete disclosure and description of how to make and use the invention, and are not intended to limit the scope of what the inventors regard as their invention.

EXAMPLES

Example 1

BAC Recombineering

Overall strategy: A mouse model of the invention can be achieved by inserting ~960 kb of the human heavy chain locus containing all the V, D and J-regions upstream of the mouse constant region and 473 kb of the human kappa region upstream of the mouse constant region. Alternatively, or in tandem, the human lambda region is inserted upstream of the mouse constant region. This insertion is achieved by gene targeting in ES cells using techniques well known in the art.

High fidelity insertion of intact V-D-J regions into each locus in their native (wild-type) configuration is suitably achieved by insertion of human bacterial artificial chromosomes (BACs) into the locus. Suitably the BACs are trimmed so that in the final locus no sequence is duplicated or lost compared to the original. Such trimming can be carried out by recombineering.

The relevant human BACs, suitably trimmed covering these loci are on average 90 kb in size.

In one approach the full complement of human D and J-elements as well as seven or eight human V-regions are covered by the first BACs to be inserted in the experimental insertion scheme described below. The first BACs to be inserted in the IgH and IgK loci may contain the following V-regions. IgH: V6-1, VII-1-1, V1-2, VIII-2-1, V1-3, V4-4, V2-5 and IgK: V4-1, V5-2, V7-3, V2-4, V1-5, V1-6, V3-7, V1-8.

Suitably the performance of each locus is assessed after the first BAC insertion using chimaeric mice and also after each subsequent BAC addition. See below for detailed description of this performance test.

Nine additional BAC insertions will be required for the IgH locus and five for IgK to provide the full complement of human V-regions covering all 0.96 Mb and 0.473 Mb of the IgH and IgK loci, respectively.

Not all BACs retain their wild-type configuration when inserted into the ES cell genome. Thus, high density genomic arrays were deployed to screen ES cells to identify those with intact BAC insertions (Barrett, M. T., Scheffer, A., Ben-Dor, A., Sampas, N., Lipson, D., Kincaid, R., Tsang, P., Curry, B., Baird, K., Meltzer, P. S., et al. (2004). Comparative genomic hybridization using oligonucleotide microarrays and total genomic DNA. Proceedings of the National Academy of Sciences of the United States of America 101, 17765-17770). This screen also enables one to identify and select against ES clones in which the ES cell genome is compromised and thus not able to populate the germ line of chimeric animals. Other suitable genomic tools to facilitate this assessment include sequencing and PCR verification.

Thus in one aspect the correct BAC structure is confirmed before moving to the next step.

It is implicit from the description above that in order to completely engineer the loci with 90 kb BACs, it is necessary to perform a minimum of 10 targeting steps for IgH and 5 steps for the IgK. Mice with an IgL locus can be generated in a similar manner to the IgK locus. Additional steps are required to remove the selection markers required to support gene targeting. Since these manipulations are being performed in ES cells in a step-wise manner, in one aspect germ line transmission capacity is retained throughout this process.

Maintaining the performance of the ES cell clones through multiple rounds of manipulation without the need to test the germ line potential of the ES cell line at every step may be important in the present invention. The cell lines currently in use for the KOMP and EUCOMM global knockout projects have been modified twice prior to their use for this project and their germ line transmission rates are unchanged from the parental cells (these lines are publicly available, see World Wide Web (www) komp.org and World Wide Web (www) eucomm.org). This cell line, called JM8, can generate 100% ES cell-derived mice under published culture conditions (Pettitt, S. J., Liang, Q., Rairdan, X. Y., Moran, J. L., Prosser, H. M., Beier, D. R., Lloyd, K. C., Bradley, A., and Skarnes, W. C. (2009). Agouti C57BL/6N embryonic stem cells for mouse genetic resources. Nature Methods). These cells have demonstrated ability to reproducibly contribute to somatic and germ line tissue of chimaeric animals using standard mouse ES cell culture conditions. This capability can be found with cells cultured on a standard feeder cell line (SNL) and even feeder-free, grown only on gelatine-coated tissue culture plates. One particular sub-line, JM8A3, maintained the ability to populate the germ line of chimeras after several serial rounds of sub-cloning. Extensive genetic manipulation via, for example, homologous recombination—as would be the case in the present invention—cannot compromise the pluripotency of the cells. The ability to generate chimeras with such high percentage of ES cell-derived tissue has other advantages. First, high levels of chimerism correlates with germ line transmission potential and provide a surrogate assay for germ line transmission while only taking 5 to 6 weeks. Second, since these mice are 100% ES cell derived the engineered loci can be directly tested, removing the delay caused by breeding. Testing the integrity of the new Ig loci is possible in the chimera since the host embryo will be derived from animals that are mutant for the RAG-1 gene as described in the next section.

Another cell line that may be used is an HPRT-ve cell line, such as AB2.1, as disclosed in Ramirez-Solis R, Liu P and Bradley A, "Chromosome engineering in mice," Nature, 1995; 378; 6558; 720-4.

RAG-1 complementation: While many clones will generate 100% ES derived mice some will not. Thus, at every step mice are generated in a RAG-1-deficient background. This provides mice with 100% ES-derived B- and T-cells which can be used directly for immunization and antibody production. Cells having a RAG-2 deficient background, or a combined RAG-1/RAG-2 deficient background may be used, or equivalent mutations in which mice produce only ES cell-derived B cells and/or T cells.

In order that only the human-mouse IgH or IgK loci are active in these mice, the human-mouse IgH and IgK loci can be engineered in a cell line in which one allele of the IgH or IgK locus has already been inactivated. Alternatively the inactivation of the host Ig locus, such as the IgH or IgK locus, can be carried out after insertion.

Figure 19:
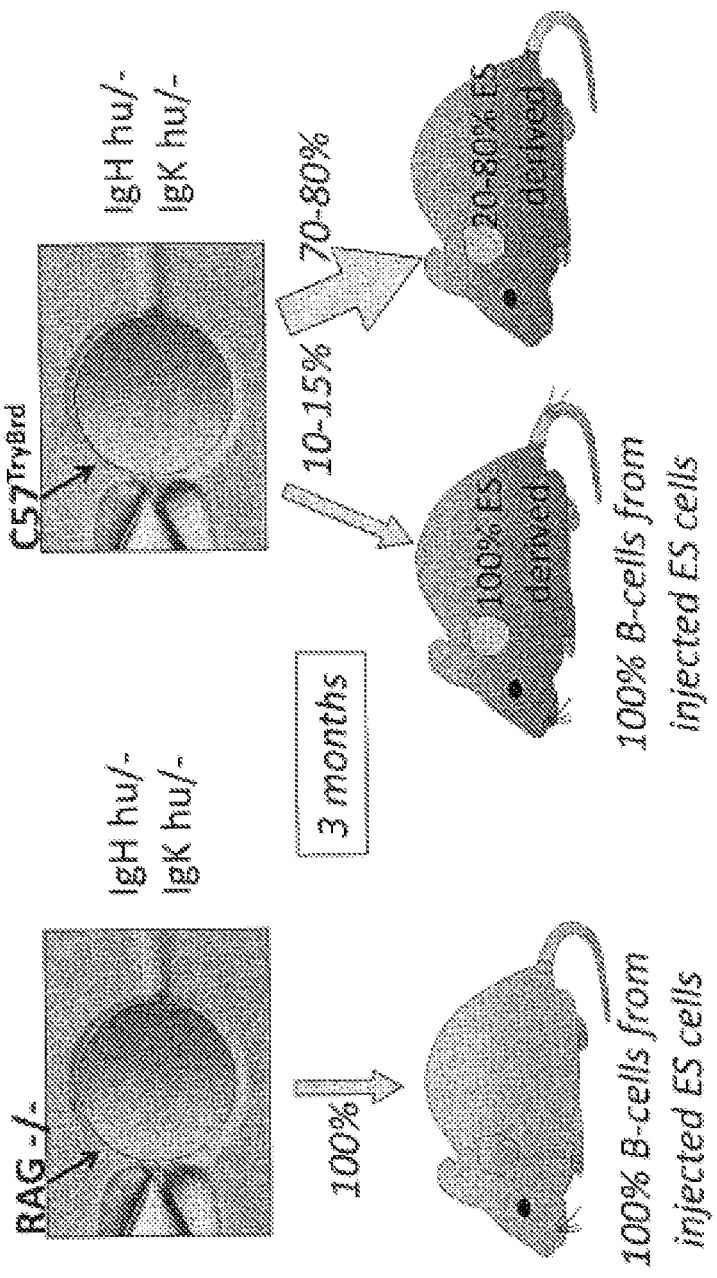
FIGS. 19 and 20 show the principles behind antibody generation in chimaeric mice
Figure 20:
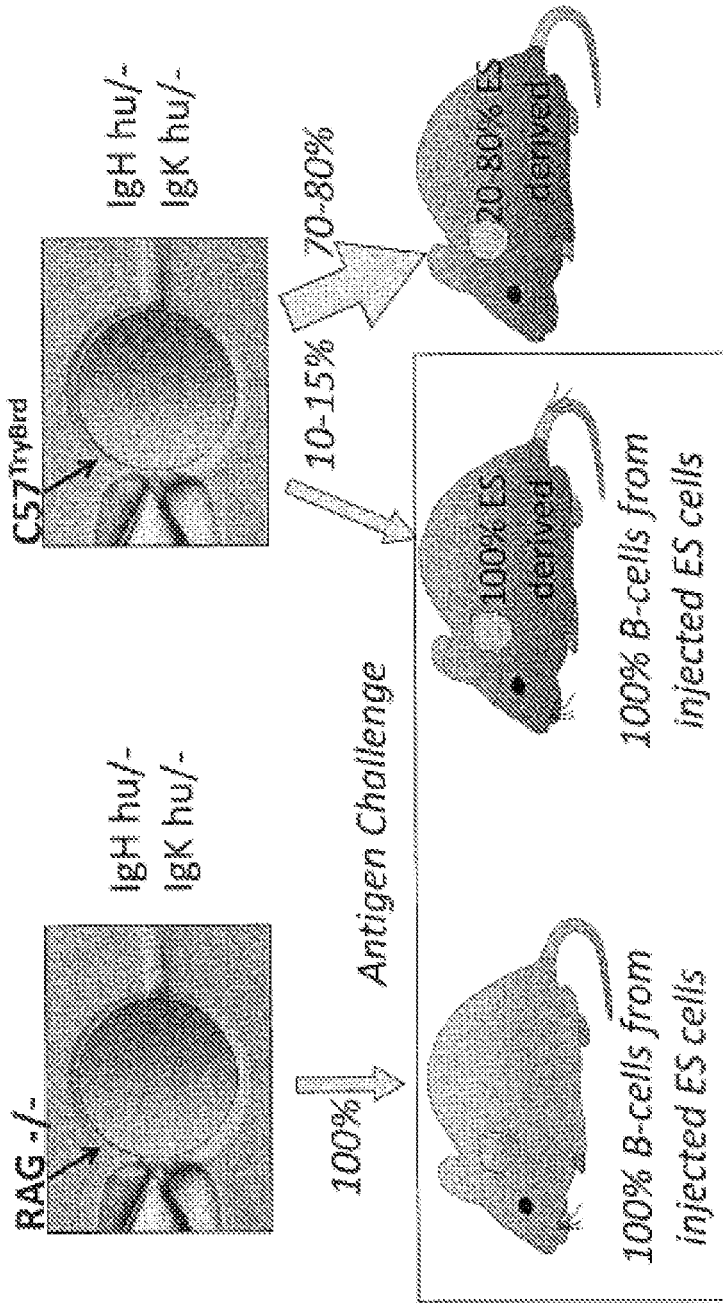
Figure 21:
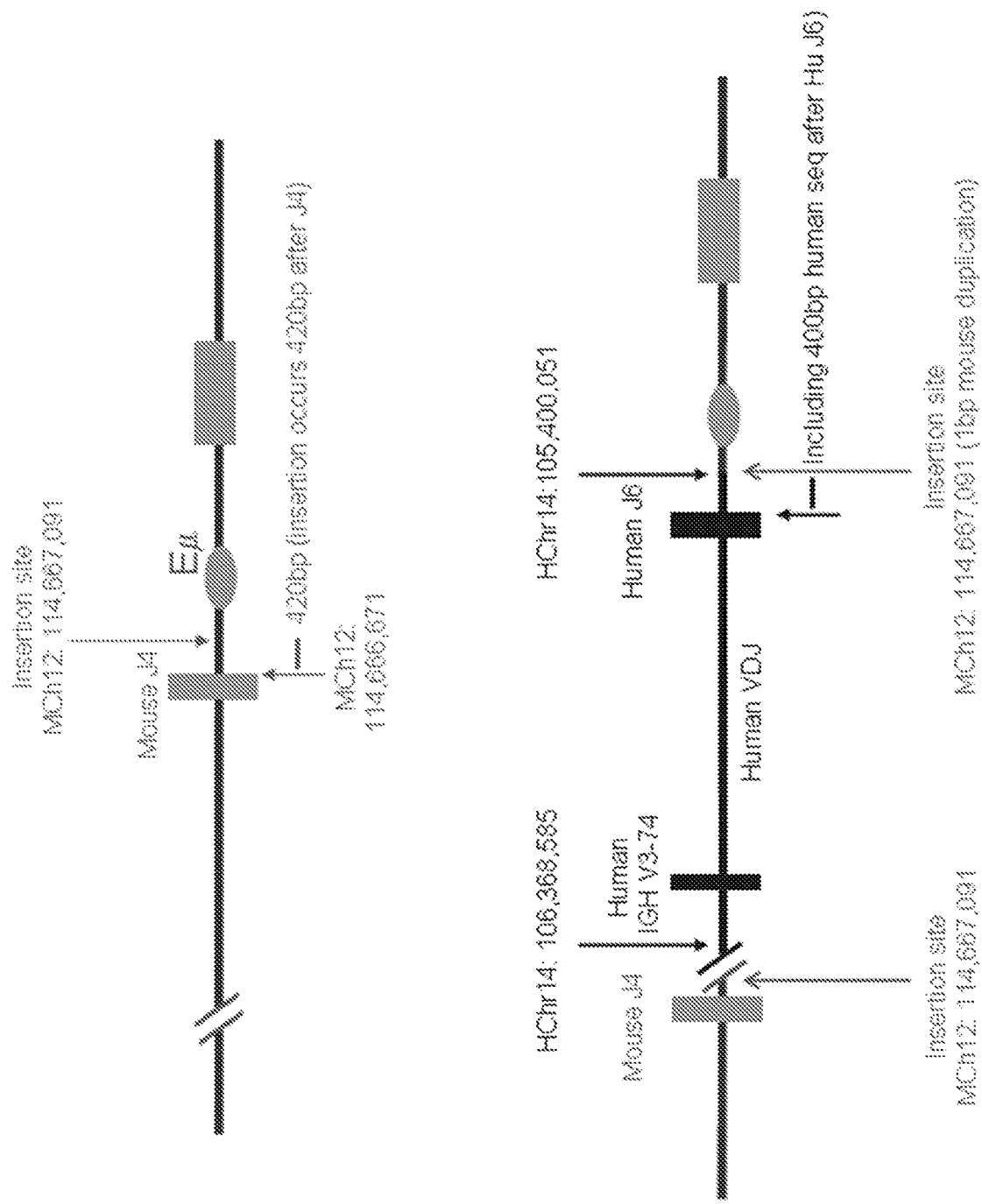
FIG. 21 shows a possible insertion site for the human DNA in a mouse chromosome FIGS. 22-26 disclose an alternative iterative process for insertion of a series of human BACs into a mouse Ig locus

Mouse strains that have the RAG-1 gene mutated are immunodeficient as they have no mature B- or T-lymphocytes (U.S. Pat. No. 5,859,307). T- and B-lymphocytes only differentiate if proper V(D)J recombination occurs. Since RAG-1 is an enzyme that is crucial for this recombination, mice lacking RAG-1 are immunodeficient. If host embryos are genetically RAG-1 homozygous mutant, a chimera produced by injecting such an embryo will not be able to produce antibodies if the animal's lymphoid tissues are derived from the host embryo. However, JM8 cells and AB2.1 cells, for example, generally contribute in excess of 80% of the somatic tissues of the chimeric animal and would therefore usually populate the lymphoid tissue. JM8 cells have wild-type RAG-1 activity and therefore antibodies produced in the chimeric animal would be encoded by the engineered JM8 ES cell genome only. Therefore, the chimeric animal can be challenged with an antigen by immunization and subsequently produce antibodies to that antigen. This allows one skilled in the art to test the performance of the engineered human/mouse IgH and IgK loci as described in the present invention. See FIGS. 19 and 20.

One skilled in the art would use the chimeric animal as described to determine the extent of antibody diversity (see e.g. Harlow, E. & Lane, D. 1998, $5^{th}$ edition, *Antibodies: A Laboratory Manual*, Cold Spring Harbor Lab. Press, Plainview, N.Y.). For example, the existence in the chimeric animal's serum of certain antibody epitopes could be ascertained by binding to specific anti-idiotype antiserum, for example, in an ELISA assay. One skilled in the art could also sequence the genomes of B-cell clones derived from the chimeric animal and compare said sequence to wild-type sequence to ascertain the level of hypermutation, such hypermutation indicative of normal antibody maturation.

One skilled in the art would also use said chimeric animal to examine antibody function wherein said antibodies are encoded from the engineered Ig loci (see e.g. Harlow, E. & Lane, D. 1998, $5^{th}$ edition, Antibodies: A Laboratory Manual, Cold Spring Harbor Lab. Press, Plainview, N.Y.). For example, antisera could be tested for binding an antigen, said antigen used to immunize the chimeric animal. Such a measurement could be made by an ELISA assay. Alternatively, one skilled in the art could test for neutralization of the antigen by addition of the antisera collected from the appropriately immunized chimeric animal.

It is well known to those skilled in the art that positive outcomes for any of these tests demonstrate the ability of the engineered Ig loci, the subject of the instant invention, to encode antibodies with human variable regions and mouse constant regions, said antibodies capable of functioning in the manner of wild-type antibodies.

Experimental Techniques: Recombineering for the production of vectors for use in homologous recombination in ES cells is disclosed in, for example, WO9929837 and WO0104288, and the techniques are well known in the art. In one aspect the recombineering of the human DNA takes place using BACs as a source of said human DNA. Human BAC DNA will be isolated using QIAGEN®, BAC purification kit. The backbone of each human BAC will be modified using recombineering to the exact same or similar configuration as the BAC already inserted into the mouse IgH region. The genomic insert of each human BAC will be trimmed using recombineering so that once the BACs are inserted, a seamless contiguous part of the human V(D)J genomic region will form at the mouse IgH or IgK locus. BAC DNA transfection by electroporation and genotyping will be performed accordingly to standard protocols (Prosser, H. M., Rzadzinska, A. K., Steel, K. P., and Bradley, A. (2008). "Mosaic complementation demonstrates a regulatory role for myosin VIla in actin dynamics of stereocilia." Molecular and Cellular Biology 28, 1702-1712; Ramirez-Solis, R., Davis, A. C., and Bradley, A. (1993). "Gene targeting in embryonic stem cells." Methods in Enzymology 225, 855-878). Recombineering will be performed using the procedures and reagents developed by Pentao Liu and Don Court's laboratories (Chan, W., Costantino, N., Li, R., Lee, S. C., Su, Q., Melvin, D., Court, D. L., and Liu, P. (2007). "A recombineering based approach for high-throughput conditional knockout targeting vector construction." Nucleic Acids Research 35, e64).

These and other techniques for gene targeting and recombination of BAC-derived chromosomal fragments into a non-human mammal genome, such as a mouse are well-known in the art and are disclosed in, for example, in World Wide Web (www) eucomm.org/information/targeting and World Wide Web (www) eucomm.org/information/publications.

Cell culture of C57BL/6N-derived cell lines, such as the JM8 male ES cells will follow standard techniques. The JM8 ES cells have been shown to be competent in extensively contributing to somatic tissues and to the germline, and are being used for large mouse mutagenesis programs at the Sanger Institute such as EUCOMM and KOMP (Pettitt, S. J., Liang, Q., Rairdan, X. Y., Moran, J. L., Prosser, H. M., Beier, D. R., Lloyd, K. C., Bradley, A., and Skarnes, W. C. (2009). "Agouti C57BL/6N embryonic stem cells for mouse genetic resources." Nature Methods). JM8 ES cells ($1.0 \times 10^7$) will be electroporated (500 µF, 230V; Bio-Rad®) with 10 µg I-SceI linearized human BAC DNA. The transfectants will be selected with either Puromycin (3 µg/ml) or G418 (150 µg/ml). The selection will begin either 24 hours (with G418) or 48 hours (with Puromycin) post electroporation and proceed for 5 days. 10 µg linearized human BAC DNA can yield up to 500 Puromycin or G418 resistant ES cell colonies. The antibiotic resistant ES cell colonies will be picked into 96-well cell culture plates for genotyping to identify the targeted clones.

Once targeted mouse ES cell clones are identified, they will be analyzed by array Comparative Genomic Hybridization (CGH) for total genome integrity (Chung, Y. J., Jonkers, J., Kitson, H., Fiegler, H., Humphray, S., Scott, C., Hunt, S., Yu, Y., Nishijima, I., Velds, A., et al. (2004). "A whole-genome mouse BAC microarray with 1-Mb resolution for analysis of DNA copy number changes by array comparative genomic hybridization." Genome research 14, 188-196.and Liang, Q., Conte, N., Skarnes, W. C., and Bradley, A. (2008). "Extensive genomic copy number variation in embryonic stem cells." Proceedings of the National Academy of Sciences of the United States of America 105, 17453-17456). ES cells that have abnormal genomes do not contribute to the germline of the chimeric mice efficiently. BAC integrity will be examined by PCR-amplifying each known functional V gene in the BAC. For example, in one approach the first human BAC chosen for the IgH locus has 6 functional V genes. To confirm the integrity of this BAC for the presence of these 6 IGH V genes, at least 14 pairs of PCR primers will be designed and used to PCR-amplify genomic DNA from the targeted ES cells. The human wild-type size and sequence of these fragments will ensure that the inserted BAC has not been rearranged.

More detailed CGH will also confirm the integrity of the inserted BACs. For example, one skilled in the art could use an oligo aCGH platform, which is developed by Agilent Technologies, Inc. This platform not only enables one to study genome-wide DNA copy number variation at high resolution (Barrett, M. T., Scheffer, A., Ben-Dor, A., Sampas, N., Lipson, D., Kincaid, R., Tsang, P., Curry, B., Baird, K., Meltzer, P. S., et al. (2004). "Comparative genomic hybridization using oligonucleotide microarrays and total genomic DNA." Proceedings of the National Academy of Sciences of the United States of America 101, 17765-17770), but permit examination of a specific genome region using custom designed arrays. Comparing the traditional aCGH techniques which rely on cDNA probes or whole BAC probes, the 60-mer oligonucleotides probes can ensure specific hybridization and high sensitivity and precision that is needed in order to detect the engineered chromosome alterations that were made. For example, oligos designed to hybridize at regular intervals along the entire length of the inserted BAC would detect even quite short deletions, insertions or other rearrangements. Also, this platform provides the greatest flexibility for customized microarray designs. The targeted ES cell genomic DNA and normal human individual genomic DNA will be labelled separately with dyes and hybridized to the array. Arrays slides will be scanned using an Aglient Technologies DNA microarray scanner. Reciprocal fluorescence intensities of dye Cy5 and dye Cy3 on each array image and the log 2 ratio values will be extracted by using Bluefuse software (Bluegnome). Spots with inconsistent fluorescence patterns ("confidence"<0.29 or "quality"=0) will be excluded before normalizing all log 2 ratio values. Within an experiment, Log 2 ratio between −0.29 and +0.29 for the signal from any oligo probe are regarded as no copy number change. The log 2 ratio threshold for "Duplication" is usually >0.29999, and for deletion is <0.29999.

Once the first human BAC is inserted into the mouse IgH locus and confirmed to be in its intact, native configuration, the FRT-flanked BAC backbone will be excised by using Flp site-specific recombinase. If regular Flp-catalyzed FRT recombination is not high enough, one can use Flo, an improved version of Flpo recombinase which in certain tests is 3-4 times more efficient than the original Flp in ES cells. After the BAC backbone is excised, ES cells will become sensitive to Puromycin (or G418) and resistant to FIAU (for loss of the TK cassette). The excision events will be further characterized by PCR amplification of the junction fragment using human genomic DNA primers. These FRT-flanked BAC backbone-free ES cells will be used for the next round of human BAC insertion and for blastocyst injection.

Targeting of the genome of an ES cell to produce a transgenic mouse may be carried out using a protocol as explained by reference to the attached FIGS. 1-18.

FIG. 1 illustrates three basic backbone vectors; an initiating cassette and 2 large insert vectors 1 and 2 respectively. The initiating cassette comprises sequences homologous to the desired site of insertion into the mouse genome, those sites flanking a selectable marker and stuffer primer sequence for PCR based genotyping to confirm correct insertion of BACs. The Stuffer-primer sequence provides the basis for genotyping each BAC addition step. This sequence is considered to provide a robust well validated sequence template for PCR primer and may be located at the ISceI site, ideally ~1 kb from the BAC insert.

The large insert vectors comprise human DNA on plasmids with selectable markers and a unique restriction site for linearisation of the plasmid to aid in homologous recombination into the genome of the ES cell.

Figure 2:
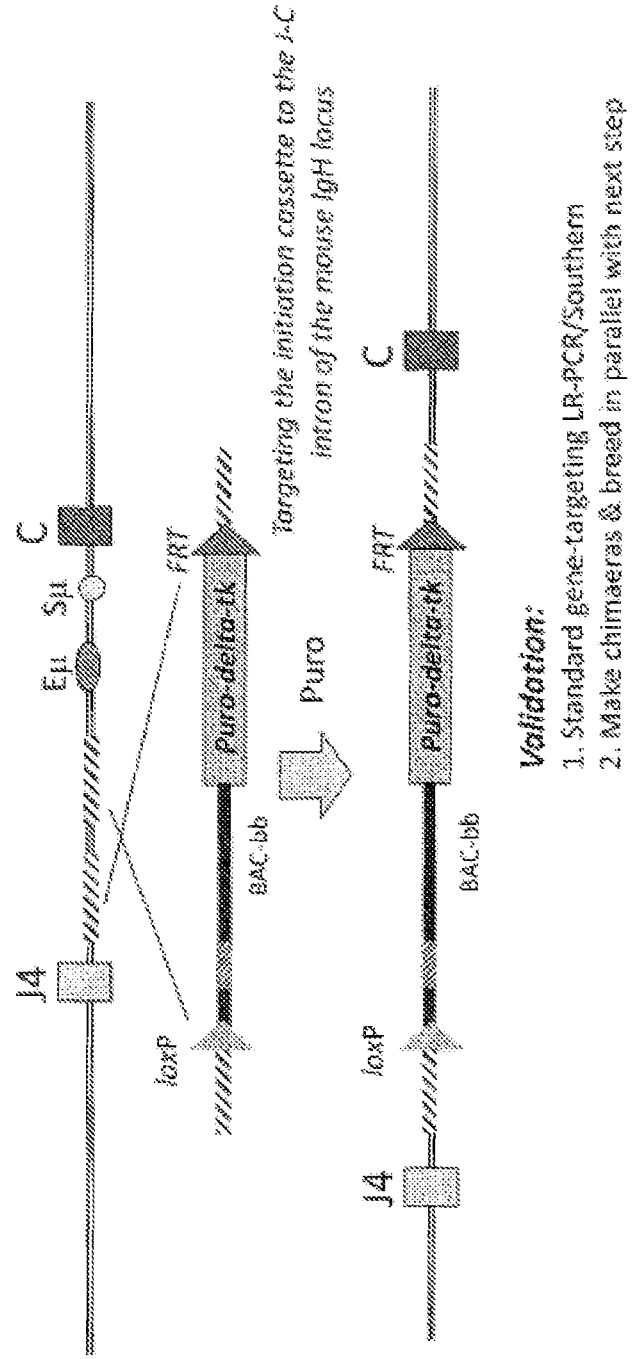

FIG. 2 illustrates insertion of an initiating cassette into the mouse genome by Homologous recombination between the mouse J4 and C alpha exons. Puromycin selection allows identification of ES cells with insertion of the cassette. pu(Delta)tk is a bifunctional fusion protein between puromycin N-acetyltransferase (Puro) and a truncated version of herpes simplex virus type 1 thymidine kinase (DeltaTk). Murine embryonic stem (ES) cells transfected with pu(Delta)tk become resistant to puromycin and sensitive to 1-(-2- deoxy-2-fluoro-1-beta-D-arabino-furanosyl)-5-iodouracil (FIAU). Unlike other HSV1 tk transgenes, puDeltatk is readily transmitted through the male germ line. Thus pu(Delta)tk is a convenient positive/negative selectable marker that can be widely used in many ES cell applications.

Figure 3:
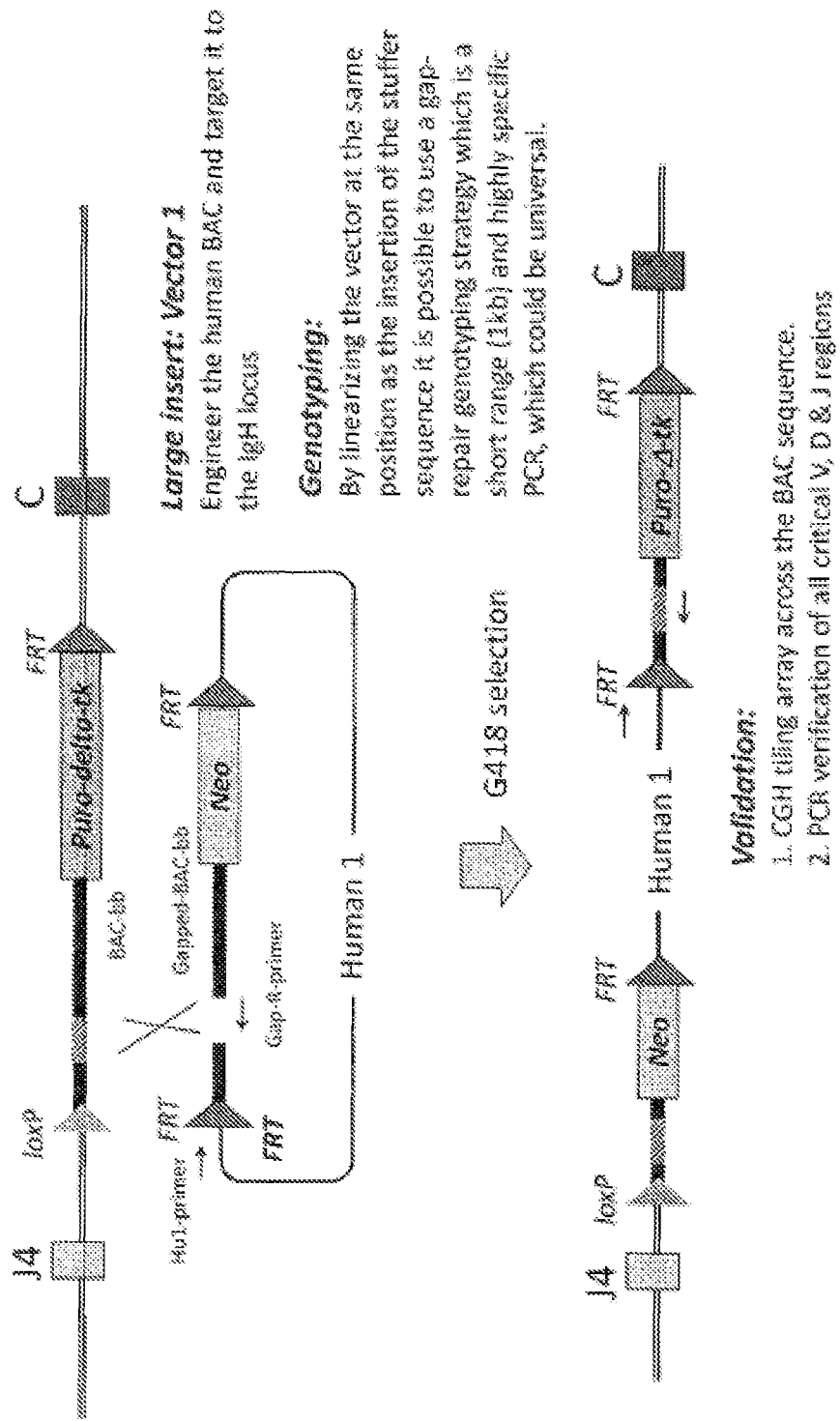

FIG. 3 illustrates targeting of the large insert vector 1 to the mouse ES cell genome. Linearisation of the vector is made at the same position as the stuffer primer sequence which allows for a gap repair genotyping strategy, well known in the art—see Zheng et al NAR 1999, Vol 27, 11, 2354-2360. In essence, random insertion of the targeting vector into the genome will not 'repair' the gap whereas a homologous recombination event will repair the gap. Juxtaposition of appropriate PCR primer sequences allows colonies to be screened individually for a positive PCR fragment indicating proper insertion. Positive selection using G418 allows for identification of mouse ES cells containing the neo selection marker. PCR verification can be made of all critical V, D and J regions. Array comparative genomic hybridization can be used to validate the BAC structure.

Figure 4:
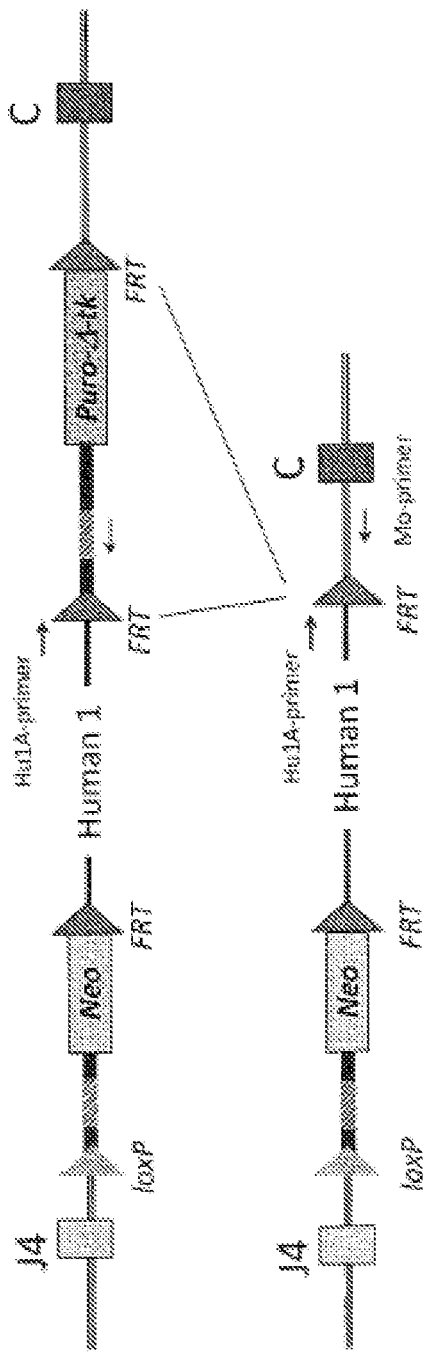

FIG. 4 illustrates the puro-delta-tk cassette and the BAC plasmid backbone is deleted using Flpe and select in FIAU. Since Flpe works inefficiently in mouse ES cells (5% deletion with transient Flpe expression), it is expected that in most cases, the recombination occurs between the two FRT sites flanking the BAC backbone. Flpo can also be tested to find out the recombination efficiency between two FRT sites that are 10 kb away.

Given that the FRT deletion step is selectable it is possible to pool FIAU resistant clones and proceed immediately to the next step in parallel with clonal analysis. Alternatively it may be desirable to show by short range PCR that the human sequences are now adjacent to those of the mouse as shown (Hu-primer 1 and Mo-primer)

At this stage a 200 kb human locus will have been inserted.

Figure 5:
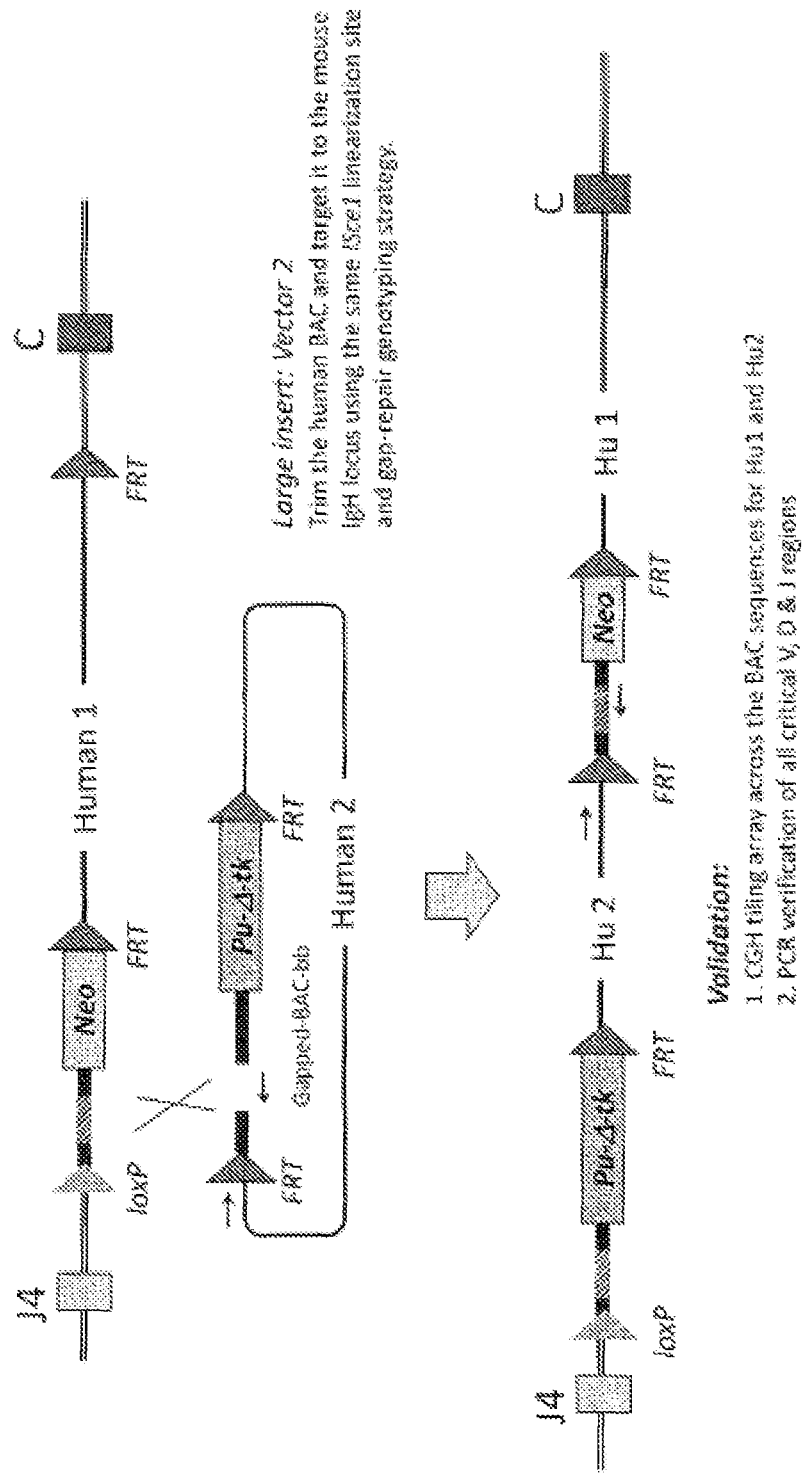

FIG. 5 illustrates a second large insert vector is targeted into the ES cell chromosome. The human BAC is targeted to the mouse IgH locus using the same initiation cassette insertion followed by IScel BAC linearization, BAC targeting to the initiation cassette and gap-repair genotyping strategy. Verification of the BAC insertion is carried out as before.

Figure 6:
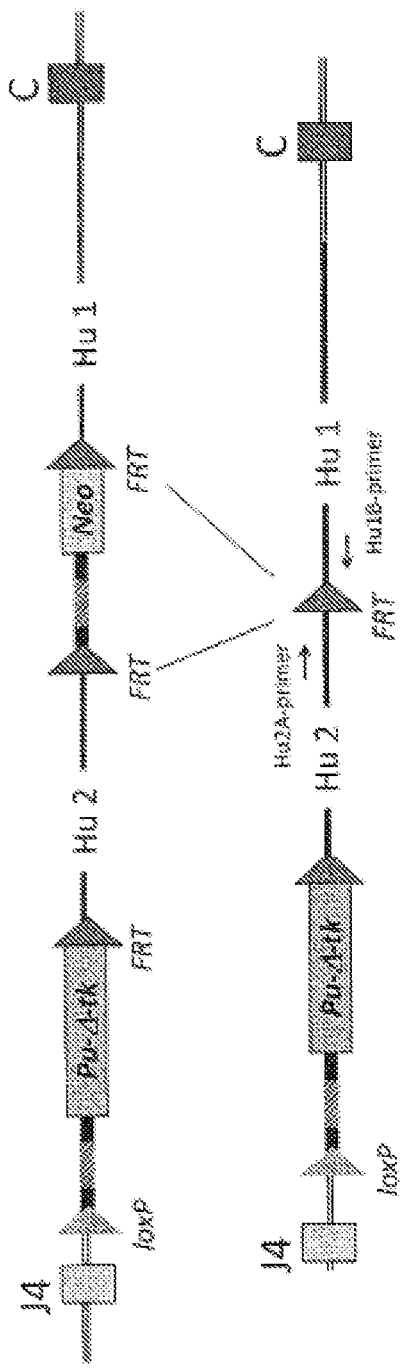

FIG. 6 illustrates the FRTY flanked BAC backbone of large insert vector 2 and the neo marker are deleted via Flpo. Note that this is not selectable, thus it will be necessary for clonal analysis at this point. This will enable confirmation of the juxtaposition of the human 2 insert with human 1 and other validation efforts.

At this stage a ~200 kb human locus will have been inserted.

Figure 7:
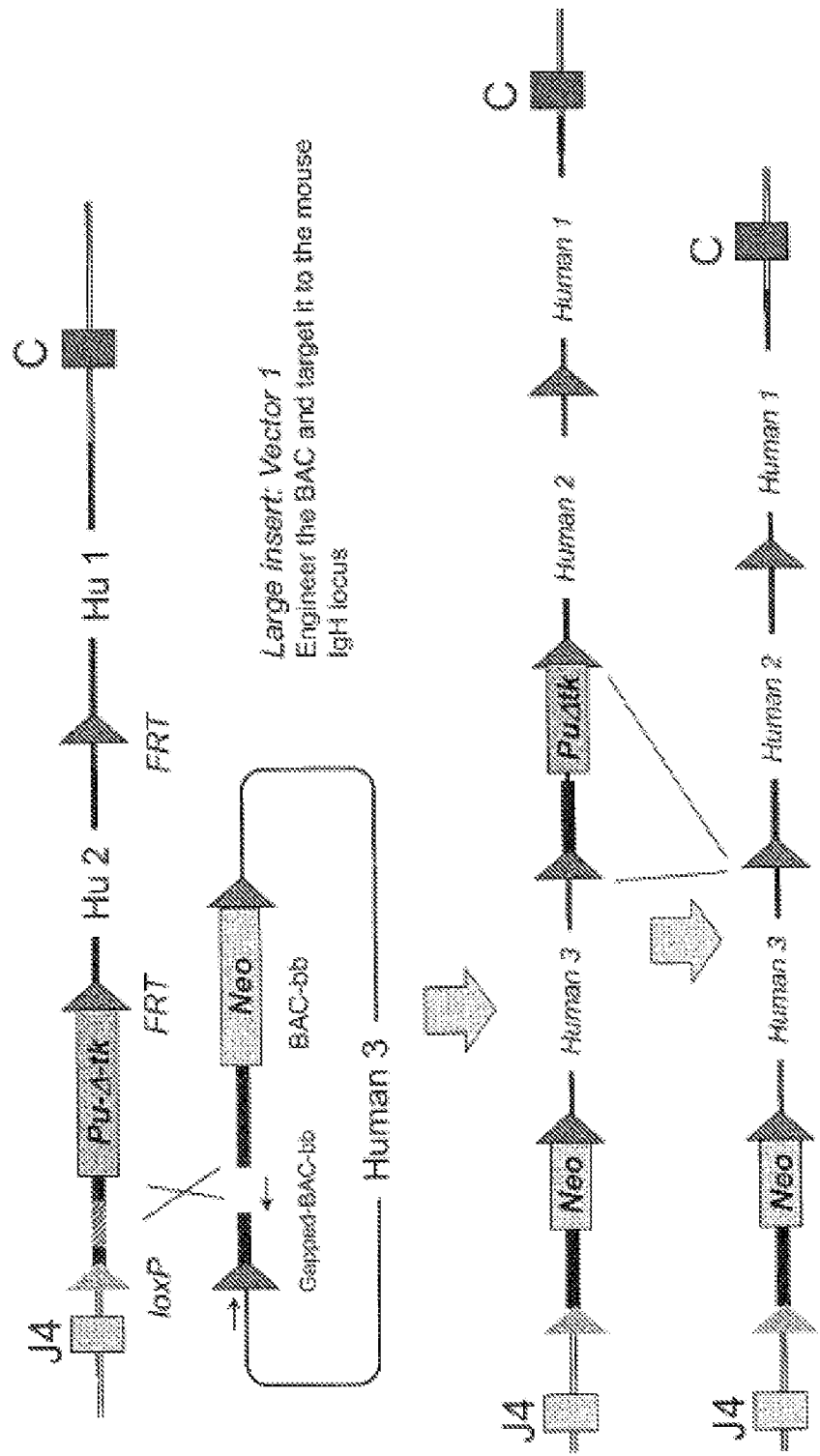

FIG. 7 illustrates the next large insert vector targeted to the mouse IgH locus. The pu-delta TK cassette is then removed, as for FIG. 4. The process can be repeated to incorporate other BACs.

Figure 8:
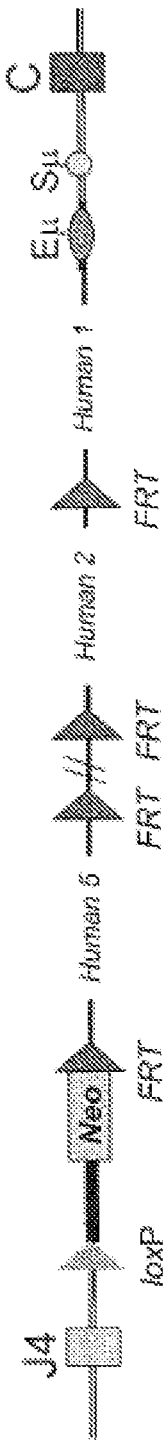
Figure 9:
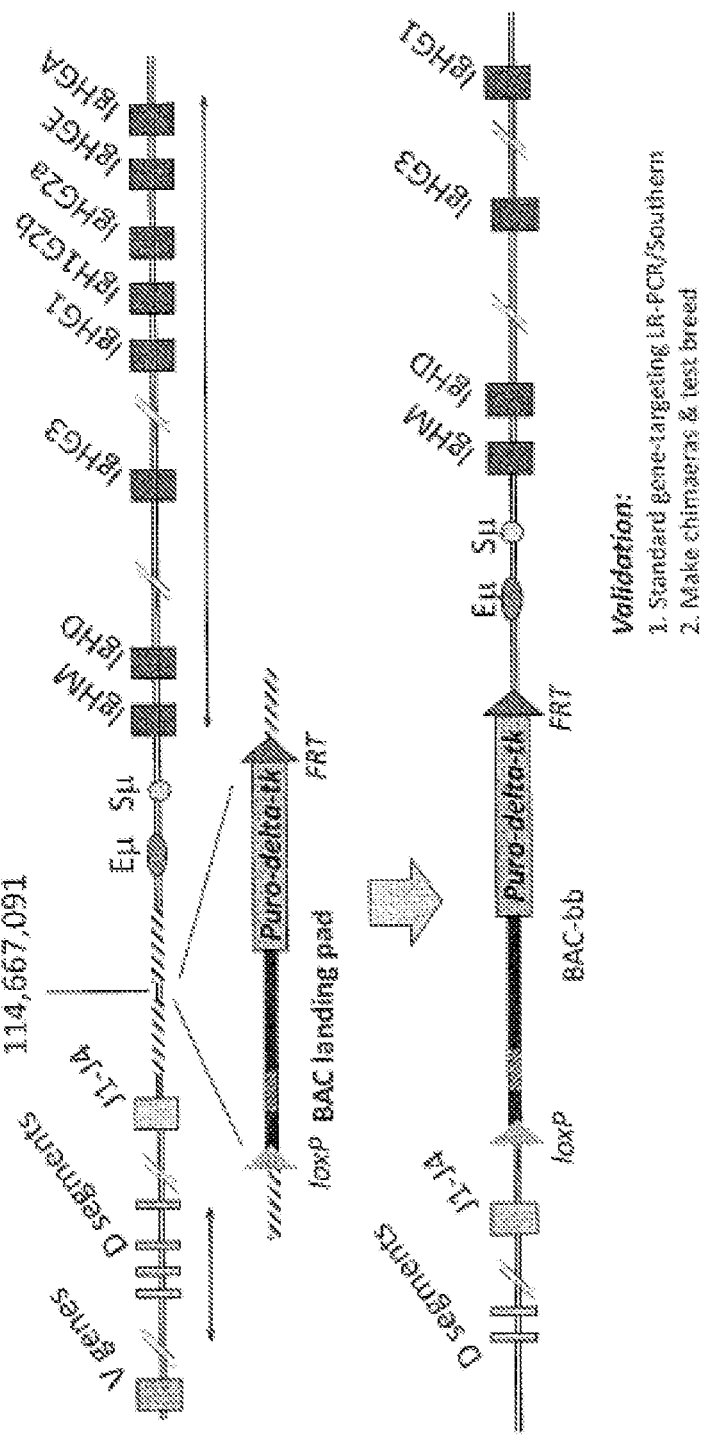
FIGS. 9-18 show in more detail the process of FIGS. 1-8 for the IgH and kappa locus
Figure 10:
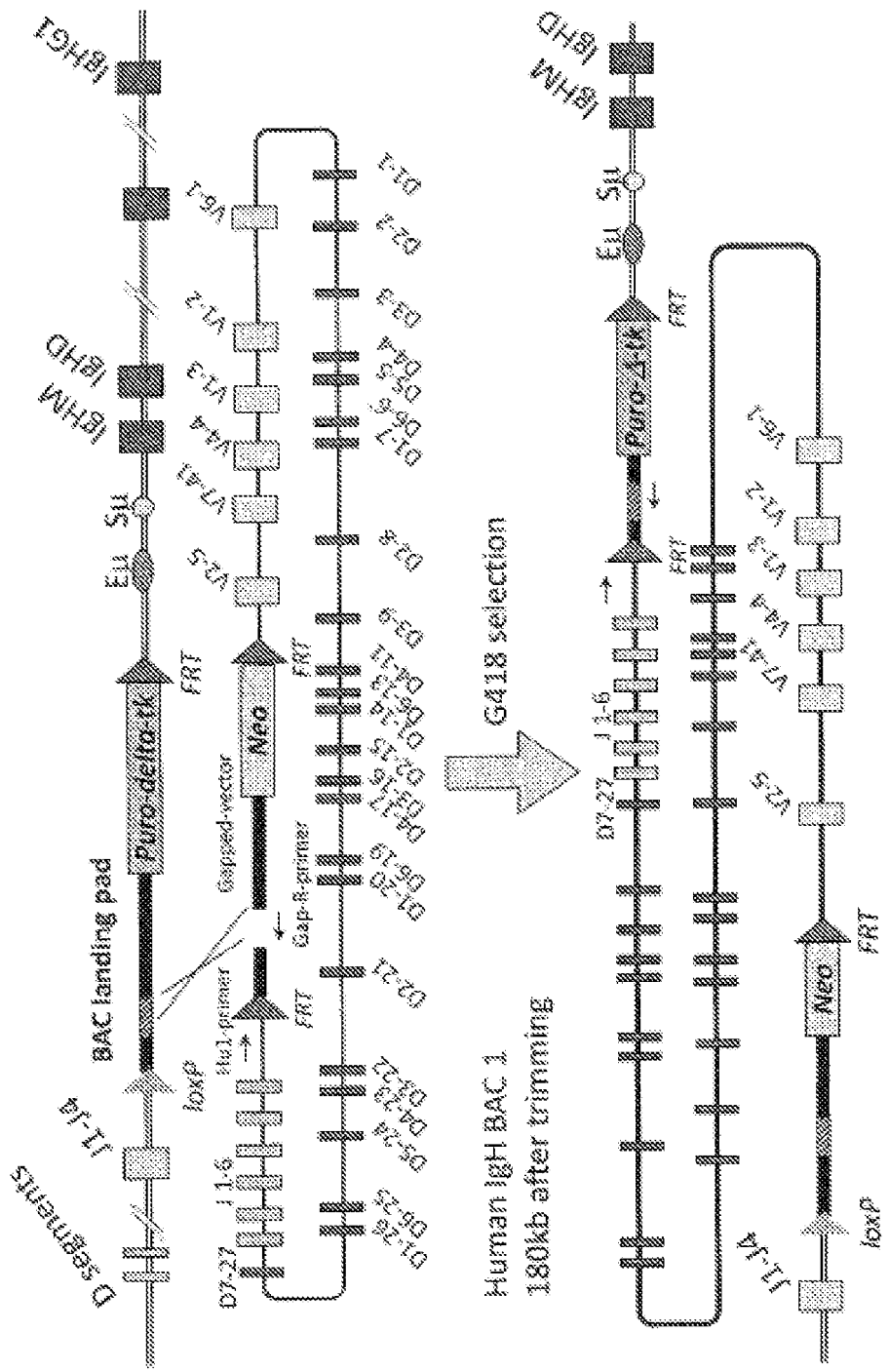
Figure 11:
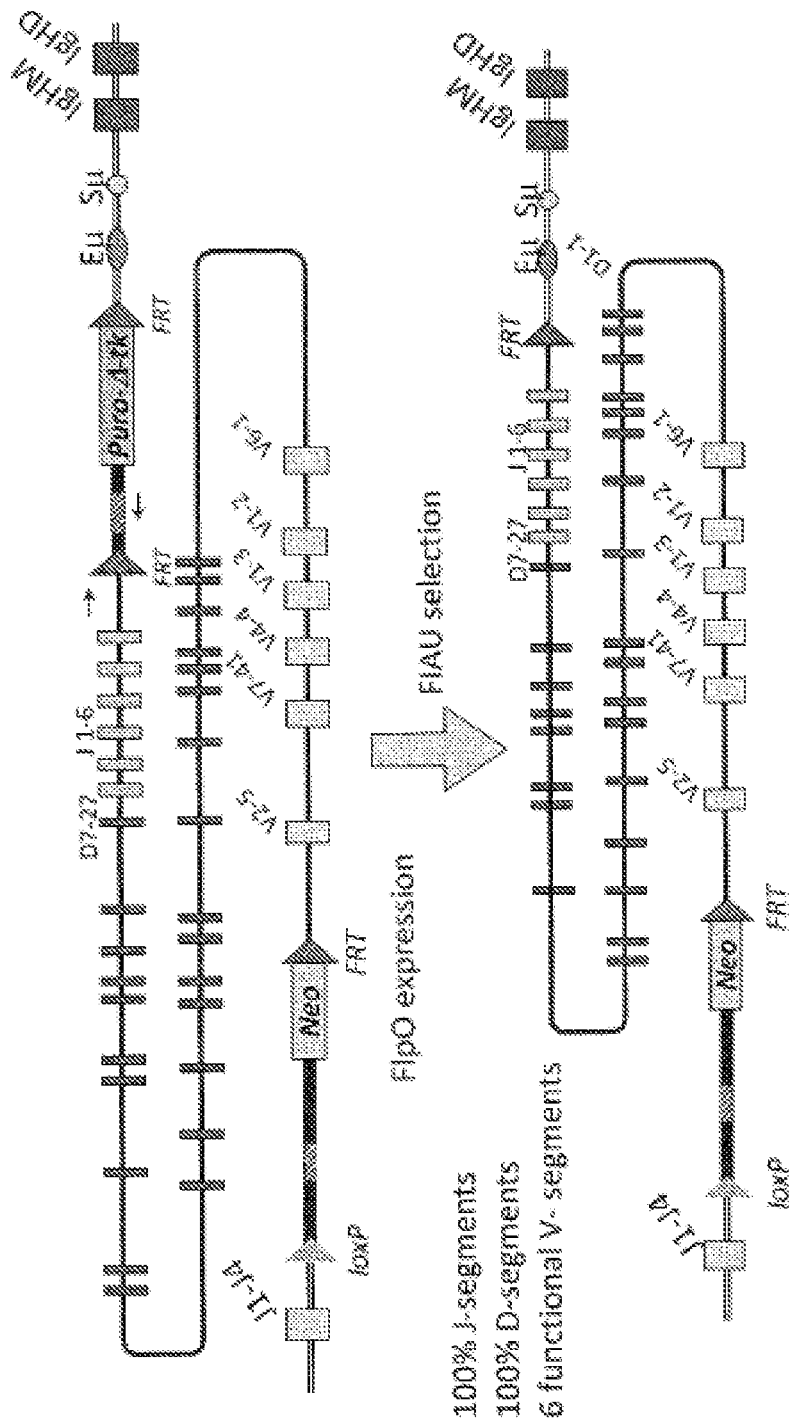
Figure 12:
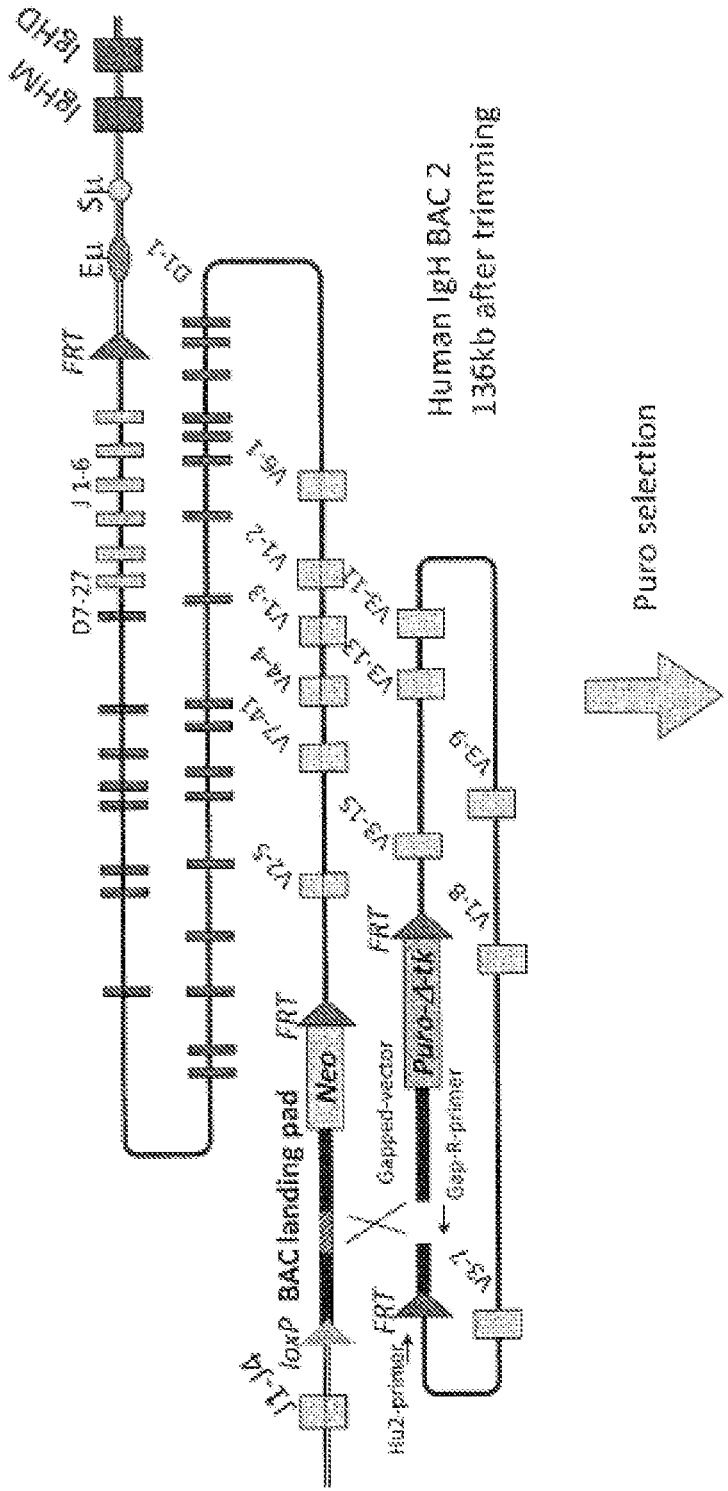
Figure 13:
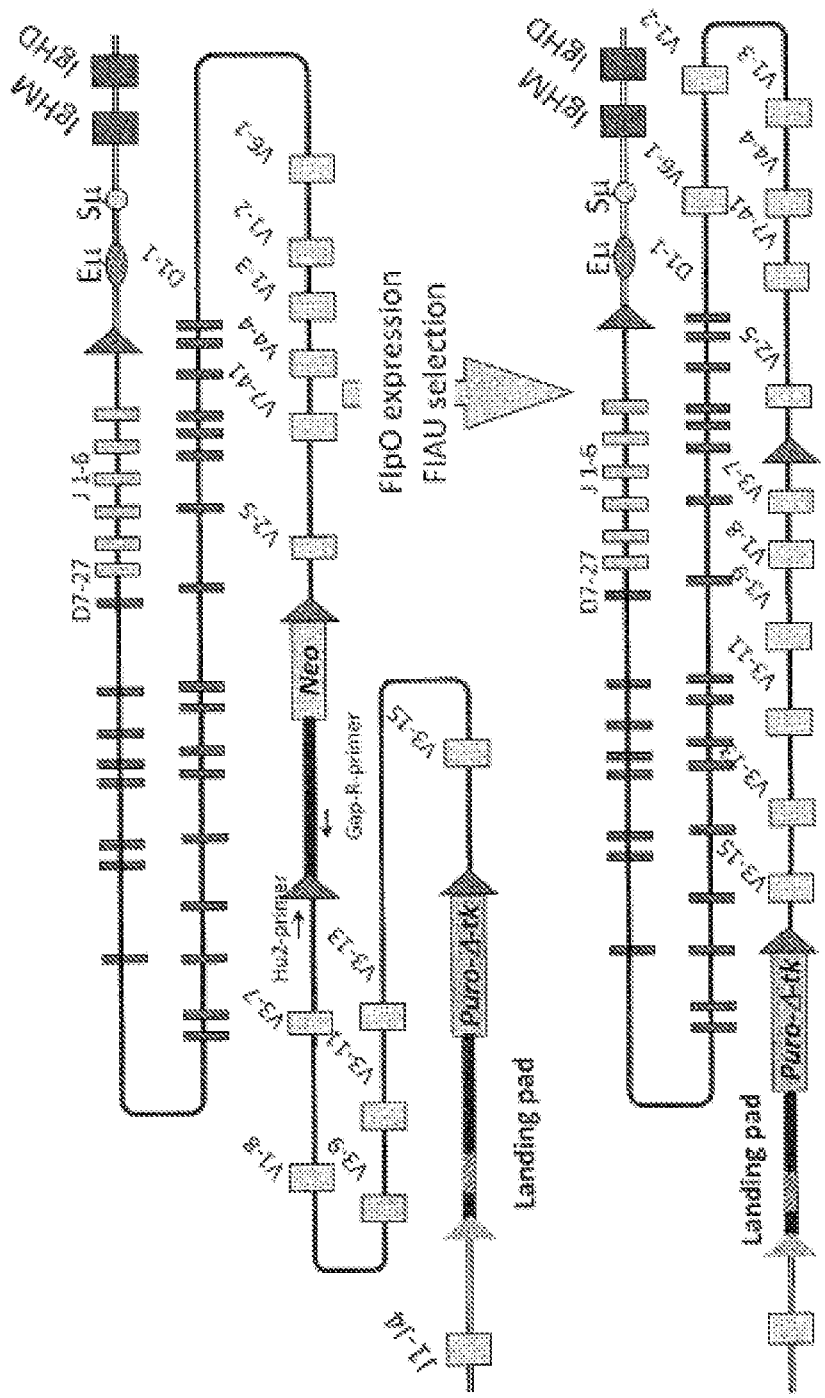
Figure 14:
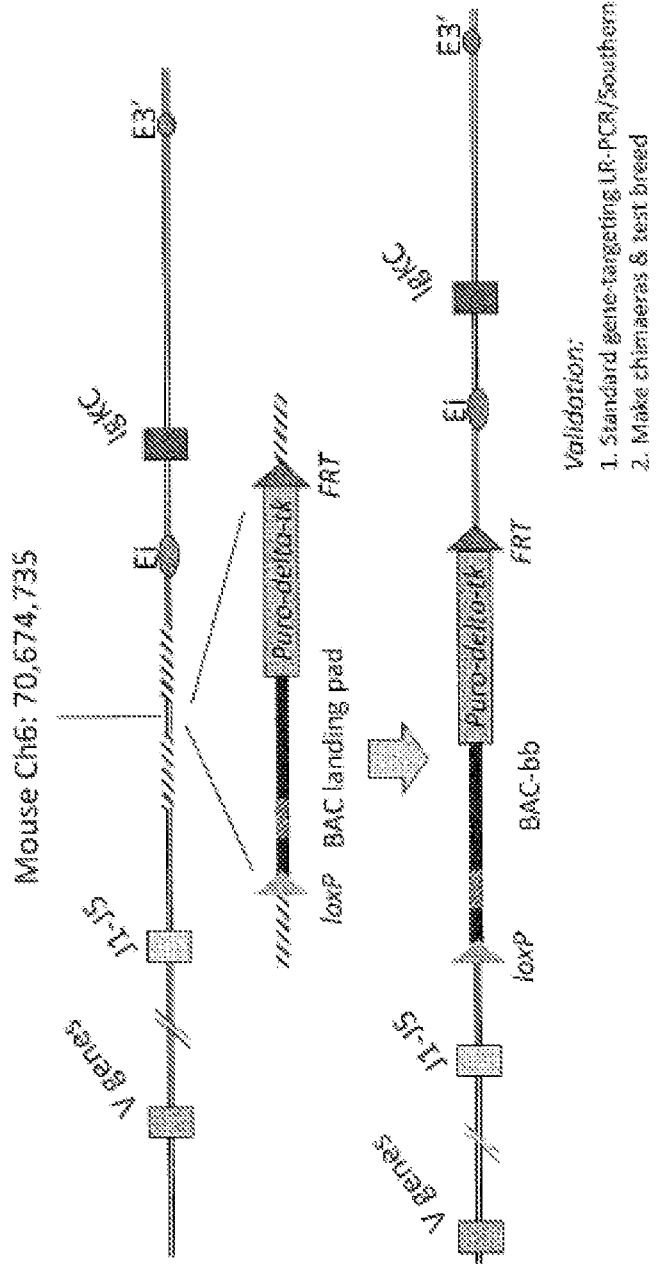
Figure 15:
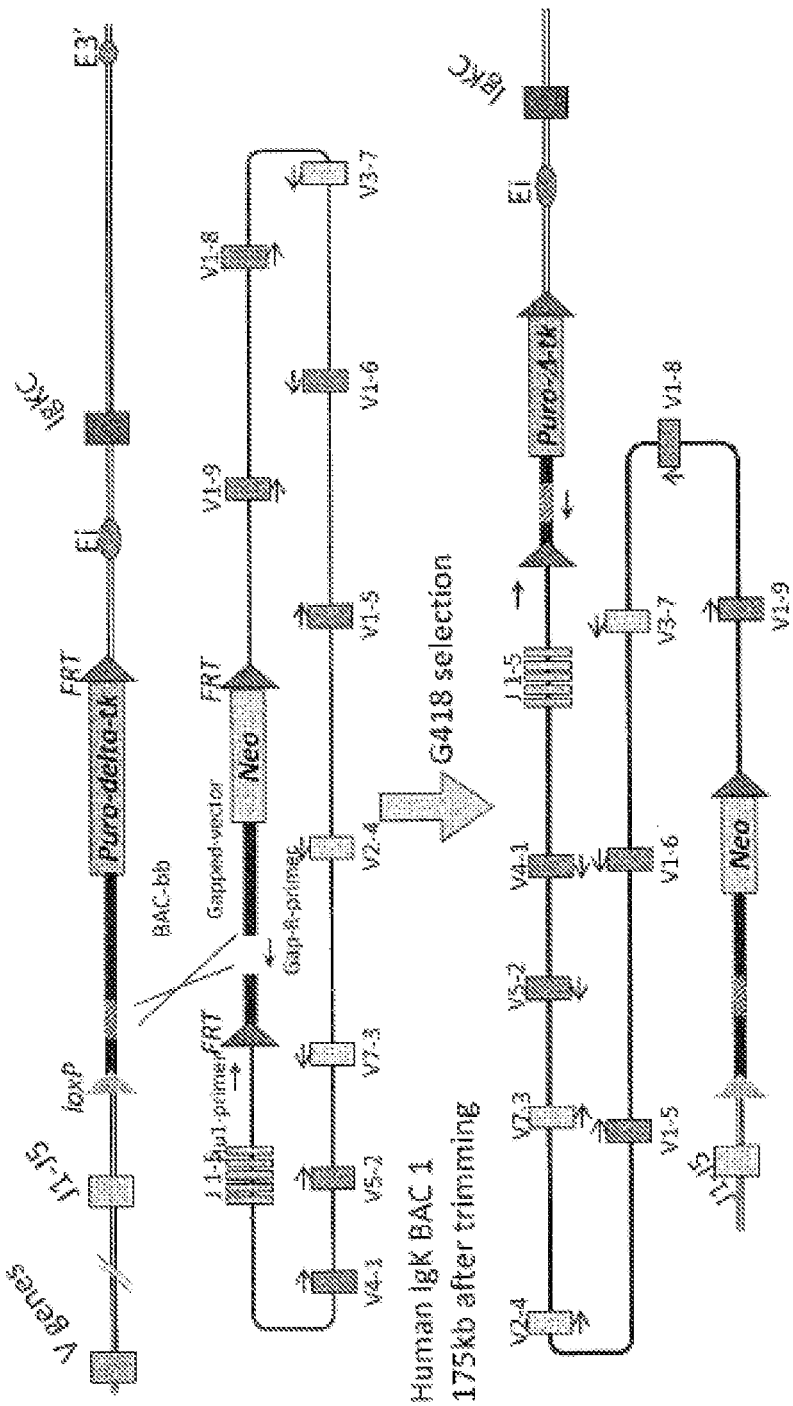
Figure 16:
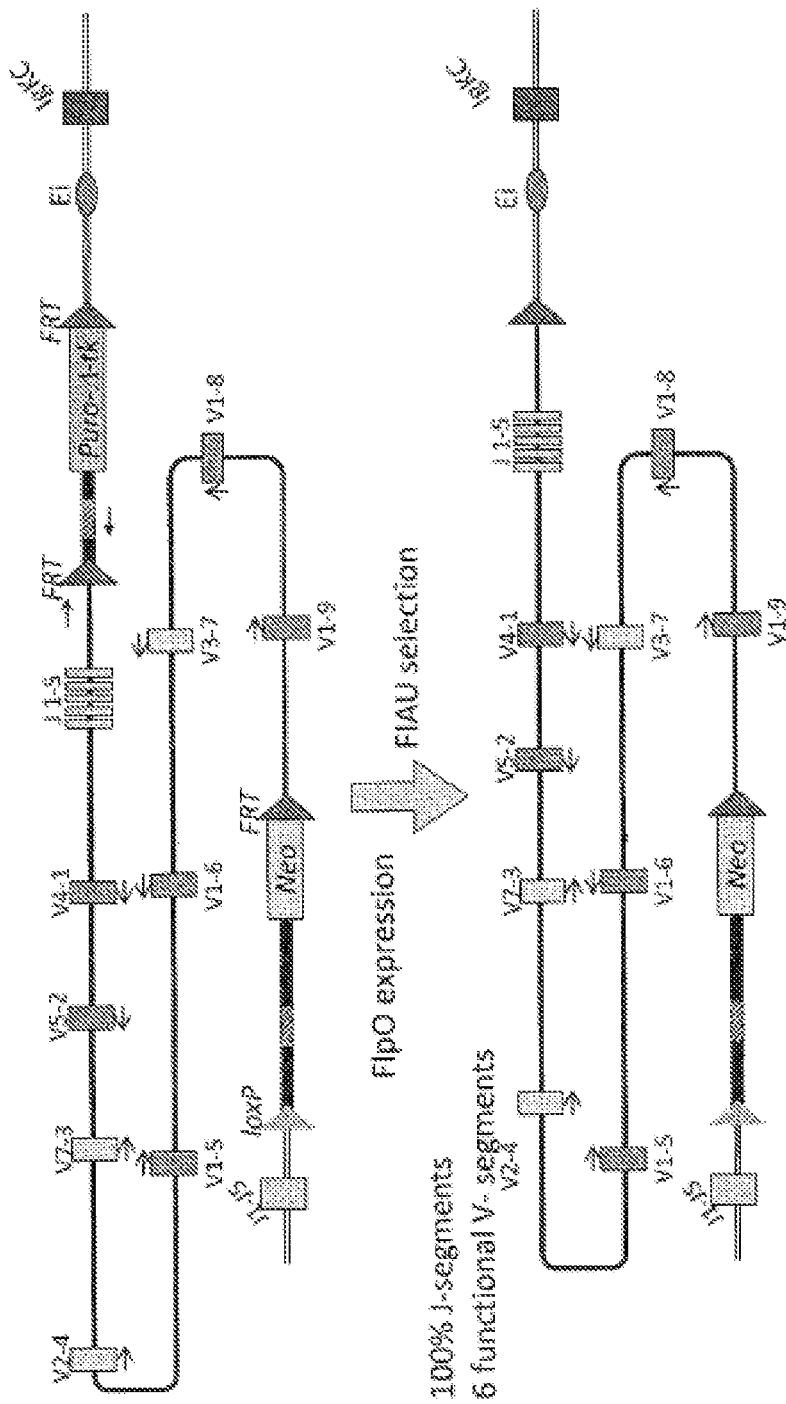
Figure 17:
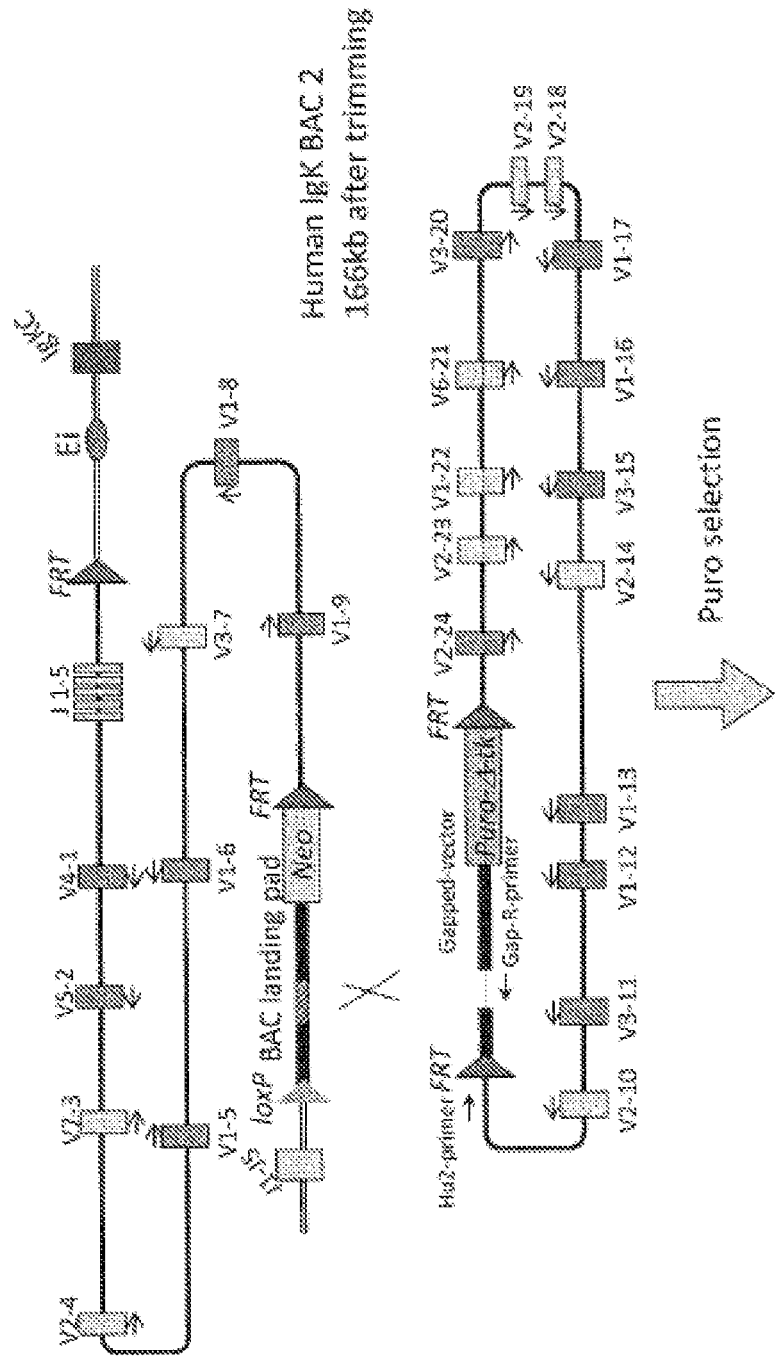
Figure 18:
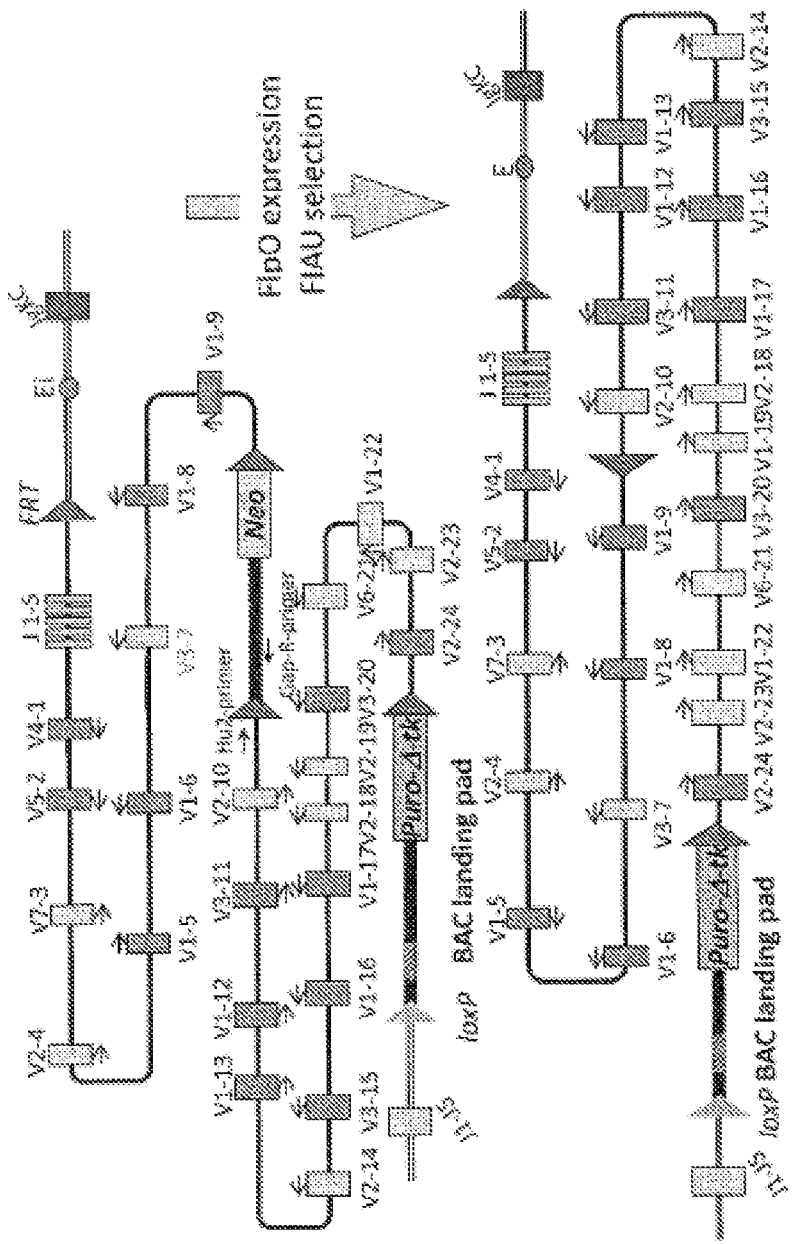

FIG. 8 illustrates the final predicted ES cell construct.

FIGS. 9-18 provide a further level of detail of this process.

Example 2

Site-Specific Recombination

In a further method of the invention site specific recombination can also be employed. Site-specific recombination (SSR) has been widely used in the last 20-years for the integration of transgenes into defined chromosomal loci. SSR involves recombination between homologous DNA sequences.

The first generation of SSR-based chromosomal targeting involved recombination between (i) a single recombination target site (RT) such as loxP or FRT in a transfected plasmid with (ii) a chromosomal RT site provided by a previous integration. A major problem with this approach is that insertion events are rare since excision is always more efficient than insertion. A second generation of SSR called RMCE (recombinase-mediated cassette exchange) was introduced by Schlake and Bode in 1994 (Schlake, T.; J. Bode (1994). "Use of mutated FLP-recognition-target-(FRT-)sites for the exchange of expression cassettes at defined chromosomal loci". Biochemistry 33: 12746-12751). Their method is based on using two heterospecific and incompatible RTs in the transfected plasmid which can recombine with compatible RT sites on the chromosome resulting in the swap of one piece of DNA for another—or a cassette exchange. This approach has been successfully exploited in a variety of efficient chromosomal targeting, including integration of BAC inserts of greater than 50 kb (Wallace, H. A. C. et al. (2007). "Manipulating the mouse genome to engineering precise functional syntenic replacements with human sequence". Cell 128: 197-209; Prosser, H. M. et al. (2008). "Mosaic complementation demonstrates a regulatory role for myosin VIIa in actin dynamics of Stereocilia". Mol. Cell. Biol. 28: 1702-12).

The largest insert size of a BAC is about 300-kb and therefore this places an upper limit on cassette size for RMCE.

In the present invention a new SSR-based technique called sequential RMCE (SRMCE) was used, which allows continuous insertion of BAC inserts into the same locus.

The method comprises the steps of
1 insertion of DNA forming an initiation cassette (also called a landing pad herein) into the genome of a cell;
2 insertion of a first DNA fragment into the insertion site, the first DNA fragment comprising a first portion of a human DNA and a first vector portion containing a first selectable marker or generating a selectable marker upon insertion;
3 removal of part of the vector DNA;
4 insertion of a second DNA fragment into the vector portion of the first DNA fragment, the second DNA fragment containing a second portion of human DNA and a second vector portion, the second vector portion containing a second selectable marker, or generating a second selectable marker upon insertion;
5 removal of any vector DNA to allow the first and second human DNA fragments to form a contiguous sequence; and
6 iteration of the steps of insertion of a part of the human V(D)J DNA and vector DNA removal, as necessary, to produce a cell with all or part of the human VDJ or VJ region sufficient to be capable of generating a chimaeric antibody in conjunction with a host constant region, wherein the insertion of at least one DNA fragment uses site specific recombination.

Figure 22:
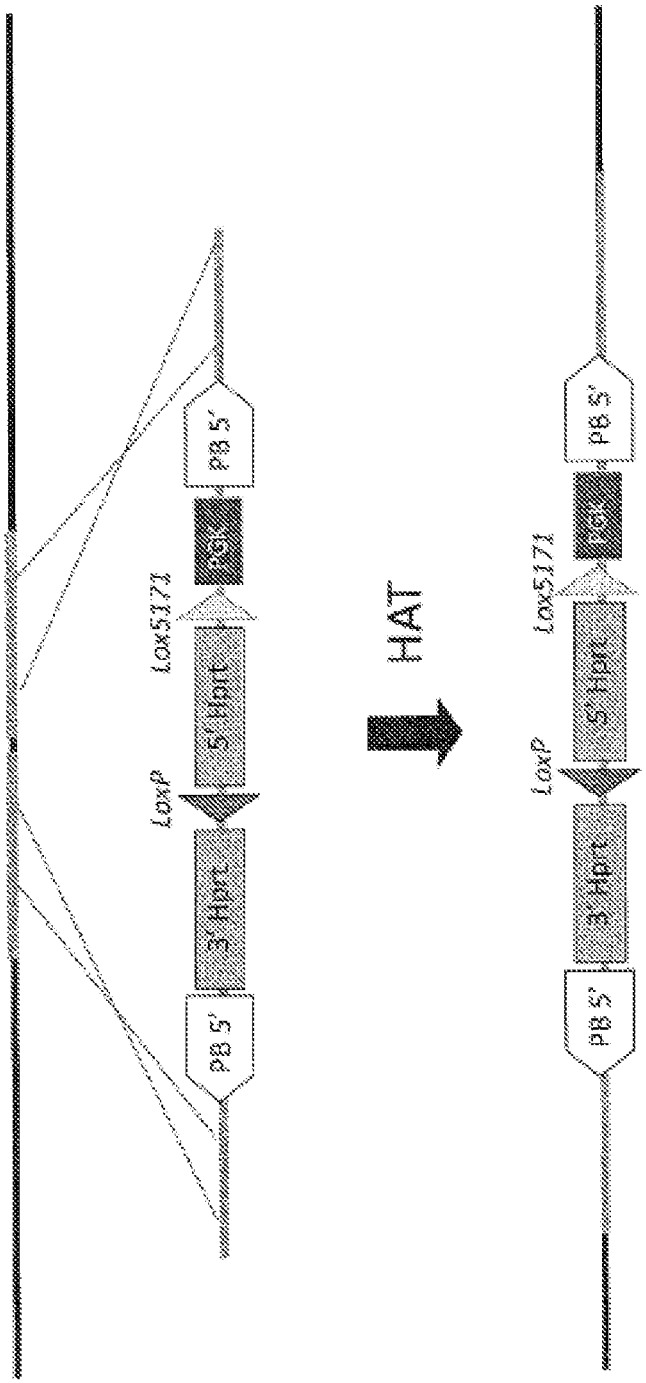

In one specific aspect the approach utilizes three heterospecific and incompatible loxP sites. The method is comprised of the steps as follows, and illustrated in FIGS. 22-26:
1. Targeting a landing pad into the defined locus. An entry vector containing an HPRT mini-gene flanked by inverted piggyBac (PB) ITRs is targeted into defined region (for example: a region between IGHJ and Eμ or IGKJ and Eκ or IGLC1 and Eλ3-1) to serve as a landing pad for BAC targeting. The HPRT mini-gene is comprised of two synthetic exons and associated intron. The 5' HPRT exon is flanked by two heterospecific and incompatible loxP sites (one wild-type and the other a mutated site, lox5171) in inverted orientation to each other (FIG. 22). These two loxP sites provide recombination sites for the BAC insertion through RMCE.

Figure 23:
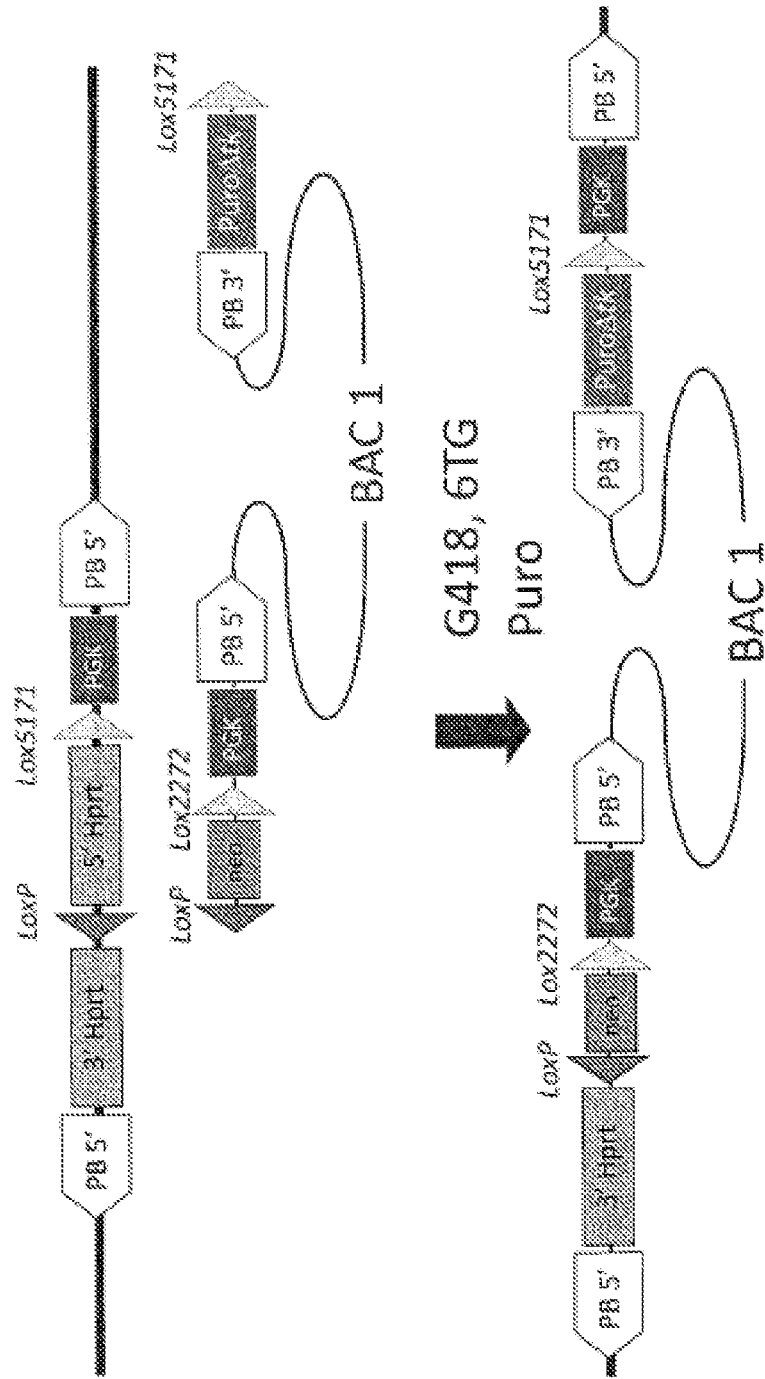

2. Insertion of the $1^{st}$ modified BAC into the targeted landing pad. The $1^{st}$ BAC has a length of DNA to be inserted into the genome flanked by engineered modifications. The 5' modification (loxP-neo gene-lox2272-PGK promoter—PB 5'LTR) and 3' modification (PB3'LTR-puroΔTK gene—lox5171) is depicted in FIG. 23 along with the relative orientations of the lox sites and PB LTRs. With transient CRE expression from a co-electroporated vector, the DNA sequence would be inserted into the defined locus through RMCE. The cells in which a correct insertion has occurred can be selected as follows: (i) Puromycin-resistance (the puroΔTK gene has acquired a promoter—"PGK"—from the landing pad), (ii) 6TG-resistance (the HPRT mini-gene has been disrupted), and (iii) G418-resistance (selects for any insertion via the 5' region PGK-neo arrangement). Any combination of these selection regimes can be used. G418- and 6TG-resistance select for correct events on the 5' end while puro-resistance selects for correct events on the 3' end.

3. Curing (removing) the 3' modification of the $1^{st}$ insertion. A properly inserted $1^{st}$ BAC results the 3' end having a puroΔTK gene flanked by inverted PB LTRs (FIG. 24)—essentially a proper transposon structure. This transposon can then be removed by the transient expression of the piggyBac transposase (from an electroporated vector). Cells with the correct excision event can be selected by FIAU resistance—i.e., no thymidine kinase activity from the puroΔTK gene. This completely removes the 3' modification leaving no trace nucleotides.

Figure 25:
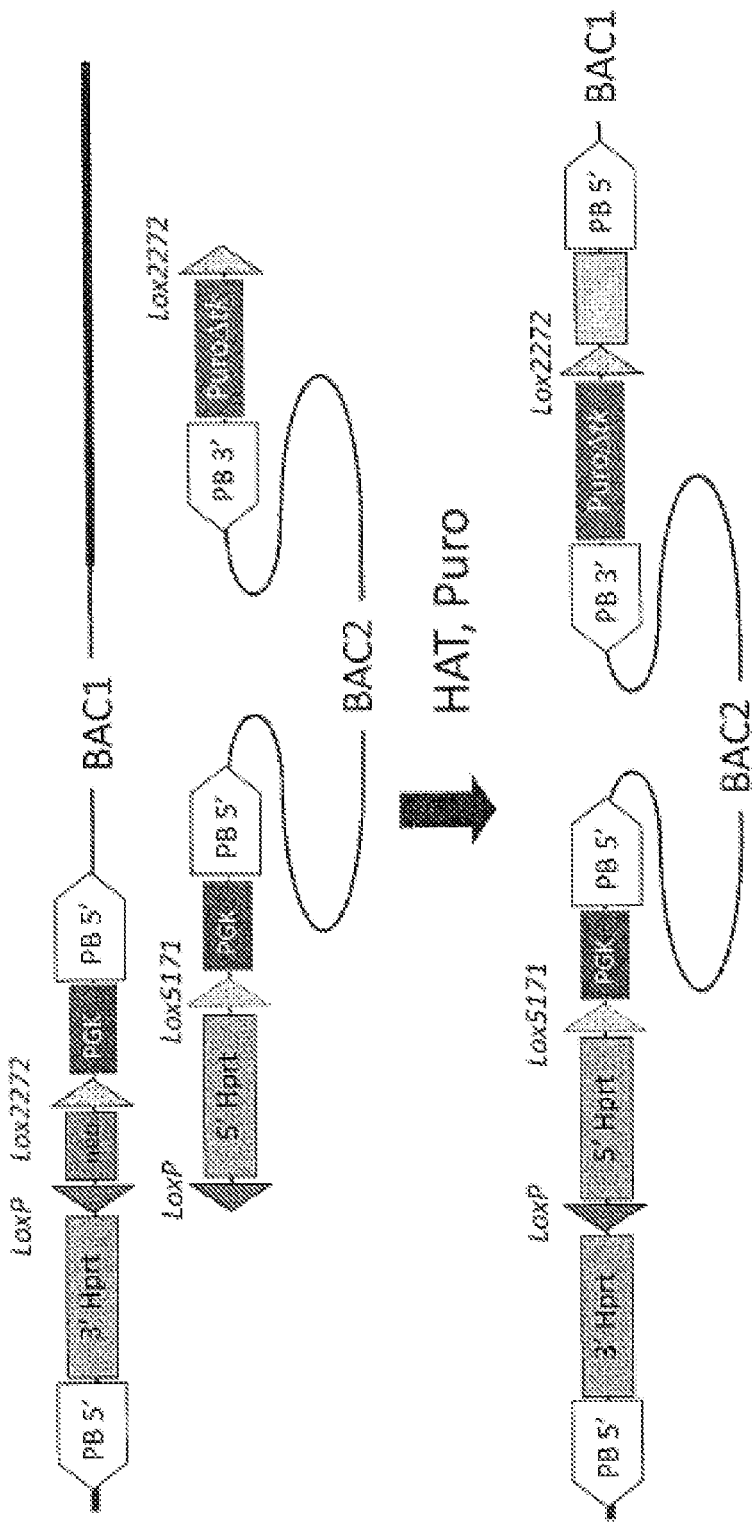
Figure 26:
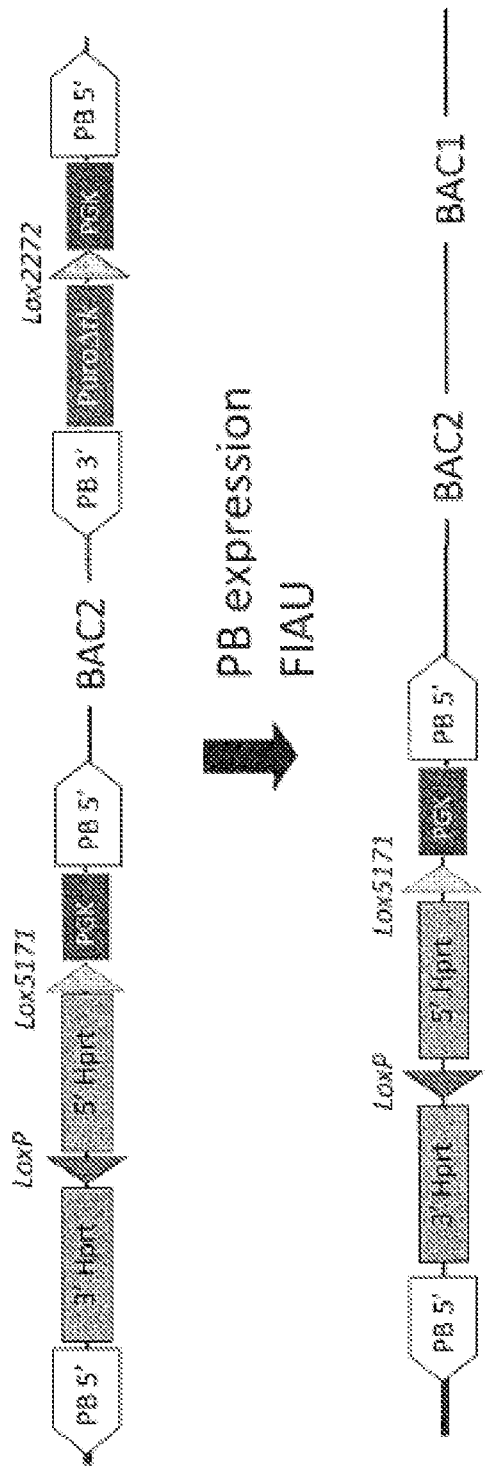

4. Insertion of a $2^{nd}$ modified BAC into the 5' end of $1^{st}$ insertion. The $2^{nd}$ BAC has a length of DNA to be inserted into the genome (usually intended to be contiguous with the DNA inserted with the $1^{st}$ BAC) flanked by engineered modifications. The 5' modification (loxP-HPRT mini gene 5' portion-lox5171-PGK promoter-PB5'LTR) and 3' modification (PB3'LTR-puroΔTK-lox2272) is depicted in FIG. 25 along with the relative orientations of the lox sites and PB LTRs. With transient CRE expression from a co-electroporated vector, the DNA sequence would be inserted into the defined locus through RMCE. The cells in which a correct insertion has occurred can be selected as follows: (i) HAT-resistance (the HPRT mini-gene is reconstituted by a correct insertion event, i.e.: the 5' and 3' exon structures are brought together), and (ii) puromycin-resistance (puroΔTK gene has acquired a promoter—"PGK"—from the landing pad).

5. Curing (removing) the 3' modification of the $2^{nd}$ insertion. A properly inserted $2^{nd}$ BAC results the 3' end having a puroΔTK gene flanked by inverted PB LTRs (FIG. 26)—essentially a proper transposon structure, exactly analogous to the consequence of a successful $1^{st}$ BAC insertion. And therefore this transposon can likewise be removed by the transient expression of the piggyBac transposase (from an electroporated vector). Cells with the correct excision event can be selected by FIAU resistance—i.e., no thymidine kinase activity from the puroΔTK gene. This completely removes the 3' modification leaving no trace nucleotides.

6. After curing of the 3' modification of the $2^{nd}$ BAC insertion, the landing pad becomes identical to the original. This entire process, steps 2 through 5, can be repeated multiple times to build up a large insertion into the genome. When complete, there are no residual nucleotides remaining other than the desired insertion.

Figure 27:
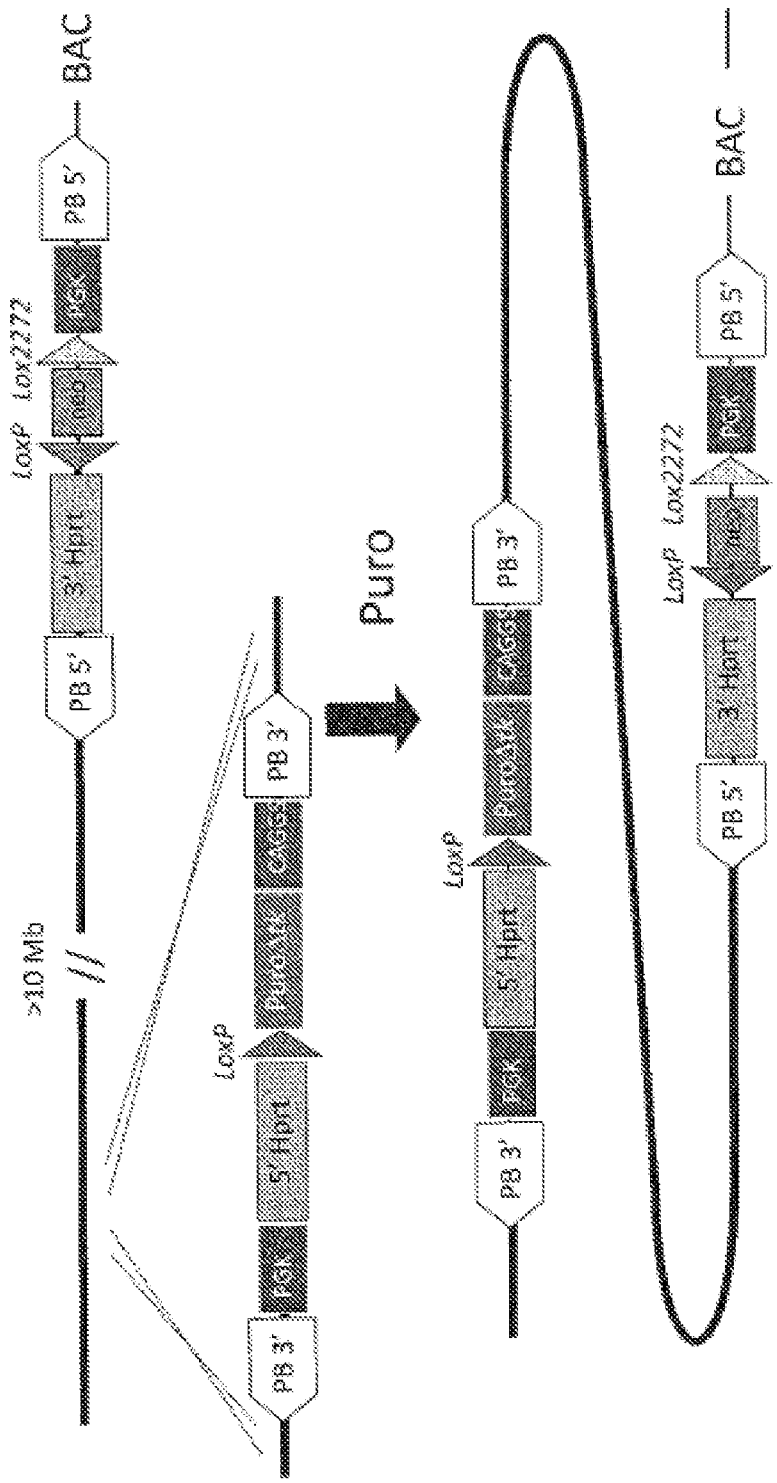
FIGS. 27-29 illustrate a mechanism for inversion of the host VDJ region

With the insertion of an odd number of BACs into the Ig loci, the endogenous VDJ or VJ sequences can be inactivated through an inversion via chromosomal engineering as follows (see FIGS. 27-29):

1. Targeting a "flip-over" cassette into a 5' region 10 to 40 megabases away from the endogenous VDJ or VJ. The flip-over vector (PB3'LTR-PGK promoter-HPRT mini gene 5' portion-loxP-puroΔTK-CAGGS promoter-PB3'LTR) is depicted in FIG. 27 along with the relative orientations of the lox sites and PB LTRs.

Figure 28:
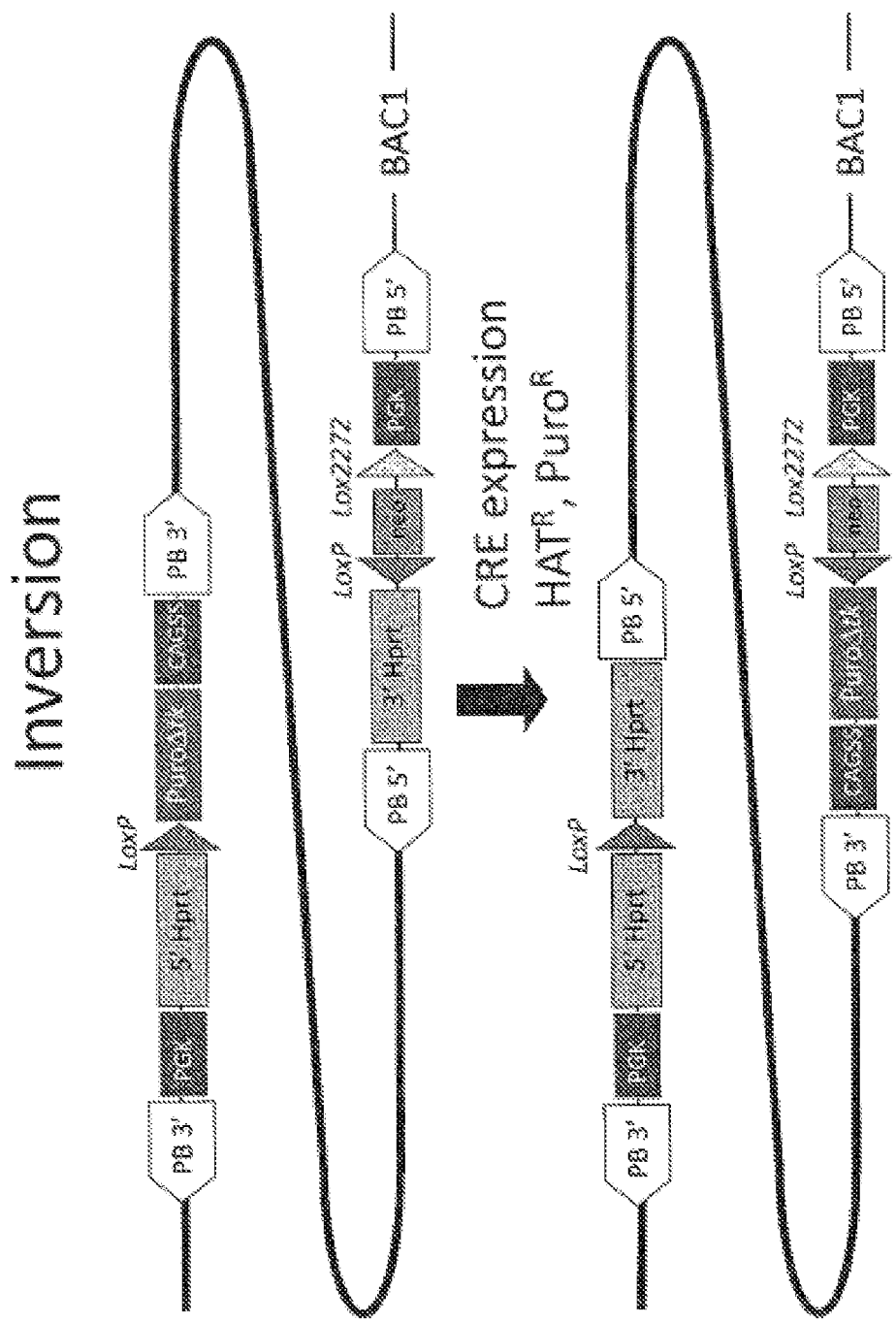

2. Transient CRE expression will result in recombination between the loxP site in the "flip-over" cassette and the loxP site in the 5' modification. This 5' modification is as described in Steps 2 and 3 above—essentially the modification resulting from insertion of an odd number of BACs, after the 3' modification has been cured. The loxP sites are inverted relative to one another and therefore the described recombination event results in an inversion as depicted in FIG. 28. Cells with the correct inversion will be HAT-resistance since the HPRT mini-gene is reconstituted by a correct inversion.

Figure 29:
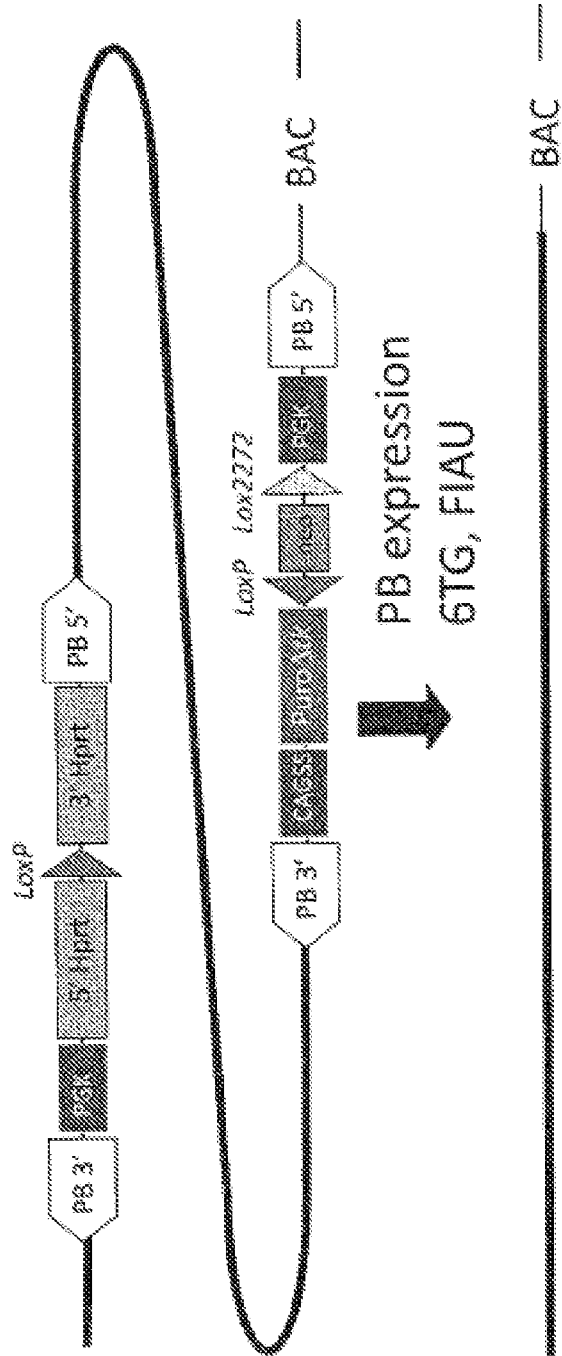

3. A correct inversion also leaves two transposon structures flanking the "flip-over" cassette and the 5' modification. Both can be excised with transient piggyBAC transposase expression, leaving no remnant of either modification (FIG. 29). Cells with the correct excisions can be selected as follows: (i) 6TG-resistance (the HPRT mini-gene is deleted) and (ii) FIAU-resistance (the puroΔTK gene is deleted). An inversion as described in the Ig loci would move the endogenous IGH-VDJ or IGK-VJ region away from the Eμ or Eκ enhancer region, respectively, and lead to inactivation of the endogenous IGH-VDJ or IGK-VJ regions.

The methods of insertion of the invention suitably provide one or more of:

Selection at both 5' and 3' ends of the inserted DNA fragment;

Efficient curing of the 3' modification, preferably by transposase mediated DNA excision;

Inactivation of endogenous IGH or IGK activity through an inversion; and

Excision of modifications, leaving no nucleotide traces remaining in the chromosome.

Example 3

Insertion of a Test Vector into the Genome at a Defined Location

Figure 30:
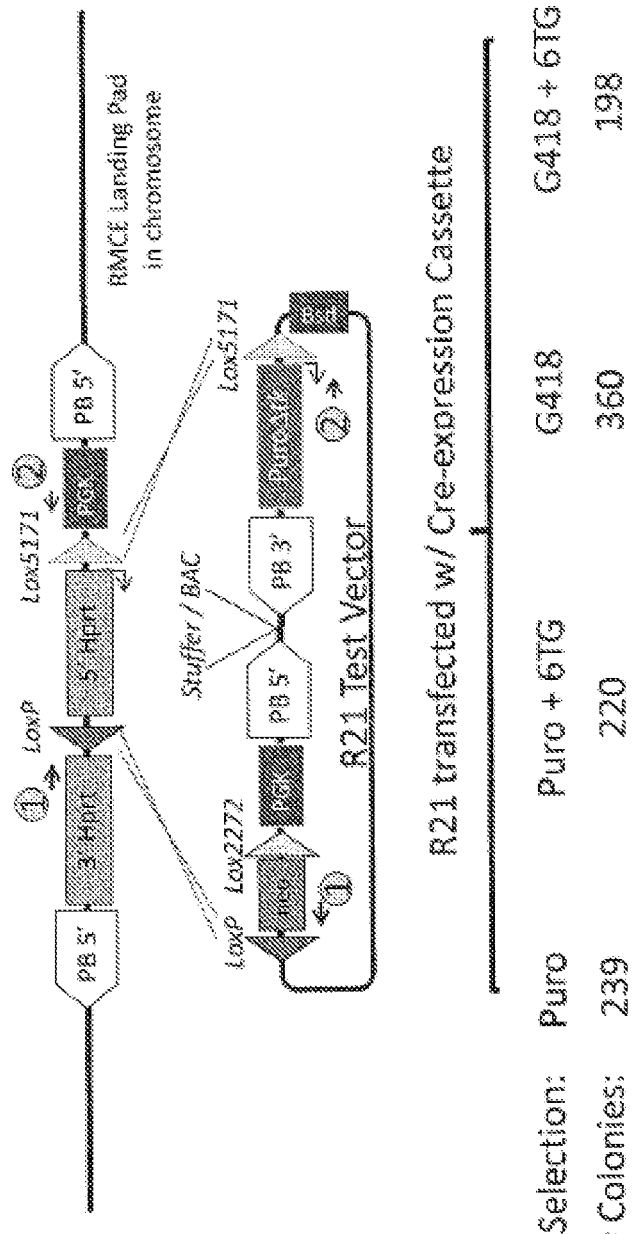
FIG. 30 illustrates proof of principle for insertion of a plasmid using an RMCE approach

Proof of concept of the approach is disclosed in FIG. 30. In FIG. 30 a landing pad as shown in FIG. 22 was inserted into the genome of a mouse by homologous recombination, followed by insertion of the R21 plasmid into that landing pad via cre-mediated site specific recombination. The insertion event generated a number of general insertion events, 360 G418 resistant colonies, of which ~220 were inserted into the desired locus, as demonstrated by disruption of the HRPT minilocus.

Figure 31:
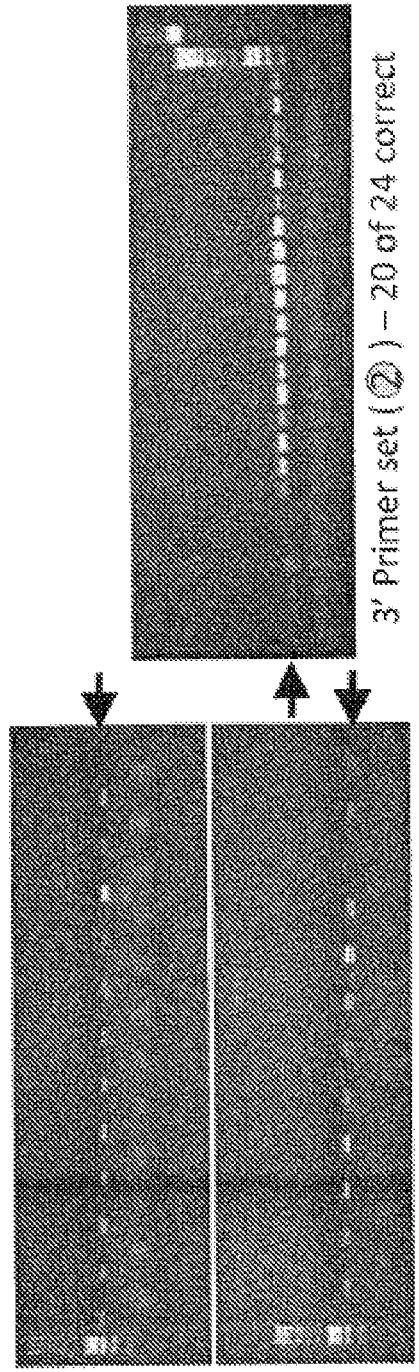
FIG. 31 illustrates sequential RMCE—Integration into Landing Pad

The R21 vector mimics the 1st BAC insertion vector at the 5' and 3' ends, including all selection elements and recombinase target sites. In place of BAC sequences, there is a small 'steer' sequence. This vector will both test all the principals designed in the invention and allow easy testing of the results in that PCR across the stuffer is feasible and therefore allows both ends of the insertion to be easily tested. R21 was co-electroporated with a cre-expressing vector into the ES cells harbouring the landing pad in the IGH locus. Four sets of transformed cells were transfected in parallel and then placed under different selection regimes as indicated in FIG. 30. G418 selection (neo gene expression) resulted in the largest number of colonies due to there being no requirement for specific landing-pad integration. Any integration of R21 into the genome will provide neo expression leading to G418-resistance. Puro selection resulted in a similar colony number to Puro+6TG or G418+6TG, suggesting that the stringency of Puro selection is due to the PuroΔTK lacking a promoter in the vector. Puro expression is only acquired when an integration occurs near a promoter element—in this design most likely specifically in the landing pad. These conclusions are supported by the results from junction PCR which is shown in FIG. 31.

Figure 32:
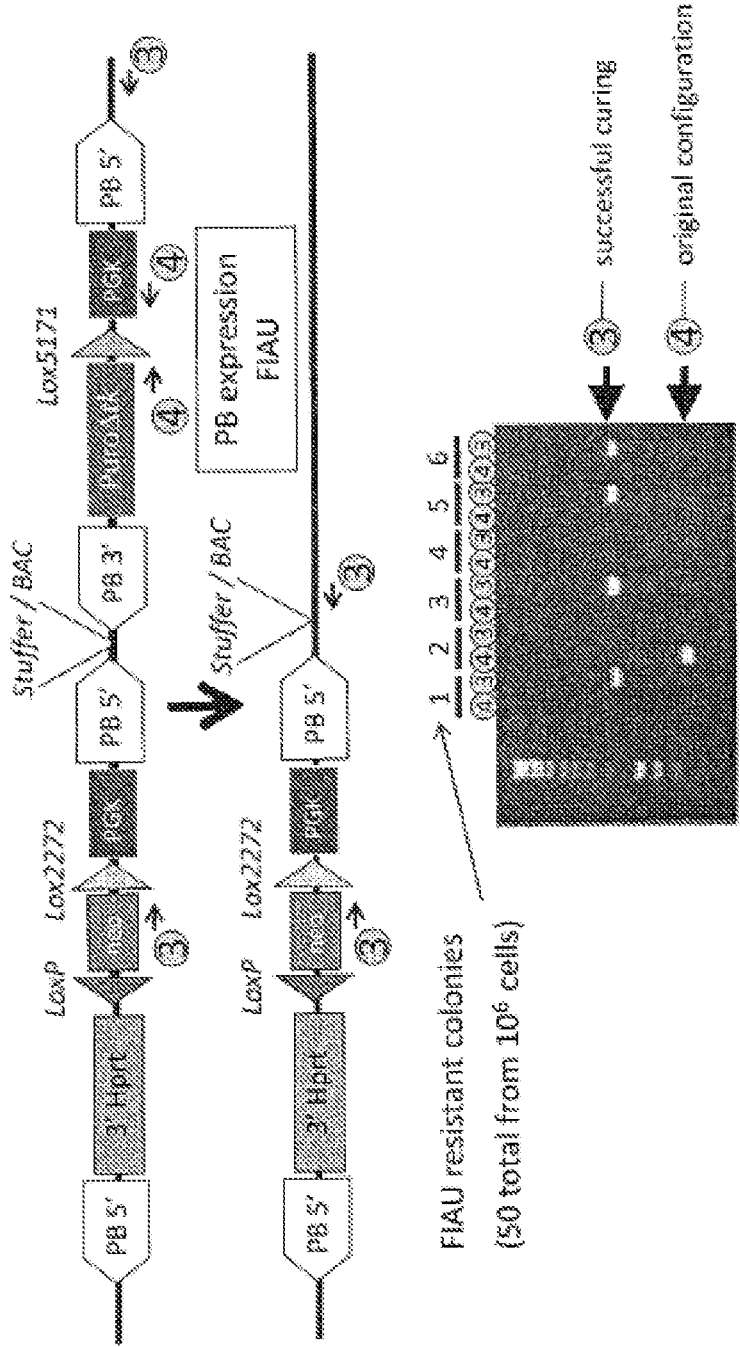
FIG. 32 illustrates confirmation of Successful Insertion into Landing Pad

The next step in the invention is to 'cure' the 3' end of the integrated BAC vector, leaving a seamless transition between the insertion and the flanking genome. This curing was demonstrated by expanding an individual clone from above (R21 inserted into the landing pad) and expressing piggyBac recombinase in this clone via transfection of an expressing plasmid. FIAU was used to select colonies in which the 3' modification was excised—i.e., through loss of the 'PGK-puroΔTK' element between the piggyBac terminal repeats. Fifty such clones resulted from a transfection of $10^6$ cells; of these six were tested for the expected genomic structure. Successful curing resulted in positive PCR between the primer set labelled "3" in FIG. 32. Of the 6 clones, 4 had correct excisions, 1 clone remained in the original configuration and 1 other had a deletion.

These data demonstrate iterative insertion of DNA into a landing pad at a defined genomic locus using the approaches outlined above.

Example 4

Insertion of Large Parts of the Human IG Loci into Defined Positions in the Mouse Genome Example 3 demonstrated that the design of the claimed invention was capable of providing for the insertion of a test vector into the genome at a defined location, in this case the R21 vector into the mouse IGH locus. The use of the appropriate selection media and the expression of cre-recombinase resulted in a genomic alteration with the predicted structure.

The same design elements described in this invention were built into the 5' and 3' ends of a BAC insert. Said insert comprised human sequences from the IGH locus and was approximately 166-kb. This engineered BAC was electroporated along with a cre-expressing plasmid DNA into mouse ES cells harbouring the landing pad at the mouse IGH locus. The transfected cell population was grown in puro-containing media to select for appropriate insertion events.

Figure 33:
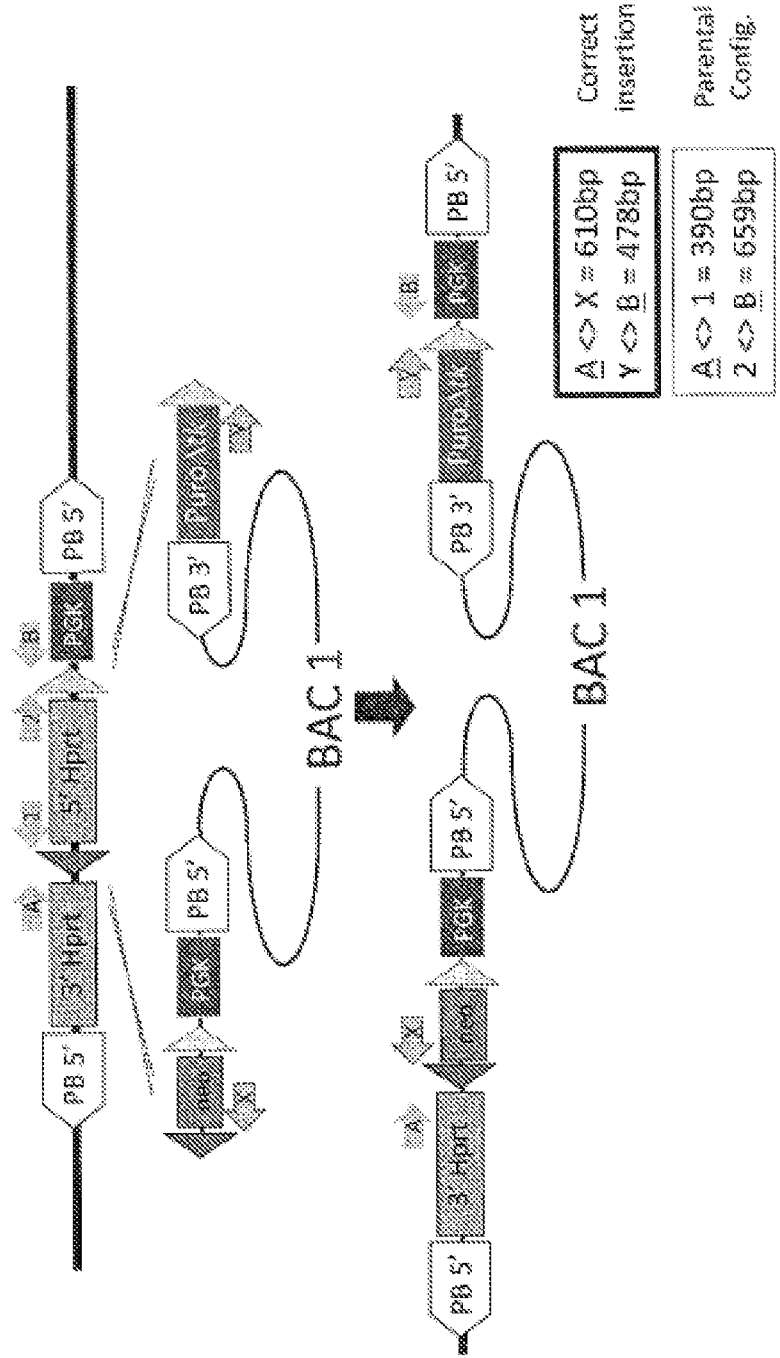
FIG. 33 illustrates PCR Confirmation of 3' End Curing
Figure 34:
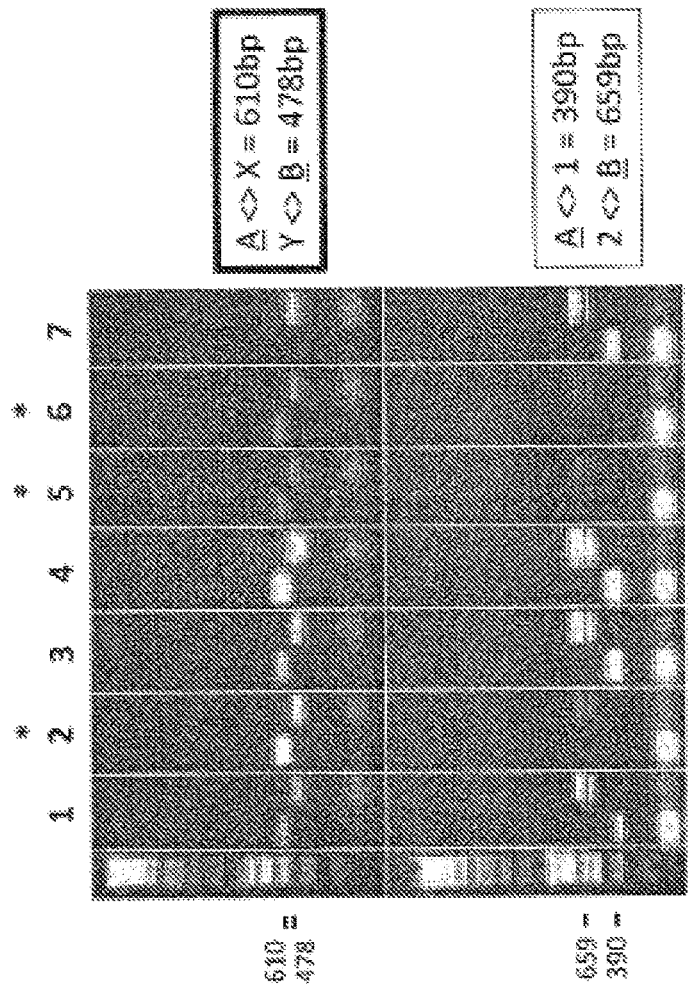
FIG. 34 illustrates insertion of BAC #1 and PCR Diagnostics

Seven resulting clones were isolated and further analysed. The expected recombination event and resulting structure are depicted in FIG. 33. Based upon data from the R21 experiment outlined in Example 3, a stringent selection for correct clones was expected when the transfected population was selected in puro-containing media. This is because the puro-coding region requires a promoter element and this is preferentially supplied by the landing pad after recombination. Accordingly, the majority of the 7 isolated clones had inserted correctly into the genome at the landing pad as determined by the diagnostic PCR. The primers for diagnosing a correct insertion are depicted in FIG. 33. Correct junctions are present in the genome if a 610-bp fragment is amplified between primers 'A' and 'X' and a 478-bp fragment is amplified between primers 'Y' and 'B' (FIGS. 33 and 34). Note that there are amplified fragments between 'A' and '1' primers and '2' and 'B' primers indicating the presence of parental genome (that is, the landing pad alone). These result from parental cells present internally in the cell colonies under puro-selection that escape the selection due to the geometry of a colony. After passaging the colony through puro-containing media, these parental junction fragments disappear indicating that the parental cells are removed from the population. In addition, all the clones were shown to be resistant to 6-TG as expected if the HPRT gene is inactivated by the correct insertion event.

These data indicate that the disclosed strategy for inserting large parts of the human IG loci into defined positions in the mouse genome will enable the construction of a mouse with a plurality of the variable regions of human IG regions upstream of the mouse constant regions as described.

Example 5

Inserted Loci are Functional in Terms of Gene Rearrangement, Junctional Diversity as Well as Expression Bacterial artificial chromosomes (BACs) were created, wherein the BACs had inserts of human Ig gene segments (human V, D and/or J gene segments). Using methods described herein, landing pads were used in a method to construct chimaeric Ig loci in mouse embryonic stem cells (ES cells), such that chimaeric IgH and IgK loci were provided in which human gene segments are functionally inserted upstream of endogenous constant regions. To test if the human IgH-VDJ or IgK-VJ gene segments in the chimaera mice derived from human BAC-inserted ES cell clones appropriately rearrange and express, RT-PCR was performed for the RNA samples of white blood cells from those mice with the primer pairs of human variable (V) region and mouse constant (C) region. The sequences of oligos are shown as follows (Table 1). Each V oligo is paired with C oligo (HV with Cμ; KV with Cκ) for PCR reaction.

TABLE 1

| Oligo | Sequence |
| --- | --- |
| HV2-5 | AGATCACCTTGAAGGAGTCTGGTCC (SEQ ID NO 7) |
| HV4-4 | TGGTGAAGCCTTCGGAGACCCTGTC (SEQ ID NO 8) |
| HV1-3 | CACTAGCTATGCTATGCATTGGGTG (SEQ ID NO 9) |
| HV1-2 | ATGGATCAACCCTAACAGTGGTGGC (SEQ ID NO 10) |
| HV6-1 | GGAAGGACATACTACAGGTCCAAGT (SEQ ID NO 11) |
| Cμ | TAGGTACTTGCCCCCTGTCCTCAGT (SEQ ID NO 12) |
| KV1-9 | AGCCCAGTGTGTTCCGTACAGCCTG (SEQ ID NO 13) |
| KV1-8 | ATCCTCATTCTCTGCATCTACAGGA (SEQ ID NO 14) |

TABLE 1-continued

| Oligo | Sequence |
|---|---|
| KV1-6 | GGTAAGGATGGAGAACACTGGCAGT (SEQ ID NO 15) |
| KV1-5 | TTAGTAGCTGGTTGGCCTGGTATCA (SEQ ID NO 16) |
| Cκ | CTTTGCTGTCCTGATCAGTCCAACT (SEQ ID NO 17) |

Using the one-step formulation of SuperScript™ III One-Step RT-PCR System with Platinum® Taq High Fidelity (Invitrogen™; World Wide Web (www) invitrogen.com/site/us/en/home/References/protocols/nucleic-acid-amplification-and-expression-profiling/per-protocol/superscript-3-one-step-rt-per-systenn-with-platinum-taq-high-fidelity.html#prot3), both cDNA synthesis and PCR amplification were achieved in a single tube using gene-specific primers and target RNAs.

The RT-PCR results showed most of the human IGH-VDJ or IGK-VJ gene segments appropriately rearrange and express in the chimaera mice. To investigate the details about the diversity generated from VDJ/VJ rearrangement, those specific RT-PCR fragments were cloned into a common vector for sequencing.

Figure 35:
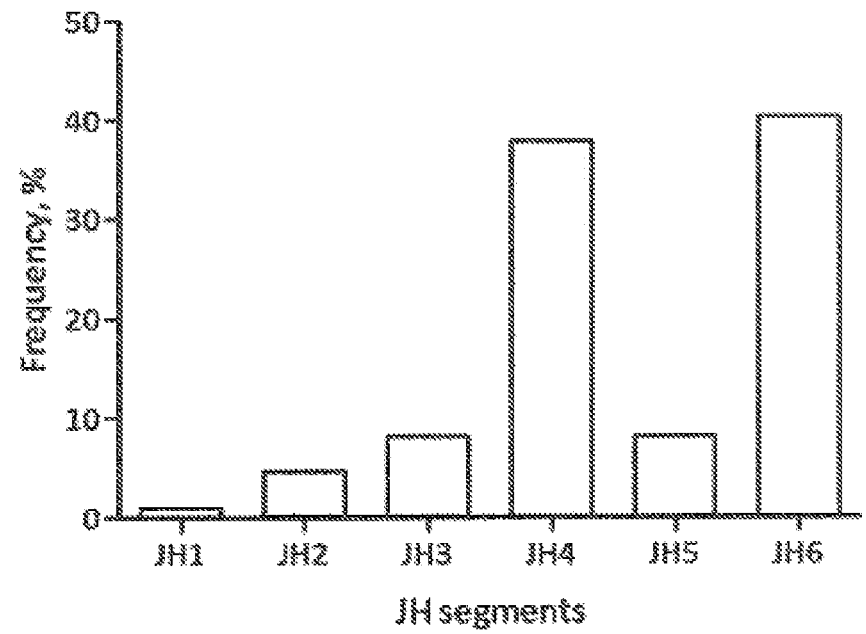
FIG. 35 illustrates JH and JK usage
Figure 35:
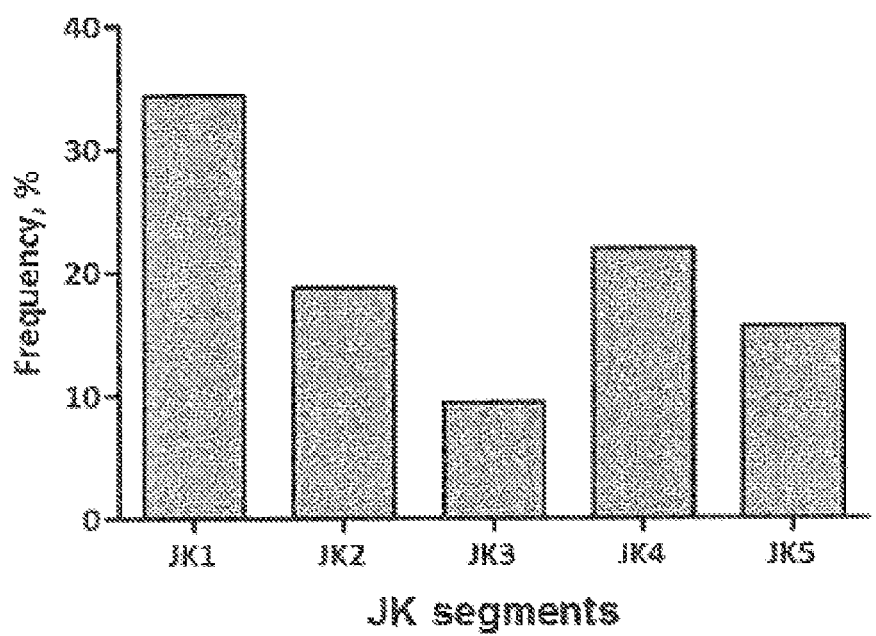
Figure 36:
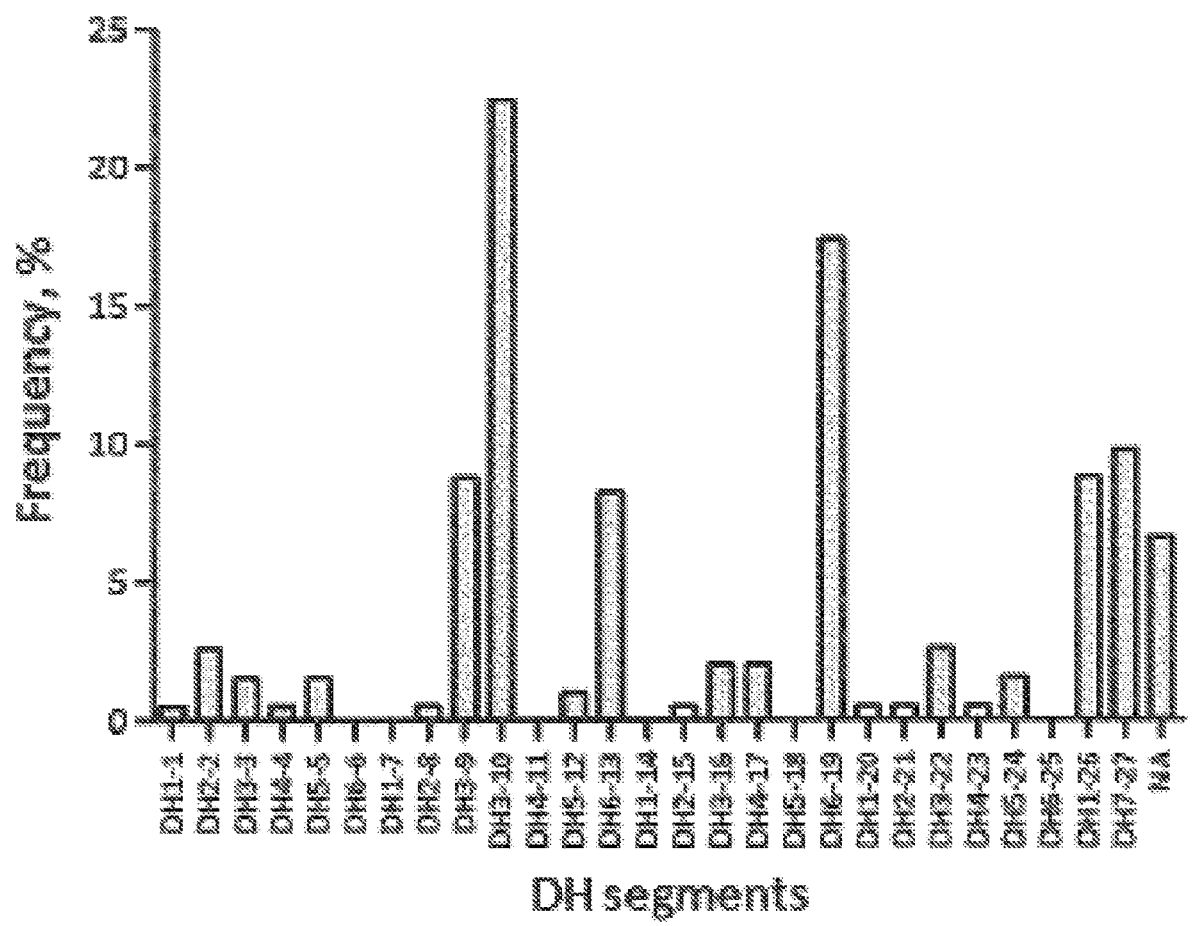
FIG. 36 illustrates DH usage
Figure 37:
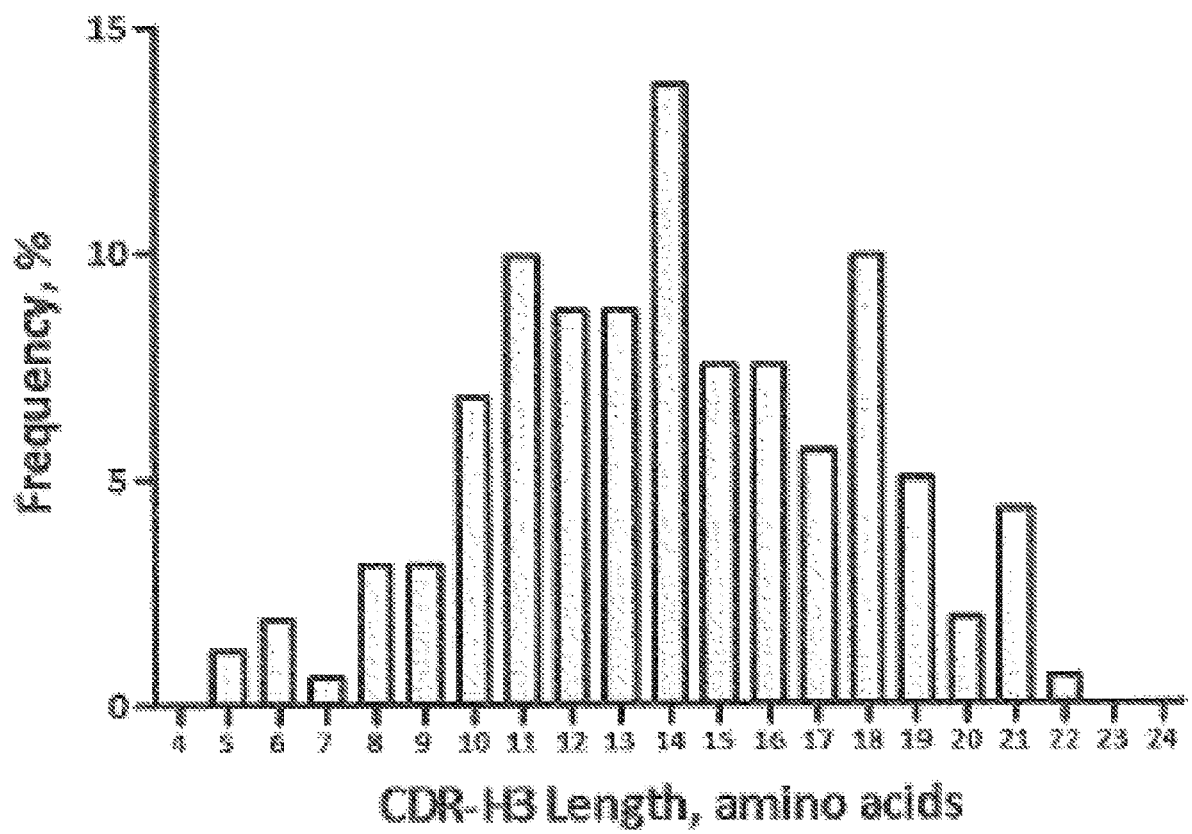
FIG. 37 illustrates the distribution of CDR-H3 length in human VDJCμ transcripts from chimera mice
Figure 38:
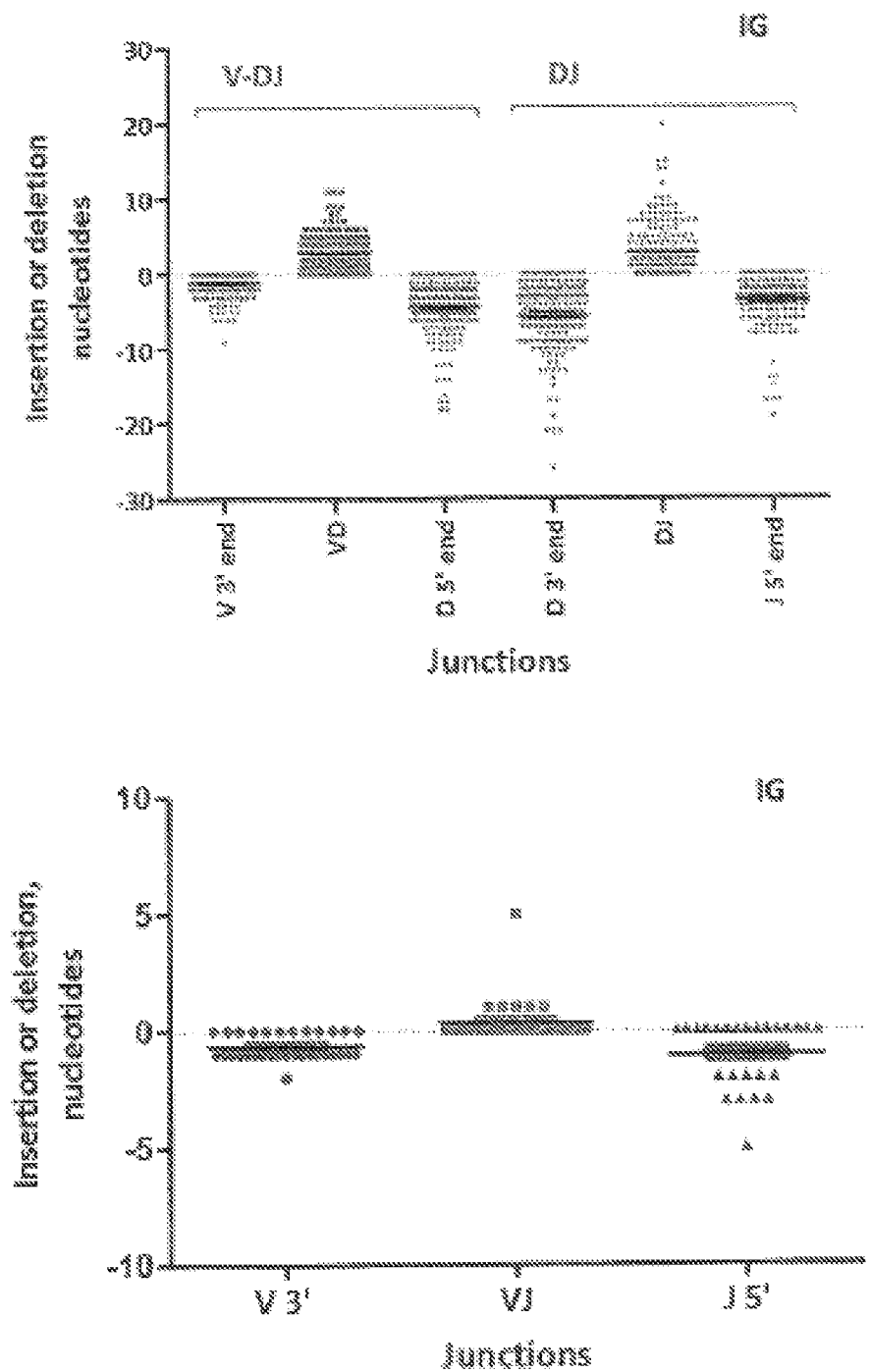
FIG. 38 illustrates the distribution of nucleotide numbers of deletion and insertion in IGH-VDJ or IGK-VJ junctions

Sequencing results indicate that JH, DH, and JK usages (FIG. 35 and FIG. 36) are similar to human results. In addition, the results from the IGH-VDJCμ transcripts show that the range and mean of CDR-H3 length (FIG. 37) are similar to that observed in human. The junctional diversity generated from exonuclease and nucleotide addition activities (FIG. 38) was also observed. The IGH rearrangement possessed a higher frequency of these activities compared to the IGK one. These data suggest that the inserted loci are functional in terms of gene rearrangement, junctional diversity as well as expression.

Example 6

Productive VJ Rearrangement and Somatic Hypermutation can be Obtained

Figure 41:
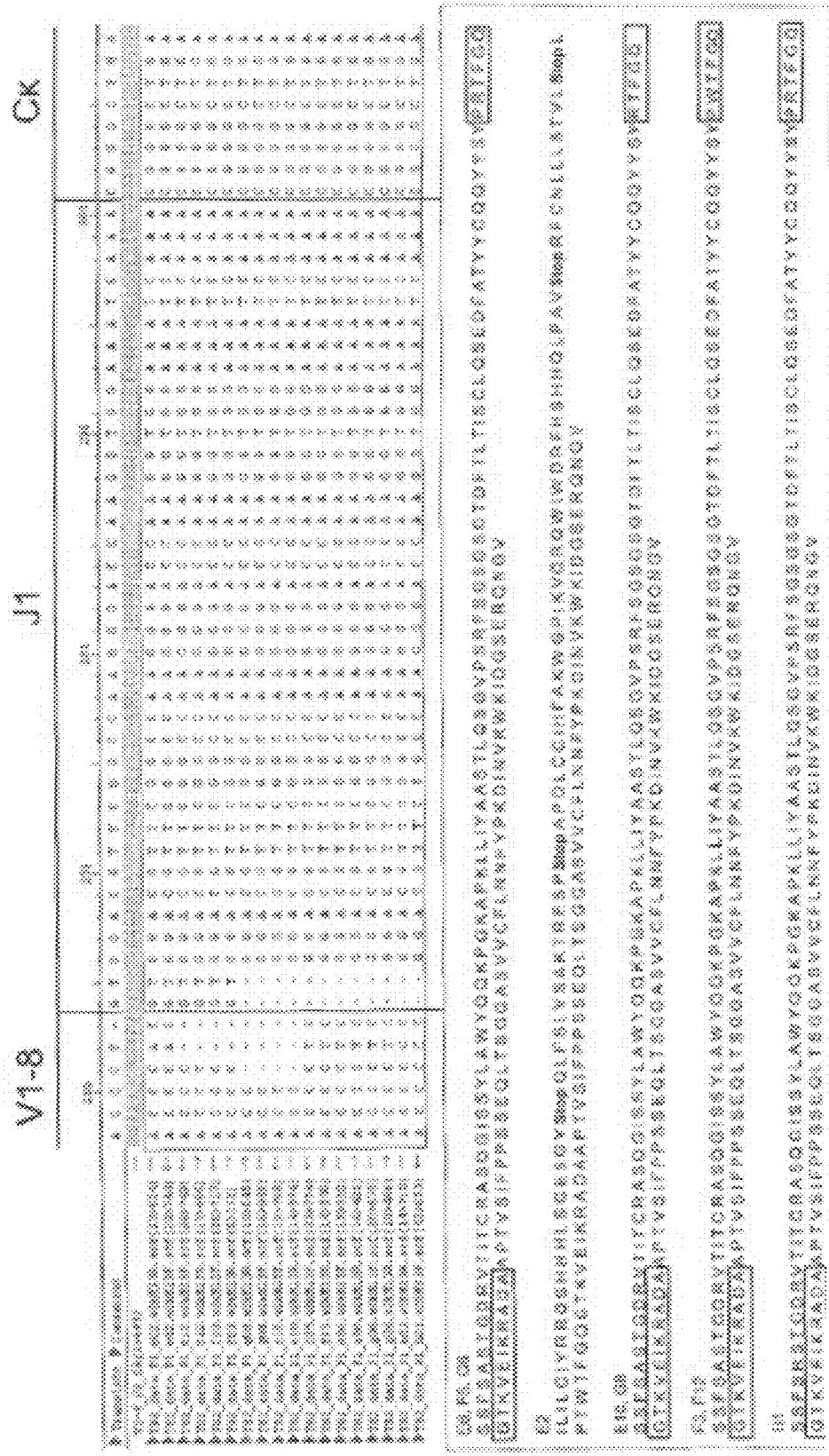
FIG. 41 illustrates Nucleotide Gain or Loss at VJ Joints Generates IGK Variants
Figure 42:
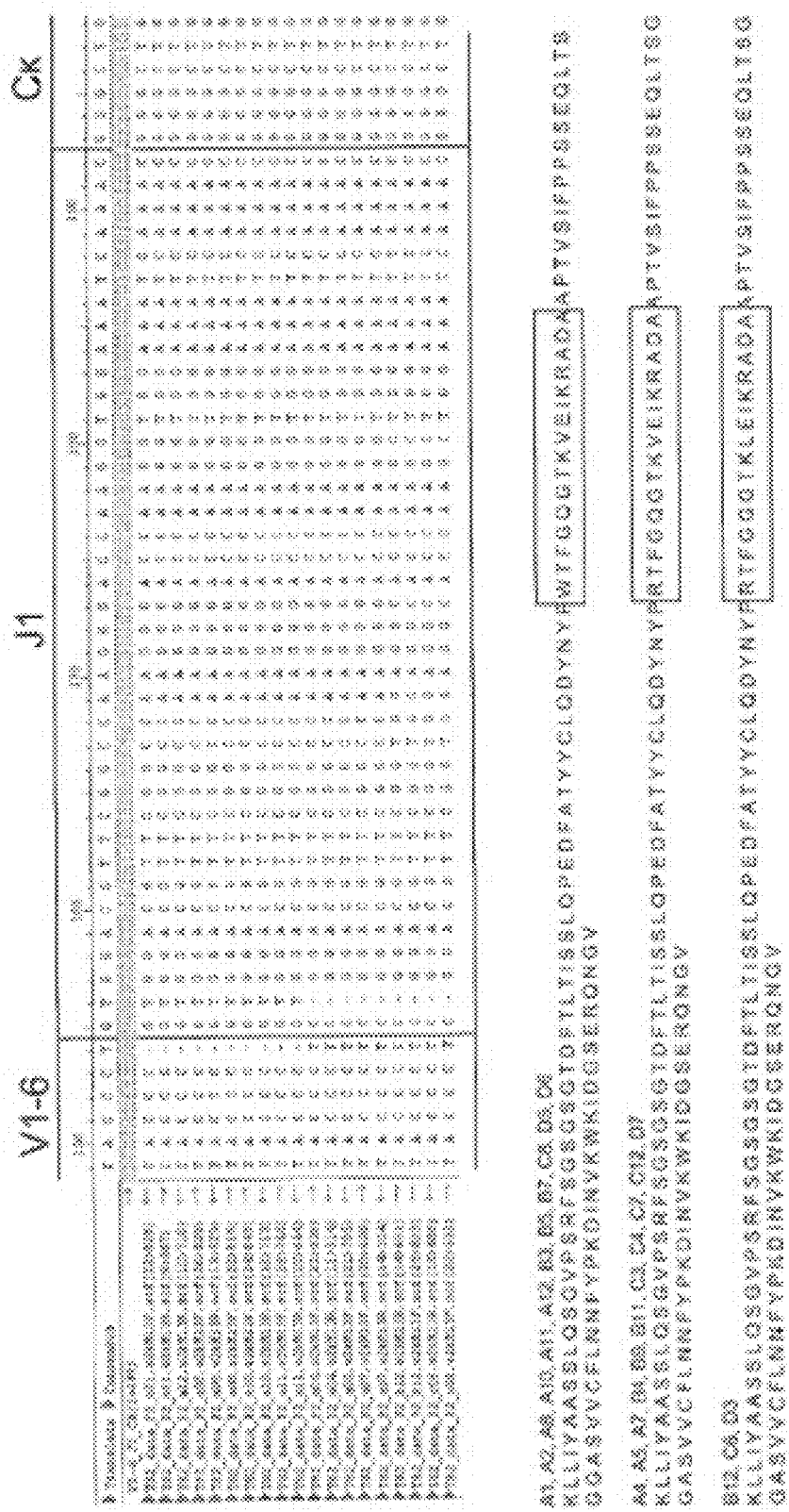
FIG. 42 illustrates Hypermutaion in J Regions Generates IGK Variants
Figure 43:
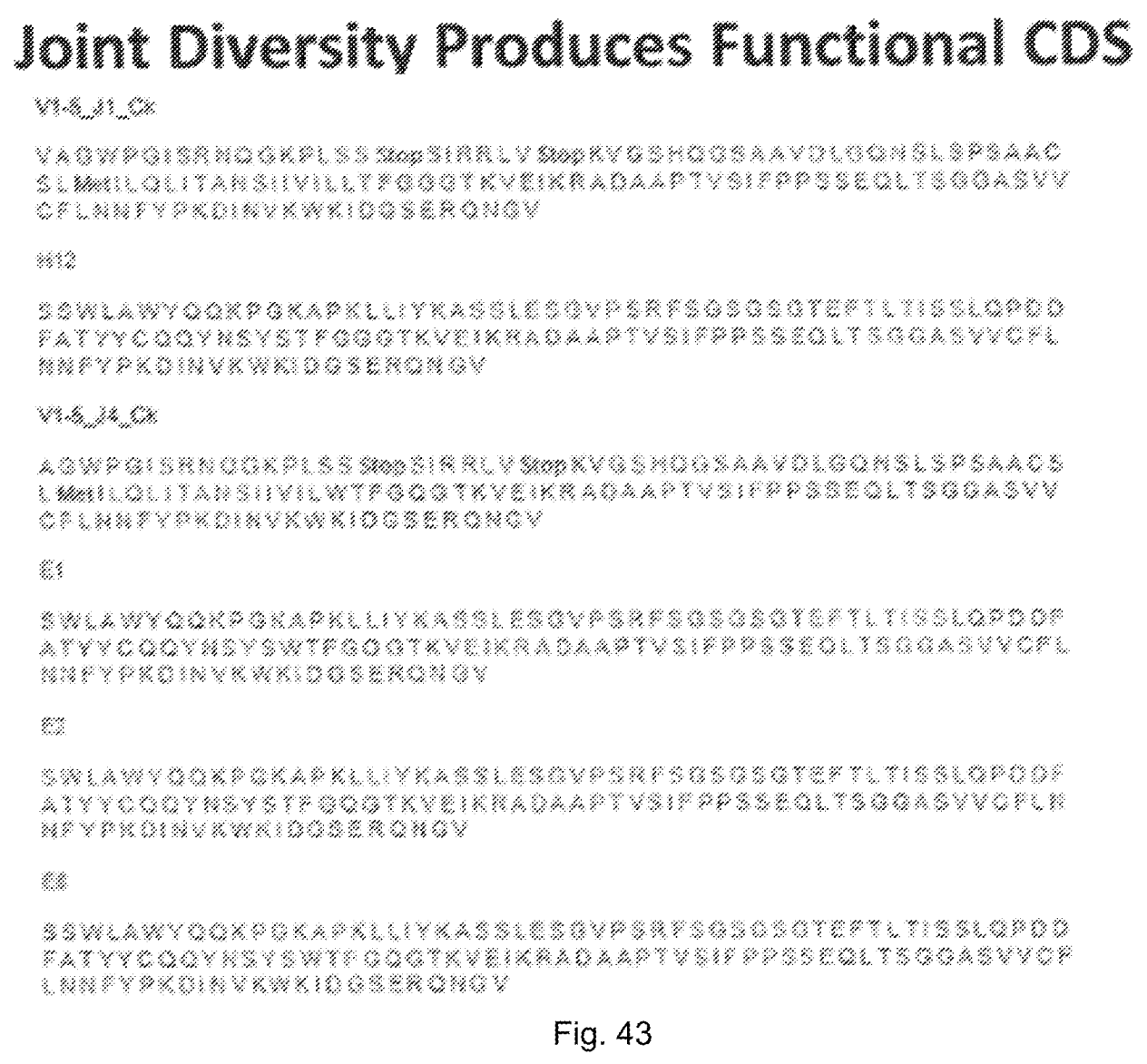

FIG. 41 shows an analysis of kappa mRNA from mice B-cells bearing rearranged VJ, the VJ having been rearranged from human germline kappa V1-8 and J1, and demonstrates that both that productive VJ rearrangement and somatic hypermutation can be obtained, the latter as seen from the changes in antibodies encoded by mRNA with respect to the germline sequences. The same is displayed for V1-6 and J1 in FIG. 42. Importantly, the recombination eliminates stop codons that are encoded by the combination of (unmutated) human germline gene segments, thereby allowing for antibody-encoding mRNA sequences. FIG. 43 demonstrates that inserted human kappa V1-5 J1 and V1-5 J4 can produce functional coding sequences in vivo and junctional diversity.

Example 7

Figure 44:
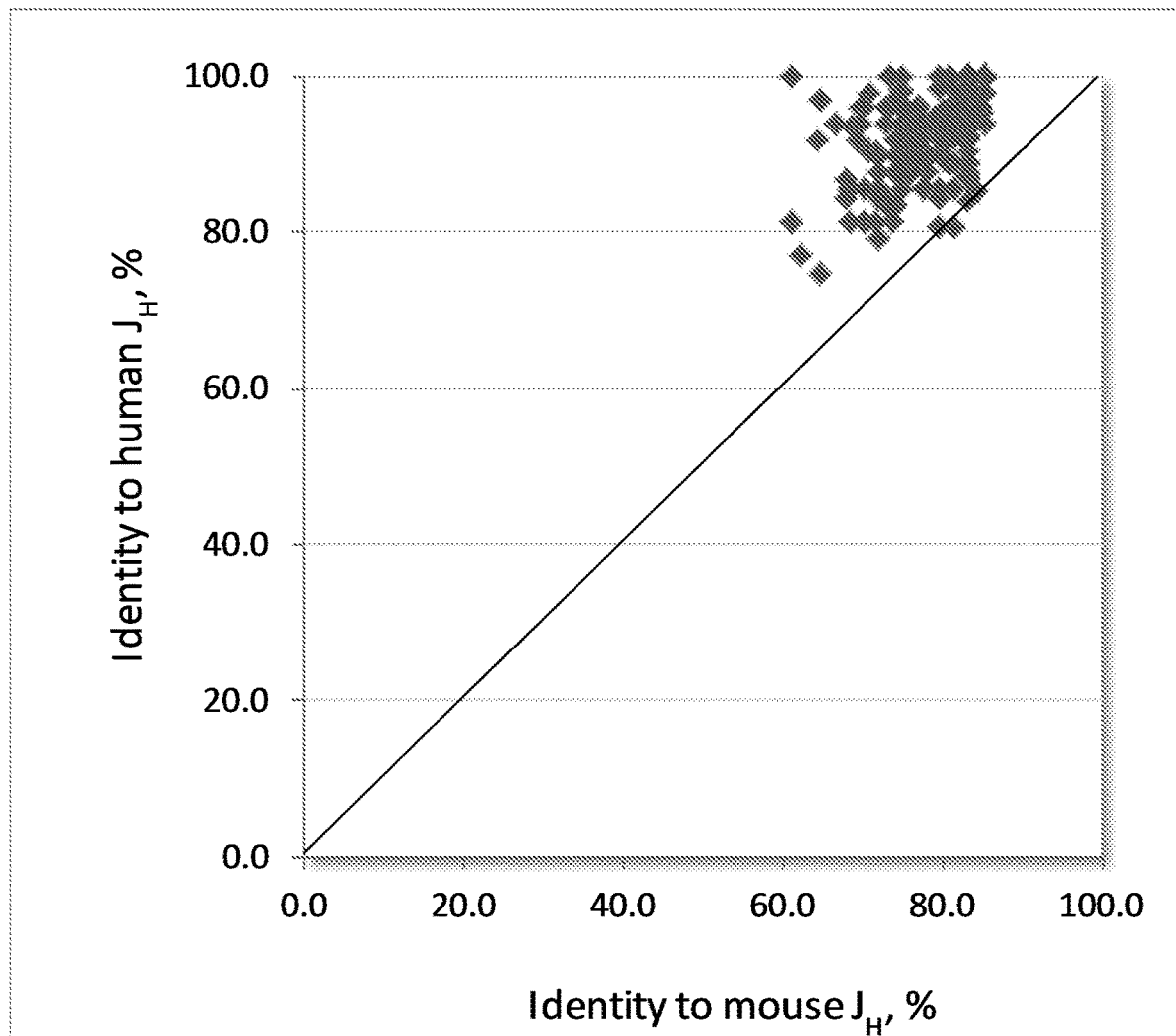
FIG. 44 illustrates a plot of identity of $J_H$ gene segment use a 5'-RACE Cμ-specific library generated from the splenic B lymphocytes of transgenic mice according to the invention in which endogenous gene segment use has been inactivated by inversion

Inactivation of Use of Endogenous IGHV Gene Segments for Expressed Rearranged Heavy Chain by Inversion Introduction A 5'-RACE Cμ-specific library was generated from the splenic B lymphocytes of transgenic mice, denoted S1 mice. These mice comprise transgenic heavy chain loci, each locus containing the six most 3' functional human $V_H$ gene segments ($V_H$2-5, 7-4-1, 4-4, 1-3, 1-2, 6-1), and all the human D and $J_H$ gene segments inserted into the endogenous heavy chain locus between endogenous IGHJ4 and Eμ (mouse chromosome 12: between coordinates 114666435 and 114666436). The human DNA was obtained from a bacterial artificial chromosome (BAC) containing the sequence of human chromosome 14 from coordinate 106328951 to coordinate 106494908. Further details on the construction of transgenic antibody loci using sRMCE is given elsewhere herein and in WO2011004192 (which is incorporated herein by reference). 4×96-well plates of clones were randomly picked for sequencing to determine the usage of the gene segments. All detected immunoglobulin heavy chains were rearranged from mouse $V_H$ or human $V_H$ with human D-$J_H$. No mouse D and $J_H$ segments were detected in rearranged products (FIG. 44).

This result indicates that insertion of human $V_H$-D-$J_H$ gene segments into an endogenous locus between the last endogenous J region (in this case, $J_H$4) and the Eμ enhancer effectively inactivates the use of endogenous D and $J_H$ gene segments for expressed rearranged immunoglobulin heavy chains.

Figure 45:
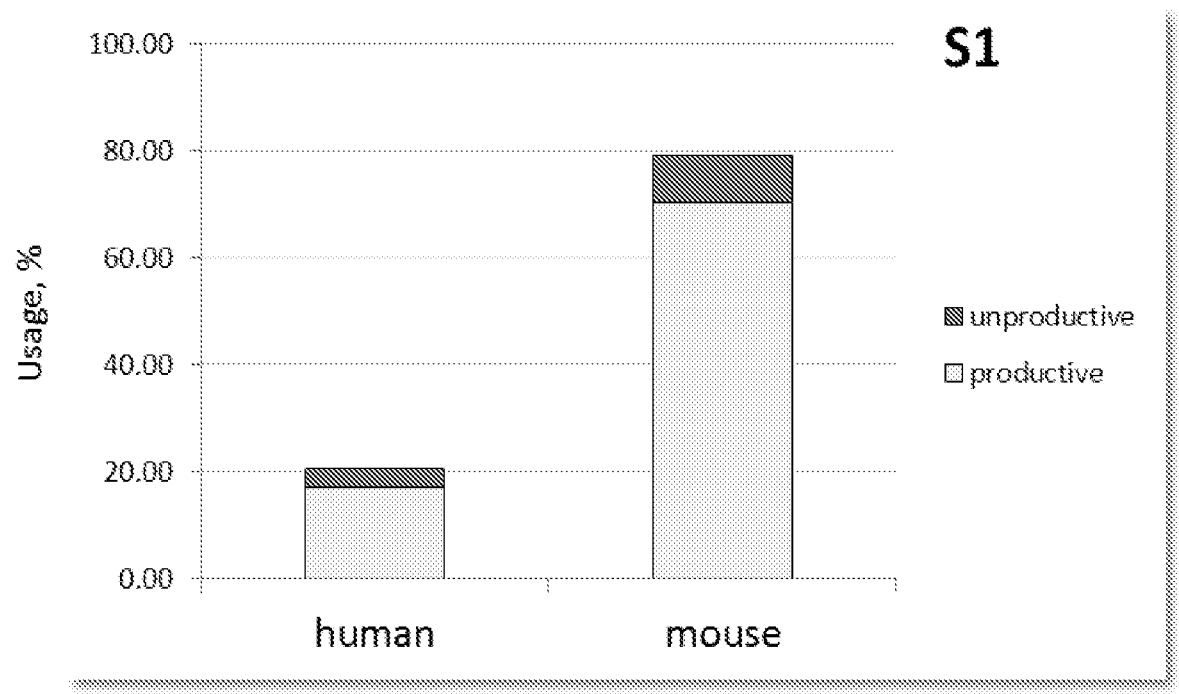
FIG. 45 illustrates the ratio of mouse $V_H$ to human $V_H$ usage as determined from antibody sequences from splenic B lymphocytes of transgenic mice according to the invention in which endogenous gene segment use has been inactivated by inversion

The ratio of mouse $V_H$ to human $V_H$ usage was around 3 to 1 (FIG. 45). To completely eliminate mouse $V_H$ use for antibody generation, the endogenous mouse $V_H$-D-$J_H$ was inverted and moved to a distant region of the same chromosome. The rearrangement of mouse $V_H$s to human D-$J_H$ segments was totally blocked by effects of inversion and distance from the heavy chain locus.

Figure 46:
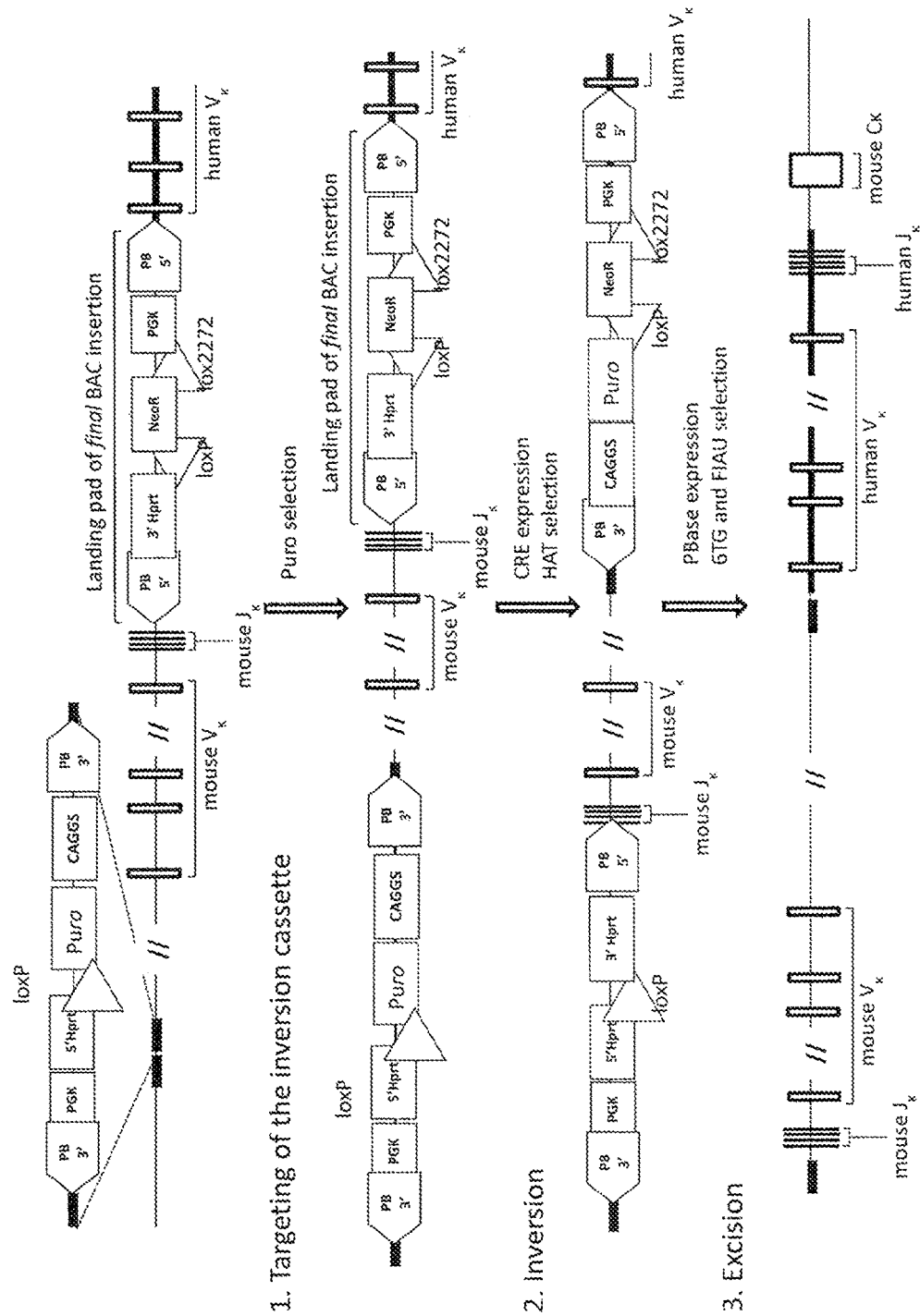
FIG. 46 illustrates inversion strategy schematic

The inversion strategy included three steps: (a) targeting of an inversion cassette, (b) inversion of endogenous VDJ and (c) excision of markers (FIG. 46).

(a) Targeting of the Inversion Cassette:

The inversion cassette consists of four components: a CAGGS promoter-driven puromycin-resistant-delta-thymidine kinase (puroΔtk) gene, a 5' HPRT gene segment under the PGK promoter control, a loxP site between them and inversely oriented to another loxP site already in the heavy chain locus, and two flanking piggyback LTRs (PB3'LTRs). The inversion targeting cassette was inserted to a region that is 5' and distant to the endogenous IGH locus at chromosome 12 as shown in FIG. 46. The targeted ES clones were identified and confirmed by PCR.

(b) Inversion:

Following the insertion, transient expression of cre from a transfected plasmid resulted in inversion of a section of chromosome 12 fragment including the endogenous $V_H$-D-$J_H$ locus and intervening sequences through recombination of two inverted loxP sites, i.e., those in the inversion cassette and the landing pad for the BAC insertion respectively. The invertants were selected by HAT and confirmed by junction PCRs cross the two recombined loxP sites.

(c) Excision of Markers:

The inversion rearranged the relative orientation of the PB3'LTRs from the inversion cassette and PB5'LTR from the landing pad to generate two piggyBac transposon structures flanking the inverted region. With transient expression of piggyBac transposase (PBase), these two transposons were excised from the chromosome (and thus the mouse cell genome). The cured ES clones were selected by 1-(-2-deoxy-2-fluoro-1-b-D-arabinofuranosyl)-5-iodouracil (FIAU) and 6TG, and confirmed by junction PCRs cross the excised regions.

Methods

Tissue culture: The procedures for ES cell culture, electroporation and drug selection have been described previously (Ramirez-Solis, R., A. C. Davis, and A. Bradley. 1993. Gene targeting in mouse embryonic stem cells. Methods Enzymol. 225:855-878).

Figure 47:
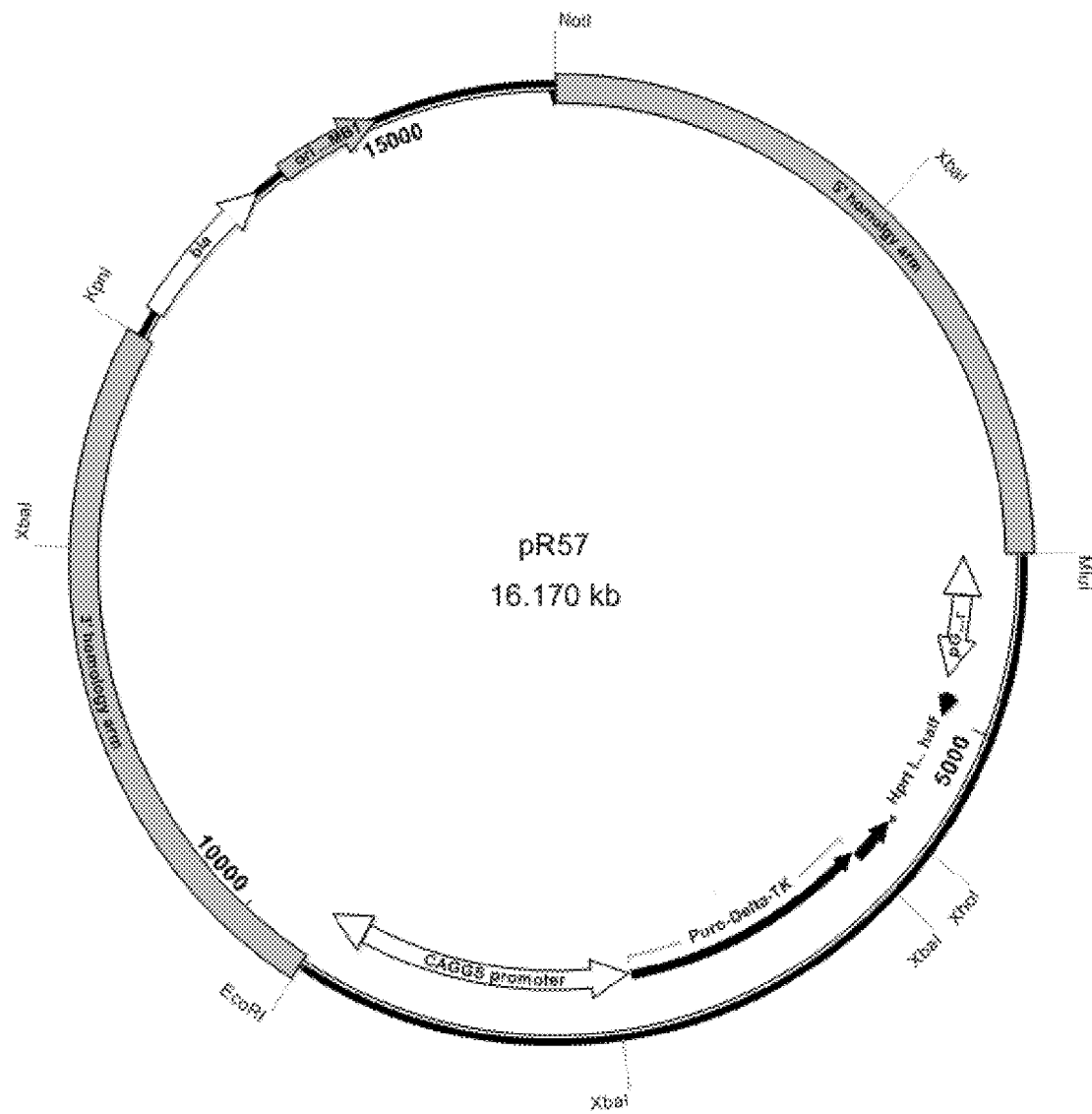
FIG. 47 illustrates targeting construct R57 for inversion

Targeting of the Locus for Inversion: Briefly, 51 cell line (S1.11.1) was cultured in M15 medium (Knockout™ DMEM supplemented with 15% fetal bovine serum, 2 mM glutamine, antibiotics, and 0.1 mM 2-mercaptoethonal). Targeting construct R57 (FIG. 47) was linearized outside the region of homology by NotI. A total of 20 μg of the linearized construct was electroporated into 51 cell lines (AB2.1-derived) with a Bio-Rad® Gene Pulser™, and 107 cells were plated onto three 90-mm-diameter SNL76/7 feeder plates containing M15 medium. At 24 h after electroporation, M15 containing puromycin (3 μg of the active ingredient per ml) was added to each 90-mm-diameter plate, and the cells were maintained under selection for 9 days. 96 puromycin-resistant clones were then picked and expanded in 96-well plates. The targeting events were identified by long-range PCR.

Cre-loxP mediated inversion: 12 positive clones were pooled together and cultured in a 6-well tissue culture plate with M15 medium. The cells were transfected with 10 μg of pCAGGS-Cre plasmid for the inversion of mouse endogenous locus and then plated onto three 90-mm-diameter SNL76/7 feeder plates containing M15 medium. At 24 h after electroporation, M15 containing 1XHAT (hypoxanthine-aminopterin-thymidine) was added to each 90-mm-diameter plate, and the cells were maintained under selection for 7 days and then treated with 1XHT (hypoxanthine-thymidine) for 2 days. 48 HAT resistant colonies were picked and genotyped by PCR amplification of the junctions after Cre-loxP mediated inversion.

HyPBase-mediated marker excision: 12 positive clones were pooled together and cultured in 6-well tissue culture plate using M15 medium. The cells were transfected with 5 μg of HyPBase plasmid to activate the PB transposon LTRs flanking two selection markers (Hprt-mini gene and PGK-puroΔtk gene) and plated onto one 90-mm-diameter SNL76/7 feeder plates containing M15 medium. At 72 h after electroporation, a serial dilution of the cells was then plated onto three 90-mm-diameter SNL76/7 feeder plates containing M15 supplemented with 1-(-2-deoxy-2-fluoro-1-b-D-arabinofuranosyl)-5-iodouracil (FIAU). Cells were maintained under selection for 10 days, and FIAU-resistant colonies were counted, picked, and expanded in 96-well plates. Positive clones were identified by PCR amplification of the junctions after excision of the selection markers. Positive clones were then expanded for blastocyst microinjection.

Generation of chimera and breeding: Mouse chimaeras were generated by microinjection of ES cells into C57/BL6 blastocysts and transfered into pseudopregnant recipients. Male chimaeras were test-crossed with C57/BL6 mice. Agouti F1 offspring were genotyped by S1 3' junction PCR. Test-cross positive heterozygotes were further intercrossed to generate homozygotes.

Determination of VH-D-JH usage by rapid amplification of 5'-cDNA ends (5' RACE) PCR: Total RNA was extracted from the spleen of S1inv1 mouse (KMSF30.1d) with TRIzol® Reagent (Invitrogen™, Life Technologies Ltd™) and treated with DNase I. Rapid amplification of 5'-cDNA ends (5' RACE) PCR was performed using 5'/3' RACE kit (2nd Generation, Roche) following the protocol supplied by the manufacturer. The first-strand cDNA was synthesised using primer E1554 (5'-ATGACTTCAGTGTTGTTCTGGTAG-3'; SEQ ID No 25) which is located at the mouse endogenous Cμ region. The synthesised first cDNA strand was purified using High Pure PCR Product Purification Kit (Roche). Poly(A) tail was added following the protocol supplied with the 5'/3' RACE kit (2nd Generation, Roche). The 5' end of the $V_H$-D-$J_H$ rearranged transcript was amplified by nested PCR with forward primers Oligo dT, which is included in the kit, and nested Cμ-specific reverse primers E1555 (5'-CACCAGAT-TCTTATCAGAC-3'; SEQ ID No 26). Following reaction, the 5' RACE PCR product was checked on a 1% agarose gel and purified using QIAquick® Gel Extraction Kit (QIAGEN) as the protocol supplied with the kit, then cloned into pDrive vector using QIAGEN PCR Cloning Kit (QIAGEN) for sequencing analysis.

Results

Figure 48:
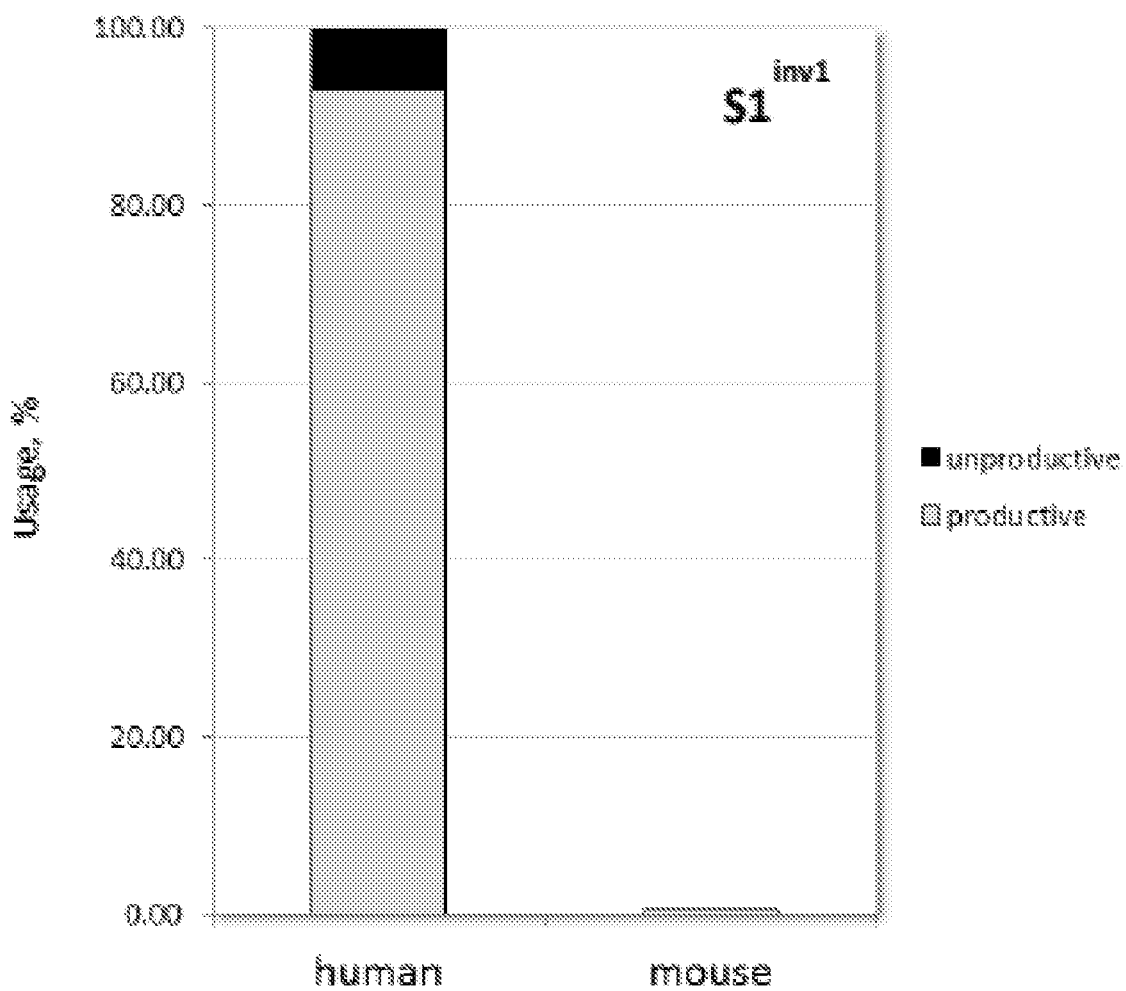
FIG. 48 illustrates sequence analysis from a Cμ-specific 5'-RACE library of splenic B lymphocytes of $S1^{inv1}$ (one human IGH BAC (i.e., multiple human VH, all functional human D and JH) with an inverted endogenous IGH locus) mouse shows that practically all the transcripts came from rearranged human $V_H$-D-$J_H$ gene segments

The sequence analysis from a Cμ-specific 5'-RACE library of splenic B lymphocytes of S1$^{inv1}$ (one human IGH BAC (i.e., multiple human VH, all functional human D and JH) with an inverted endogenous IGH locus version 1) mouse shows that practically all the transcripts came from rearranged human $V_H$-D-$J_H$ gene segments (FIG. 48). Mouse $V_H$ usage was rarely detected (0.4%), and no mouse D and $J_H$ usage was detected. Human $V_H$ usage was 99.6% and only human D and $J_H$ were used; it was hypothesized that the rare mouse $V_H$ usage was due to trans-switching with another chromosome and not due to use of moue $V_H$ from the inverted sequences. The inversion resulted in complete inactivation of the endogenous $V_H$ use.

Figure 49:
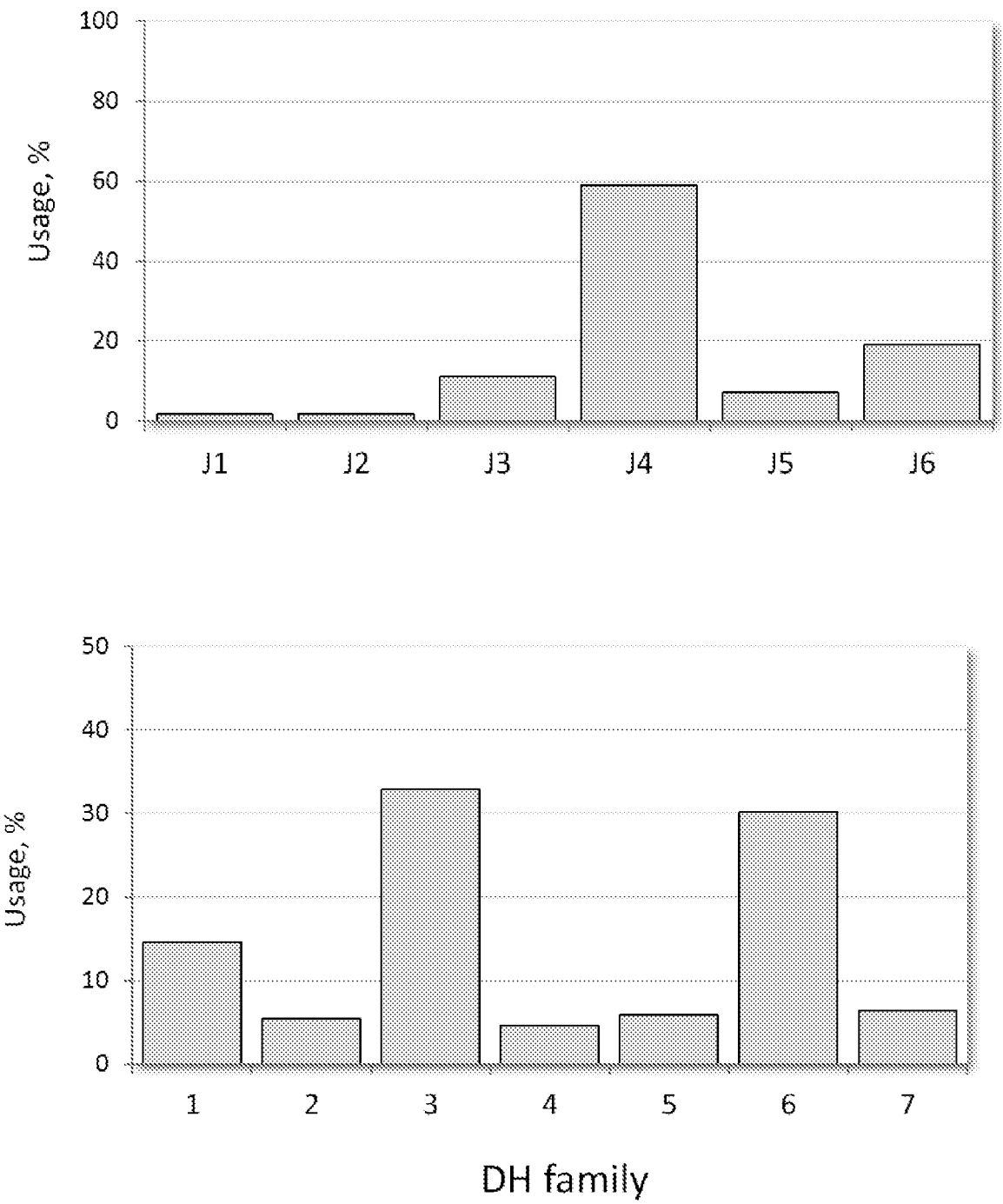
FIG. 49 illustrates that the $S1^{inv1}$ mouse shows a similar usage of both D and $J_H$ gene segments to human

This result indicates that inversion is an effective way to inactivate the rearrangement of endogenous $V_H$ gene segments. The S1$^{inv1}$ mouse also shows a similar usage of both D and $J_H$ gene segments to human (FIG. 49) (Link, J M et al. Mol. Immunol. 2005. 42, 943-955). Thus, a mouse was produced that comprises a transgenic heavy chain locus that expresses heavy chains comprising human variable regions, but no mouse variable regions, and furthermore the human variable regions demonstrated a normal, human sequence distribution corresponding to human D and J usage observed in humans.

Example 8

Inactivation of Use of Endogenous IGHV Gene Segments for Expressed Rearranged Heavy Chain by Insertion of Human IgH Genomic DNA Introduction Insertion of human BACs with $V_H$-D-$J_H$ gene segments into an endogenous mouse heavy chain locus between $J_H$4 and Eμ in chromosome 12 allows human $V_H$-D-$J_H$ gene segments to effectively use mouse Eμ and 3' enhancers and rearrange to generate chimeric antibody with human variable region and mouse constant region. Meanwhile, the endogenous $V_H$-D-$J_H$ gene segments are pushed away from endogenous enhancers and constant regions. This distance effect results in inactivation of mouse D and $J_H$ use for expressed rearranged antibody products. As the distance increases by stepwise BAC insertion, it is expected that the mouse VH usage would be significantly reduced.

Results

Insertion of human DNA from a 1$^{st}$ human BAC (BAC comprising a the sequence of mouse Chromosome 14 from coordinate 106328951 to coordinate 106494908; containing six most 3' functional $V_H$ gene segments ($V_H$2-5, 7-4-1, 4-4, 1-3, 1-2, 6-1), and all the human D and $J_H$ gene segments) into the heavy chain endogenous locus of a AB2.1 ES cell genome between endogenous IGHJ4 and Eμ (at mouse chromosome 12: between coordinates 114666435 and 114666436) effectively inactivates the use of endogenous D and $J_H$ gene segments for expressed rearranged immunoglobulin heavy chain (FIG. 44). The rearranged transcripts with mouse $V_H$ gene segments are reduced in the resulting S1 mouse. The proportion of transcripts using mouse $V_H$ is around 75% of all observed sequences (FIG. 45).

Figure 24:
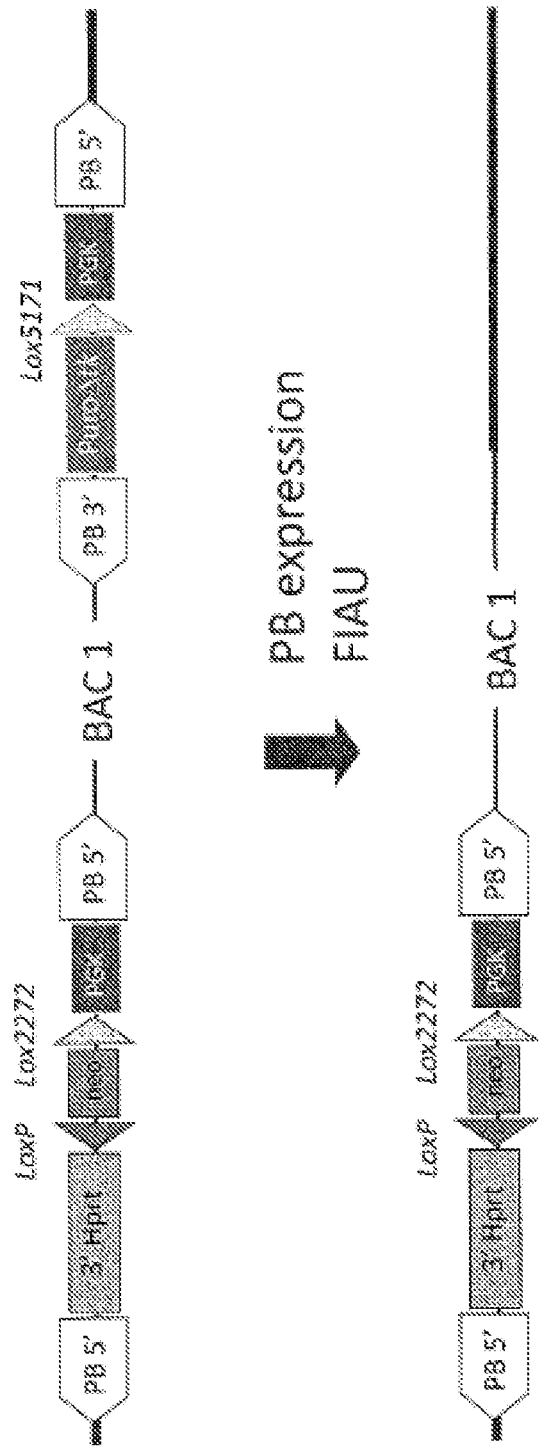
Figure 50:
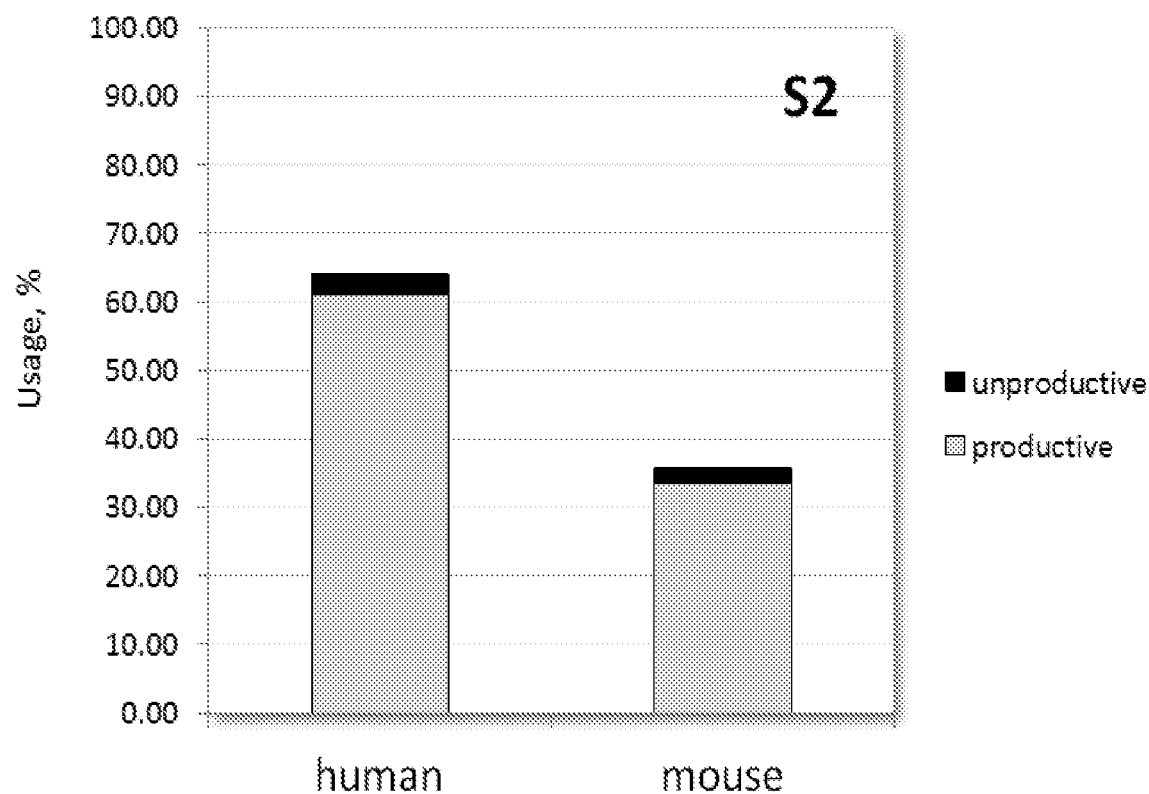
FIG. 50 illustrates that mouse $V_H$ usage is further significantly reduced following insertion of the $2^{nd}$ human BAC into the endogenous heavy chain locus

Following the 1$^{st}$ BAC DNA insertion, human DNA from a 2$^{nd}$ human BAC (Chr14: 106494909-106601551) (BAC comprising a the sequence of mouse Chromosome 14 from coordinate 106494909 to coordinate 106601551; containing 5 more functional VH gene segments ($V_H$3-13, 3-11, 3-9, 1-8, 3-7)) was inserted into the landing pad left behind after curing following the 1$^{st}$ BAC insertion (see, e.g., FIG. 24). The mouse $V_H$ usage is further significantly reduced following this insertion of the 2$^{nd}$ BAC into the locus. The proportion of transcripts using mouse VH was further reduced to 35% of all observed sequences (FIG. 50).

This result indicate that the endogenous $V_H$-D-$J_H$ gene segments could be inactivated (i.e., not used for expressed rearranged heavy chains) through insertion of human VDJ sequences from one or more BACs. As the distance increases by stepwise BAC insertion, it is expected that the mouse VH usage would be significantly reduced.

Example 9

Normal Class Switch and Hypermutation in Transgenic Mice of the Invention

Introduction

The B cell arm of the immune system has evolved to produce high affinity, antigen-specific antibodies in response to antigenic challenge. Antibodies are generated in B lymphocytes by a process of gene rearrangement in which variable (V), diversity (D; for the IGH locus) and joining (J) gene segments are recombined, transcribed and spliced to a Cμ (for IGH) or a $C_K$ or Cλ (for IGL) constant region gene segment to form an IgM antibody. Depending on the stage of B cell development, IgM is either located on the cell surface or secreted. The recombination process generates a primary antibody repertoire with sufficient germ line diversity to bind a wide range of antigens. However, it is usually not large enough to provide the high affinity antibodies that are required for an effective immune response to an antigen such as an infectious agent. Therefore, the immune system adopts a two-stage diversification process to increase diversity further. When challenged with antigens, B cells undergo selection and maturation by a process called somatic mutation. B cells expressing antibodies which bind to antigen undergo multiple rounds of diversification, clonal expansion and antigen selection in the germinal centres (GCs) of the secondary lymphoid organs. During this process, the rearranged variable regions of the immunoglobulin genes acquire somatic hypermutation through nucleotide substitution, addition or deletion. This stepwise process creates a secondary repertoire from the weak binders selected originally from the primary repertoire and combines rapid proliferation of antigen-reactive B cells with intense selection for quality of binding, eventually giving rise to high affinity antibodies with broad epitope coverage. During this process, antibodies undergo class switching in which the Cμ constant region is replaced by $C_\gamma$, Cα or Cε to produce respectively IgG, A or E classes of antibody with different effector functions.

Insertion of 1$^{st}$ human BAC (Chr14: 106328951-106494908) containing six most 3' functional $V_H$ gene segments ($V_H$2-5, 7-4-1, 4-4, 1-3, 1-2, 6-1), and all the D and $J_H$ gene segments into the locus between endogenous IGHJ4 and Eμ (Chr12: 114666435 and 114666436) produces transgenic mice that generate chimeric immunoglobulin heavy chains containing human variable and mouse constant regions. This result demonstrates that human immunoglobulin gene segments are able to be rearranged and expressed in mice. Here, RT-PCR experiments and sequence analysis were performed to further demonstrate that immunized transgenic mice have proper class switch and hypermutation for generated antibodies.

Methods

RT-PCR and sequence analysis: Wild type or S1 chimera mice at 6-8 weeks of age were primed by intraperitoneal injection of 10$^6$ sheep RBCs suspended in phosphate buffer saline (PBS). The immunized mice were boosted twice with the same amount of sheep RBCs two and four weeks after priming. Four days after the last boost, peripheral blood cells were collected from the immunized mice. Total RNA was isolated from peripheral blood cells with TRIzol® reagent (Invitrogen™) and treated with DNase I. Reverse transcription polymerase chain reaction (RT-PCR) was performed using SuperScript® III First-Strand Synthesis System (Invitrogen™) following the protocol supplied by the manufacturer. The 1st strand cDNA was synthesized with the specific Cγ primers ($C_\gamma$1, $C_\gamma$2a, $C_\gamma$2b), following by PCR with specific human V primers (VH1-2,3, VH4-4, VH6-1) and $C_\gamma$ primers (Table 2). Following reaction, the RT-PCR product was checked on a 1% agarose gel and purified using QIAquick® Gel Extraction Kit (QIAGEN) as the protocol supplied with the kit, then cloned into pDrive vector using QIAGEN PCR Cloning Kit (QIAGEN) for sequencing analysis.

TABLE 2

| | | |
|---|---|---|
| ELP1352_ Cγ1 | 5'-AGAGCGGCCGCTGGGCAACGTTGCAGGTGACGGTC-3' | SEQ ID No 27 |
| ELP1353_ Cγ2b | 5'-AGAGCGGCCGCTTTGTCCACCGTGGTGCTGCTGG-3' | SEQ ID No 28 |
| ELP1354_ Cγ2a | 5'-AGAGCGGCCGCACATTGCAGGTGATGGACTGGC-3' | SEQ ID No 29 |
| ELP1356_ VH4-4 | 5'-AGGACGCGTGAAACACCTGTGGTTCTTCCTCCTGC-3' | SEQ ID No 30 |
| ELP1357_ VH1-2,3 | 5'-AGGACGCGTCACCATGGACTGGACCTGGAGGAT-3' | SEQ ID No 31 |
| ELP1358_ VH6-1 | 5'-AGGACGCGTATGTCTGTCTCCTTCCTCATCTTCC-3' | SEQ ID No 32 |

Results

Figure 51:
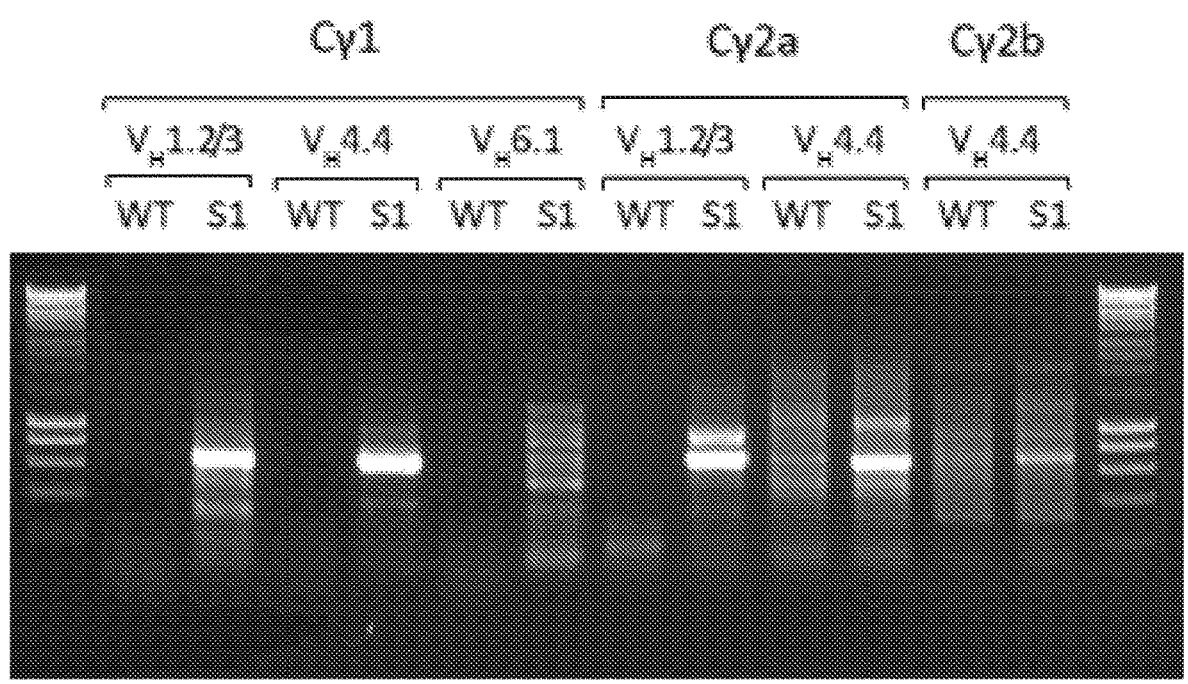
FIG. 51 illustrates a gel showing that normal class-switching (to IgG-type) was observed in transcripts from mice of the invention. The rearranged transcripts were detected using RT-PCR with human VH-specific and mouse Cγ-specific primers for amplification from peripheral blood cells of immunized transgenic mice
Figure 52:
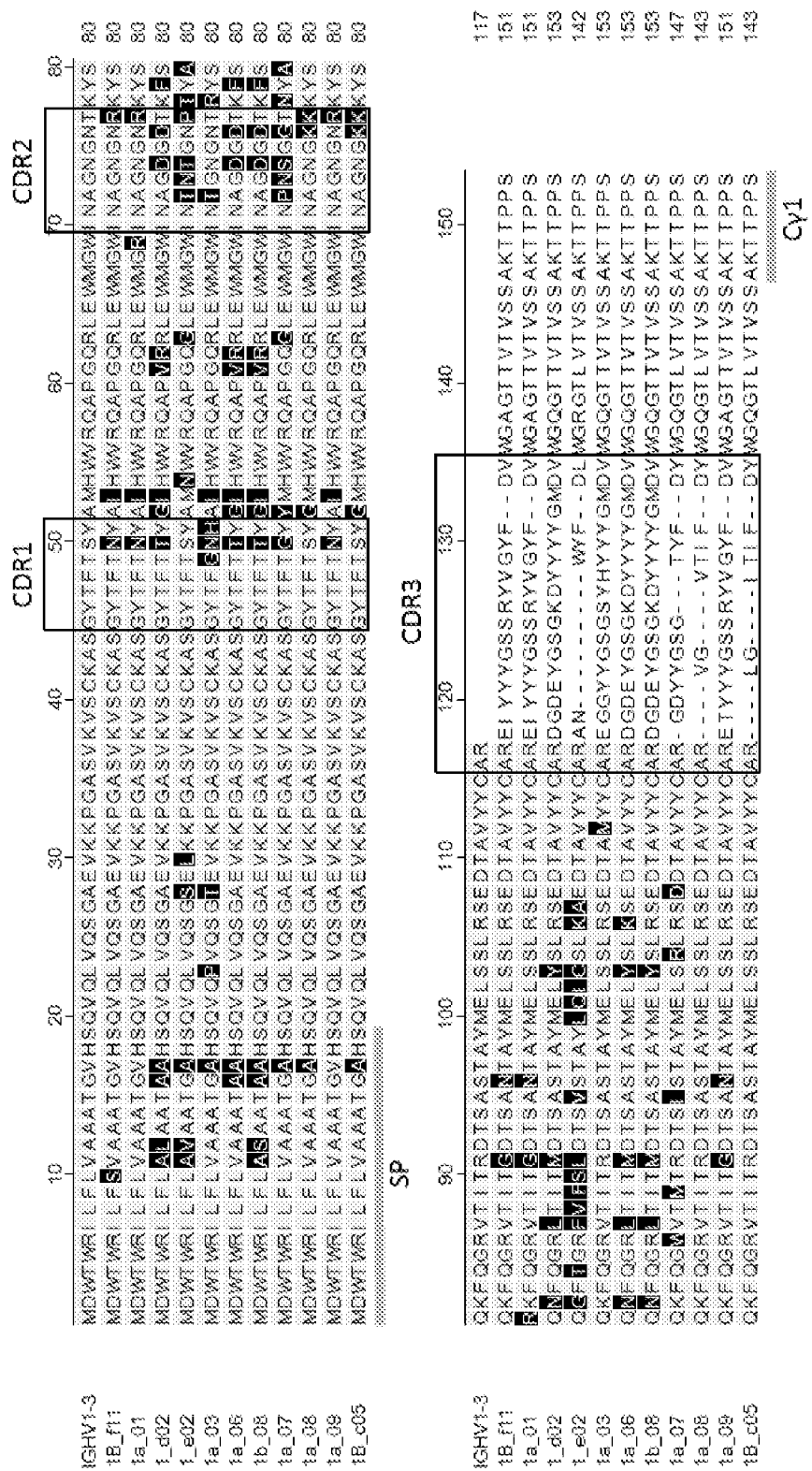
FIG. 52 illustrates sequence analysis amplified fragments demonstrate hypermutation occurred within the human variable regions of these IGγ chains from mice of the invention

The rearranged transcripts were detected using RT-PCR with human VH-specific and mouse $C_\gamma$-specific primers for amplification from peripheral blood cells of immunized transgenic mice (FIG. 51). Further sequence analysis of these amplified fragments demonstrated hypermutation happened within the human variable regions of these IGγ chains (FIG. 52). These results indicate that loci of the invention comprising insertion of human IGH BAC containing $V_H$, D and $J_H$ gene segments into the locus between endogenous IGHJ4 and Eμ regions has normal class switching and hypermutation functionality (IgM to IgG) following antigen challenge.

Example 10

Normal B Cell Compartments in Transgenic Mice of the Invention

Introduction

In mice, about $2 \times 10^7$ bone marrow immature B cells are produced daily. Among them, only 10-20% of these cells survive to exit the bone marrow and enter the spleen. The immature splenic B cell population is divided into two distinct subsets: transitional 1 (T1) and transitional 2 (T2) B cells. In vivo experiments indicate that T1 cells give rise to T2 cells, whereas T2 cells can further differentiate into mature (M) B cells. In contrast to immature B cells (3-4 days old), mature B cells are long-lived (15-20 weeks old) and are ready to respond to antigens (Pillai S et al; Immunol. Reviews. 2004. 197: 206-218). Thus, the component of mature B cell population is directly linked to the efficiency of humoral immune response.

The T1, T2 and M cell populations can be categorized by their cell surface IgM and IgD levels. A normal phenotype of splenic B cell compartment is required to mount a robust immune response.

Methods

Flow cytometric analysis of mature B lymphocytes: To obtain a single cell suspension from spleen, the spleens of mice listed below were gently passaged through a 30 μm cell strainer. Single cells were resuspended in PBS supplemented with 3% heat inactivated foetal calf serum (FCS; Gibco®). The following antibodies were used for staining:

Antibody against B220/CD45R conjugated with allophycocyanin (APC) (eBioscience, clone RA3-6B2), antibody against IgD receptor conjugated with phycoerythrin (PE) (eBioscience, clone 11-26) and IgM receptor conjugated with fluorescein isothiocyanate (FITC) (eBioscience, clone 11/41).

$5 \times 10^6$ cells were used for each staining. To each vial containing splenocytes a cocktail of antibodies was added consisting of: IgD (PE) (eBioscience, clone 11-26), IgM (FITC) and B220/CD45R (APC). Cells were incubated at 6° C. for 15 minutes, washed to remove excess of unbound antibodies and analysed using a fluorescence-activated cell sorting (FACS) analyser from Miltenyi Biotech. B-cells were gated as $B220^+IgM^+IgD^-$ for T1 population, $B220^+IgM^+IgD^+$ for T2 population and $B220^+IgM^-IgD^+$ for M population. Percentage of cells was calculated using gating system.

Results

Four different genotypes of mice were generated:—
Wild type (WT);
A transgenic mouse homozygous for a heavy chain transgene comprising insertion of the $1^{st}$ BAC human DNA noted above in which there are 6 human VH, all functional human D and JH gene segments (S1/S1);
A transgenic mouse homozygous for a heavy chain transgene comprising insertion of a human VH, all functional human D and JH gene segments (H1/H1); and
A transgenic mouse homozygous for a kappa chain transgene comprising insertion of 6 functional human Vκ and 5 functional Jκ gene segments (K1/K1).

Figure 53:
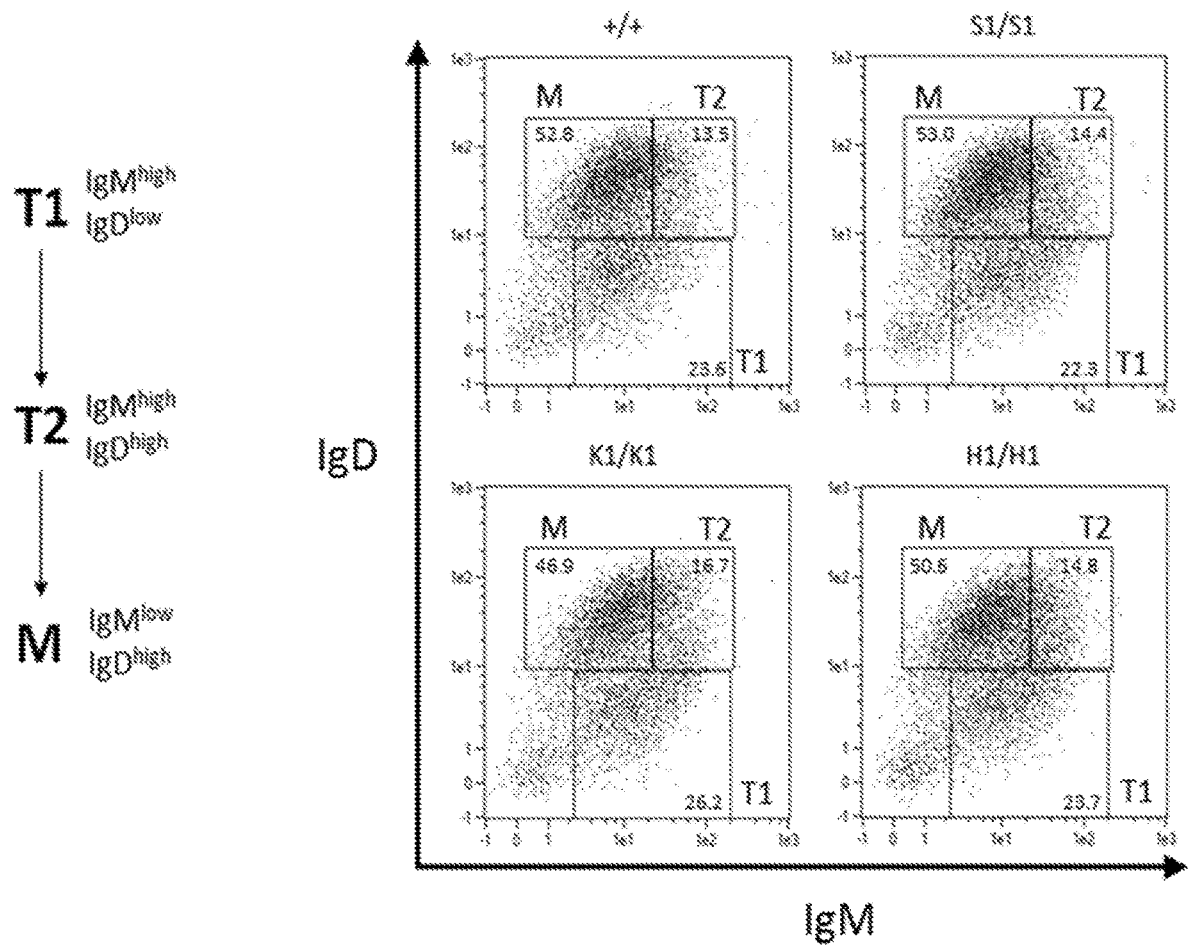
FIG. 53 illustrates Flow cytometric analysis showing normal B-cell compartments in transgenic mice of the invention
Figure 54A:
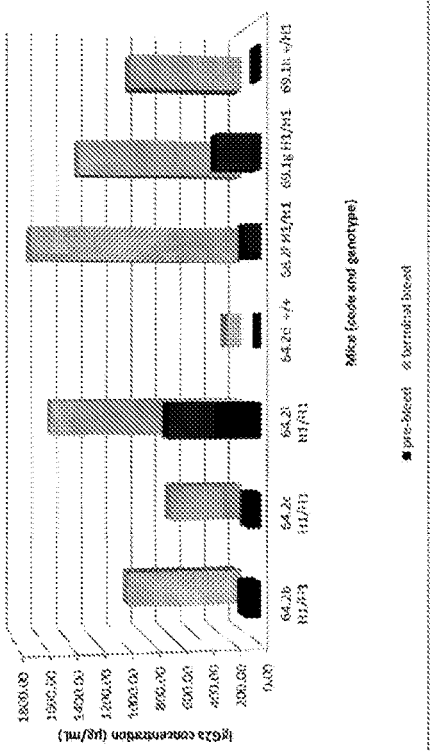
FIGS. 54A-54D illustrate normal IgH isotypes in transgenic mice (H1) immunised with 100 μg Cholera Toxin B subunit.
Figure 54B:
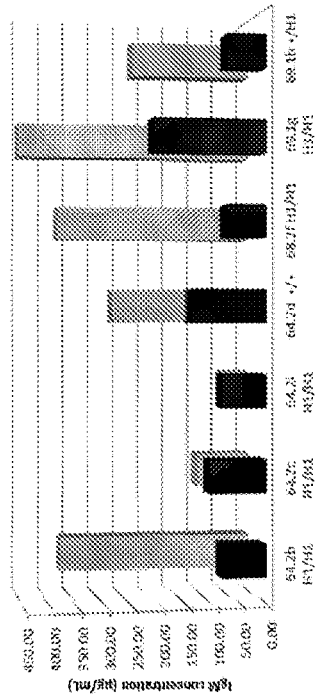
Figure 54C:
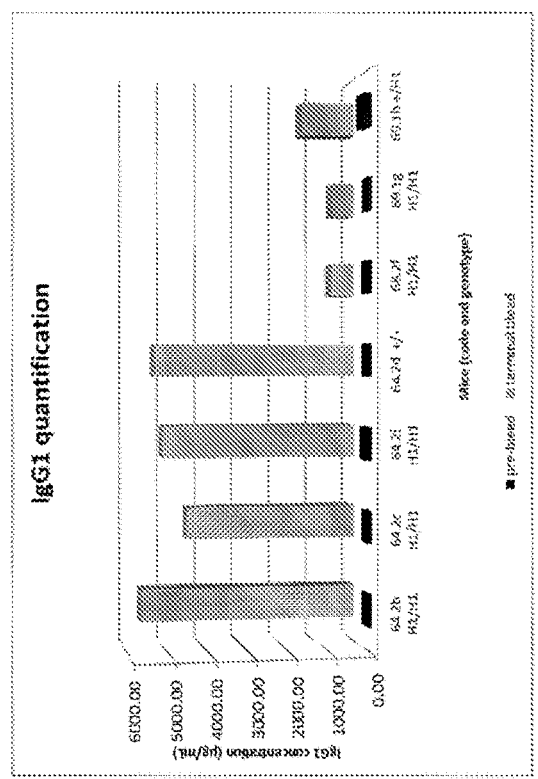
Figure 54D:
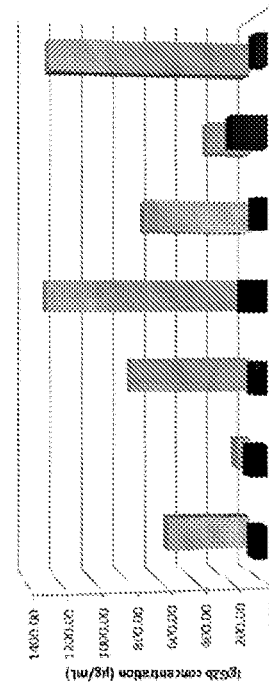

Spleens from these naïve mice were collected and analysed for their B cell compartments. The number and percentages of T1, T2 and M cells among those mice are similar (FIG. 53), indicating that genetic manipulation of endogenous IG loci in transgenic mice according to the invention do not compromise their B cell development. These data help to establish that animals according to the invention provide a robust platform for antibody discovery.

Example 11

Normal IgH Isotypes & Serum Levels in Transgenic Animals of the Invention

Figure 55A:
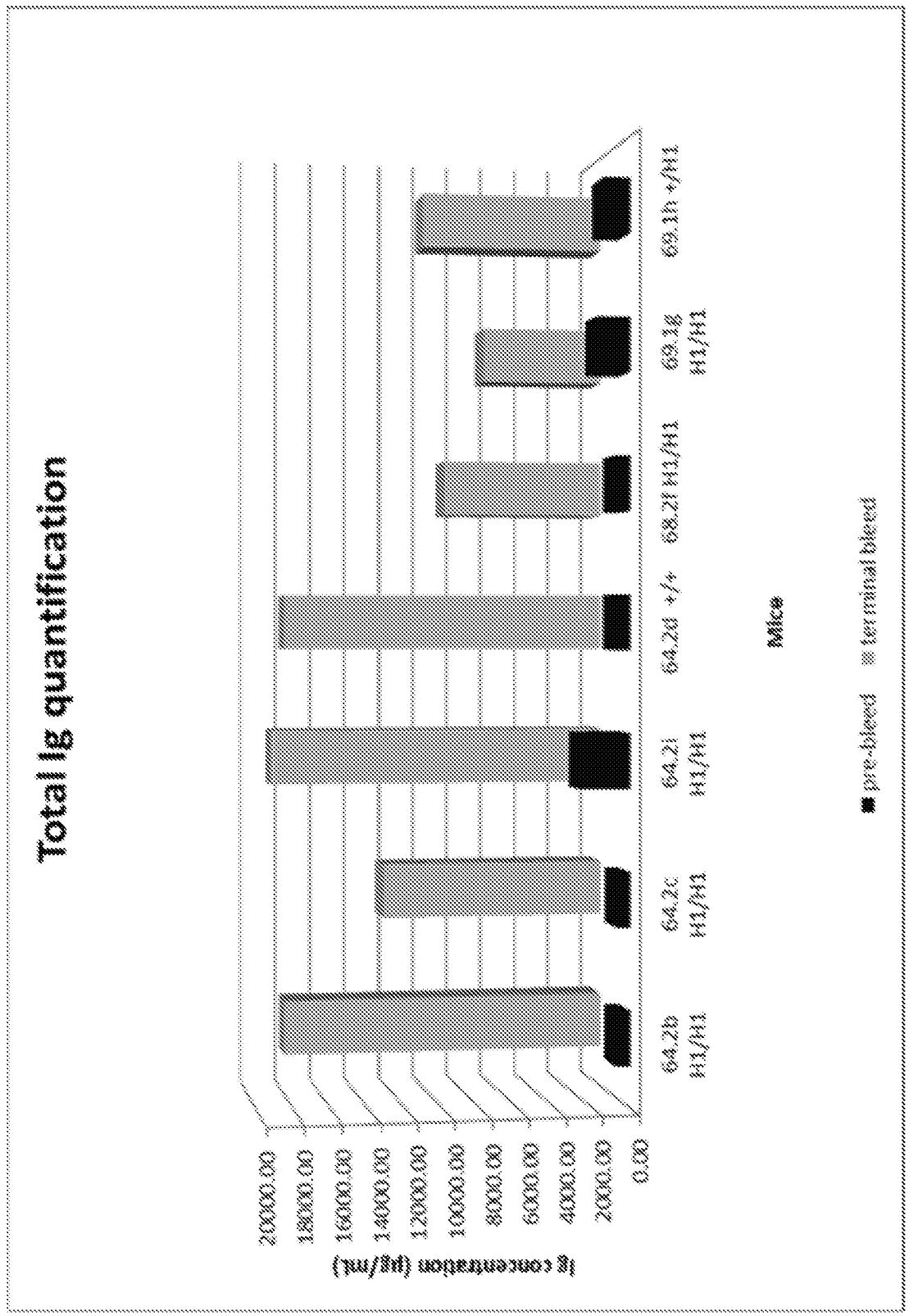
FIG. 55A and FIG. 55B illustrate normal IgH isotypes and serum levels are obtained in transgenic H1 and S1 animals, respectively, of the invention following immunisation with antigens.
Figure 55B:
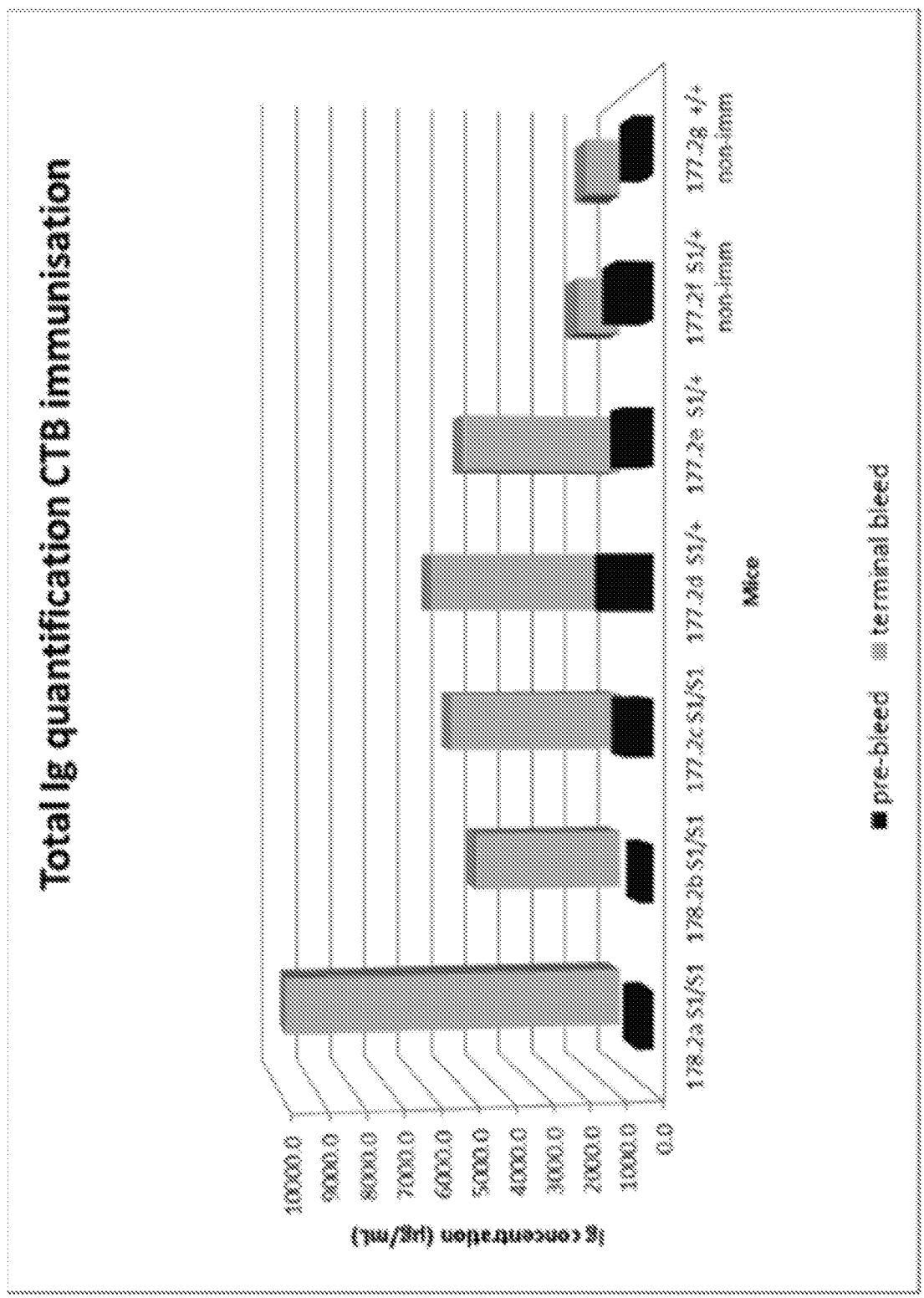

Transgenic mice (H1) carrying all human JH, all human DH and human Vh2-5 under control of a rat switch region or mice (S1) carrying all human JH, all human DH and human Vh2-5, Vh7-41, Vh4-4, Vh1-3, Vh1-2 and Vh6-1 under control of a mouse switch region were immunised with 100 μg Cholera Toxin B subunit (CTB; Sigma-Aldrich® C9903) emulsified in Complete Freund's Adjuvant CFA; Sigma-Aldrich® F 5881). At least three animals were injected sc or ip and then boosted with 25 μg antigen in Incomplete Freund's Adjuvant (IFA; Sigma-Aldrich® F 5506) at (i) 14 days and 21 days or (ii) 28 days after priming. Blood was taken before priming at day "−1" (pre-bleeds) and on the day the spleens were taken (usually 4d after last boost). Serum was analysed by ELISA using an antigen independent assessment of Ig isotypes. This assay detects total serum antibodies of all species. Specific detection for mouse IgG1, IgG2a, IgG2b and IgM was used ((Anti-mouse IgG1 HRP AbD Serotec STAR132P, Anti-mouse IgG2a HRP AbD Serotec STAR133P, Anti-mouse IgG2b HRP AbD Serotec STAR134P, Anti-mouse IgM HRP Abcam® ab97230) and concentrations were read off a standard curve produced for each isotype using polyclonal isotype controls (IgG1, Kappa murine myeloma Sigma-Aldrich® M9269, IgG2a, Kappa murine myeloma Sigma-Aldrich® M9144, IgG2b, Kappa from murine myeloma Sigma-Aldrich® M8894, IgM, Kappa from murine myeloma Sigma-Aldrich® M3795). Results (FIGS. 54 & 55 for H1 homozygous and S1 homozygous and heterozygous mice) showed that even with these relatively short immunisation regimes mice showed an increase in overall IgG levels after immunisation over pre-bleeds. In cases where control mice (+/+) not carrying any human immunoglobulin genes were included and immunised, these mice showed comparable changes in total observed Ig levels (FIG. 54). Individual isotype levels were more variable between animals possibly showing various stages of class switching. IgM levels never exceeded 800 µg/ml whereas IgG levels reached more than 6 mg/ml in some animals. Non-immunised controls showed no such increases in switched isotype Ig levels.

These results demonstrate that mice comprising multiple human VDJ gene segments under the control of a rat Sp rat or mouse switch are able to undergo productive recombination and class switching in response to antigen challenge and that the mice produce antibody levels that are broadly comparable to unmodified mice The transgenic mice are able to produce antibodies of each of the IgG1, IgG2a, IgG2b and IgM isotypes after immunisation. Titers for CTB-specific Ig in pre-bleeds and terminal bleeds were determined and all immunised animals showed at CTB-specific titres of at least 1/100 000.

Example 12

Generation of Anti-Ovalbumin Antibodies with Sub-50 nm Affinities from Animals of the Invention Transgenic mice carrying all human JH, all human DH and human Vh2-5 under control of a rat Sp switch region were immunised with 25 µg ovalbumin (OVA; Sigma-Aldrich® A7641) in Sigma-Aldrich® adjuvant (Sigma Adjuvant System® S6322) ip and then boosted with the same amount of OVA in adjuvant at day 14 and day 21. Spleenocytes were taken 4 days later and fused using 1 ml polyethyleneglycol (PEG Average MW1450; Sigma-Aldrich® P7306) with a myeloma line. Fused hybridoma cells were plated on 5 96-well plates and after selection with hypoxanthine-aminopterin-thymidine (HAT) wells tested for expression of OVA-specific antibodies by ELISA. Clones positive by ELISA were re-tested by surface plasmon resonance (SPR) and binding kinetics determined using the ProteOn™ XPR36 (Bio-Rad®). Briefly, anti-mouse IgG (GE Biacore™ BR-1008-38) was coupled to a GLM biosensor chip by primary amine coupling, this was used to capture the antibodies to be tested directly from tissue culture supernatants. Ovalbumin was used as the analyte and passed over the captured antibody surface at 1024 nM, 256 nM, 64 nM, 16 nM, 4 nM with a 0 nM (i.e. buffer alone) used to double reference the binding data. Regeneration of the anti-mouse IgG capture surface was by 10 mM glycine pH1.7, this removed the captured antibody and allowed the surface to be used for another interaction. The binding data was fitted to 1:1 model inherent to the ProteOn™ XPR36 analysis software. The run was carried out 1×HBS-EP (10 mM Hepes, 150 mM NaCl, 3 mM EDTA, 0.05% polysorbate, pH7.6 (Teknova H8022)) used as running buffer and carried out at 25° C.

For 8 positive clones, heavy chain V-regions were recovered by RT-PCR (Access RT-PCR System, A1250, Promega) using forward primers specific for Ig signal sequences (Wardemann et al Science 301, 1374 (2003)) and the following reverse primers for the constant regions of mouse IgG (Table 3):

TABLE 3

| Primer Name | Sequence | bp | |
|---|---|---|---|
| mIgG1_2 rev | GGGGCCAGTGGATAGACAGAT | 21 | SEQ ID No 33 |
| mIgG2b rev | CAGTGGATAGACTGATGG | 18 | SEQ ID No 34 |
| mIgG2a_2 rev | CAGTGGATAGACCGATGG | 21 | SEQ ID No 35 |
| mCH1 unirev | KCAGGGGCCAGTGGATAGAC | 20 | SEQ ID No 36 |
| mCH1 unirev_2 | TARCCYTTGACMAGGCATCC | 20 | SEQ ID No 37 |

RT-PCR products were either directly sequenced using the same primer pairs or cloned in to TA plasmids (TOPO® TA Cloning® Kit for Sequencing, K4595-40, Invitrogen™) and submitted for plasmid sequencing. Results (Table 4, below) show that CDRH3 sequences had variable CDRs except for two identical clones (16C9 and 20B5) that also had near identical KD kinetic values. The determined equilibrium binding constant KD ranged from 0.38 nM to 40.60 nM, as determined by SPR at 25° C.

These results demonstrate that mice comprising multiple human VDJ gene segments under the control of a rat Cµ switch are able to undergo productive recombination and produce high affinity antigen-specific antibodies whose CDR3 regions have sequences encoded by human gene segments (human JH was separately identified by V-Quest, IMGT).

TABLE 4

| KD [nM] | clone code | CDR3 and FR4 (underlined) according to Kabat definition | |
|---|---|---|---|
| 0.38 | 16C9 | QEVINYYYYGMDV<u>WGQGTTVTVSS</u> | SEQ ID No 38 |
| 0.52 | 20B5 | QEVINYYYYGMDV<u>WGQGTTVTVSS</u> | SEQ ID No 39 |
| 5.89 | 19F4 | LEMATINYYYYGMDV<u>WGQGTMVTVSS</u> | SEQ ID No 40 |
| 39.70 | 19E1 | QEFGNYYYYGMDV<u>WGQGTTVTVSS</u> | SEQ ID No 41 |
| 3.10 | 19G8 | QEDGNPYYFGMDF<u>WGQGTTVTVSS</u> | SEQ ID No 42 |
| 8.95 | 20H10 | GSSYYYDGMDV<u>WGQGTTVTVSS</u> | SEQ ID No 43 |
| 4.46 | 18D10 | LENDYGYYYYGMDV<u>WGQGTTVTVSS</u> | SEQ ID No 44 |
| 40.60 | 16F2 | RGGLSPLYGMDV<u>WGQGTTVTVSS</u> | SEQ ID No 45 |

Example 13

Generation of Anti-Cholera Toxin B Antibodies with Human Vh Regions from Animals of the Invention Transgenic mice carrying all human JH, all human DH and human Vh2-5, Vh7-41, Vh4-4, Vh1-3, Vh1-2 and Vh6-1 under control of a mouse Sp switch region were immunised and fused as described in Example 11. Fused hybridoma cells were plated on 5 96-well plates and after selection with hypoxanthine-aminopterin-thymidine (HAT) or G418 (Gibco® Cat No 10131-027, Lot 503317) and wells tested for expression of CTB-specific antibodies by ELISA. Clones positive by ELISA were re-tested by surface plasmon resonance SPR and binding kinetics determined using the ProteOn XPR36™ (Bio-Rad®).

Briefly, anti-mouse IgG (GE Biacore™ BR-1008-38) was coupled to a GLM biosensor chip by primary amine coupling, this was used to capture the antibodies to be tested directly from tissue culture supernatants. Cholera toxin B was used as analyte and passed over the captured antibody surface at 256 nM, 64 nM, 16 nM, 4 nM and 1 nM, with a 0 nM (i.e. buffer alone) used to double reference the binding data. Regeneration of the anti-mouse IgG capture surface was by 10 mM glycine pH1.7, this removed the captured antibody and allowed the surface to be used for another interaction. The binding data was fitted to 1:1 model inherent to the ProteOn XPR36™ analysis software. The run was carried out 1×HBS-EP (10 mM Hepes, 150 mM NaCl, 3 mM EDTA, 0.05% polysorbate, pH7.6 (Teknova H8022)) used as running buffer and carried out at 37° C.

From the clones initially identified by ELISA, binding to CTB was confirmed by SPR. However, due to the pentameric nature of the cholera toxin B, the majority of fits to the 1:1 model were poor and the equilibrium binding constant KDs could not be accurately determined. Where fits were acceptable, equilibrium binding constant KDs determined ranged from 0.21 nM to 309 nM but due to the pentameric nature of cholera toxin B these are likely to be the result of multimeric interactions and therefore apparent affinities with possible avidity components.

Clones identified by SPR for binding to CTB were subjected to RT-PCR as described in Example 12 to recover the Vh regions. RT-PCR products were directly sequenced using the same primer pairs. Results were obtained for only 14 clones presumably because the human primers described in Wardemann et al were not designed to amplify mouse Vh regions and therefore may have failed to amplify certain mouse Vh classes. Results showed that 3 of the 14 CTB-specific recovered heavy chain V-region sequences were human V, D and J regions as identified by V-Quest, IMGT (Table 5).

TABLE 5

Alignment of heavy chain CDRs and J-region of 3 clones identified as binding to CTB and preferentially matching with human reference sequences from IMGT database; note that the KD values given here are apparent values due to the avidity of the CTB-antibody interaction

| Vh region | Clone Name | CDR1 | CDR2 | CDR3 | J regions | KD [nM] |
|---|---|---|---|---|---|---|
| IGHV4-4*02 | — | SSNWWS (SEQ ID NO 51) | EIYHSGSTNYHPSLKS (SEQ ID NO 56) | n/a | IGHJ2*01 YWYFDLWGRGTLVTVSS (SEQ ID NO 64) | — |
| | 12D10 | SGNWWS (SEQ ID NO 52) | EIYHSGNTNYNPSLKS (SEQ ID NO 57) | GPLTGEKYYFDL (SEQ ID NO 61) | -YYFDLWGRGTLVTVSS (SEQ ID NO 65) | 0.27 |
| | 1283 | RSNWWS (SEQ ID NO 53) | EIYHSGSTNYNPSLKS (SEQ ID NO 58) | IGDWYFDL (SEQ ID NO 62) | -WYFDLWGRGTLVTVSS (SEQ ID NO 66) | 0.85 |
| IGHV6-1*01 | — | SHSAAWN (SEQ ID NO 54) | RTYYRSKWYNDYAVSVKS (SEQ ID NO 59) | n/a | JGHJ3*01 DAFDVWGQGTMVTVSS (SEQ ID NO 67) | — |
| | 4A12 | SNSAAWN (SEQ ID NO 55) | RTYYRSKWYNDYKVSVKS (SEQ ID NO 60) | EGSHSGSGWYLDAFDI (SEQ ID NO 63) | DAFDIWGQGTKVTVSS (SEQ ID NO 68) | 1.61 |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The invention claimed is:

1. A method for producing a biological sample selected from the group consisting of:
   (i) a polypeptide comprising a human kappa variable region,
   (ii) an Ig kappa light chain comprising a human kappa variable region,
   (iii) an antibody comprising a human kappa variable region,
   (iv) a cell expressing a polypeptide comprising a human kappa variable region,
   (v) a cell expressing an Ig kappa light chain comprising a human kappa variable region,
   (vi) a cell expressing an antibody comprising a human kappa variable region,
   (vii) nucleic acid encoding a polypeptide comprising a human kappa variable region,
   (viii) nucleic acid encoding an Ig kappa light chain comprising a human kappa variable region,
   (ix) nucleic acid encoding a human kappa variable region, and
   (x) nucleic acid encoding a human kappa variable region and a mouse constant region, the method comprising the steps of:
   (a) delivering an antigen to a transgenic mouse having a germline comprising a homozygous recombinant immunoglobulin light chain kappa (Igκ) locus comprising unrearranged human Igκ variable region gene segments at an endogenous mouse kappa light chain locus upstream of a kappa enhancer and a constant (C) region comprising an endogenous Cκ gene segment; wherein said recombinant Igκ locus comprises in 5' to 3' transcriptional orientation: unrearranged human Igκ variable region gene segments, a chimeric JC intron comprising truncated human Igκ JC intronic DNA, truncated mouse Igκ JC intronic DNA comprising said kappa enhancer, and said constant (C) region; wherein said human Igκ variable region gene segments in said recombinant Igκ locus are operably linked to said C region, and wherein said unrearranged Igκ variable region gene segments comprise human Vκ4-1, Vκ5-2, Vκ7-3, Vκ2-4, Vκ1-5, Vκ1-6, Vκ3-7, Vκ1-8, Vκ1-9, Jκ1, Jκ2, Jκ3, Jκ4, and Jκ5 gene segments;
   wherein said mouse genome is homozygous for a chimeric IgH locus comprising unrearranged human IgH variable region gene segments, at an endogenous IgH locus upstream of an enhancer and a constant (C) region comprising an endogenous CH gene segment, wherein said unrearranged human variable region gene segments comprise unrearranged human VH region gene segments comprising a plurality of human VH, JH, and D gene segments in said chimeric IgH locus are operably linked to said enhancer and said C region, wherein said germline comprises all or part of mouse IgH variable region DNA upstream of said unrearranged human VH region gene segments comprising the human VH, D and JH gene segments;
   wherein said mouse is non-functional to express fully mouse Ig comprising a mouse VH region and a mouse CH region;
   wherein said transgenic mouse prior to said antigen delivery comprises B cells comprising said recombinant Igκ locus, and
   wherein after said antigen delivery, said transgenic mouse comprises B cells comprising antibody specific for said antigen and comprising light chain comprising a human kappa variable region,
   wherein said IgH locus of said transgenic mouse is capable of undergoing V, D, J joining and,
   wherein said mouse following delivery of said antigen, is capable of producing a plurality of antibodies specific for said antigen comprising a chimeric Ig heavy chain comprising a plurality of human IgH chain variable regions, and
   wherein said recombinant immunoglobulin light chain kappa (Igκ) locus of said transgenic mouse is capable of undergoing V, J joining and,
   wherein said mouse following delivery of said antigen, is capable of producing a plurality of antibodies specific for said antigen comprising a chimeric Igκ chain comprising a plurality of human Igκ chain variable regions,
   wherein said transgenic mouse is capable of breeding with another said transgenic mouse to provide subsequent generation mice,
   wherein said subsequent generation mouse comprises: (i) in its germline said homozygous IgH locus, (ii) in its germline comprising all or part of mouse IgH variable region DNA upstream of said unrearranged human VH region gene segments, and capable of breeding to subsequent generations, and wherein said subsequent generation mouse is capable of breeding with a said subsequent generation mouse to further subsequent generations, and (b) isolating from said mouse of step (a) or a cell of said mouse of step (a) said biological sample.

2. The method of claim 1, wherein the biological sample comprises said polypeptide comprising said human kappa variable region, further comprising the step of adding a human kappa constant region to the carboxy terminus of said human kappa variable region to provide a fully human Igκ polypeptide.

3. The method of claim 1, wherein said isolated biological sample comprises a cell which is a B cell comprising said antigen-specific antibody, and said method further comprises the step of preparing a hybridoma from said B cell.

4. The method of claim 3, wherein said method further comprises the step of:
isolating nuclei acid from said hybridoma, wherein said nucleic acid encodes a polypeptide selected from the group consisting of: said human kappa variable region, a light chain polypeptide comprising said human kappa variable region, or said antigen-specific antibody comprising said human kappa variable region.

5. The method of claim 4, further comprising combining nucleic acid encoding a human kappa variable region with nucleic acid encoding a human constant region, thereby producing a nucleic acid encoding a human Igκ polypeptide.

6. The method of claim 5, further comprising inserting said nucleic acid encoding said fully human Igκ peptide into the genome of a cell, thereby providing a cell capable of expressing said human Igκ polypeptide.

7. The method of claim 6, further comprising the step of: expressing said human Igκ polypeptide from said cell, and optionally isolating the expressed polypeptide.

8. The method of claim 5, further comprising the step of: expressing in vitro said human Igκ polypeptide from said nucleic acid encoding said human Igκ polypeptide, and optionally isolating the expressed polypeptide.

9. The method of claim 1, wherein said isolated biological sample comprises a cell which is a B cell comprising said human kappa variable region, or a B cell expressing said antigen-specific antibody, and said method further comprises the step of isolating nucleic acid from a B-cell, wherein said nucleic acid encodes said human kappa variable region, or said antigen-specific antibody comprising said Igκ polypeptide.

10. The method of claim 9, further comprising combining nucleic acid encoding said human kappa region with nucleic acid encoding a human constant region, thereby producing a nucleic acid encoding a human Igκ polypeptide.

11. The method of claim 10, further comprising the step of: expressing in vitro or in vivo from a cell said human Igκ polypeptide from said nucleic acid encoding said human Igκ polypeptide, and optionally isolating the expressed polypeptide.

12. The method of claim 1, wherein said isolated biological sample comprises nucleic acid encoding said human kappa variable region, and said method further comprises the step of:
combining said nucleic acid encoding said human kappa variable region to nucleic acid encoding a human C region polypeptide to produce nucleic acid encoding a fully human polypeptide comprising said human kappa variable region and said human C region.

13. The method of claim 12, further comprising the step of: expressing said fully human polypeptide from said nucleic acid encoding said human polypeptide comprising said human kappa variable region and said human C region.

14. The method of claim 11, further comprising isolating said fully human polypeptide and combining said polypeptide with a human heavy chain polypeptide to provide an antibody.

15. The method of claim 1, wherein said antigen is a human antigen.

16. method of claim 1, wherein said enhancer is a mouse kappa enhancer.

17. The method of claim 16, wherein said human Jκ gene segments comprise a 3' human Jκ gene segment and wherein the distance from said 3' human Jκ gene segment to said mouse IgK JC intronic DNA is less than 2 kb.

18. The method of claim 16, wherein the distance between said mouse IgK JC intronic DNA and said mouse enhancer comprises 782 bp.

19. The method of claim 16, wherein DNA between said mouse IgK JC intronic DNA and said enhancer comprises mouse 129 strain JC intronic DNA.

20. The method of claim 1, wherein 100% of B-cells of said mouse after antigen delivery comprise Vκ and Jκ gene segments.

* * * * *

SEQUENCE LISTING

<160> NUMBER OF SEQ ID NOS: 68

<210> SEQ ID NO 1
<211> LENGTH: 4272
<212> TYPE: DNA
<213> ORGANISM: Rattus norvegicus

<400> SEQUENCE: 1

| | | | | | |
|---|---|---|---|---|---|
| agatctgccc | atctcaggct | agttaaatta | gttcatccca | gtttggccca | acttacccca | 60 |
| tctagagtag | cgaaactaat | ctgagcctag | ctaagtccag | tttagtttaa | tgtagcccag | 120 |
| cttggcacag | gctaatacat | actgctacag | tttggtctag | cctaccctaa | ttaagctgat | 180 |
| ccaggcctgg | gtagacctag | ctcatctcag | cccagttaag | gttatccagt | acatctcttt | 240 |
| ccagttcagc | tcaggttacc | ataccttatc | tcaattcagc | tcagctagtg | taattcatct | 300 |
| tagttcatcc | cctaccccctc | tagactccct | gttgatctta | actcagttta | gacatggcca | 360 |
| acaaagcctg | gcccaactca | ggccaggtta | gtgtagctca | gcataagcag | tctagccttg | 420 |
| ctcagtctag | ctcacccttc | ctcatctaaa | ttcaactcag | ctatgccggc | cctgcagcag | 480 |
| gtcccctcag | ctcacccaag | tccaaccagt | tcagtctggc | tcatttaagt | cttgacaatc | 540 |
| cccaattcat | cccagctcag | cttagcataa | ctcaggcagt | ccattcttag | cccaacccag | 600 |
| tttagcccag | tttatcccag | ttcatcctgg | ctgtactcag | tgcaactcga | ttcatgttct | 660 |
| cccaggccac | ctcagcccag | ttcatggtag | ctcatctgag | cccaacttat | cccagctcat | 720 |
| cccaaaccac | ctcacctaag | ccctgctcag | cctagctcat | ctgagcctag | ttcaacctct | 780 |
| ctcatcctgc | cagctagccc | agtttagtcc | acatcatctt | gcaaagctca | accagcccaa | 840 |
| gtcagccggg | tccagctcat | tcatgtccaa | accagctcag | tcatgctcat | cctaactcag | 900 |
| cctcaccatc | atccacatca | gctagcccag | ttcagctgag | ctcatcccag | cccacttcaa | 960 |
| tcacagctca | tttaagtaca | gctcacccca | gctctattta | gctcaagcta | gcttatttag | 1020 |
| cctacttcat | cccagctcag | cccagccaac | tcaactcatc | ctagctcagc | taaaccctgc | 1080 |
| tcagctcacc | caagcaaagc | tgactccaac | ccagatcctt | tcagctcagc | tcacccagct | 1140 |
| caggccagct | cacccatccc | agctcaccca | gcttagctca | cccagcccag | ctcagcccag | 1200 |
| ctcacccagc | ccagctcagc | ccagctcacc | cagcccagct | cagcccagct | cagctcagct | 1260 |
| cagctcagct | cagctcagct | cacccagctc | agctcagcca | gctcagctca | cccagctca | 1320 |
| gtccagctca | gttcagctca | cccagctcag | ctcacccaa | tcagctcac | tcaactcagc | 1380 |
| tcacccaact | cagctcagct | cagttcaccc | agctcagctc | acccagccca | gcacagctca | 1440 |
| tctcacccag | ctcagctcac | ccagcccagc | tcacccagc | tcaccccagc | tcagctcagc | 1500 |
| tcaccccagc | tcagcccagc | tcagctcacc | cagctcagct | cacccaactc | agctcagctc | 1560 |
| agttcaccca | gctcagctca | cccagcccag | cacagctcat | ctcacccagc | ccagctcacc | 1620 |
| ccagctcacc | ccagctcagc | tcagctcagc | ccagctcacc | cagctcagct | cagctcaccc | 1680 |
| cagctcagct | cacccagctc | agctcaccca | gcccagctca | gctcagctca | cccagctca | 1740 |
| gcccagctca | gctcacccag | ctcagctcac | ccagcccagc | tcaccccagc | tcaccccagc | 1800 |
| tcagtccagc | tcagttcagc | tcacccagct | cagctcaccc | aactcaactc | agctcagttc | 1860 |
| acccagctca | gctcagctca | cccagctcag | cccagctcag | cccagctcag | ttcagctcac | 1920 |
| cccagctcag | ttcacccagc | tcagctcacc | cagcccagct | cagcccagct | caccccagct | 1980 |
| cagctcaacc | agatcagctc | agcccagctc | acctagttt | agttcacccca | gcccagctca | 2040 |
| ccccagctca | gctcacccca | actcagctca | cccagctcat | cccagctcag | ccagctaatc | 2100 |

```
ccagctcagc tcaccccagc tcagctcacc cagctcagct cacccaactc agctcacccc      2160
agctcacccc agctcatccc agctcatccc agttcagacc tgttcagctc atctcacccc      2220
agctcagctc accccagttc agctcaccta gcccaactca ccccagctca gtccagctca      2280
gttcagctca ccccaactca tctcacccag ctcagctcac cccagctcat ccagctcag       2340
ctcaccccag ttcagccctg ttcagctcat ctcacccagc tcagctcatc cagcccagct      2400
caccccagct caccccagct cagtccagct cagttcagct cacccagctc agctcaccca      2460
actcaactca gctcagttca cccagctcag ctcagctcac cccagctcac ccagctcagt      2520
tcagctcacc ccagctcagt tcacccagct cagctcaccc agcccagctc aaccagatca      2580
gctcagccca gctcacccta gtttagttca cccagcccag ctcaccccag ctcagctcac      2640
cccaactcag ctcacctagc tcatcccagc tcagctcacc ccagctcagc tcaccccagc      2700
tcatctcacc ccagctcagc tcacccagct catcccagct cagctcagcc agctcatcc       2760
cagccctgct catcccagct cagctcagct cagcccagct cagcccagct cagcccagct      2820
cagcccagct cagcccagct cagctcaacc cagctcagct cacccagccc agctcagccc      2880
agctcaccca gctcagctca ccccagctca gctcaccccca gctcatctca cccagctcag      2940
ctcacccagc tcagcccagc tcagctcagc tcacccagct catctcaccc agctcagctc      3000
accccagctc atcccagctc agctcacccc agttcagccc tgttcagctc atctcacccc      3060
agctcagctc acccagttca gctcatccca gcccatccca gctcagctca gcccagctca      3120
gcccagctca gccagcccca gcccagccca gctcagctca gcccagctca gcccagctca      3180
gtccagctca gcttagccca gcccagctca gctcagccca gctcagccca gctcagccca      3240
gctcagctca cccagctcac cccagctcag cccagctcag cccagctcag ctcacccagc      3300
tcaccccacc ccagctcacc ccagttcagc ccagctcagc ccagctcagc ccagcccagc      3360
ccagcccagc ccagcccagc tcagcccagc tcagctcagc ccagcccagc tcagctcagc      3420
ccagctcagc ccagctcatc ccagctcagc tcaccccagc tcagcccagc tcagcccagc      3480
tcagctcacc cagctcaccc caccccagct caccccagtt cagcccagct catccagctc      3540
agctcacccc cagctctgct cacccagctc agctcagctt acccagctca gctcaactca      3600
cccagctcag ctcacccagc tcagctcagc tcaccccagc ccagctcagc tcagctcacc      3660
ccagctctgc tcacccagct cagctcagct cacctcagct ctgctcaccc agctcagctc      3720
aaccacctca ggtcagccca gctcaccccca gcttacccca gctcacccag ctcagctcag      3780
ctcacccagc tcagctcacc cagctcagct caccccagct taccccagct caccccagct      3840
cagctaaccc agctcagctc acccagctca gctcacccag ctcagctcat cccagctcac      3900
cccagctacc acagagtagc tcatgctagc tcagctcacc ccagcacaac acagcccaac      3960
acagctcagt tcagagcagt ccagtagagt ttagctccaa tcagcccaga tcaagacaat      4020
tcattccaat ttggctatct tggttaagtc agcctagttt agcttagccg gcctagctca      4080
attcagctca ttgcagtcta cctcgttcct gctcaagtcc agctttggct acctcagagt      4140
aatcatctca gcttagcaca tttttgaagg gctcagggaa gcctacacat ctcagtccaa      4200
ctgtgcttaa ctagagccta gcttcctagc caggctgtca accttgttca ctaaattttg      4260
ctcagcaagc tt                                                         4272
```

<210> SEQ ID NO 2
<211> LENGTH: 22190
<212> TYPE: DNA

<213> ORGANISM: Artificial Sequence
<220> FEATURE:
<223> OTHER INFORMATION: Tragetting Vector (long version)

<400> SEQUENCE: 2

```
gcggccgcaa cctgggcaaa tgggagctta gcaacaatgt aggggggctgg acctagactt      60
cctacacatt tgtagcagat gtgcagcttg gtcttcatgt gtgtattacc ctaacatttg     120
gagcaggagc tgtctctgac tctgttgcct gccattggat ccccttcccc tgcttgggct     180
gccttgtttg gccttagtag gaaaggatgt gcttagtcct gctgtgactt gatgtcccta     240
ggcagaatga tacccaggg gggctcccca tctctgagga gatgggcaaa gggtaatggt      300
tggagggact tgtgaggctg ggactgggag gagagaaagg agacagctgt aactggaatg     360
atgttaagtg aacaaatgaa tggatagatt agatagacag atagacagac agacagacag     420
acagacagac agacagacag acagatagaa agatagatag ataaggggaa aaagaaacgt     480
agctgagcaa gccagagaga gcaagccaaa taagcagcat tcctccatga cttttccttc     540
agctcctgcc tatgagtctg ccttgacttc cctcagtgat tggttgtaag ttaaaaggtg     600
aaataaaccc tttctttgac aagttgcttt tggttctgat ttttatcaca gcaagagaaa     660
atcaaactag aacaaacatg tattttttcct ggcacatgtc catagtaagg cagaaatgat    720
cttcagacct agaccataga tactacagag agcagaagtg tagataggtg gacttactgt     780
atgattgtaa tccaagtaaa tctacatagc tagagagcta gaggaaaggc caaagcttcc     840
tctgggaggt cagatcctgt cgcactgtag ccaataaggc atattgcatc acaggaaagg     900
actaagaccc aggctggcaa tagtgtctgt atcttaacta gacctctcta gtgagtgagg     960
aaggaagttt gtgagagccc agactgtggg ctcggaaggt acctgccatg cccctgttag    1020
taactgagta ctacagcagg agcaggtgtt ctctagaaag cctgagacaa ctctacttct    1080
tctctcaaga gaccacctaa tacaggcctg agaaacaga ctctggaaat agatgggact    1140
taaggagcta agatctagag ctcatctaca gagcagaatc ccagccaaga gaacaaagaa    1200
tactggctct ctctcctgtt ccctactcct agagttctaa acacactat agggaaggga    1260
gcctctagac ctccgtccat tcccccatctt gctcattcca tcttcccatg tccccaggtc    1320
tccaagccac agacactacc tttcctattc acccacctttt ctgtgtccct aggtccccag    1380
gccatagtca cctccccca cacacacccc actcaccctg ccccatctat gcccctagat    1440
gcttacttac cagagtcttt tgtctgacgt ggggctacaa gcatctatgc tccctaagca    1500
cctactgctg acctgtagga cccagctctg aaccaactca tataagtaaa tacagactct    1560
cccctgtctt aggatggcct cctggatcag gaggagacca ctgccaaaga accttctctc    1620
agagcactga actcctcccc tgtaccactt aggacagacc tgagacctat tattactgat    1680
taccagagct ctggcagtga ccacggagga gataggtcca ccctggacac aggaaacaca    1740
gcagcagaga tactgctcca tcacaacagt agagtgacac tttagacttt aatttgggtc    1800
actttcctgc tgcagaggtg ggatcagaaa gcaaagagca gtatgagtgc ctgataggca    1860
cccaagtaca ctatagagta ctcatggtga ataaggtacc tccatggctt cccagggagg    1920
ggcactgccc cacccccacc atcacagacc tttctccata gttgataact cagacacaag    1980
tgaatgacag atggacctcc atctactctt atttaaaaa gaagacaaac cccacaggct    2040
cgagaacttt agcgactgtt ttgagagaaa tcattggtcc ctgactcaag agatgactgg    2100
cagattgggg atcagaatac ccatactctg tggctagtgt gaggtttaag cctcagagtc    2160
cctgtggtct ctgactggtg caaggttttg actaagcgga gcaccacagt gctaactggg    2220
```

```
accacggtga cacgtggctc aacaaaaacc ttctgtttgg agctctccag gggcagcctg    2280
agctatgagg aagtagagag gcttgagaaa tctgaggaag aaaagagtag atctgagagg    2340
aaaggtagct ttctggaggt caggagacag tgcagagaag aacgagttac tgtggacagg    2400
tcttagatgg ggaaagaatg agcaaatgca agcatcagaa gggtggatgc aatgtcctgc    2460
caaggactta ccaagaggat ccccggacag agcaggcagg tggagttgac tgagaggaca    2520
gggtaggtgc aggtccctct ctcgtttcct ttctccttct cctgtttcct tcctctcttg    2580
tcacaggtct cactatgcta gccaaggcta gcctgaaaga ttaccatcct acagatgggc    2640
ccatccagtt gagttaaggt ggagatctct ccaaacatct gagtttctga ggcttggatg    2700
ccactgggga cgccaaggga ctttgggctg ggtttggttg gccccagatg aagggctact    2760
tcactgggtc tataattact ctgatgtcta ggaccagggg gctcaggtca ctcaggtcag    2820
gtgagtcctg catctgggga ctgtgggggtt caggtgtcct aaggcaggat gtggagagag    2880
ttttagtata ggaacagagg cagaacagag actgtgctac tggtacttcg atgtctgggg    2940
cgcagggacc acggtcaccg tctcctcagg taagctggct ttttctttc tgcacattcc    3000 attctgaaat gggaaaagat attctcagat ctccccatgt caggccatct gccacactct    3060
gcatgctgca gaagcttttc tgtaaggata gggtcttcac tcccaggaaa agaggcagtc    3120
agaggctagc tgcctgtgga acagtgacaa tcatggaaaa taggcattta cattgttagg    3180
ctacatgggt agatgggttt tgtacaccc actaaagggg tctatgatag tgtgactact    3240
ttgactactg ggccaaggc accactctca cagtctcctc aggtgagtcc ttacaacctc    3300
tctcttctat tcagcttaaa tagattttac tgcatttgtt gggggggaaa tgtgtgtatc    3360
tgaatttcag gtcatgaagg actagggaca ccttgggagt cagaaagggt cattgggagc    3420
cctggctgat gcagacagac atcctcagct cccagacttc atggccagag atttataggg    3480
atcctggcca gcattccgc taggtccctc tcttctatgc tttctttgtc cctcactggc    3540
ctccatctga gatcatcctg gagccctagc caaggatcat ttattgtcag gggtctaatc    3600
attgttgtca caatgtgcct ggtttgctta ctggggccaa gggactctgg tcactgtctc    3660
tgcaggtgag tcctaacttc tcccattcta aatgcatgtt ggggggattc tgagccttca    3720
ggaccaagat tctctgcaaa cgggaatcaa gattcaaccc ctttgtccca aagttgagac    3780
atgggtctgg gtcagggact ctctgcctgc tggtctgtgg tgacattaga actgaagtat    3840
gatgaaggat ctgccagaac tgaagcttga agtctgaggc agaatcttgt ccagggtcta    3900
tcggactctt gtgagaatta ggggctgaca gttgatggtg acaatttcag ggtcagtgac    3960
tgtctggttt ctctgaggtg aggctggaat ataggtcacc ttgaagacta agagggggtc    4020
caggggcttc tgcacaggca gggaacagaa tgtggaacaa tgacttgaat ggttgattct    4080
tgtgtgacac caggaattgg cataatgtct gagttgccca ggggtgattc tagtcagact    4140
ctggggtttt tgtcgggtat agaggaaaaa tccactattg tgattactat gctatggact    4200
actggggtca aggaacctca gtcaccgtct cctcaggtaa gaatggcctc tccaggtctt    4260 tattttttaac ctttgttatg gagttttctg agcattgcag actaatcttg gatatttgtc    4320
cctgagggag ccggctgaga gaagttggga aataaactgt ctagggatct cagagccttt    4380
aggacagatt atctccacat ctttgaaaaa ctaagaatct gtgtgatggt gttggtggag    4440
tccctggatg atgggatagg gactttggag gctcatttga gggagatgct aaaacaatcc    4500
tatggctgga gggatagttg gggctacgcg ttttaaccc tagaaagata gtctgcgtaa    4560
```

```
aattgacgca tgcattcttg aaatattgct ctctctttct aaatagcgcg aatccgtcgc    4620
tgtgcattta ggacatctca gtcgccgctt ggagctcccg tgaggcgtgc ttgtcaatgc    4680
ggtaagtgtc actgattttg aactataacg accgcgtgag tcaaaatgac gcatgattat    4740
cttttacgtg acttttaaga tttaactcat acgataatta tattgttatt tcatgttcta    4800
cttacgtgat aacttattat atatatattt tcttgttata gatatcgcta gtggatccgg    4860
ctggttcttt ccgcctcaga aggtactttt tttttttttt tttttttttt tttttttttt    4920
tttttttttt tttttttttt tttttaaat ttttgggaat ttattgattt gcatttaaaa     4980
gggaactgct gacaaagatt cactggtaat aatttgaaca agttggaaaa tacagtcaac    5040
attactgaaa cactactaaa ataattccag gacagaacaa aacttcttag atgctgtctt    5100
tgatgtgaaa attgactgct tcttacttttt ctaacacacg gtggtataat taacaatatt    5160
caatcacttc tattctttcc tgcatatata aaaattaaaa taccaattaa aaaactaata    5220
tatcttctct ttatttctta cagatatgag ttcaatgttt cactcaatag tgctgtggtt    5280
taagagaatt ttttcattta caagttaaac aacaatccgc ccaaagggaa ctgatagtct    5340
ataggctcat agtgcaaata aacagtttag gaatgcagca actgacattt ctaaagtaca    5400
aaacagataa aattcttaga agatacatgc aaaaagctct actaagcaga tggccacaga    5460
actagaacat tgataatttt actggcgatg tcaataggac tccagatgtt tccaaactca    5520
acttgaactc tcatcttagg cttttgtattt tgcttttcca gtttcactaa tgacacaaac    5580
atgattcaaa tccctgaagt attcattata gtcaagggca tatcctacaa caaacttgtc    5640
tggaatttca aatccaacaa agtctggctt atatccaaca cttcgtgggg tccttttcac    5700
cagcaagctt gcgaccttga ccatctttgg attatactgc ctgaccaagg aaagcaaagt    5760
ctgcattgtt ttgccagtgt caattatatc ttccacaatc aagacattct ttccagttaa    5820
agttgagaga tcatctccac caattacttt tatgtcccct gttgactggt cattacaata    5880
gctcttcagt ctgataaaat ctacagtcat aggaatggat ctatcactat ttctattcag    5940
tgctttgatg taatccagca ggtcagcaaa gaatttatag ccccccttga gcacacagag    6000
ggctacaatg tgatggcctc ccatctcctt catcacatct cgagcaagac gttcagtcct    6060
acagaaataa aatcaggaat ttaatagaaa gtttcataca ttaaacttta taacaaacac    6120
ctcttagtca ttaaacttcc acaccaacct gggcaatata gtgagacccc atgcctgcaa    6180
aaaaaaaaaa attagccagg catggtagca tgtacctgta gtcccagcta cttgagaggt    6240
gaggtgggaa aatcactttta gtgcaggatg ttgaggctgg agtgaactgt gattgtgcca    6300
ctgcactcca gcctggacaa tagagcaaga ccttgtctca aaaaaatgca ttaaaaattt    6360 ttttaaatc ttccacgtaa cacatccttt gccctcatgt ttcataaggt aaaaaatttg      6420
ataccttcaa aaaaaccaag cataccacta tcataatttt ttttaaatgc aaataaaaac    6480
aagataccat tttcacctat cagactggca ggttctgatt aaatgaaatt tcttggataa    6540
tatacaatat taagagagac tgtagaaact gggccagtgg ctcatgcctg taatcccagc    6600
actttgggag gctgggtaac atggcgaacc ctgtttctac aaaataaaaa tattagctgg    6660
gagtggtggc gcacacctat agtcccagct actcaggagg ctgaggtgga aggatcgctt    6720
gaacccagga ggttgagact gcagtgaact gtgatcattc tgctgcactg caccccagcc    6780
tgggcaacag agaccttgtc tcaaaaaaaa aaaaaaaga dacaaattgt gaagagaaag    6840
gtactctcat ataacatcag gagtataaaa tgattcaact tcttagagga aaatttggca    6900
ataccaaaat attcaataaa ctctttcccc ttgacccaga aattccactt gaataaagct    6960
```

```
gaacaagtac caaacatgta aaagaatgtt tcttctagta cagtcggtaa gaacaaaata    7020
gtgtctatca atagtggact ggttaaatca gttatggtat ctccataaga cagaatgcta    7080
tgcaaccttt aaaatatatt agatagctct agacagtgga tcccctcgag ggacctaata    7140
acttcgtata gcatacatta tacgaagtta tattaagggt tattgaatat gtcgactaga    7200
cacactaata ttaaaagtgt ccaataacat ttaaaactat actcatacgt taaaatataa    7260
atgtatatat gtacttttgc atatagtata catgcatagc cagtgcttga gaagaaatgt    7320
gtacagaagg ctgaaggag agaactttag tcttcttgtt tatggcctcc atagttagaa    7380
tattttataa cacaaatatt ttgatattat aattttaaaa taaaaacaca gaatagccag    7440
acatacaatg caagcattca ataccaggta aggttttca ctgtaattga cttaacagaa    7500
aattttcaag ctagatgtgc ataataataa aaatctgacc ttgccttcat gtgattcagc    7560
cccagtccat taccctgttt aggactgaga atgcaagac tctggctaga gttccttctt    7620
ccatctccct tcaatgttta ctttgttctg gtccctacag agtcccacta taccacaact    7680
gatactaagt aattagtaag gccctcctct tttatttta ataaagaaga ttttagaaag    7740
catcagttat ttaataagtt ggcctagttt atgttcaaat agcaagtact cagaacagct    7800
gctgatgttt gaaattaaca caagaaaaag taaaaaacct catttaaga tcttacttac    7860 ctgtccataa ttagtccatg gggaataaac acccttcca aatcctcagc ataatgatta    7920
ggtatgcaaa ataaatcaag gtcataacct ggttcatcat cactaatcac gacgccaggg    7980
ctgcgggtcg ccataacgga gccggccggc gcgcgggctg aataacttcg tataatgtgt    8040
actatacgaa gttatttgtt caggaggagg aagccggtgg cggagcagag gaggaggcgg    8100
aggcgcagca agaccccccc ccccctgcag gtcgaaaggc ccggagatga ggaagaggag    8160
aacagcgcgg cagacgtgcg cttttgaagc gtgcagaatg ccgggcctcc ggaggacctt    8220
cgggcgcccg ccccgcccct gagcccgccc ctgagcccgc cccggaccc acccttccc    8280 agcctctgag cccagaaagc gaaggagcaa agctgctatt ggccgctgcc ccaaaggcct    8340
acccgcttcc attgctcagc ggtgctgtcc atctgcacga gactagtgag acgtgctact    8400
tccatttgtc acgtcctgca cgacgcgagc tgcggggcgg gggggaactt cctgactagg    8460
ggaggagtag aaggtggcgc gaaggggcca ccaaagaacg gagccggttg gcgcctaccg    8520
gtggatgtga atgtgtgcg aggccagagg ccacttgtgt agcgccaagt gcccagcggg    8580
gctgctaaag cgcatgctcc agactgcctt gggaaaagcg cctcccctac ccggtagata    8640
tctataacaa gaaaatatat atataataag ttatcacgta agtagaacat gaaataacaa    8700
tataattatc gtatgagtta aatcttaaaa gtcacgtaaa agataatcat gcgtcatttt    8760
gactcacgcg gtcgttatag ttcaaaatca gtgacactta ccgcattgac aagcacgcct    8820
cacgggagct ccaagcggcg actgagatgt cctaaatgca cagcgacgga ttcgcgctat    8880
ttagaaagag agagcaatat ttcaagaatg catgcgtcaa ttttacgcag actatctttc    8940
tagggttaaa agaattcgat atcaagctta tcgatgtagt tggagatttt cagtttttag    9000
aataaaagta ttagttgtgg aatatacttc aggaccacct ctgtgacagc atttatacag    9060
tatccgatgc atagggacaa agagtggagt ggggcacttt ctttagattt gtgaggaatg    9120
ttccgcacta gattgtttaa aacttcattt gttggaagga gagctgtctt agtgattgag    9180
tcaagggaga aaggcatcta gcctcggtct caaaagggta gttgctgtct agagaggtct    9240
ggtggagcct gcaaaagtcc agctttcaaa ggaacacaga agtatgtgta tggaatatta    9300
```

```
gaagatgttg cttttactct taagttggtt cctaggaaaa atagttaaat actgtgactt    9360
taaaatgtga gagggttttc aagtactcat ttttttaaat gtccaaaatt tttgtcaatc    9420
aatttgaggt cttgtttgtg tagaactgac attacttaaa gtttaaccga ggaatgggag    9480
tgaggctctc tcatacccta ttcagaactg acttttaaca ataataaatt aagtttaaaa    9540
tatttttaaa tgaattgagc aatgttgagt tggagtcaag atggccgatc agaaccagaa    9600
cacctgcagc agctggcagg aagcaggtca tgtggcaagg ctatttgggg aagggaaaat    9660
aaaaccacta ggtaaacttg tagctgtggt ttgaagaagt ggttttgaaa cactctgtcc    9720
agccccacca aaccgaaagt ccaggctgag caaaacacca cctgggtaat ttgcatttct    9780
aaaataagtt gaggattcag ccgaaactgg agaggtcctc ttttaactta ttgagttcaa    9840
ccttttaatt ttagcttgag tagttctagt ttccccaaac ttaagtttat cgacttctaa    9900
aatgtattta gaattcattt tcaaaattag gttatgtaag aaattgaagg actttagtgt    9960
ctttaatttc taatatattt agaaaacttc ttaaaattac tctattattc ttccctctga   10020
ttattggtct ccattcaatt cttttccaat acccgaagca tttacagtga ctttgttcat   10080
gatctttttt agttgtttgt tttgccttac tattaagact ttgacattct ggtcaaaacg   10140
gcttcacaaa tcttttcaa gaccactttc tgagtattca ttttaggaga atacttttt   10200 ttttaaatga atgcaattat ctagacttat ttcagttgaa catgctggtt ggtggttgag   10260
aggacactca gtcagtcagt gacgtgaagg gcttctaagc cagtccacat gctctgtgtg   10320
aactccctct ggccctgctt attgttgaat gggccaaagg tctgagacca ggctgctgct   10380
gggtaggcct ggactttggg tctcccaccc agacctggga atgtatggtt gtggcttctg   10440
ccacccatcc acctggctgc tcatggacca gccagcctcg gtggctttga aggaacaatt   10500
ccacacaaag actctggacc tctccgaaac caggcaccgc aaatggtaag ccagaggcag   10560
ccacagctgt ggctgctgct cttaaagctt gtaaactgtt tctgcttaag agggactgag   10620
tcttcagtca ttgctttagg gggagaaaga gacatttgtg tgtcttttga gtaccgttgt   10680
ctgggtcact cacatttaac tttccttgaa aaactagtaa agaaaaatg ttgcctgtta   10740 accaataatc atagagctca tggtattttg aggaaatctt agaaaacgtg tatacaattg   10800
tctggaatta tttcagttaa gtgtattagt tgaggtactg atgctgtctc tacttcagtt   10860
atacatgtgg gtttgaattt tgaatctatt ctggctcttc ttaagcagaa aatttagata   10920
aaatggatac ctcagtggtt tttaatggtg ggtttaatat agaaggaatt taaattggaa   10980
gctaatttag aatcagtaag gagggaccca ggctaagaag gcaatcctgg gattctgaa   11040 gaaaagatgt ttttagtttt tatagaaaac actactacat tcttgatcta caactcaatg   11100
tggtttaatg aatttgaagt tgccagtaaa tgtacttcct ggttgttaaa gaatggtatc   11160
aaaggacagt gcttagatcc aaggtgagtg tgagaggaca ggggctgggg tatggatacg   11220
cagaaggaag gccacagctg tacagaattg agaaagaata gagacctgca gttgaggcca   11280
gcaggtcggc tggactaact ctccagccac agtaatgacc cagacagaga aagccagact   11340
cataaagctt gctgagcaaa atttagtgaa caaggttgac agcctggcta ggaagctagg   11400
ctctagttaa gcacagttgg actgagatgt gtaggcttcc ctgagccctt caaaaatgtg   11460
ctaagctgag atgattactc tgaggtagcc aaagctggac ttgagcagga acgaggtaga   11520
ctgcaatgag ctgaattgag ctaggccggc taagctaaac taggctgact taaccaagat   11580
agccaaattg gaatgaattg tcttgatctg ggctgattgg agctaaactc tactggactg   11640
ctctgaactg agctgtgttg ggctgtgttg tgctggggtg agctgagcta gcatgagcta   11700
```

```
ctctgtggta gctggggtga gctgggatga gctgagctgg gtgagctgag ctgggtgagc    11760
tgagctgggt tagctgagct ggggtgagct ggggtaagct ggggtgagct gagctgggtg    11820
agctgagctg ggtgagctga gctgagctgg gtgagctggg gtaagctggg gtgagctggg    11880
ctgacctgag gtggttgagc tgagctgggt gagcagagct gaggtgagct gagctgagct    11940
gggtgagcag agctggggtg agctgagctg agctgggctg gggtgagctg agctgagctg    12000
ggtgagctga gctgggtgag ttgagctgag ctgggtaagc tgagctgagc tgggtgagca    12060
gagctggggg tgagctgagc tggatgagct gggctgaact ggggtgagct ggggtggggt    12120
gagctgggtg agctgagctg ggctgagctg ggctgagctg gggtgagctg agctgggatg    12180
agctgggctg agctgggctg agctgagctg gctgggctg agctgagctg gctgagctg    12240
```

```
ctgagctggg tgaactgagc tgagctgagt tgggtgagct gagctgggtg agctgagctg    14100
ggctgagctg gggtgagctg agctgagctg gggtgagctg gggtgagctg ggctgggtga    14160
gctgagctgg gtgagatgag ctgtgctggg ctgggtgagc tgagctgggt gaactgagct    14220
gagctgagtt gggtgagctg agttgagtga gctgagttgg gtgagctgag ctggggtgag    14280
ctgaactgag ctggactgag ctggggtgag ctgagctggc tgagctgagc tgggtgagct    14340
gagctgagct gagctgagct gagctgagct gggctgagct gggctgggtg agctgggctg    14400
agctgggctg ggtgagctgg gctgagctgg gctgggtgag ctaagctggg tgagctggga    14460
tgggtgagct ggcctgagct gggtgagctg agctgaaagg atctgggttg gagtcagctt    14520
tgcttgggtg agctgagcag ggtttagctg agctaggatg agttgagttg gctgggctga    14580
gctgggatga agtaggctaa ataagctagc ttgagctaaa tagagctggg gtgagctgta    14640
cttaaatgag ctgtgattga agtgggctgg gatgagctca gctgaactgg gctagctgat    14700
gtggatgatg gtgaggctga gttaggatga gcatgactga gctggtttgg acatgaatga    14760
gctggacccg gctgacttgg gctggttgag ctttgcaaga tgatgtggac taaactgggc    14820
tagctggcag gatgagagag gttgaactag gctcagatga gctaggctga gcagggctta    14880
ggtgaggtgg tttgggatga gctgggataa gttgggctca gatgagctac catgaactgg    14940
gctgaggtgg cctgggagaa catgaatcga gttgcactga gtacagccag gatgaactgg    15000
gataaactgg gctaaactgg gttgggctaa gaatggactg cctgagttat gctaagctga    15060
gctgggatga attggggatt gtcaagactt aaatgagcca gactgaactg gttggacttg    15120
ggtgagctga ggggacctgc tgcagggccg gcatagctga gttgaattta gatgaggaag    15180
ggtgagctag actgagcaag gctagactgc ttatgctgag ctacactaac ctggcctgag    15240
ttgggccagg ctttgttggc catgtctaaa ctgagttaag atcaacaggg agtctagagg    15300
ggtaggggat gaactaagat gaattacact agctgagctg aattgagata aggtatggta    15360
acctgagctg aactggaaag agatgtactg gataaccttta actgggctga gatgagctag    15420
gtctacccag gcctggatca gcttaattag ggtaggctag accaaactgt agcagtatgt    15480
attagcctgt gccaagctgg gctacattaa actaaactgg acttagctag gctcagatta    15540
gtttcgctac tctagatggg gtaagttggg ccaaactggg atgaactaat ttaactagcc    15600
tgagatgggc agatctgaat gagcagagct gggatgaact gaatgagttt caccaggcct    15660
ggaccagtta ggctaggacc tcgttctata gaggcagact gtgtgctaca gtggagtttc    15720
aagatgattc catgagtcct ccccgccccc aacataaccc accttcctcc taccctacaa    15780
gcctgtctgg tgtgtaaatc ccagctttgt gtgctgatac agaagcctga gcccctcccc    15840
cacctccacc tacctattac tttgggatga gaatagttct cccagccagt gtctcagagg    15900
gaagccaagc aggacaggcc caaggctact tgagaagcca ggatctaggc ctctccctga    15960
gaacgggtgt tcatgcccct agagttggct gaagggccag atccacctac tctagaggca    16020
tctctccctg tctgtgaagg cttccaaagt cacgttcctg tggctagaag gcagctccat    16080
agccctgctg cagtttcgtc ctgtatacca ggttcaccta ctaccatatc tagccctgcc    16140
tgccttaaga gtagcaacaa ggaaatagca gggtgtagag ggatctcctg tctgacagga    16200
ggcaagaaga cagattctta cccctccatt tctctttat ccctctctgg tcctcagaga    16260
gtcagtcctt cccaaatgtc ttcccccctcg tctcctgcga gagccccctg tctgataaga    16320
atctggtggc catgggctgc ctggcccggg acttcctgcc cagcaccatt tccttcacct    16380
ggaactacca gaacaacact gaagtcatcc agggtatcag aaccttccca acactgagga    16440
```

```
caggggggcaa gtacctagcc acctcgcagg tgttgctgtc tcccaagagc atccttgaag    16500
gttcagatga atacctggta tgcaaaatcc actacggagg caaaaacaaa gatctgcatg    16560
tgcccattcc aggtaagaac caaaccctcc cagcagggt gcccaggccc aggcatggcc     16620
cagagggagc agcggggtgg ggcttaggcc aagctgagct cacaccttga cctttcattc    16680
cagctgtcgc agagatgaac cccaatgtaa atgtgttcgt cccaccacgg gatggcttct   16740
ctggccctgc accacgcaag tctaaactca tctgcgaggc cacgaacttc actccaaaac    16800
cgatcacagt atcctggcta aaggatggga agctcgtgga atctggcttc accacagatc    16860
cggtgaccat cgagaacaaa ggatccacac cccaaaccta caaggtcata agcacactta    16920
ccatctctga aatcgactgg ctgaacctga atgtgtacac ctgccgtgtg gatcacaggg    16980
gtctcacctt cttgaagaac gtgtcctcca catgtgctgc cagtgagtgg cctgggataa    17040
gcccaatgcc tagccctccc agattaggga agtcctccta caattatggc caatgccacc    17100
cagacatggt catttgctcc ttgaactttg gctccccaga gtggccaagg acaagaatga    17160
gcaataggca gtagaggggt gagaatcagc tggaaggacc agcatcttcc cttaagtagg    17220
tttgggggat ggagactaag ctttttttcca acttcacaac tagatatgtc ataacctgac    17280
acagtgttct cttgactgca ggtccctcca cagacatcct aaccttcacc atccccccct    17340
cctttgccga catcttcctc agcaagtccg ctaacctgac ctgtctggtc tcaaacctgg    17400
caacctatga aaccctgaat atctcctggg cttctcaaag tggtgaacca ctggaaacca    17460
aaattaaaat catggaaagc catcccaatg gcaccttcag tgctaagggt gtggctagtg    17520
tttgtgtgga agactggaat aacaggaagg aatttgtgtg tactgtgact cacagggatc    17580
tgccttcacc acagaagaaa ttcatctcaa aacccaatgg taggtatccc cccttccctt    17640
cccctccaat tgcaggaccc ttcctgtacc tcatagggag ggcaggtcct cttccaccct    17700
atcctcacta ctgtcttcat ttacagaggt gcacaaacat ccacctgctg tgtacctgct    17760
gccaccagct cgtgagcaac tgaacctgag ggagtcagcc acagtcacct gcctggtgaa    17820
gggcttctct cctgcagaca tcagtgtgca gtggcttcag agagggcaac tcttgcccca    17880
agagaagtat gtgaccagtg ccccgatgcc agagcctggg gccccaggct tctactttac    17940
ccacagcatc ctgactgtga cagaggagga atggaactcc ggagagacct atacctgtgt    18000
tgtaggccac gaggccctgc cacacctggt gaccgagagg accgtggaca agtccactgg    18060
taaacccaca ctgtacaatg tctccctgat catgtctgac acaggcggca cctgctattg    18120
accatgctag cgctcaacca ggcaggccct gggtgtccag ttgctctgtg tatgcaaact    18180
aaccatgtca gagtgagatg ttgcatttta taaaattag aaataaaaaa aatccattca    18240
aacgtcactg gttttgatta tacaatgctc atgcctgctg agacagttgt gttttgcttg    18300
ctctgcacac accctgcata cttgcctcca ccctggccct tcctctacct tgccagtttc    18360
ctccttgtgt gtgaactcag tcaggcttac aacagacaga gtatgaacat gcgattcctc    18420
cagctacttc tagatatatg gctgaaagct tgcctaacct ggtgcaggca gcattcaggc    18480
acatatatag acacacatgc atttatacat agatatatag gtacacatgt gtagacacat    18540
acatgaatgt gtattcatgg acacacagac aaagtacac atatatacac atgagttcat    18600
gcgcacacac atgcatggac acttacaaac gccttcagag acaaataggc atagacacac    18660
aaccactcac agaaacagat accaaatatgc atggtcctgt gtacacagaa acagactata    18720
ggcaaatata cacaaataaa ctatatagat acaaagatat gcatatacac acatgtacag    18780
```

```
aaacatcttc acatgtgtac actaacatgt ggacaggtat agcacacaga tacacctgga    18840
ctctgaccag ggctgtaatc tccaaggctc acggctcaga gagcctacac taggctgggt    18900
cactgatact cctcaggagc ccactctatg attgggagag ataaccccag gtacaaagta    18960
tgcctatctg tctcaacacc atggggcaga agatactcca ctaaccaccc atgacagaaa    19020
gttagccttg gctgtgtctc cattaataga acacctcaga agaccaatgt gaaattgcct    19080
aacccactca cacccaccct gatctccagt tcaaaatgca gaaaacataa tgcagttgtc    19140
caaaagatgc cccaaccaca cacacacaca cacacacaca cacacacaca cacacacaca    19200
cacacataca cacacacaca ccatcaagga gcctctgtaa ggagtcacca cccaataaca    19260
ctgcctcttt gggctcatat cctggacatt cttcatattc atatccattt ggggcctagg    19320
ctttagatat ccccaagggc tcatctttac agggatcaga gatcccaata aatgccctgg    19380
tcccacagcc tccctcaggt atctgtctgt ttatctcttg gtacctttct tagacgttag    19440
gtggcacttt tcggggaaat gtgcgcggaa cccctatttg tttattttc taaatacatt    19500 caaatatgta tccgctcatg agacaataac cctgataaat gcttcaataa tattgaaaaa    19560
ggaagagtat gagtattcaa catttccgtg tcgcccttat tccctttttt gcggcatttt    19620
gccttcctgt ttttgctcac ccagaaacgc tggtgaaagt aaaagatgct gaagatcagt    19680
tgggtgcacg agtgggttac atcgaactgg atctcaacag cggtaagatc cttgagagtt    19740
ttcgccccga agaacgtttt ccaatgatga gcacttttaa agttctgcta tgtggcgcgg    19800
tattatcccg tgttgacgcc gggcaagagc aactcggtcg ccgcatacac tattctcaga    19860
atgacttggt tgagtactca ccagtcacag aaaagcatct tacggatggc atgacagtaa    19920
gagaattatg cagtgctgcc ataaccatga gtgataacac tgcggccaac ttacttctga    19980
caacgatcgg aggaccgaag gagctaaccg ctttttttgca caacatgggg gatcatgtaa    20040
ctcgccttga tcgttgggaa ccggagctga atgaagccat accaaacgac gagcgtgaca    20100
ccacgatgcc tgcagcaatg gcaacaacgt tgcgcaaact attaactggc gaactactta    20160
ctctagcttc ccggcaacaa ttaatagact ggatggaggc ggataaagtt gcaggaccac    20220
ttctgcgctc ggcccttccg gctggctggt ttattgctga taaatctgga gccggtgagc    20280
gtgggtctcg cggtatcatt gcagcactgg ggccagatgg taagccctcc cgtatcgtag    20340
ttatctacac gacggggagt caggcaacta tggatgaacg aaatagacag atcgctgaga    20400
taggtgcctc actgattaag cattggtaac tgtcagacca agtttactca tatatacttt    20460
agattgattt aaaacttcat ttttaattta aaaggatcta ggtgaagatc cttttgata    20520 atctcatgac caaaatccct taacgtgagt tttcgttcca ctgagcgtca ccccgtag    20580 aaaagatcaa aggatcttct tgagatcctt ttttctgcg cgtaatctgc tgcttgcaaa    20640
caaaaaaacc accgctacca gcggtggttt gtttgccgga tcaagagcta ccaactcttt    20700
ttccgaaggt aactggcttc agcagagcgc agataccaaa tactgtcctt ctagtgtagc    20760
cgtagttagg ccaccacttc aagaactctg tagcaccgcc tacatacctc gctctgctaa    20820
tcctgttacc agtggctgct gccagtggcg ataagtcgtg tcttaccggg ttggactcaa    20880
gacgatagtt accggataag gcgcagcggt cgggctgaac ggggggttcg tgcacacagc    20940
ccagcttgga gcgaacgacc tacaccgaac tgagatacct acagcgtgag ctatgagaaa    21000
gcgccacgct tcccgaaggg agaaaggcgg acaggtatcc ggtaagcggc agggtcggaa    21060
caggagagcg cacgagggag cttccagggg gaaacgcctg gtatctttat agtcctgtcg    21120
ggtttcgcca cctctgactt gagcgtcgat ttttgtgatg ctcgtcaggg gggcggagcc    21180
```

```
tatgaaaaa cgccagcaac gcggcctttt tacggttcct ggccttttgc tggccttttg    21240
ctcacatgtt ctttcctgcg ttatccctg attctgtgga taaccgtatt accgcctttg    21300
agtgagctga taccgctcgc cgcagccgaa cgaccgagcg cagcgagtca gtgagcgagg    21360
aagcggaaga gcgcctgatg cggtatttc tccttacgca tctgtgcggt atttcacacc    21420
gcatatggtg cactctcagt acaatctgct ctgatgccgc atagttaagc cagtatacac    21480
tccgctatcg ctacgtgact gggtcatggc tgcgccccga cacccgccaa cacccgctga    21540
cgcgccctga cgggcttgtc tgctcccggc atccgcttac agacaagctg tgaccgtctc    21600
cgggagctgc atgtgtcaga ggttttcacc gtcatcaccg aaacgcgcga ggcagctgcg    21660
gtaaagctca tcagcgtggt cgtgaagcga ttcacagatg tctgcctgtt catccgcgtc    21720
cagctcgttg agtttctcca gaagcgttaa tgtctggctt ctgataaagc gggccatgtt    21780
aagggcggtt ttttcctgtt tggtcactga tgcctccgtg taagggggat ttctgttcat    21840
gggggtaatg ataccgatga aacgagagag gatgctcacg atacgggtta ctgatgatga    21900
acatgcccgg ttactggaac gttgtgaggg taaacaactg gcggtatgga tgcggcggga    21960
ccagagaaaa atcactcagg gtcaatgcca gcgcttcgtt aatacagatg taggtgttcc    22020
acagggtagc cagcagcatc ctgcgatgca gatccggaac ataatggtgc agggcgctga    22080
cttccgcgtt tccagacttt acgaaacacg gaaaccgaag accattcatg ttgttgctca    22140
ggtcgcagac gttttgcagc agcagtcgct tcacgttcgc tcgcgtatcg             22190

<210> SEQ ID NO 3
<211> LENGTH: 14130
<212> TYPE: DNA
<213> ORGANISM: Artificial Sequence
<220> FEATURE:
<223> OTHER INFORMATION: Targetting vector (short version)

<400> SEQUENCE: 3
gcggccgcaa cctgggcaaa tgggagctta gcaacaatgt agggggctgg acctagactt      60
cctacacatg tgtaacagat gtgcagcttg gtcttcatgt gtgtattacc ctaacatttg     120
gagcaggagc tgtctctgac tctgttgcct gccattggat ccccttcccc tgcttgggct     180
gccttgtttg gccttagtag gaaaggatgt gcttagtcct gctgtgactt gatgtcccta     240
ggcagaatga taccccaggg gggctcccca tctctgagga gatgggcaaa gggtaatggt     300
tggagggact tgtgaggctg ggactgggag gagagaaagg agacagctgt aactggaatg     360
atgttaagtg aacaaatgaa tggatagatt agatagacag atagacagac agacagacag     420
acagacagac agacagacag acagacagat agaaagatag atagataagg ggaaaaagaa     480
acgtagctga gcaagccaga gagagcaagc caaataagca gcattcctcc atgacttttc     540
cttcagctcc tgcctatgag tctgccttga cttccctcag tgattggttg taagttaaaa     600
ggtgaaataa accctttctt tgacaagttg cttttggttc tgatttttat cacagcaaga     660
gaaaatcaaa ctagaacaaa catgtatttt tcctggcaca tgtccatagt aaggcagaaa     720
tgatcttcag acctgacca tagatactac agagagcaga agtgtagata ggtggactta     780
ctgtatgatt gtaatccaag taaatctaca tagctagaga gctagaggaa aggccaaagc     840
ttcctctggg aggtcagatc ctgtcgcact gtagccaata aggcatattg catcacagga     900
aaggactaag acccaggctg gcaatagtgt ctgtatctta actagatctc tctagtgagt     960
gaggaagtaa atttgtgaga gcccagactg tgggctcgga aggtacctgc catgcccctg    1020
```

| | |
|---|---|
| ttagtaactg agtactacag caggagcagg tgttctctag aaagcctgag acaactctac | 1080 |
| ttcttctctc aagagaccac ctaatacagg cctgagagaa cagactctgg aaatagatgg | 1140 |
| gacttacgga gctaagatct agagctcatc tacagagcag aatcccagcc aagagaacaa | 1200 |
| agaatactga ctctctcctg ttccctactc ctagagttct aaaacacact atagggaagg | 1260 |
| gagcctctag acctccgtcc attccccatc ttgctcattc catcttccca tgtccccagg | 1320 |
| tctccaagcc acagacacca cctttcctat tcacccacct ttctgtgtcc ctaggtcccc | 1380 |
| aggccatagt cacctccccc cacacccgc tcaccctgcc ccatctatgc ccctagatgc | 1440 |
| ttacttacca gagtcttttg tctgacgtgg ggctacaagc atctatgctc cctaagcacc | 1500 |
| tactgctgac ctgtaggacc cagctctgaa ccaactcata taagtaaata cagactctcc | 1560 |
| cctgtcttag gatggccccc tgggtcagga ggagaccact gccaaggaac cttctcttag | 1620 |
| agcactgaac tcctcccctg taccacttag cacagacctg agacctatta ttactgatta | 1680 |
| ccagagctct ggcagtgacc acggaggaga tagatccacc ctggacacag gaaacacagc | 1740 |
| accagagata ctgcttcatc acaacagtag agtgacactt tagactttaa tttgggtcac | 1800 |
| tttcctgctg tagaggtggg atcagaaagc aaagagcagt atgagtgcct gataggcacc | 1860 |
| caagtacact atagagtact catggtgaat aaggtacctc catggcttcc cagggagggg | 1920 |
| cactgcccca cccccaccat cacagaccctt tctccatagt tgataactca gacacaagtg | 1980 |
| aatgacagat ggacctccat ctgctcttat tttaaaaaga agacaaaccc cacaggctcg | 2040 |
| agaactttag cgactgttttt gagagaaatc attggtccct gactcaagag atgactggca | 2100 |
| gattggggat cagaataccc atactctgtg gctagtgtga ggtttaagcc tcagagtccc | 2160 |
| tgtggtctct gactggtgca aggttttgac taagcggagc accacagtgc taactgggac | 2220 |
| cacggtgaca cgtggctcaa caaaaaacctt ctgtttggag ctctccaggg gcagcctgag | 2280 |
| ctatgaggaa gtagagaggc ttgagaaatc tgaggaagaa aagagtagat ctgagaggaa | 2340 |
| aggtagcttt ctggaggtca ggagacagtg cagagaagaa cgagttactg tggacaggtc | 2400 |
| ttagatgggg aaagaatgag caaatgcaag catcagaagg gtggatgcaa tgtcctgcca | 2460 |
| aggacttacc aagaggatcc ccggacagag caggcaggtg gagttgactg agaggacagg | 2520 |
| ataggtgcag gtccctctct tgtttccttt ctccttctcc tgtttccttc ttctcttgtc | 2580 |
| acaggtctca ctatgctagc caaggctagc ctgaaagatt accatcctac agatgggccc | 2640 |
| atccagttga attaaggtgg agatctctcc aaacatctga gtttctgagg cttggatgcc | 2700 |
| actggggacg ccaagggact ttgggatggg tttggttggc cccagatgaa gggctacttc | 2760 |
| actgggtcta taattactct gatgtctagg accagggggc tcaggtcact caggtcaggt | 2820 |
| gagtcctgca tctggggact gtggggttca ggtggcctaa ggcaggatgt ggagagagtt | 2880 |
| ttagtatagg aacagaggca gaacagagac tgtgctactg gtacttcgat gtctgggca | 2940 |
| cagggaccac ggtcaccgtc tcctcaggta agctggcttt tttctttctg cacattccat | 3000 |
| tctgaaacgg gaaaagatat tctcagatct ccccatgtca ggccatctgc cacactctgc | 3060 |
| atgctgcaga agcttttctg taaggatagg gtcttcactc ccaggaaaag aggcagtcag | 3120 |
| aggctagctg cctgtggaac agtgacaatc atggaaaata ggcatttaca ttgttaggct | 3180 |
| acatgggtag atgggttttt gtacacccac taaagggggtc tatgatagtg tgactacttt | 3240 |
| gactactggg gccaaggcac cactctcaca gtctcctcag gtgagtcctt acaacctctc | 3300 |
| tcttctattc agcttaaata gattttactg catttgttgg gggggaaatg tgtgtatctg | 3360 |
| aatttcaggt catgaaggac tagggacacc ttgggagtca gaaagggtca ttgggagccc | 3420 |

```
tggctgacgc agacagacat cctcagctcc catacttcat ggccagagat ttatagggat    3480
cctggccagc attgccgcta ggtccctctc ttctatgctt tctttgtccc tcactggcct    3540
ccatctgaga tcatcctgga gccctagcca aggatcattt attgtcaggg gtctaatcat    3600
tgttgtcaca atgtgcctgg tttgcttact ggggccaagg gactctggtc actgtctctg    3660
caggtgagtc ctaacttctc ccattctaaa tgcatgttgg ggggattctg ggccttcagg    3720
accaagattc tctgcaaacg ggaatcaaga ttcaacccct tgtcccaaa gttgagacat     3780 gggtctgggt cagggactct ctgcctgctg gtctgtggtg acattagaac tgaagtatga    3840
tgaaggatct gccagaactg aagcttgaag tctgaggcag aatcttgtcc agggtctatc    3900
ggactcttgt gagaattagg ggctgacagt tgatggtgac aatttcaggg tcagtgactg    3960
tctggtttct ctgaggtgag gctggaatat aggtcacctt gaagactaaa gaggggtcca    4020
ggggcttctg cacaggcagg aacagaatg tggaacaatg acttgaatgg ttgattcttg      4080
tgtgacacca ggaattggca taatgtctga gttgcccagg ggtgattcta gtcagactct    4140 ggggttttg tcgggtatag aggaaaaatc cactattgtg attactatgc tatggactac      4200
tggggtcaag gaacctcagt caccgtctcc tcaggtaaga atggcctctc caggtcttta    4260
tttttaacct ttgttatgga gttttctgag cattgcagac taatcttgga tatttgtccc    4320
tgagggagcc ggctgagaga agttgggaaa taaactgtct agggatctca gagcctttag    4380
gacagattat ctccacatct ttgaaaaact aagaatctgt gtgatggtgt tggtggagtc    4440
cctggatgat gggataggga ctttggaggc tcatttgaag aagatgctaa aacaatccta    4500
tggctggagg atagttggg gctacgcgtt tttaaccta gaaagatagt ctgcgtaaaa       4560
ttgacgcatg cattcttgaa atattgctct ctctttctaa atagcgcgaa tccgtcgctg    4620
tgcatttagg acatctcagt cgccgcttgg agctcccgtg aggcgtgctt gtcaatgcgg    4680
taagtgtcac tgattttgaa ctataacgac cgcgtgagtc aaaatgacgc atgattatct    4740
tttacgtgac ttttaagatt taactcatac gataattata ttgttatttc atgttctact    4800
tacgtgataa cttattatat atatatttc ttgttataga tatcgctagt ggatcctggt     4860
tctttccgcc tcagaaggta ctttttttttt tttttttttt tttttttttt tttttttttt   4920
tttttttttt tttttttttt taaattttg ggaatttatt gatttgcatt taaaagggaa     4980
ctgctgacaa agattcactg gtaataattt gaacaagttg gaaaatacag tcaacattac    5040
tgaaacacta ctaaaataat tccaggacag aacaaaactt cttagatgct gtctttgatg    5100
tgaaaattga ctgcttctta cttttctaac acacggtggt ataattaaca atattcaatc    5160
acttctattc tttcctgcat atataaaaat taaaatacca attaaaaaac taatatatct    5220
tctctttatt tcttacagat atgagttcaa tgtttcactc aatagtgctg tggtttaaga    5280
gaattttttc atttacaagt taaacaacaa tccgcccaaa gggaactgat agtctatagg    5340
ctcatagtgc aaataaacag tttaggaatg cagcaactga catttctaaa gtacaaaaca    5400
gataaaattc ttagaagata catgcaaaaa gctctactaa gcagatggcc acagaactag    5460
aacattgata attttactgg cgatgtcaat aggactccag atgtttccaa actcaacttg    5520
aactctcatc ttaggctttg tattttgctt ttccagtttc actaatgaca caaacatgat    5580
tcaaatccct gaagtattca ttatagtcaa gggcatatcc tacaacaaac ttgtctggaa    5640
tttcaaatcc aacaaagtct ggcttatatc caacacttcg tggggtcctt ttcaccagca    5700
agcttgcgac cttgaccatc tttggattat actgcctgac caaggaaagc aaagtctgca    5760
```

```
ttgttttgcc agtgtcaatt atatcttcca caatcaagac attctttcca gttaaagttg    5820
agagatcatc tccaccaatt acttttatgt cccctgttga ctggtcatta caatagctct    5880
tcagtctgat aaaatctaca gtcataggaa tggatctatc actatttcta ttcagtgctt    5940
tgatgtaatc cagcaggtca gcaaagaatt tatagccccc cttgagcaca cagagggcta    6000
caatgtgatg gcctcccatc tccttcatca catctcgagc aagacgttca gtcctacaga    6060
aataaaatca ggaatttaat agaaagtttc atacattaaa ctttataaca aacacctctt    6120
agtcattaaa cttccacacc aacctgggca atatagtgag accccatgcc tgcaaaaaaa    6180
aaaaaattag ccaggcatgg tagcatgtac ctgtagtccc agctacttga gaggtgaggt    6240
gggaaaatca ctttagtgca ggatgttgag gctggagtga actgtgattg tgccactgca    6300
ctccagcctg gacaatagag caagaccttg tctcaaaaaa atgcattaaa aattttttt     6360
aaatcttcca cgtaacacat cctttgccct catgtttcat aaggtaaaaa atttgatacc    6420
ttcaaaaaaa ccaagcatac cactatcata atttttttta aatgcaaata aaacaagat     6480
accattttca cctatcagac tggcaggttc tgattaaatg aaatttcttg gataatatac    6540
aatattaaga gagactgtag aaactgggcc agtggctcat gcctgtaatc ccagcacttt    6600
gggaggctgg gtaacatggc gaaccctgtt tctacaaaat aaaaatatta gctgggagtg    6660
gtggcgcaca cctatagtcc cagctactca ggaggctgag gtggaaggat cgcttgaacc    6720
caggaggttg agactgcagt gaactgtgat cattctgctg cactgcaccc cagcctgggc    6780
aacagagacc ttgtctcaaa aaaaaaaaa aagagacaa attgtgaaga gaaaggtact     6840
ctcatataac atcaggagta taaatgatt caacttctta gaggaaaatt tggcaatacc     6900
aaaatattca ataaactctt tccccttgac ccagaaattc cacttgaata agctgaaca     6960
agtaccaaac atgtaaaaga atgtttcttc tagtacagtc ggtaagaaca aaatagtgtc    7020
tatcaatagt ggactggtta aatcagttat ggtatctcca taagacagaa tgctatgcaa    7080
cctttaaaat atattagata gctctagaca gtggatcccc tcgagggacc taataacttc    7140
gtatagcata cattatacga agttatatta agggttattg aatatgtcga ctagacacac    7200
taatattaaa agtgtccaat aacatttaaa actatactca tacgttaaaa tataaatgta    7260
tatatgtact tttgcatata gtatacatgc atagccagtg cttgagaaga aatgtgtaca    7320
gaaggctgaa aggagagaac tttagtcttc ttgtttatgg cctccatagt tagaatattt    7380
tataacacaa atattttgat attataattt taaaataaaa acacagaata gccagacata    7440
caatgcaagc attcaatacc aggtaaggtt tttcactgta attgacttaa cagaaaattt    7500
tcaagctaga tgtgcataat aataaaaatc tgaccttgcc ttcatgtgat tcagccccag    7560
tccattaccc tgtttaggac tgagaaatgc aagactctgg ctagagttcc ttcttccatc    7620
tcccttcaat gtttactttg ttctggtccc tacagagtcc cactatacca caactgatac    7680
taagtaatta gtaaggccct cctctttat ttttaataaa gaagatttta gaaagcatca     7740
gttatttaat aagttggcct agtttatgtt caaatagcaa gtactcagaa cagctgctga    7800
tgtttgaaat taacacaaga aaagtaaaa aacctcattt taagatctta cttacctgtc     7860
cataattagt ccatggggaa taaacaccct ttccaaatcc tcagcataat gattaggtat    7920
gcaaaataaa tcaaggtcat aacctggttc atcatcacta atcacgacgc cagggctgcg    7980
ggtcgcccata acggagccgg ccggcgcgcg ggctgaataa cttcgtataa tgtgtactat    8040
acgaagttat ttgttcagga ggaggaagcc ggtggcggag cagaggagga ggcggaggcg    8100
cagcaagacc cccccccccc tgcaggtcga aaggcccgga gatgaggaag aggagaacag    8160
```

```
cgcggcagac gtgcgctttt gaagcgtgca gaatgccggg cctccggagg accttcgggc    8220
gcccgccccg ccccctgagcc cgcccctgag cccgcccccg gacccacccc ttcccagcct    8280
ctgagcccag aaagcgaagg agccaaagct gctattggcc gctgcccaa aggcctaccc     8340 gcttccattg ctcagcggtg ctgtccatct gcacgagact agtgagacgt gctacttcca    8400
tttgtcacgt cctgcacgac gcgagctgcg gggcggggggg gaacttcctg actaggggag   8460
gagtagaagg tggcgcgaag gggccaccaa agaacggagc cggttggcgc ctaccggtgg    8520
atgtggaatg tgtgcgaggc cagaggccac ttgtgtagcg ccaagtgccc agcggggctg    8580
ctaaagcgca tgctccagac tgccttggga aaagcgcctc ccctacccgg tagatatcta    8640
taacaagaaa atatatatat aataagttat cacgtaagta gaacatgaaa taacaatata    8700
attatcgtat gagttaaatc ttaaaagtca cgtaaaagat aatcatgcgt cattttgact    8760
cacgcggtcg ttatagttca aaatcagtga cacttaccgc attgacaagc acgcctcacg    8820
ggagctccaa gcggcgactg agatgtccta aatgcacagc gacggattcg cgctatttag    8880
aaagagagag caatatttca agaatgcatg cgtcaatttt acgcagacta tctttctagg    8940
gttaaaagaa ttcgtagttg gagattttca gttttttagaa taaaagtatt agctgcggaa    9000
tatacttcag gaccacctct gtgacagcat ttatacagta tccgatgcat agggacaaag    9060
agtggagtgg ggcactttct ttagatttgt gaggaatgtt ccacactaga ttgttttaaaa   9120 cttcatttgt tggaaggaga gctgtcttag tgattgagtc aagggagaaa ggcatctagc    9180
ctcggtctca aaagggtagt tgctgtctag agaggtctgg tggagcctgc aaaagtccag    9240 cttttcaaagg aacacagaag tatgtgtatg gaatattaga agatgttgct tttactctta   9300
agttggttcc taggaaaaat agttaaatac tgtgacttta aaatgtgaga gggttttcaa    9360
gtactcattt ttttaaatgt ccaaaatttt tgtcaatcaa tttgaggtct tgtttgtgta    9420
gaactgacat tacttaaagt ttaaccgagg aatgggagtg aggctctctc atacccatt     9480 cagaactgac ttttaacaat aataaattaa gtttaaaata tttttaaatg aattgagcaa    9540
tgttgagttg gagtcaagat ggccgatcag aaccagaaca cctgcagcag ctggcaggaa    9600
gcaggtcatg tggcaaggct atttggggaa gggaaaataa aaccactagg taaacttgta    9660
gctgtggttt gaagaagtgg tttttgaaaca ctctgtccag ccccaccaaa ccgaaagtcc   9720
aggctgagca aaacaccacc tgggtaattt gcatttctaa aataagttga ggattcagcc    9780
gaaactggag aggtcctctt ttaacttatt gagttcaacc ttttaatttt agcttgagta    9840
gttctagttt cccaaaactt aagtttatcg acttctaaaa tgtatttaga attcattttc    9900
aaaattaggt tatgtaagaa attgaaggac tttagtgtct ttaatttcta atatatttag    9960
aaaacttctt aaaattactc tattattctt ccctctgatt attggtctcc attcaattct   10020
tttccaatac ccgaagcatt tacagtgact ttgttcatga tcttttttag ttgtttgttt   10080
tgccttacta ttaagacttt gacattctgg tcaaaacggc ttcacaaatc ttttttcaaga  10140 ccactttctg agtattcatt ttaggagaaa tactttttttt ttaaatgaat gcaattatct   10200
agacttattt cggttgaaca tgctggtggg tggttgagag gacactcagt cagtcagtgg   10260
cgtgaagggc ttctaagcca gtccacatgc tctgtgtgaa ctccctctgg ccctgcttat   10320
tgttgaatgg gccaaaggtc tgagaccagg ctgctgctgg gtaggcctgg actttgggtc   10380
tcccacccag acctgggaat gtatggttgt ggcttctgcc acccatccac ctggctgctc   10440
atggaccagc cagcctcggt ggctttgaag gaacaattcc acacaaagac tctggacctc   10500
```

```
tccgaaacca ggcaccgcaa atggtaagcc agaggcagcc acagctgtgg ctgctgctct   10560
taaagcttgt aaactgtttc tgcttaagag ggactgagtc ttcagtcatt gctttagggg   10620
gagaaagaga catttgtgtg tcttttgagt accgttgtct gggtcactca catttaactt   10680
tccttgaaaa actagtaaaa gaaaaatgtt gcctgttaac caataatcat agagctcatg   10740
gtattttgag gaaatcttag aaaacgtgta tacaattgtc tggaattatt tcagttaagt   10800
gtattagttg aggtactgat gctgtctcta cttcagttat acatgtgggt ttgaattttg   10860
aatctattct ggctcttctt aagcagaaaa tttagataaa atggatacct cagtggtttt   10920
taatggtggg tttaatatag aaggaattta aatttggaagc taatttagaa tcagtaagga   10980
gggacccagg ctaagaaggc aatcctggga ttctggaaga aaagatgttt ttagttttta   11040
tagaaaacac tactacattc ttgatctaca actcaatgtg gtttaatgaa tttgaagttg   11100
ccagtaaatg tacttcctgg ttgttaaaga atggtatcaa aggacagtgc ttagatccaa   11160
ggtgagtgtg agaggacagg ggctggggta tggatacgca gaaggaaggc cacagctgta   11220
cagaattgag aaagaataga gacctgcagt tgaggccagc aggtcggctg gactaactct   11280
ccagccacag taatgaccca gacagagaag gccagactca taaagcttta tcgataccgt   11340
cgacctcgag ggggggcccg gtacctttct tagacgtcag gtggcacttt tcggggaaat   11400
gtgcgcggaa cccctatttg tttattttc taaatacatt caaatatgta tccgctcatg   11460
agacaataac cctgataaat gcttcaataa tattgaaaaa ggaagagtat gagtattcaa   11520
catttccgtg tcgcccttat tcccttttt gcggcatttt gccttcctgt ttttgctcac   11580
ccagaaacgc tggtgaaagt aaaagatgct gaagatcagt tgggtgcacg agtgggttac   11640
atcgaactgg atctcaacag cggtaagatc cttgagagtt ttcgccccga agaacgtttt   11700
ccaatgatga gcacttttaa agttctgcta tgtggcgcgg tattatcccg tgttgacgcc   11760
gggcaagagc aactcggtcg ccgcatacac tattctcaga atgacttggt tgagtactca   11820
ccagtcacag aaaagcatct tacgatggca atgacagtaa gagaattatg cagtgctgcc   11880
ataaccatga gtgataacac tgcggccaac ttacttctga caacgatcgg aggaccgaag   11940
gagctaaccg cttttttgca acatgggga tcatgtaa ctcgccttga tcgttgggaa   12000
ccggagctga atgaagccat accaaacgac gagcgtgaca ccacgatgcc tgcagcaatg   12060
gcaacaacgt tgcgcaaact attaactggc gaactactta ctctagcttc ccggcaacaa   12120
ttaatagact ggatggaggc ggataaagtt gcaggaccac ttctgcgctc ggcccttccg   12180
gctggctggt ttattgctga taaatctgga gccggtgagc gtgggtctcg cggtatcatt   12240
gcagcactgg ggccagatgg taagccctcc cgtatcgtag ttatctacac gacggggagt   12300
caggcaacta tggatgaacg aaatagacag atcgctgaga taggtgcctc actgattaag   12360
cattggtaac tgtcagacca agtttactca tatatacttt agattgattt aaaacttcat   12420
ttttaattta aaaggatcta ggtgaagatc ctttttgata atctcatgac caaaatccct   12480
taacgtgagt tttcgttcca ctgagcgtca gaccccgtag aaaagatcaa aggatcttct   12540
tgagatcctt ttttttctgcg cgtaatctgc tgcttgcaaa caaaaaaacc accgctacca   12600
gcggtggttt gtttgccgga tcaagagcta ccaactcttt ttccgaaggt aactggcttc   12660
agcagagcgc agataccaaa tactgtcctt ctagtgtagc cgtagttagg ccaccacttc   12720
aagaactctg tagcaccgcc tacatacctc gctctgctaa tcctgttacc agtggctgct   12780
gccagtggcg ataagtcgtg tcttaccggg ttggactcaa gacgatagtt accggataag   12840
gcgcagcggt cgggctgaac ggggggttcg tgcacacagc ccagcttgga gcgaacgacc   12900
```

```
tacaccgaac tgagatacct acagcgtgag ctatgagaaa gcgccacgct tcccgaaggg      12960
agaaaggcgg acaggtatcc ggtaagcggc agggtcggaa caggagagcg cacgagggag      13020
cttccagggg gaaacgcctg gtatctttat agtcctgtcg ggtttcgcca cctctgactt      13080
gagcgtcgat ttttgtgatg ctcgtcaggg gggcggagcc tatggaaaaa cgccagcaac      13140
gcggcctttt tacggttcct ggccttttgc tggccttttg ctcacatgtt ctttcctgcg      13200
ttatcccctg attctgtgga taaccgtatt accgcctttg agtgagctga taccgctcgc      13260
cgcagccgaa cgaccgagcg cagcgagtca gtgagcgagg aagcggaaga gcgcctgatg      13320
cggtattttc tccttacgca tctgtgcggt atttcacacc gcatatggtg cactctcagt      13380
acaatctgct ctgatgccgc atagttaagc cagtatacac tccgctatcg ctacgtgact      13440
gggtcatggc tgcgcccga cacccgccaa caccgctga cgcgcctga cgggcttgtc       13500 tgctcccggc atccgcttac agacaagctg tgaccgtctc cgggagctgc atgtgtcaga      13560
ggttttcacc gtcatcaccg aaacgcgcga ggcagctgcg gtaaagctca tcagcgtggt      13620
cgtgaagcga ttcacagatg tctgcctgtt catccgcgtc cagctcgttg agtttctcca      13680
gaagcgttaa tgtctggctt ctgataaagc gggccatgtt aagggcggtt ttttcctgtt      13740
tggtcactga tgcctccgtg taaggggat  ttctgttcat gggggtaatg ataccgatga      13800
aacgagagag gatgctcacg atacgggtta ctgatgatga acatgcccgg ttactggaac      13860
gttgtgaggg taaacaactg gcggtatgga tgcggcggga ccagagaaaa atcactcagg      13920
gtcaatgcca gcgcttcgtt aatacagatg taggtgttcc acagggtagc cagcagcatc      13980
ctgcgatgca gatccggaac ataatggtgc agggcgctga cttccgcgtt tccagacttt      14040
acgaaacacg gaaaccgaag accattcatg ttgttgctca ggtcgcagac gttttgcagc      14100
agcagtcgct tcacgttcgc tcgcgtatcg                                      14130
```

<210> SEQ ID NO 4
<211> LENGTH: 3551
<212> TYPE: DNA
<213> ORGANISM: Mus musculus
<220> FEATURE:
<221> NAME/KEY: misc_feature
<222> LOCATION: (1399)..(1498)
<223> OTHER INFORMATION: n is a, c, g, or t

<400> SEQUENCE: 4

```
aagcttgctg agcaaaatta agggaacaag gttgagagcc ctagtaagcg aggctctaaa        60
aagcatggct gagctgagat gggtgggctt ctctgagcgc ttctaaaatg cgctaaactg       120
aggtgattac tctgaggtaa gcaaagctgg gcttgagcca aaatgaagta gactgtaatg       180
aactggaatg agctgggccg ctaagctaaa ctaggctggc ttaaccgaga tgagccaaac       240
tggaatgaac ttcattaatc taggttgaat agagctaaac tctactgcct acactggact       300
gttctgagct gagatgagct ggggtgagct cagctatgct acgctgtgtt ggggtgagct       360
gatctgaaat gagctactct ggagtagctg agatggggtg agatggggtg agctgagctg       420
ggctgagctg gactgagctg agctagggtg agctgagctg ggtgagctga gctaagctgg       480
ggtgagctga gctgagcttg actgagctag ggtgagctgg actgagctgg ggtgagctga       540
gctgagctgg ggtaagctgg gatgagctgg ggtgagctga gctgagctga agtgagctga       600
gctgggctga gctggggtga gctggggtgg gctgagctgg ggtgagctgg gctgagctgg       660
ggtgagctga gctggggtga gctgagctga gctggggtga gctgagctga gctggggtga       720
```

```
gctgagctgg ggtgagctga gctgagctgg gctgagctga ggtgagctga gctggggtga    780
gctgagctgg ggtgagctga gctgagctgg ggtaagctgg gatgagctgg ggtgagctga    840
gctgagctgg agtgagctga gctgggctga gctggggtga gctggggtga gctgagctgg    900
ggtgagctga gctgagctgg gctgagctga ggtgagctga gctggggtga gctgagctga    960
gctggggtga gctgagctga gctggggtga gctgagctgg ggtgagctga gctggggtga   1020
gctgagctga gctggggtga gctgagctgg ggtgagctga gctgagctgg ggtgagctga   1080
gctgagctgg ggtgagctga gctgagctga gctggggtga gctgagctga gctggggtga   1140
gctgagctga gctggggtga gctgagctgg ggtgagctgg gctgagctga gctgggctga   1200
gctgagctga gctgagctga gctggggtga gctgagctgg gctgagctgg ggtgagctgg   1260
gctgagctgg ggtgagctga gctggggtga gctgagctga gctggggtga gctgagctga   1320
gctggggtga gctgagctgg ggtgagctga gctgagctgg gctgagctga gctgagctgg   1380
ggtgagctga gctgagctnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnag   1500
ctgagctgag ctgagctgag ctgagctggg gtgagctggg gtgagctgag ctggggtgag   1560
ctgagctgag ctggggtgag ctgagctgag ctgagctgag ctgagctgag ctgggtgagc   1620
tgagctgagc tgagctgggg tgagctgagc tggggtgagc tgagctgagc tggggtgagc   1680
tgagctgggg tgagctgagc tgagctgggg tgagctgggg tgagctgggg tgagctgggg   1740
tgagctgagc tgaactgggg tgagctgggc tgagctgggg tgagctgagc tgagctgggc   1800
tgagctgggg tgagctgggg tgagctgggg tgagctgagc tgagctaggg tgagctgagc   1860
tgagctaggg tgagctgagc tgagctgggg tgagctgagc tgagctgggg tgagctgagc   1920
tgagctgggg tgagctgagc tgagctgggg tgagctgagc tgagctgggg tgagcttggc   1980
tgagctgggg tgagctgggg tgagctgagc tggggtgagc tggggtaagc tgagctgagc   2040
tggggtgagc tgagctgagc tggggtgagc tggggtgagc tgagctgagc tgagctgggt   2100
gatctgagct gagctgagct gggtgagctg agctgagctg agctgggtga gctgagctga   2160
gctgagctga gctgggtgag ctgagctgag ctgagctgag ctgagctgag ctggggtgag   2220
ctgggctgag ctgagctgag ctggggtgag ctgagctgag ctgagctgag ctggggtgag   2280
ctgggctgag ctggggtgag ctgggctgag ctgagctggg tgagctgagc tgaactgagc   2340
tgagctgggt gagctgagct gagctgagct gggtgagctg agctgggctg agctgagctg   2400
ggtgagctga gctgaactga gctgagctgg gtgagctgag ctgagctgag ctgggtgagc   2460
tgagctgggg tgagctgagc tgagctgggg tgagctgagc tgagctgagc tgggtgagct   2520
gagctggggt gagctgagct gagctggggt gagctgagct gagctggggt gagctgagct   2580
gagctggggt gagctgagct gagctggggt gagctgagct agggtgaact gggctgggtg   2640
agctggagtg agctgagctg aggtgaactg gggtgagccg ggatgttttg agttgagctg   2700
gggtaagatg agctgaactg gggtaagatg ggatgagctg tggtgagggg agctggattg   2760
aactgagctg tgtgagctga gctggggtca gctgagcaag agtgagtaga gctggctggc   2820
cagaaccaga atcaattagg ctaagtgagc cagattgcgc tggatcagc tgtactcaga    2880
tgagctggga tgaggtaggc tgggatgagc tgggctagct gacatggatt atgtgaggct   2940
gagctagcat gggctggcct agctgatgag ctaagcttga atgaacgggg ctgagctgga   3000
ctcagatgtg ctagactgag ctgtactgga tgatctggtg tagggtgatc tggactcaac   3060
tgggctggct gatgggatgc cccaggttga actaggctca gataagttag gctgagtagg   3120
```

| | |
|---|---|
| gcctggttga gatggttcgg gatgagctgg gaaaagatgg actgggacca tgaactgggc | 3180 |
| tgagctgggt tgggagacca tgaattgagc tgaactgagt gcagctggga taaactgggt | 3240 |
| tgagctaaga atagactacc tgaattgtgc caaactgggc tgggatcaat tggaaattat | 3300 |
| caggatttag atgagccgga ctaaactatg ctgagctgga ctggttggat gtgttgaact | 3360 |
| ggcctgctgc tgggctggca tagctgagtt gaacttaaat gaggaaggat gagcaaggct | 3420 |
| agcctgcttg catagagctg aactttagcc tagcctgagc tggaccagcc tgagctgagt | 3480 |
| aggtctaaac tgagttaaaa atcaacaggg ataatttaac agctaattta caagcctga | 3540 |
| ggtctgagat t | 3551 |

<210> SEQ ID NO 5
<211> LENGTH: 2484
<212> TYPE: DNA
<213> ORGANISM: Mus musculus

<400> SEQUENCE: 5

| | |
|---|---|
| aagcttgctg agcaaaatta agggaacaag gttgagagcc ctagtaagcg aggctctaaa | 60 |
| aagcacagct gagctgagat gggtgggctt ctctgagtgc ttctaaaatg cgctaaactg | 120 |
| aggtgattac tctgaggtaa gcaaagctgg gcttgagcca aaatgaagta gactgtaatg | 180 |
| aactggaatg agctgggccg ctaagctaaa ctaggctggc ttaaccgaga tgagccaaac | 240 |
| tggaatgaac ttcattaatc taggttgaat agagctaaac tctactgcct acactggact | 300 |
| gttctgagct gagatgagct ggggtgagct cagctatgct acgctgtgtt ggggtgagct | 360 |
| gatctgaaat gagatactct ggagtagctg agatggggtg agatggggtg agctgagctg | 420 |
| ggctgagcta gactgagctg agctaggggt agctgagctg ggtgagctga gctaagctgg | 480 |
| ggtgagctga gctgagcttg gctgagctag ggtgagctgg gctgagctgg ggtgagctga | 540 |
| gctgagctgg ggtaagctgg gatgagctgg ggtgagctga gctgagctgg agtgagctga | 600 |
| gctgggctga gctggggtga gctgggctga gctgggctga gctgggctga gctggggtga | 660 |
| gctgagctgg ggtgagctga gctgagctgg ggtgagctga gctgagctgg ggtgagctgg | 720 |
| ggtgagctga gctggggtga gctgagctga gctggggtga gctgagctgg ggtgagctga | 780 |
| gctgagctgg ggtgagctga gctgagctga gctgagctga gctggggtga gctgagctga | 840 |
| gctgagctgg ggtgagctgg ggtgagctga gctgagctgg agtgagctga gctgggctga | 900 |
| gctggggtga gctgggctga gctggggtga gctgagctga gctgagctga gctggggtga | 960 |
| gctgagctga gctggggtga gctgagctgg ggtgagctgg gctgagctga gctgagctga | 1020 |
| gctgagctga gctgagctga gctgagctga gctgagctga gctgagctga gctgagctga | 1080 |
| gctgagctgg ggtgagctga gctgagctgg gctgagctgg ggtgagctgg gctgagctgg | 1140 |
| gctgagctga gctgggctgg ggtgagctga gctggggtga gctgagctga gctgggctga | 1200 |
| gctgagctga gctggggtga gctgagctga gctggggtga gctgagctga gctgagctgg | 1260 |
| ggtgagctga gctgggctga gcagggctga gctggggtga gctgagctga gctggggtga | 1320 |
| gctgggctga gctgggctga gctgagctga gctgggctga gctgggctga gctgggctga | 1380 |
| gctgggctga gctgggctga gctggggtga gctgagctga gctggggtga gctggggtga | 1440 |
| gctgagctgg ggtgagctga gctggggtga gctgagctga gctggggtga gctgagctgg | 1500 |
| ggtgagctga gctgagctgg ggtgagctga gctgagctgg ggtgagctga gctagggtga | 1560 |
| actgggctgg gtgagctgga gtgagctgag ctgaggtgaa ctgggggtgag ccgggatgtt | 1620 |

| | |
|---|---|
| ttgagttgag ctggggtaag atgagctgaa ctggggtaaa ctgggatgag ctgtggtgag | 1680 |
| cggagctgga ttgaactgag ctgtgtgagc tgagctgggg tcagctgagc aagagtgagt | 1740 |
| agagctggct ggccagaacc agaatcaatt aggctaagtg agccagattg tgctgggatc | 1800 |
| agctgtactc agatgagctg ggatgaggta ggctgggatg agctgggcta gctgacatgg | 1860 |
| attatgtgag gctgagctag catgggctgg cctagctgat gagctaagct tgaatgagcg | 1920 |
| gggctgagct ggactcagat gtgctagact gagctgtact ggatgatctg tgtagggtg | 1980 |
| atctggactc aactgggctg gctgatggga tgcgccaggt tgaactaggc tcagataagt | 2040 |
| taggctgagt agggcctggt tgagatggtt cgggatgagc tgggaaaaga tggactcgga | 2100 |
| ccatgaactg ggctgagctg ggttgggaga ccatgaattg agctgaactg agtgcagctg | 2160 |
| ggataaactg ggttgagcta agaatagact acctgaattg tgccaaactc ggctgggatc | 2220 |
| aattggaaat tatcaggatt tagatgagcc ggactaaact atgctgagct ggactggttg | 2280 |
| gatgtgttga actggcctgc tgctgggctg gcatagctga gttgaactta aatgaggaag | 2340 |
| gctgagcaag gctagcctgc ttgcatagag ctgaacttta gcctagcctg agctggacca | 2400 |
| gcctgagctg agtaggtcta aactgagtta aaaatcaaca gggataattt aacagctaat | 2460 |
| ttaacaagcc tgaggtctga gatt | 2484 |

<210> SEQ ID NO 6
<211> LENGTH: 4515
<212> TYPE: DNA
<213> ORGANISM: Artificial Sequence
<220> FEATURE:
<223> OTHER INFORMATION: 5' homology arm of targetting vector

<400> SEQUENCE: 6

| | |
|---|---|
| aacctgggca atgggagct tagcaacaat gtaggggct ggacctagac ttcctacaca | 60 |
| tgtgtaacag atgtgcagct tggtcttcat gtgtgtatta ccctaacatt tggagcagga | 120 |
| gctgtctctg actctgttgc ctgccattgg atccccttcc cctgcttggg ctgccttgtt | 180 |
| tggccttagt aggaaaggat gtgcttagtc ctgctgtgac ttgatgtccc taggcagaat | 240 |
| gatacccag gggggctccc catctctgag gagatgggca aagggtaatg gttggaggga | 300 |
| cttgtgaggc tgggactggg aggagagaaa ggagacagct gtaactggaa tgatgttaag | 360 |
| tgaacaaatg aatggataga ttagatagac agatagacag acagacagac agacagacag | 420 |
| acagacagac agacagacag atagaaagat agatagataa ggggaaaag aaacgtagct | 480 |
| gagcaagcca gagagagcaa gccaaataag cagcattcct ccatgacttt tccttcagct | 540 |
| cctgcctatg agtctgcctt gacttccctc agtgattggt tgtaagttaa aaggtgaaat | 600 |
| aaaccctttc tttgacaagt tgcttttggt tctgattttt atcacagcaa gagaaaatca | 660 |
| aactagaaca aacatgtatt tttcctggca catgtccata gtaaggcaga aatgatcttc | 720 |
| agacctagac catagatact acagagagca gaagtgtaga taggtggact tactgtatga | 780 |
| ttgtaatcca agtaaatcta catagctaga gagctagagg aaaggccaaa gcttcctctg | 840 |
| ggaggtcaga tcctgtcgca ctgtagccaa taaggcatat tgcatcacag gaaaggacta | 900 |
| agacccaggc tggcaatagt gtctgtatct taactagatc tctctagtga gtgaggaagt | 960 |
| aaatttgtga gagcccagac tgtgggctcg gaaggtacct gccatgcccc tgttagtaac | 1020 |
| tgagtactac agcaggagca ggtgttctct agaaagcctg agacaactct acttcttctc | 1080 |
| tcaagagacc acctaataca ggcctgagag aacagactct ggaaatagat gggacttacg | 1140 |
| gagctaagat ctagagctca tctacagagc agaatcccag ccaagagaac aaagaatact | 1200 |

```
gactctctcc tgttccctac tcctagagtt ctaaaacaca ctatagggaa gggagcctct    1260
agacctccgt ccattcccca tcttgctcat tccatcttcc catgtcccca ggtctccaag    1320
ccacagacac cacctttcct attcacccac ctttctgtgt ccctaggtcc ccaggccata    1380
gtcacctccc cccacacccc gctcaccctg ccccatctat gccctagat gcttacttac     1440 cagagtcttt tgtctgacgt ggggctacaa gcatctatgc tccctaagca cctactgctg    1500
acctgtagga cccagctctg aaccaactca tataagtaaa tacagactct cccctgtctt    1560
aggatggccc cctgggtcag gaggagacca ctgccaagga accttctctt agagcactga    1620
actcctcccc tgtaccactt aggacagacc tgagacctat tattactgat taccagagct    1680
ctggcagtga ccacggagga gatagatcca ccctggacac aggaaacaca gcaccagaga    1740
tactgcttca tcacaacagt agagtgacac tttagacttt aatttgggtc actttcctgc    1800
tgtagaggtg ggatcagaaa gcaaagagca gtatgagtgc ctgataggca cccaagtaca    1860
ctatagagta ctcatggtga ataaggtacc tccatggctt cccagggagg ggcactgccc    1920 caccccacc atcacagacc tttctccata gttgataact cagacacaag tgaatgacag      1980
atggacctcc atctgctctt attttaaaaa gaagacaaac cccacaggct cgagaacttt    2040
agcgactgtt ttgagagaaa tcattggtcc ctgactcaag agatgactgg cagattgggg    2100
atcagaatac ccatactctg tggctagtgt gaggtttaag cctcagagtc cctgggtct     2160 ctgactggtg caaggttttg actaagcgga gcaccacagt gctaactggg accacggtga    2220
cacgtggctc aacaaaaacc ttctgtttgg agctctccag gggcagcctg agctatgagg    2280
aagtagagag gcttgagaaa tctgaggaag aaaagagtag atctgagagg aaaggtagct    2340
ttctggaggt caggagacag tgcagagaag aacgagttac tgtggacagg tcttagatgg    2400
ggaaagaatg agcaaatgca agcatcagaa gggtggatgc aatgtcctgc caaggactta    2460
ccaagaggat ccccggacag agcaggcagg tggagttgac tgagaggaca ggataggtgc    2520
aggtccctct cttgtttcct ttctccttct cctgtttcct tcttctcttg tcacaggtct    2580
cactatgcta gccaaggcta gcctgaaaga ttaccatcct acagatgggc ccatccagtt    2640
gaattaaggt ggagatctct ccaaacatct gagtttctga ggcttggatg ccactgggga    2700
cgccaaggga ctttgggatg ggtttggttg gccccagatg aagggctact tcactgggtc    2760
tataattact ctgatgtcta ggaccagggg gctcaggtca ctcaggtcag gtgagtcctg    2820
catctgggga ctgtggggtt caggtggcct aaggcaggat gtggagagag ttttagtata    2880
ggaacagagg cagaacagag actgtgctac tggtacttcg atgtctgggg cacagggacc    2940
acggtcaccg tctcctcagg taagctggct tttttctttc tgcacattcc attctgaaac    3000
gggaaaagat attctcagat ctccccatgt caggccatct gccacactct gcatgctgca    3060
gaagcttttc tgtaaggata gggtcttcac tcccaggaaa agaggcagtc agaggctagc    3120
tgcctgtgga acagtgacaa tcatggaaaa taggcattta cattgttagg ctacatgggt    3180
agatgggttt ttgtacaccc actaaagggg tctatgatag tgtgactact ttgactactg    3240
gggccaaggc accactctca cagtctcctc aggtgagtcc ttacaacctc tctcttctat    3300
tcagcttaaa tagattttac tgcatttgtt gggggggaaa tgtgtgtatc tgaatttcag    3360
gtcatgaagg actagggaca ccttgggagt cagaaagggt cattgggagc cctggctgac    3420
gcagacagac atcctcagct cccatacttc atggccagag atttataggg atcctggcca    3480
gcattgccgc taggtccctc tcttctatgc tttctttgtc cctcactggc ctccatctga    3540
```

| | | |
|---|---|---|
| gatcatcctg gagccctagc caaggatcat ttattgtcag gggtctaatc attgttgtca | 3600 |
| caatgtgcct ggtttgctta ctggggccaa gggactctgg tcactgtctc tgcaggtgag | 3660 |
| tcctaacttc tcccattcta aatgcatgtt ggggggattc tgggccttca ggaccaagat | 3720 |
| tctctgcaaa cgggaatcaa gattcaaccc ctttgtccca aagttgagac atgggtctgg | 3780 |
| gtcagggact ctctgcctgc tggtctgtgg tgacattaga actgaagtat gatgaaggat | 3840 |
| ctgccagaac tgaagcttga agtctgaggc agaatcttgt ccagggtcta tcggactctt | 3900 |
| gtgagaatta ggggctgaca gttgatggtg acaatttcag ggtcagtgac tgtctggttt | 3960 |
| ctctgaggtg aggctggaat ataggtcacc ttgaagacta agaggggtc cagggcttc | 4020 |
| tgcacaggca gggaacagaa tgtggaacaa tgacttgaat ggttgattct tgtgtgacac | 4080 |
| caggaattgg cataatgtct gagttgccca ggggtgattc tagtcagact ctggggtttt | 4140 |
| tgtcgggtat agaggaaaaa tccactattg tgattactat gctatggact actggggtca | 4200 |
| aggaacctca gtcaccgtct cctcaggtaa gaatggcctc tccaggtctt tattttaac | 4260 |
| cttgttatg gagttttctg agcattgcag actaatcttg gatatttgtc cctgagggag | 4320 |
| ccggctgaga aagttggga aataaactgt ctagggatct cagagccttt aggacagatt | 4380 |
| atctccacat ctttgaaaaa ctaagaatct gtgtgatggt gttggtggag tccctggatg | 4440 |
| atgggatagg gactttggag gctcatttga agaagatgct aaaacaatcc tatggctgga | 4500 |
| gggatagttg gggct | 4515 |

```
<210> SEQ ID NO 7
<211> LENGTH: 25
<212> TYPE: DNA
<213> ORGANISM: Artificial Sequence
<220> FEATURE:
<223> OTHER INFORMATION: Oligonucleotide HV2-5

<400> SEQUENCE: 7
agatcacctt gaaggagtct ggtcc                                  25

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide HV4-4

<400> SEQUENCE: 8
tggtgaagcc ttcggagacc ctgtc                                  25

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide HV1-3

<400> SEQUENCE: 9
cactagctat gctatgcatt gggtg                                  25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide HV1-2

<400> SEQUENCE: 10
```

-continued

```
atggatcaac cctaacagtg gtggc                                        25

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide HV6-1

<400> SEQUENCE: 11
ggaaggacat actacaggtc caagt                                        25

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide C

<400> SEQUENCE: 12
taggtacttg ccccctgtcc tcagt                                        25

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide KV1-9

<400> SEQUENCE: 13
agcccagtgt gttccgtaca gcctg                                        25

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide KV1-8

<400> SEQUENCE: 14
atcctcattc tctgcatcta cagga                                        25

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide KV1-6

<400> SEQUENCE: 15
ggtaaggatg gagaacactg gcagt                                        25

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide KV1-5

<400> SEQUENCE: 16
ttagtagctg gttggcctgg tatca                                        25

<210> SEQ ID NO 17
<211> LENGTH: 25
<212> TYPE: DNA
```

```
<213> ORGANISM: Artificial Sequence
<220> FEATURE:
<223> OTHER INFORMATION: Oligonucleotide Ck

<400> SEQUENCE: 17
ctttgctgtc ctgatcagtc caact                                              25

<210> SEQ ID NO 18
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(10)
<223> OTHER INFORMATION: Repeated 148 times

<400> SEQUENCE: 18
gagctgagct                                                               10

<210> SEQ ID NO 19
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(10)
<223> OTHER INFORMATION: Repeat 25 times

<400> SEQUENCE: 19
ggggtggggt                                                               10

<210> SEQ ID NO 20
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(5)
<223> OTHER INFORMATION: Repeat 82 times

<400> SEQUENCE: 20
gggctgggct                                                               10

<210> SEQ ID NO 21
<211> LENGTH: 6
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR, RT, or PW

<400> SEQUENCE: 21

Xaa Xaa Thr Phe Gly Gln
1               5

<210> SEQ ID NO 22
<211> LENGTH: 17
<212> TYPE: PRT
<213> ORGANISM: Artificial Sequence
<220> FEATURE:
```

```
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa= PR, RT, or PW

<400> SEQUENCE: 22

Xaa Xaa Thr Phe Gly Gln Gly Thr Lys Val Glu Ile Lys Arg Ala Asp
1               5                   10                  15

Ala

<210> SEQ ID NO 23
<211> LENGTH: 6
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR or PW

<400> SEQUENCE: 23

Xaa Xaa Thr Phe Gly Gln
1               5

<210> SEQ ID NO 24
<211> LENGTH: 17
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR or PW

<400> SEQUENCE: 24

Xaa Xaa Thr Phe Gly Gln Gly Thr Lys Val Glu Ile Lys Arg Ala Asp
1               5                   10                  15

Ala

<210> SEQ ID NO 25
<211> LENGTH: 24
<212> TYPE: DNA
<213> ORGANISM: Artificial Sequence
<220> FEATURE:
<223> OTHER INFORMATION: Primer E1554

<400> SEQUENCE: 25
atgacttcag tgttgttctg gtag                                          24

<210> SEQ ID NO 26
<211> LENGTH: 19
<212> TYPE: DNA
<213> ORGANISM: Artificial Sequence
<220> FEATURE:
<223> OTHER INFORMATION: Primer E1555

<400> SEQUENCE: 26
caccagattc ttatcagac                                                19

<210> SEQ ID NO 27
<211> LENGTH: 35
<212> TYPE: DNA
<213> ORGANISM: Artificial Sequence
<220> FEATURE:
```

```
<223> OTHER INFORMATION: ELP1352_Cy1

<400> SEQUENCE: 27
agagcggccg ctgggcaacg ttgcaggtga cggtc                              35

<210> SEQ ID NO 28
<211> LENGTH: 34
<212> TYPE: DNA
<213> ORGANISM: Artificial Sequence
<220> FEATURE:
<223> OTHER INFORMATION: ELP1353_Cy2b

<400> SEQUENCE: 28
agagcggccg ctttgtccac cgtggtgctg ctgg                               34

<210> SEQ ID NO 29
<211> LENGTH: 33
<212> TYPE: DNA
<213> ORGANISM: Artificial Sequence
<220> FEATURE:
<223> OTHER INFORMATION: ELP1354_Cy2a

<400> SEQUENCE: 29
agagcggccg cacattgcag gtgatggact ggc                                33

<210> SEQ ID NO 30
<211> LENGTH: 35
<212> TYPE: DNA
<213> ORGANISM: Artificial Sequence
<220> FEATURE:
<223> OTHER INFORMATION: ELP1356_VH4-4

<400> SEQUENCE: 30
aggacgcgtg aaacacctgt ggttcttcct cctgc                              35

<210> SEQ ID NO 31
<211> LENGTH: 33
<212> TYPE: DNA
<213> ORGANISM: Artificial Sequence
<220> FEATURE:
<223> OTHER INFORMATION: ELP1357_VH1-2,3

<400> SEQUENCE: 31
aggacgcgtc accatggact ggacctggag gat                                33

<210> SEQ ID NO 32
<211> LENGTH: 34
<212> TYPE: DNA
<213> ORGANISM: Artificial Sequence
<220> FEATURE:
<223> OTHER INFORMATION: ELP1358_VH6-1

<400> SEQUENCE: 32
aggacgcgta tgtctgtctc cttcctcatc ttcc                               34

<210> SEQ ID NO 33
<211> LENGTH: 21
<212> TYPE: DNA
<213> ORGANISM: Artificial Sequence
<220> FEATURE:
<223> OTHER INFORMATION: mIgG1_2 rev

<400> SEQUENCE: 33
ggggccagtg gatagacaga t                                             21
```

```
<210> SEQ ID NO 34
<211> LENGTH: 18
<212> TYPE: DNA
<213> ORGANISM: Artificial Sequence
<220> FEATURE:
<223> OTHER INFORMATION: mIgG2b rev

<400> SEQUENCE: 34
cagtggatag actgatgg                                                 18

<210> SEQ ID NO 35
<211> LENGTH: 18
<212> TYPE: DNA
<213> ORGANISM: Artificial Sequence
<220> FEATURE:
<223> OTHER INFORMATION: mIgG2a_2 rev

<400> SEQUENCE: 35
cagtggatag accgatgg                                                 18

<210> SEQ ID NO 36
<211> LENGTH: 20
<212> TYPE: DNA
<213> ORGANISM: Artificial Sequence
<220> FEATURE:
<223> OTHER INFORMATION: mCH1 unirev
<220> FEATURE:
<221> NAME/KEY: misc_feature
<222> LOCATION: (1)..(1)
<223> OTHER INFORMATION: K = G or T

<400> SEQUENCE: 36
kcagggccca gtggatagac                                               20

<210> SEQ ID NO 37
<211> LENGTH: 20
<212> TYPE: DNA
<213> ORGANISM: Artificial Sequence
<220> FEATURE:
<223> OTHER INFORMATION: mCH1 unirev_2
<220> FEATURE:
<221> NAME/KEY: misc_feature
<222> LOCATION: (3)..(3)
<223> OTHER INFORMATION: R = A or G
<220> FEATURE:
<221> NAME/KEY: misc_feature
<222> LOCATION: (6)..(6)
<223> OTHER INFORMATION: Y = C or T
<220> FEATURE:
<221> NAME/KEY: misc_feature
<222> LOCATION: (12)..(12)
<223> OTHER INFORMATION: M = A or C

<400> SEQUENCE: 37
tarccyttga cmaggcatcc                                               20

<210> SEQ ID NO 38
<211> LENGTH: 24
<212> TYPE: PRT
<213> ORGANISM: Artificial Sequence
<220> FEATURE:
<223> OTHER INFORMATION: 16C9

<400> SEQUENCE: 38

Gln Glu Val Ile Asn Tyr Tyr Tyr Tyr Gly Met Asp Val Trp Gly Gln
 1               5                  10                  15

Gly Thr Thr Val Thr Val Ser Ser
            20
```

<210> SEQ ID NO 39
<211> LENGTH: 24
<212> TYPE: PRT
<213> ORGANISM: Artificial Sequence
<220> FEATURE:
<223> OTHER INFORMATION: 20B5

<400> SEQUENCE: 39

Gln Glu Val Ile Asn Tyr Tyr Tyr Gly Met Asp Val Trp Gly Gln
1               5                   10                  15

Gly Thr Thr Val Thr Val Ser Ser
            20

<210> SEQ ID NO 40
<211> LENGTH: 26
<212> TYPE: PRT
<213> ORGANISM: Artificial Sequence
<220> FEATURE:
<223> OTHER INFORMATION: 19F4

<400> SEQUENCE: 40

Leu Glu Met Ala Thr Ile Asn Tyr Tyr Tyr Gly Met Asp Val Trp
1               5                   10                  15

Gly Gln Gly Thr Met Val Thr Val Ser Ser
            20                  25

<210> SEQ ID NO 41
<211> LENGTH: 24
<212> TYPE: PRT
<213> ORGANISM: Artificial Sequence
<220> FEATURE:
<223> OTHER INFORMATION: 19E1

<400> SEQUENCE: 41

Gln Glu Phe Gly Asn Tyr Tyr Tyr Gly Met Asp Val Trp Gly Gln
1               5                   10                  15

Gly Thr Thr Val Thr Val Ser Ser
            20

<210> SEQ ID NO 42
<211> LENGTH: 24
<212> TYPE: PRT
<213> ORGANISM: Artificial Sequence
<220> FEATURE:
<223> OTHER INFORMATION: 19G8

<400> SEQUENCE: 42

Gln Glu Asp Gly Asn Pro Tyr Tyr Phe Gly Met Asp Phe Trp Gly Gln
1               5                   10                  15

Gly Thr Thr Val Thr Val Ser Ser
            20

<210> SEQ ID NO 43
<211> LENGTH: 22
<212> TYPE: PRT
<213> ORGANISM: Artificial Sequence
<220> FEATURE:
<223> OTHER INFORMATION: 20H10

<400> SEQUENCE: 43

Gly Ser Ser Tyr Tyr Tyr Asp Gly Met Asp Val Trp Gly Gln Gly Thr
1               5                   10                  15

Thr Val Thr Val Ser Ser
            20

<210> SEQ ID NO 44
<211> LENGTH: 25
<212> TYPE: PRT
<213> ORGANISM: Artificial Sequence
<220> FEATURE:
<223> OTHER INFORMATION: 18D10

<400> SEQUENCE: 44

Leu Glu Asn Asp Tyr Gly Tyr Tyr Tyr Gly Met Asp Val Trp Gly
1               5                   10                  15

Gln Gly Thr Thr Val Thr Val Ser Ser
            20                  25

<210> SEQ ID NO 45
<211> LENGTH: 23
<212> TYPE: PRT
<213> ORGANISM: Artificial Sequence
<220> FEATURE:
<223> OTHER INFORMATION: 16F2

<400> SEQUENCE: 45

Arg Gly Gly Leu Ser Pro Leu Tyr Gly Met Asp Val Trp Gly Gln Gly
1               5                   10                  15

Thr Thr Val Thr Val Ser Ser
            20

<210> SEQ ID NO 46
<211> LENGTH: 15
<212> TYPE: DNA
<213> ORGANISM: Artificial Sequence
<220> FEATURE:
<223> OTHER INFORMATION: Rat Switch

<400> SEQUENCE: 46
gggctgggct gggct                                                         15

<210> SEQ ID NO 47
<211> LENGTH: 20
<212> TYPE: DNA
<213> ORGANISM: Artificial Sequence
<220> FEATURE:
<223> OTHER INFORMATION: Rat Switch

<400> SEQUENCE: 47
gggctgggct gggctgggct                                                    20

<210> SEQ ID NO 48
<211> LENGTH: 25
<212> TYPE: DNA
<213> ORGANISM: Artificial Sequence
<220> FEATURE:
<223> OTHER INFORMATION: Rat Switch

<400> SEQUENCE: 48
gggctgggct gggctgggct gggct                                              25

<210> SEQ ID NO 49
<211> LENGTH: 30
<212> TYPE: DNA
<213> ORGANISM: Artificial Sequence
<220> FEATURE:
<223> OTHER INFORMATION: Rat Switch

<400> SEQUENCE: 49

```
gggctgggct gggctgggct gggctgggct                                           30

<210> SEQ ID NO 50
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(5)
<223> OTHER INFORMATION: Repeat 6 to 81 times

<400> SEQUENCE: 50
gggctgggct                                                                 10

<210> SEQ ID NO 51
<211> LENGTH: 6
<212> TYPE: PRT
<213> ORGANISM: Artificial Sequence
<220> FEATURE:
<223> OTHER INFORMATION: IGHV4-4*02  CDR1

<400> SEQUENCE: 51

Ser Ser Asn Trp Trp Ser
1               5

<210> SEQ ID NO 52
<211> LENGTH: 6
<212> TYPE: PRT
<213> ORGANISM: Artificial Sequence
<220> FEATURE:
<223> OTHER INFORMATION: 12D10 CDR1

<400> SEQUENCE: 52

Ser Gly Asn Trp Trp Ser
1               5

<210> SEQ ID NO 53
<211> LENGTH: 6
<212> TYPE: PRT
<213> ORGANISM: Artificial Sequence
<220> FEATURE:
<223> OTHER INFORMATION: 1283 CDR1

<400> SEQUENCE: 53

Arg Ser Asn Trp Trp Ser
1               5

<210> SEQ ID NO 54
<211> LENGTH: 7
<212> TYPE: PRT
<213> ORGANISM: Artificial Sequence
<220> FEATURE:
<223> OTHER INFORMATION: IGHV6-1*01 CDR1

<400> SEQUENCE: 54

Ser Asn Ser Ala Ala Trp Asn
1               5

<210> SEQ ID NO 55
<211> LENGTH: 7
<212> TYPE: PRT
<213> ORGANISM: Artificial Sequence
<220> FEATURE:
<223> OTHER INFORMATION: 4A12 CDR1

<400> SEQUENCE: 55
```

```
Ser Asn Ser Ala Ala Trp Asn
1               5

<210> SEQ ID NO 56
<211> LENGTH: 16
<212> TYPE: PRT
<213> ORGANISM: Artificial Sequence
<220> FEATURE:
<223> OTHER INFORMATION: IGHV4-4*02 CDR2

<400> SEQUENCE: 56

Glu Ile Tyr His Ser Gly Ser Thr Asn Tyr Asn Pro Ser Leu Lys Ser
1               5                  10                  15

<210> SEQ ID NO 57
<211> LENGTH: 16
<212> TYPE: PRT
<213> ORGANISM: Artificial Sequence
<220> FEATURE:
<223> OTHER INFORMATION: 12D10 CDR2

<400> SEQUENCE: 57

Glu Ile Tyr His Ser Gly Asn Thr Asn Tyr Asn Pro Ser Leu Lys Ser
1               5                  10                  15

<210> SEQ ID NO 58
<211> LENGTH: 16
<212> TYPE: PRT
<213> ORGANISM: Artificial Sequence
<220> FEATURE:
<223> OTHER INFORMATION: 1283 CDR2

<400> SEQUENCE: 58

Glu Ile Tyr His Ser Gly Ser Thr Asn Tyr Asn Pro Ser Leu Lys Ser
1               5                  10                  15

<210> SEQ ID NO 59
<211> LENGTH: 18
<212> TYPE: PRT
<213> ORGANISM: Artificial Sequence
<220> FEATURE:
<223> OTHER INFORMATION: IGHV6-1*01 CDR2

<400> SEQUENCE: 59

Arg Thr Tyr Tyr Arg Ser Lys Trp Tyr Asn Asp Tyr Ala Val Ser Val
1               5                  10                  15

Lys Ser

<210> SEQ ID NO 60
<211> LENGTH: 18
<212> TYPE: PRT
<213> ORGANISM: Artificial Sequence
<220> FEATURE:
<223> OTHER INFORMATION: 4A12 CDR2

<400> SEQUENCE: 60

Arg Thr Tyr Tyr Arg Ser Lys Trp Tyr Asn Asp Tyr Lys Val Ser Val
1               5                  10                  15

Lys Ser

<210> SEQ ID NO 61
<211> LENGTH: 12
<212> TYPE: PRT
<213> ORGANISM: Artificial Sequence
<220> FEATURE:
```

<223> OTHER INFORMATION: 12D10 CDR3

<400> SEQUENCE: 61

Gly Pro Leu Thr Gly Glu Lys Tyr Tyr Phe Asp Leu
1               5                   10

<210> SEQ ID NO 62
<211> LENGTH: 8
<212> TYPE: PRT
<213> ORGANISM: Artificial Sequence
<220> FEATURE:
<223> OTHER INFORMATION: 1283 CDR3

<400> SEQUENCE: 62

Ile Gly Asp Trp Tyr Phe Asp Leu
1               5

<210> SEQ ID NO 63
<211> LENGTH: 16
<212> TYPE: PRT
<213> ORGANISM: Artificial Sequence
<220> FEATURE:
<223> OTHER INFORMATION: 4A12 CDR3

<400> SEQUENCE: 63

Glu Gly Ser His Ser Gly Ser Gly Trp Tyr Leu Asp Ala Phe Asp Ile
1               5                   10                  15

<210> SEQ ID NO 64
<211> LENGTH: 17
<212> TYPE: PRT
<213> ORGANISM: Artificial Sequence
<220> FEATURE:
<223> OTHER INFORMATION: IGHJ2*01 J-region

<400> SEQUENCE: 64

Tyr Trp Tyr Phe Asp Leu Trp Gly Arg Gly Thr Leu Val Thr Val Ser
1               5                   10                  15

Ser

<210> SEQ ID NO 65
<211> LENGTH: 16
<212> TYPE: PRT
<213> ORGANISM: Artificial Sequence
<220> FEATURE:
<223> OTHER INFORMATION: 12D10 J-region

<400> SEQUENCE: 65

Tyr Tyr Phe Asp Leu Trp Gly Arg Gly Thr Leu Val Thr Val Ser Ser
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: 1283 J-Region

<400> SEQUENCE: 66

Trp Tyr Phe Asp Leu Trp Gly Arg Gly Thr Leu Val Thr Val Ser Ser
1               5                   10                  15

<210> SEQ ID NO 67
<211> LENGTH: 16
<212> TYPE: PRT
<213> ORGANISM: Artificial Sequence

```
<220> FEATURE:
<223> OTHER INFORMATION: IGHJ3*01 J-Region

<400> SEQUENCE: 67

Asp Ala Phe Asp Val Trp Gly Gln Gly Thr Met Val Thr Val Ser Ser
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: 4A12 J-region

<400> SEQUENCE: 68

Asp Ala Phe Asp Ile Trp Gly Gln Gly Thr Lys Val Thr Val Ser Ser
1               5                   10                  15
```